(12) United States Patent
Putnam et al.

(10) Patent No.: US 8,470,605 B2
(45) Date of Patent: Jun. 25, 2013

(54) OPTICAL READER FOR READING ENCODED MICROPARTICLES

(75) Inventors: Martin A. Putnam, Cheshire, CT (US); Richard L. Lemoine, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 431 days.

(21) Appl. No.: 12/408,037

(22) Filed: Mar. 20, 2009

(65) Prior Publication Data

US 2010/0072278 A1 Mar. 25, 2010

Related U.S. Application Data

(60) Division of application No. 11/226,892, filed on Sep. 13, 2005, now abandoned, and a continuation-in-part of application No. 10/661,836, filed on Sep. 12, 2003, now Pat. No. 7,399,643, which is a continuation-in-part of application No. 10/645,689, filed on Aug. 20, 2003, now abandoned, said application No. 11/226,892 is a continuation-in-part of application No. 11/063,665, filed on Feb. 22, 2005, now abandoned.

(60) Provisional application No. 60/609,583, filed on Sep. 13, 2004, provisional application No. 60/610,910, filed on Sep. 17, 2004, provisional application No. 60/610,833, filed on Sep. 17, 2004, provisional application No. 60/410,541, filed on Sep. 12, 2002, provisional application No. 60/546,435, filed on Feb. 19, 2004.

(51) Int. Cl.
*G06K 7/10* (2006.01)
*G01N 33/53* (2006.01)

(52) U.S. Cl.
USPC ............ 436/174; 436/180; 436/524; 435/7.1; 435/287.2; 235/454

(58) Field of Classification Search
USPC ... 436/174, 180, 524; 435/7.1, 287.2; 422/99, 422/100, 507; 235/454
See application file for complete search history.

(56) References Cited

U.S. PATENT DOCUMENTS

| 3,074,634 A | 1/1963 | Gamo |
| 3,600,223 A | 8/1971 | Glick |

(Continued)

FOREIGN PATENT DOCUMENTS

| CH | 598661 | 5/1978 |
| DE | 2416652 | 10/1975 |

(Continued)

OTHER PUBLICATIONS

Jain KK, Nanodiagnostics: Application of Nanotechnology in Molecular Diagnostics, Expert Review of Molecular Diagnostics 3(2):153-161 (2003), XP008038849.

(Continued)

*Primary Examiner* — Krishnan S Menon
*Assistant Examiner* — Rebecca M Fritchman
(74) *Attorney, Agent, or Firm* — The Small Patent Law Group LLC; Jason P. Gross

(57) ABSTRACT

An optical reader for reading encoded microparticles. Each microparticle has an elongated body with an optically detectable code that extends along a longitudinal axis of the corresponding elongated body. The reader includes a plate that has a plurality of channels. The channels are configured to receive and align the microparticles so that the codes of the microparticles are in a common fixed orientation relative to each other. The reader also includes an illumination source for illuminating the microparticles on the plate. The codes in the microparticles reflect a portion of incident light and permit a portion of the incident light to pass through the microparticles thereby providing an output signal indicative of the code. The reader also includes a detection device that is configured to capture the output signal provided by the microparticles.

21 Claims, 83 Drawing Sheets

U.S. PATENT DOCUMENTS

| | | |
|---|---|---|
| 3,614,193 A | 10/1971 | Beiser |
| 3,791,788 A | 2/1974 | Taylor |
| 3,858,979 A | 1/1975 | Elbe |
| 3,880,497 A | 4/1975 | Bryngdahl |
| 3,891,302 A | 6/1975 | Dabby |
| 3,903,415 A | 9/1975 | Holzapfel |
| 3,916,182 A | 10/1975 | Dabby |
| 3,928,253 A | 12/1975 | Thornton et al. |
| 3,968,476 A | 7/1976 | McMahon |
| 4,011,435 A | 3/1977 | Phelps |
| 4,023,010 A | 5/1977 | Horst |
| 4,053,228 A | 10/1977 | Schiller |
| 4,053,433 A | 10/1977 | Lee |
| 4,112,037 A | 9/1978 | Parker et al. |
| 4,131,337 A | 12/1978 | Moraw |
| 4,168,146 A | 9/1979 | Grubb |
| 4,301,139 A | 11/1981 | Feingers |
| 4,386,274 A | 5/1983 | Altshuler |
| 4,400,616 A | 8/1983 | Chevillat |
| 4,445,229 A | 4/1984 | Tasto |
| 4,447,546 A | 5/1984 | Hirschfeld |
| 4,537,504 A | 8/1985 | Baltes |
| 4,560,881 A | 12/1985 | Briggs |
| 4,562,157 A | 12/1985 | Lowe |
| 4,647,544 A | 3/1987 | Nicoli |
| 4,678,752 A | 7/1987 | Thorne |
| 4,685,480 A | 8/1987 | Eck |
| 4,688,240 A | 8/1987 | Hosemann |
| 4,690,907 A | 9/1987 | Hibino |
| 4,701,754 A | 10/1987 | Provonchee |
| 4,716,121 A | 12/1987 | Block |
| 4,725,110 A | 2/1988 | Glenn |
| 4,740,468 A | 4/1988 | Weng |
| 4,740,688 A | 4/1988 | Edwards |
| 4,748,110 A | 5/1988 | Paul |
| 4,762,420 A | 8/1988 | Bowley |
| 4,767,719 A | 8/1988 | Finlan |
| 4,770,295 A | 9/1988 | Carveth et al. |
| 4,807,950 A | 2/1989 | Glenn |
| 4,815,027 A | 3/1989 | Tokumitsu |
| 4,816,659 A | 3/1989 | Bianco |
| 4,820,006 A | 4/1989 | Constant |
| 4,822,746 A | 4/1989 | Walt |
| 4,841,140 A | 6/1989 | Sullivan |
| 4,843,631 A | 6/1989 | Steinpichler |
| 4,877,747 A | 10/1989 | Stewart |
| 4,880,752 A | 11/1989 | Keck |
| 4,882,288 A | 11/1989 | North |
| 4,921,805 A | 5/1990 | Gebeyehu |
| 4,931,384 A | 6/1990 | Layton |
| 4,937,048 A | 6/1990 | Sakai |
| 4,958,376 A | 9/1990 | Leib |
| 4,992,385 A | 2/1991 | Godfrey |
| 5,002,867 A | 3/1991 | Macevicz |
| 5,003,600 A | 3/1991 | Deason |
| RE33,581 E | 4/1991 | Nicoli |
| 5,028,545 A | 7/1991 | Soini |
| 5,030,558 A | 7/1991 | Litman |
| 5,033,826 A | 7/1991 | Kolner |
| 5,048,139 A | 9/1991 | Matsumi |
| 5,065,008 A | 11/1991 | Hakamata |
| 5,067,155 A | 11/1991 | Bianco |
| 5,081,012 A | 1/1992 | Flanagan |
| 5,089,387 A | 2/1992 | Tsay |
| 5,090,807 A | 2/1992 | Tai |
| 5,091,636 A | 2/1992 | Takada |
| 5,095,194 A | 3/1992 | Barbanell |
| 5,100,238 A | 3/1992 | Nailor |
| 5,104,209 A | 4/1992 | Hill |
| 5,105,305 A | 4/1992 | Betzig |
| 5,114,864 A | 5/1992 | Walt |
| 5,115,121 A | 5/1992 | Bianco |
| 5,118,608 A | 6/1992 | Layton |
| 5,129,974 A | 7/1992 | Aurenius |
| 5,138,468 A | 8/1992 | Barbanell |
| 5,141,848 A | 8/1992 | Donovan |
| 5,143,853 A | 9/1992 | Walt |
| 5,144,461 A | 9/1992 | Horan |
| 5,160,701 A | 11/1992 | Brown, III |
| 5,166,813 A | 11/1992 | Metz |
| 5,192,980 A | 3/1993 | Dixon |
| 5,196,350 A | 3/1993 | Backman |
| 5,200,794 A | 4/1993 | Nishiguma |
| 5,218,594 A | 6/1993 | Tanno |
| 5,239,178 A | 8/1993 | Derndinger |
| 5,244,636 A | 9/1993 | Walt |
| 5,283,777 A | 2/1994 | Tanno |
| 5,291,006 A | 3/1994 | Nishiguma |
| 5,291,027 A | 3/1994 | Kita |
| 5,300,764 A | 4/1994 | Hoshino |
| 5,307,332 A | 4/1994 | Tinet |
| 5,310,686 A | 5/1994 | Sawyers |
| 5,329,352 A | 7/1994 | Jacobsen |
| 5,342,790 A | 8/1994 | Levine |
| 5,349,442 A | 9/1994 | Deason |
| 5,352,582 A | 10/1994 | Lichtenwalter |
| 5,364,797 A | 11/1994 | Olson |
| 5,367,588 A | 11/1994 | Hill |
| 5,372,783 A | 12/1994 | Lackie |
| 5,374,816 A | 12/1994 | Bianco |
| 5,374,818 A | 12/1994 | Bianco |
| 5,388,173 A | 2/1995 | Glenn |
| 5,394,234 A | 2/1995 | Bianco |
| 5,395,558 A | 3/1995 | Tsai |
| 5,410,147 A | 4/1995 | Riza |
| 5,426,297 A | 6/1995 | Dunphy |
| 5,432,329 A | 7/1995 | Colgate |
| 5,442,433 A | 8/1995 | Hoshino |
| 5,448,659 A | 9/1995 | Tsutsui |
| 5,451,528 A | 9/1995 | Raymoure |
| 5,455,178 A | 10/1995 | Fattinger |
| 5,461,475 A | 10/1995 | Lerner |
| 5,465,176 A | 11/1995 | Bianco |
| 5,468,649 A | 11/1995 | Shah |
| 5,472,515 A | 12/1995 | Roberts |
| 5,479,515 A | 12/1995 | Longacre |
| 5,506,674 A | 4/1996 | Inoue |
| 5,514,785 A | 5/1996 | Van Ness |
| 5,528,045 A | 6/1996 | Hoffman |
| 5,547,849 A | 8/1996 | Baer |
| 5,559,613 A | 9/1996 | Deveaud-Pledran |
| 5,585,639 A | 12/1996 | Dorsel |
| 5,587,832 A | 12/1996 | Krause |
| 5,607,188 A | 3/1997 | Bahns |
| 5,610,287 A | 3/1997 | Nikiforov |
| 5,620,853 A | 4/1997 | Smethers |
| 5,621,515 A | 4/1997 | Hoshino |
| 5,624,850 A | 4/1997 | Kumar |
| 5,625,472 A | 4/1997 | Mizrahi |
| 5,627,040 A | 5/1997 | Bierre |
| 5,627,663 A | 5/1997 | Horan |
| 5,633,724 A | 5/1997 | King |
| 5,633,790 A | 5/1997 | Gritter |
| 5,633,975 A | 5/1997 | Gary |
| 5,663,790 A | 9/1997 | Ekstrom |
| 5,667,976 A | 9/1997 | Van Ness |
| 5,671,308 A | 9/1997 | Inoue |
| 5,682,244 A | 10/1997 | Barlow |
| 5,700,037 A | 12/1997 | Keller |
| 5,712,912 A | 1/1998 | Tomko |
| 5,721,435 A | 2/1998 | Troll |
| 5,729,365 A | 3/1998 | Sweatt |
| 5,736,330 A | 4/1998 | Fulton |
| 5,742,432 A | 4/1998 | Bianco |
| 5,745,615 A | 4/1998 | Atkins |
| 5,745,617 A | 4/1998 | Starodubov |
| 5,759,778 A | 6/1998 | Li |
| 5,760,961 A | 6/1998 | Tompkin |
| 5,766,956 A | 6/1998 | Groger |
| 5,771,251 A | 6/1998 | Kringlebotn |
| 5,776,694 A | 7/1998 | Sheiness |
| 5,793,502 A | 8/1998 | Bianco |
| 5,798,273 A | 8/1998 | Shuler |
| 5,799,231 A | 8/1998 | Gates |
| 5,801,857 A | 9/1998 | Heckenkamp |
| 5,804,384 A | 9/1998 | Muller |
| 5,812,272 A | 9/1998 | King |

| Patent | Kind | Date | Name |
|---|---|---|---|
| 5,822,472 | A | 10/1998 | Danielzik |
| 5,824,478 | A | 10/1998 | Muller |
| 5,824,557 | A | 10/1998 | Burker |
| 5,830,622 | A | 11/1998 | Canning |
| 5,831,698 | A | 11/1998 | Depp |
| 5,837,475 | A | 11/1998 | Dorsel |
| 5,837,552 | A | 11/1998 | Cotton |
| 5,841,555 | A | 11/1998 | Bianco |
| 5,846,737 | A | 12/1998 | Kang |
| 5,861,113 | A | 1/1999 | Choquette |
| 5,874,187 | A | 2/1999 | Colvin |
| 5,881,197 | A | 3/1999 | Dong |
| 5,895,750 | A | 4/1999 | Mushahwar |
| 5,922,550 | A | 7/1999 | Everhart |
| 5,922,617 | A | 7/1999 | Wang |
| 5,925,562 | A | 7/1999 | Nova |
| 5,925,878 | A | 7/1999 | Challener |
| 5,945,679 | A | 8/1999 | Dorsel |
| 5,972,542 | A | 10/1999 | Starodubov |
| 5,976,896 | A | 11/1999 | Kumar |
| 5,981,166 | A | 11/1999 | Mandecki |
| 5,986,838 | A | 11/1999 | Thomas, III |
| 5,989,923 | A | 11/1999 | Lowe |
| 5,992,742 | A | 11/1999 | Sullivan |
| 5,998,796 | A | 12/1999 | Liu |
| 6,001,510 | A | 12/1999 | Meng |
| 6,005,691 | A | 12/1999 | Grot |
| 6,017,754 | A | 1/2000 | Chesnut |
| 6,025,129 | A | 2/2000 | Nova |
| 6,025,283 | A | 2/2000 | Roberts |
| 6,027,694 | A | 2/2000 | Boulton |
| 6,030,581 | A | 2/2000 | Virtanen |
| 6,035,082 | A | 3/2000 | Murphy |
| 6,035,083 | A | 3/2000 | Brennan et al. |
| 6,036,807 | A | 3/2000 | Brongers |
| 6,043,880 | A | 3/2000 | Andrews |
| 6,046,925 | A | 4/2000 | Tsien |
| 6,049,727 | A | 4/2000 | Crothall |
| 6,057,107 | A | 5/2000 | Fulton |
| 6,060,256 | A | 5/2000 | Everhart |
| 6,067,167 | A | 5/2000 | Atkinson |
| 6,067,392 | A | 5/2000 | Wakami |
| 6,078,048 | A | 6/2000 | Stevens |
| 6,084,995 | A | 7/2000 | Clements |
| 6,087,186 | A | 7/2000 | Cargill |
| 6,088,503 | A | 7/2000 | Chandler et al. |
| 6,096,496 | A | 8/2000 | Frankel |
| 6,096,596 | A | 8/2000 | Gonzalez |
| 6,097,485 | A | 8/2000 | Lievan |
| 6,103,535 | A | 8/2000 | Pilevar |
| 6,118,127 | A | 9/2000 | Liu |
| 6,128,077 | A | 10/2000 | Jovin |
| 6,137,931 | A | 10/2000 | Ishikawa |
| 6,143,247 | A | 11/2000 | Sheppard, Jr. |
| 6,156,501 | A | 12/2000 | McGall |
| 6,159,748 | A | 12/2000 | Hechinger |
| 6,160,240 | A | 12/2000 | Momma |
| 6,160,656 | A | 12/2000 | Mossberg |
| 6,164,548 | A | 12/2000 | Curiel |
| 6,165,592 | A | 12/2000 | Berger |
| 6,165,648 | A | 12/2000 | Colvin |
| 6,174,648 | B1 | 1/2001 | Terao |
| 6,194,563 | B1 | 2/2001 | Cruickshank |
| 6,204,068 | B1 | 3/2001 | Soini |
| 6,204,969 | B1 | 3/2001 | Jang |
| 6,214,560 | B1 | 4/2001 | Yguerabide |
| 6,218,194 | B1 | 4/2001 | Lyndin |
| 6,221,579 | B1 | 4/2001 | Everhart |
| 6,229,635 | B1 | 5/2001 | Wulf |
| 6,229,827 | B1 | 5/2001 | Fernald |
| 6,229,941 | B1 | 5/2001 | Yoon |
| 6,242,056 | B1 | 6/2001 | Spencer |
| 6,259,450 | B1 | 7/2001 | Chiabrera |
| 6,262,846 | B1 | 7/2001 | Nakai |
| 6,268,128 | B1 | 7/2001 | Collins |
| 6,277,628 | B1 | 8/2001 | Johann |
| 6,284,437 | B1 | 9/2001 | Kashyap |
| 6,284,459 | B1 | 9/2001 | Nova |
| 6,285,806 | B1 | 9/2001 | Kersey |
| 6,288,220 | B1 | 9/2001 | Kambara |
| 6,292,282 | B1 | 9/2001 | Mossberg |
| 6,292,319 | B1 | 9/2001 | Thomas, III |
| 6,301,047 | B1 | 10/2001 | Hoshino |
| 6,304,263 | B1 | 10/2001 | Chiabrera |
| 6,306,587 | B1 | 10/2001 | Royer |
| 6,309,601 | B1 | 10/2001 | Juncosa |
| 6,312,961 | B1 | 11/2001 | Voirin |
| 6,313,771 | B1 | 11/2001 | Munroe |
| 6,314,220 | B1 | 11/2001 | Mossberg |
| 6,319,668 | B1 | 11/2001 | Nova |
| 6,321,007 | B1 | 11/2001 | Sanders |
| 6,322,932 | B1 | 11/2001 | Colvin |
| RE37,473 | E | 12/2001 | Challener |
| 6,328,209 | B1 | 12/2001 | O'Boyle |
| 6,329,963 | B1 | 12/2001 | Chiabrera |
| 6,331,273 | B1 | 12/2001 | Nova |
| 6,335,824 | B1 | 1/2002 | Overbeck |
| 6,340,588 | B1 | 1/2002 | Nova |
| 6,344,298 | B1 | 2/2002 | Starodubov et al. |
| 6,352,854 | B1 | 3/2002 | Nova |
| 6,355,198 | B1 | 3/2002 | Kim |
| 6,355,432 | B1 | 3/2002 | Fodor |
| 6,356,681 | B1 | 3/2002 | Chen |
| 6,359,734 | B1 | 3/2002 | Staub |
| 6,361,958 | B1 | 3/2002 | Shieh |
| 6,363,097 | B1 | 3/2002 | Linke |
| 6,371,370 | B2 | 4/2002 | Sadler |
| 6,372,428 | B1 | 4/2002 | Nova |
| 6,383,754 | B1 | 5/2002 | Kaufman |
| 6,391,562 | B2 | 5/2002 | Kambara |
| 6,395,558 | B1 | 5/2002 | Duveneck |
| 6,399,295 | B1 | 6/2002 | Kaylor |
| 6,399,935 | B1 | 6/2002 | Jovin |
| 6,403,320 | B1 | 6/2002 | Read |
| 6,406,841 | B1 | 6/2002 | Lee |
| 6,406,848 | B1 | 6/2002 | Bridgham |
| 6,416,714 | B1 | 7/2002 | Nova |
| 6,416,952 | B1 | 7/2002 | Pirrung |
| 6,417,010 | B1 | 7/2002 | Cargill |
| 6,428,707 | B1 | 8/2002 | Berger |
| 6,428,957 | B1 | 8/2002 | Delenstarr |
| 6,429,022 | B1 | 8/2002 | Kunz |
| 6,433,849 | B1 | 8/2002 | Lowe |
| 6,436,651 | B1 | 8/2002 | Everhart |
| 6,440,667 | B1 | 8/2002 | Fodor |
| 6,456,762 | B1 | 9/2002 | Nishiki |
| RE37,891 | E | 10/2002 | Collins |
| 6,462,770 | B1 | 10/2002 | Cline |
| 6,489,606 | B1 | 12/2002 | Kersey |
| 6,496,287 | B1 | 12/2002 | Seiberle |
| 6,506,342 | B1 | 1/2003 | Frankel |
| 6,514,767 | B1 | 2/2003 | Natan |
| 6,515,753 | B2 | 2/2003 | Maher |
| 6,522,406 | B1 | 2/2003 | Rovira |
| 6,524,793 | B1 | 2/2003 | Chandler |
| 6,533,183 | B2 | 3/2003 | Aasmul |
| 6,542,673 | B1 | 4/2003 | Holter |
| 6,544,739 | B1 | 4/2003 | Fodor |
| 6,545,758 | B1 | 4/2003 | Sandstrom |
| 6,552,809 | B1 | 4/2003 | Bergeron |
| 6,560,017 | B1 | 5/2003 | Bianco |
| 6,565,770 | B1 | 5/2003 | Mayer |
| 6,573,523 | B1 | 6/2003 | Long |
| 6,576,424 | B2 | 6/2003 | Fodor |
| 6,578,712 | B2 | 6/2003 | Lawandy |
| 6,592,036 | B2 | 7/2003 | Sadler |
| 6,594,421 | B1 | 7/2003 | Johnson |
| 6,609,728 | B1 | 8/2003 | Voerman |
| 6,613,581 | B1 | 9/2003 | Wada |
| 6,618,342 | B1 | 9/2003 | Johnson |
| 6,622,916 | B1 | 9/2003 | Bianco |
| 6,628,439 | B2 | 9/2003 | Shiozawa |
| 6,632,655 | B1 | 10/2003 | Mehta |
| 6,635,470 | B1 | 10/2003 | Vann |
| 6,635,863 | B1 | 10/2003 | Nihommori |
| 6,646,243 | B2 | 11/2003 | Pirrung |
| 6,657,758 | B1 | 12/2003 | Garner |
| 6,660,147 | B1 | 12/2003 | Woudenberg |

| | | |
|---|---|---|
| 6,678,429 B2 | 1/2004 | Mossberg |
| RE38,430 E | 2/2004 | Rosenstein |
| 6,689,316 B1 | 2/2004 | Blyth |
| 6,692,031 B2 | 2/2004 | McGrew |
| 6,692,912 B1 | 2/2004 | Boles |
| 6,708,618 B1 | 3/2004 | Tsai |
| 6,750,941 B2 | 6/2004 | Satoh |
| 6,762,061 B1 * | 7/2004 | Borrelli et al. ............... 436/180 |
| 6,794,658 B2 | 9/2004 | MacAulay |
| 6,806,954 B2 | 10/2004 | Sandstrom |
| 6,858,184 B2 | 2/2005 | Pelrine |
| 6,874,639 B2 | 4/2005 | Lawandy |
| 6,881,789 B2 | 4/2005 | Bossé |
| 6,892,001 B2 | 5/2005 | Ohta |
| 6,905,885 B2 | 6/2005 | Colston |
| 6,908,737 B2 * | 6/2005 | Ravkin et al. ................. 435/6 |
| 6,919,009 B2 | 7/2005 | Stonas |
| 6,972,883 B2 | 12/2005 | Fujii et al. |
| 6,982,996 B1 | 1/2006 | Putnam |
| 7,014,815 B1 | 3/2006 | Worthington et al. |
| 7,045,049 B1 | 5/2006 | Natan |
| 7,065,032 B2 | 6/2006 | Horimai |
| 7,080,857 B2 | 7/2006 | Patton |
| 7,092,160 B2 | 8/2006 | Putnam |
| 7,106,513 B2 | 9/2006 | Moon |
| 7,122,384 B2 | 10/2006 | Prober |
| 7,126,755 B2 | 10/2006 | Moon |
| 7,164,533 B2 | 1/2007 | Moon |
| 7,190,522 B2 | 3/2007 | Moon |
| 7,215,628 B2 | 5/2007 | Horimai |
| 7,225,082 B1 | 5/2007 | Natan |
| 7,321,541 B2 | 1/2008 | Horimai |
| 7,339,148 B2 | 3/2008 | Kawano |
| 7,349,158 B2 | 3/2008 | Moon |
| 7,375,890 B2 | 5/2008 | Putnam |
| 7,399,643 B2 | 7/2008 | Moon et al. |
| 7,433,123 B2 | 10/2008 | Putnam et al. |
| 7,441,703 B2 | 10/2008 | Moon |
| 7,508,608 B2 | 3/2009 | Kersey |
| 7,602,952 B2 | 10/2009 | Kersey |
| 7,604,173 B2 | 10/2009 | Kersey |
| 7,619,819 B2 | 11/2009 | Moon |
| 7,791,802 B2 | 9/2010 | Putnam et al. |
| 7,796,333 B2 | 9/2010 | Kersey et al. |
| 2001/0007775 A1 | 7/2001 | Seul |
| 2001/0020375 A1 | 9/2001 | Novack et al. |
| 2001/0029049 A1 | 10/2001 | Walt |
| 2002/0000471 A1 | 1/2002 | Aasmul |
| 2002/0006664 A1 | 1/2002 | Sabatini |
| 2002/0018430 A1 | 2/2002 | Heckenkamp |
| 2002/0021003 A1 | 2/2002 | McGrew |
| 2002/0022273 A1 | 2/2002 | Empedocles |
| 2002/0025534 A1 | 2/2002 | Goh |
| 2002/0031783 A1 * | 3/2002 | Empedocles et al. .......... 435/7.1 |
| 2002/0034747 A1 | 3/2002 | Bruchez, Jr. |
| 2002/0039728 A1 | 4/2002 | Kain |
| 2002/0039732 A1 | 4/2002 | Bruchez |
| 2002/0074513 A1 | 6/2002 | Abel |
| 2002/0084329 A1 | 7/2002 | Kaye |
| 2002/0090650 A1 | 7/2002 | Empedocles |
| 2002/0094528 A1 | 7/2002 | Salafsky |
| 2002/0097658 A1 | 7/2002 | Worthington |
| 2002/0155490 A1 | 10/2002 | Skinner |
| 2002/0174918 A1 | 11/2002 | Fujimura et al. |
| 2002/0197456 A1 | 12/2002 | Pope |
| 2003/0008323 A1 | 1/2003 | Ravkin |
| 2003/0021003 A1 | 1/2003 | Ono |
| 2003/0032203 A1 | 2/2003 | Sabatini |
| 2003/0077038 A1 | 4/2003 | Murashima |
| 2003/0082568 A1 | 5/2003 | Phan |
| 2003/0082587 A1 | 5/2003 | Seul |
| 2003/0129654 A1 | 7/2003 | Ravkin |
| 2003/0138208 A1 | 7/2003 | Pawlak |
| 2003/0142704 A1 | 7/2003 | Lawandy |
| 2003/0142713 A1 | 7/2003 | Lawandy |
| 2003/0153006 A1 | 8/2003 | Washizu |
| 2003/0162296 A1 | 8/2003 | Lawandy |
| 2003/0184730 A1 | 10/2003 | Price |
| 2003/0203390 A1 | 10/2003 | Kaye |
| 2003/0228610 A1 | 12/2003 | Seul |
| 2004/0027968 A1 | 2/2004 | Horimai |
| 2004/0047030 A1 | 3/2004 | MacAulay |
| 2004/0062178 A1 | 4/2004 | Horimai |
| 2004/0075907 A1 | 4/2004 | Moon |
| 2004/0100636 A1 | 5/2004 | Somekh |
| 2004/0100892 A1 | 5/2004 | Horimai |
| 2004/0125370 A1 | 7/2004 | Montagu |
| 2004/0125424 A1 | 7/2004 | Moon |
| 2004/0126875 A1 | 7/2004 | Putnam |
| 2004/0132205 A1 | 7/2004 | Moon |
| 2004/0156471 A1 | 8/2004 | Sakata |
| 2004/0170356 A1 | 9/2004 | Iazikov |
| 2004/0175842 A1 | 9/2004 | Roitman |
| 2004/0209376 A1 | 10/2004 | Natan |
| 2004/0233485 A1 | 11/2004 | Moon |
| 2004/0263923 A1 | 12/2004 | Moon |
| 2005/0042764 A1 | 2/2005 | Sailor |
| 2005/0054004 A1 | 3/2005 | Alivisatos |
| 2005/0056587 A1 | 3/2005 | Allen |
| 2005/0220408 A1 | 10/2005 | Putnam |
| 2005/0227252 A1 | 10/2005 | Moon |
| 2005/0270603 A1 | 12/2005 | Putnam |
| 2006/0023310 A1 | 2/2006 | Putnam |
| 2006/0028727 A1 | 2/2006 | Moon |
| 2006/0050544 A1 | 3/2006 | Horimai |
| 2006/0057729 A1 | 3/2006 | Moon |
| 2006/0063271 A1 | 3/2006 | Putnam |
| 2006/0067179 A1 | 3/2006 | Matsumoto |
| 2006/0071075 A1 | 4/2006 | Moon |
| 2006/0072177 A1 | 4/2006 | Putnam |
| 2006/0118630 A1 | 6/2006 | Kersey |
| 2006/0119913 A1 | 6/2006 | Moon |
| 2006/0132877 A1 | 6/2006 | Kersey |
| 2006/0134324 A1 | 6/2006 | Putnam |
| 2006/0139635 A1 | 6/2006 | Kersey |
| 2006/0140074 A1 | 6/2006 | Horimai |
| 2006/0160208 A1 | 7/2006 | Putnam |
| 2007/0121181 A1 | 5/2007 | Moon |
| 2007/0236789 A1 | 10/2007 | Moon |
| 2008/0085565 A1 | 4/2008 | Moon |
| 2008/0129990 A1 | 6/2008 | Moon |
| 2008/0165656 A1 | 7/2008 | Moon et al. |
| 2008/0170664 A1 | 7/2008 | Kalman |
| 2008/0192311 A1 | 8/2008 | Horimai |
| 2009/0034078 A1 | 2/2009 | Putnam |
| 2009/0040885 A1 | 2/2009 | Horimai |
| 2009/0073520 A1 | 3/2009 | Kersey |
| 2009/0194589 A1 | 8/2009 | Moon et al. |
| 2010/0025482 A1 | 2/2010 | Moon |
| 2010/0072278 A1 | 3/2010 | Putnam |
| 2010/0099574 A1 | 4/2010 | Moon |

FOREIGN PATENT DOCUMENTS

| | | |
|---|---|---|
| EP | 0 395 300 | 10/1990 |
| EP | 0 723 149 | 7/1996 |
| EP | 0 798 573 A1 | 10/1997 |
| EP | 0 911 667 A1 | 4/1999 |
| EP | 916981 | 5/1999 |
| EP | 0 972 817 A1 | 1/2000 |
| EP | 1182054 | 2/2002 |
| EP | 1219979 | 7/2002 |
| GB | 2 118 189 | 10/1983 |
| GB | 2129551 | 5/1984 |
| GB | 2 138 821 | 10/1984 |
| GB | 2 299 235 | 9/1996 |
| GB | 2 306 484 | 5/1997 |
| GB | 2 319 838 | 6/1998 |
| GB | 2372100 | 8/2002 |
| JP | 58143254 | 8/1983 |
| JP | 58143254 A | 8/1983 |
| JP | 08102544 | 4/1986 |
| JP | 01047950 | 2/1989 |
| JP | 05307119 | 11/1993 |
| JP | 06333102 | 2/1994 |
| JP | 06333102 | 12/1994 |
| JP | 08102544 | 4/1996 |
| JP | 08272923 | 10/1996 |
| JP | 10160705 | 6/1998 |

| | | |
|---|---|---|
| JP | 11119029 | 4/1999 |
| JP | 20035521 | 2/2000 |
| JP | 00249706 | 9/2000 |
| JP | 2000249706 | 9/2000 |
| JP | 200191715 | 4/2001 |
| JP | 2002182022 | 2/2002 |
| JP | 2002513166 | 5/2002 |
| JP | 22182022 | 6/2002 |
| JP | 200300467 A | 1/2003 |
| JP | 2003004671 | 8/2003 |
| WO | WO 91/06496 | 5/1991 |
| WO | WO 93/09668 | 5/1993 |
| WO | WO 94/28119 | 12/1994 |
| WO | WO 96/24061 | 8/1996 |
| WO | WO 96/36436 | 11/1996 |
| WO | WO9636436 | 11/1996 |
| WO | WO 97/12680 | 4/1997 |
| WO | WO 97/15690 | 5/1997 |
| WO | WO 97/17258 | 5/1997 |
| WO | WO 97/31282 | 8/1997 |
| WO | WO 97/34171 | 9/1997 |
| WO | WO 98/04740 | 2/1998 |
| WO | WO 98/24549 | 6/1998 |
| WO | WO 99/02266 | 1/1999 |
| WO | WO 99/09042 | 2/1999 |
| WO | WO 99/32654 | 7/1999 |
| WO | WO 99/42209 | 8/1999 |
| WO | WO 00/08443 | 2/2000 |
| WO | WO0016893 | 3/2000 |
| WO | 0019262 | 6/2000 |
| WO | WO 00/37914 | 6/2000 |
| WO | WO 00/37969 | 6/2000 |
| WO | WO 00/39617 | 7/2000 |
| WO | WO 00/63419 | 10/2000 |
| WO | WO0061198 | 10/2000 |
| WO | WO0158583 | 8/2001 |
| WO | WO0171322 | 9/2001 |
| WO | WO 01/78889 | 10/2001 |
| WO | WO0178889 | 10/2001 |
| WO | WO02/059603 | 8/2002 |
| WO | WO2059306 | 8/2002 |
| WO | WO2064829 | 8/2002 |
| WO | WO03061983 | 7/2003 |
| WO | WO03091731 | 11/2003 |
| WO | WO2004011940 | 2/2004 |
| WO | WO2004015418 | 2/2004 |
| WO | WO 2004/025561 | 3/2004 |
| WO | WO 2004/025563 | 3/2004 |
| WO | WO2004019276 | 3/2004 |
| WO | WO2004024328 | 3/2004 |
| WO | WO2004025562 | 3/2004 |
| WO | WO 2004/034012 | 4/2004 |
| WO | WO2004046697 | 6/2004 |
| WO | WO2004066210 | 8/2004 |
| WO | WO 2005/026729 | 3/2005 |
| WO | WO 2005/027031 | 3/2005 |
| WO | WO 2005/029047 | 3/2005 |
| WO | WO 2005/033681 | 4/2005 |
| WO | WO 2005/050207 | 6/2005 |
| WO | WO 2005/079544 | 9/2005 |
| WO | WO 2006/020363 | 2/2006 |
| WO | WO 2006/055735 | 5/2006 |
| WO | WO 2006/055736 | 5/2006 |
| WO | WO 2006/076053 | 7/2006 |

OTHER PUBLICATIONS

Lide (CRC Handbook of Chemistry and Physics, 71st ed.).
Othonos, X. Lee; Superimposed Multiple Bragg Gratings, Nov. 10, 1994, vol. 30, No. 23.
Patil et al. (AAPS PharmSciTech, Mar. 24, 2006, vol. 7, pp. E1-E7).
Po Ki Yuen, Microbarcode Sorting Device; Science & Technology, Corning Incorparated, Corning, New York 14831-0007, USA.
International Search Report and Written Opinion for International Application No. PCT/US2003/26315.
International Search Report and Written Opinion for International Application No. PCT/US2003/26316.
International Search Report for International Application No. PCT/US2003/28862.
International Search Report for International Application No. PCT/US2003/28874.
International Search Report for International Application No. PCT/US2003/28875.
International Search Report for International Application No. PCT/US2003/28887.
International Search Report for International Application No. PCT/US2003/28890.
International Search Report and Written Opinion for International Application No. PCT/US2003/29164.
International Search Report for International Application No. PCT/US2003/29244.
International Search Report and Written Opinion for International Application No. PCT/US2004/01685.
International Search Report and Written Opinion for International Application No. PCT/US2004/30037.
International Search Report and Written Opinion for International Application No. PCT/US2004/30038.
International Search Report and Written Opinion for International Application No. PCT/US2004/30300.
International Search Report and Written Opinion for International Application No. PCT/US2004/32084.
International Search Report and Written Opinion for International Application No. PCT/US2004/38416.
International Search Report and Written Opinion for International Application No. PCT/US2005/05743.
International Search Report and Written Opinion for International Application No. PCT/US200S/05745.
International Search Report and Written Opinion for International Application No. PCT/US2005/26289.
International Search Report and Written Opinion for International Application No. PCT/US2005/33694.
International Search Report and Written Opinion for International Application No. PCT/US2005/41730.
International Search Report and Written Opinion for International Application No. PCT/US2005/41731.
"Compact Disc Arrayer"; V&P Scientific; Nov. 17, 2003; pp. 1-4.
"Electronically Scanned Confocal Imaging System"; IBM Technical Disclosure Bulletin; vol. 36; No. 06B; Jun. 1993; pp. 261-262.
"Ben Beune Patent Licensing Director of Philips IP&S"; Replication & Duplication—News &Technology; Jan.-Feb. 2002; pp. 1-2.
Andrew Marshall; "DNA Chips: Array of Possibilities"; Nature Biotechnology vol. 16 Jan. 1998; pp. 27-31.
Burstein Technology, Inc.; "Angel Strategies Tombstone"; 1 pg.
de Beer et al., "Forward-Scattering Degenerate Four-Wave Mixing for Sensitive Absorption Detection in Microseparation Systems Coupling to Micro-Column Liquid Chromatography"; Journal of Chromatography A. 811 (1998); pp. 35-45.
Fonjallaz et al., "Interferometric Side Diffraction Technique for the Characterisation of Fiber Gratings"; 1999 OSA Conference, Sep. 23-25; 3 pgs.
G. Kakarantzas et al.;"Transmission Filters Based on periodically Micro-tapered Fibre"; CLE0/2000/Friday Morning; 8:45 a.m.; pp. 574-575.
Hideki Kambara; Recent Progress in fluorescent DNA Analyzers and Methods; Current Topics in Analytical checmistry; vol. 1, (1998) pp. 21-36.
Ivan Oransky; "Sequencing on Compact Disc? Microgenomics of Breast Cancer; Better Binding Site Prediction"; vol. 17 / Issue 13 / 35 / Jun. 30, 2003; 13 pgs.
Kashyap R.; "Fiber Bragg Gratings"; Academic Press, Ch. 9; pp. 430-433.
Kogelnik H; "Coupled Wave Theory for Thick Hologram Gratings"; The Bell System.Technical Journal, 48(9):2909-2947 (1969).
Krug P., "Measurement of Index Modulation Along an Optical Fiber Bragg Grating"; Optics Letters, 20(17):1767-1769.
Leith et al., "Holographic Data Storage in Three-Dimensional Media"; Applied Optics, vol.5, No. 8, Aug. 1966; 21 pgs.
Mark O. Worthington; "Curriculum Vitae"; Jan. 5, 2004; 4 pgs.
Masato Mitsuhashi; "Gene Manipulation on Plastic Plates"; Nature, vol. 357, Jun. 11, 1992; pp. 519-520.

Michael C. Needels et al.; "Generation and Screening of an Oligonucleotide-Encoded Synthetic Peptide Library"; Proc Natl. Acad. Sci. USA, vol. 90;pp. 10700-10704, Nov. 1993.

Michael J. Kozal; "Extensive Polymorphisms Observed in HIV-1 Clade B Protease Gene Using High-Density Oligonucleotide Arrays"; Nature Medicine, vol. 2, No. 7, Jul. 1996; pp. 753-759.

Shelia R. Nicerwarner-Peña, "Submicrometer Metallic Barcodes"; Science, vol. 294; Oct. 5, 2001; 5 pgs.

Thomas Laurell; "Enhanced Enzyme Activity in Silicon Integrated Enzyme Reactors Utilizing Porous Silicon as the Coupling Matrix"; Sensor & Actuators B 31 (1996); pp. 161-166.

Vander Lugt; "Design Relationships for Holographic Memories"; Applied Optics, vol. 12, No. 7, Jul. 1973; pp. 1675-1685.

W.R. Rigby; "An Anodizing Process for the Production of Inorganic Microfiltration Membranes"; 2436Transactions of the Institute of Metal Finishing;68(Aug. 1990),Part 3 p. 95-98.

Yoshinobu Kohara; "DNA Probes on Beads Arrayed in a Capillary, 'Bead-Array', Exhibited High Hybridization Performance"; Nucleic Acids Research, 2002, vol. 30, No. 16 e87; 7 pgs.

"Introduction to Flow Cytometry: A Learning Guide," BD Biosciences, San Jose, CA, Apr. 2000.

Material Safety Data Sheet Aquaclean 900; Aquabond Technologies (ABT); 1 pg.

US 6,780,301, 08/2004, Natan (withdrawn)

* cited by examiner

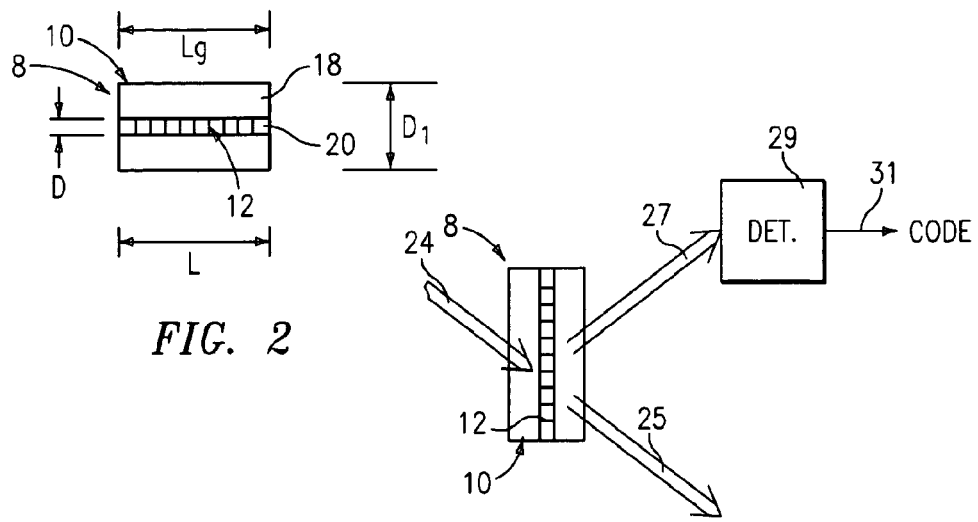
FIG. 2
FIG. 3
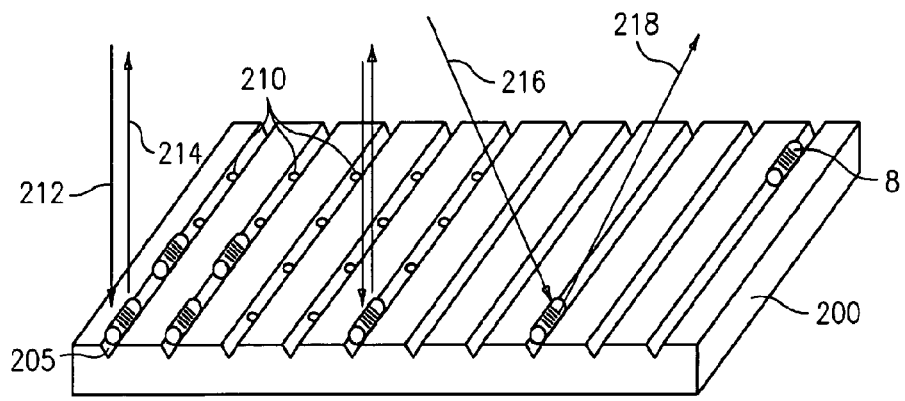
FIG. 4
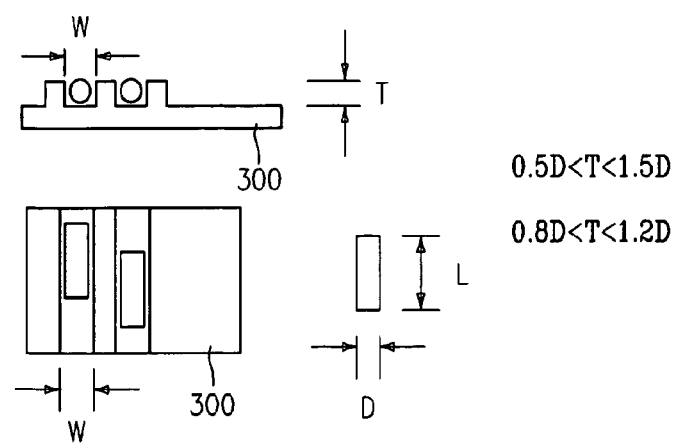
0.5D<T<1.5D
0.8D<T<1.2D
FIG. 5

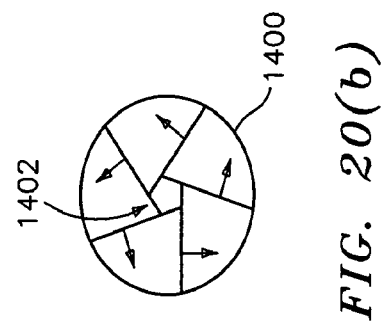
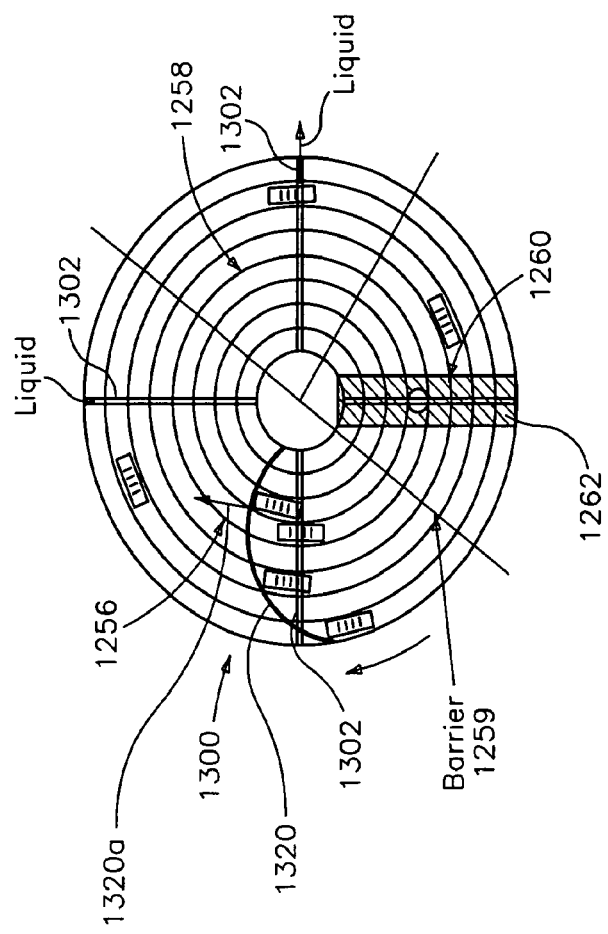

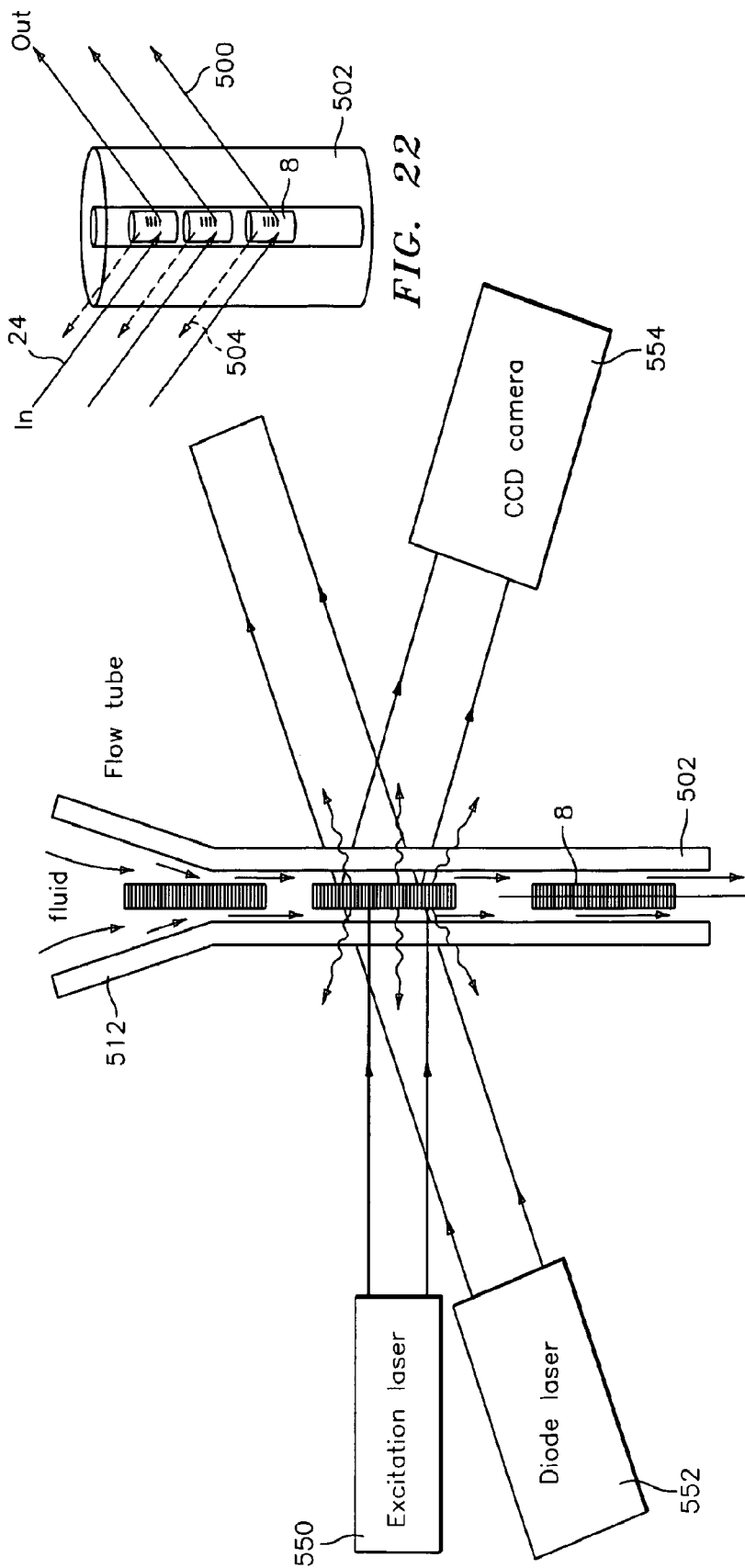

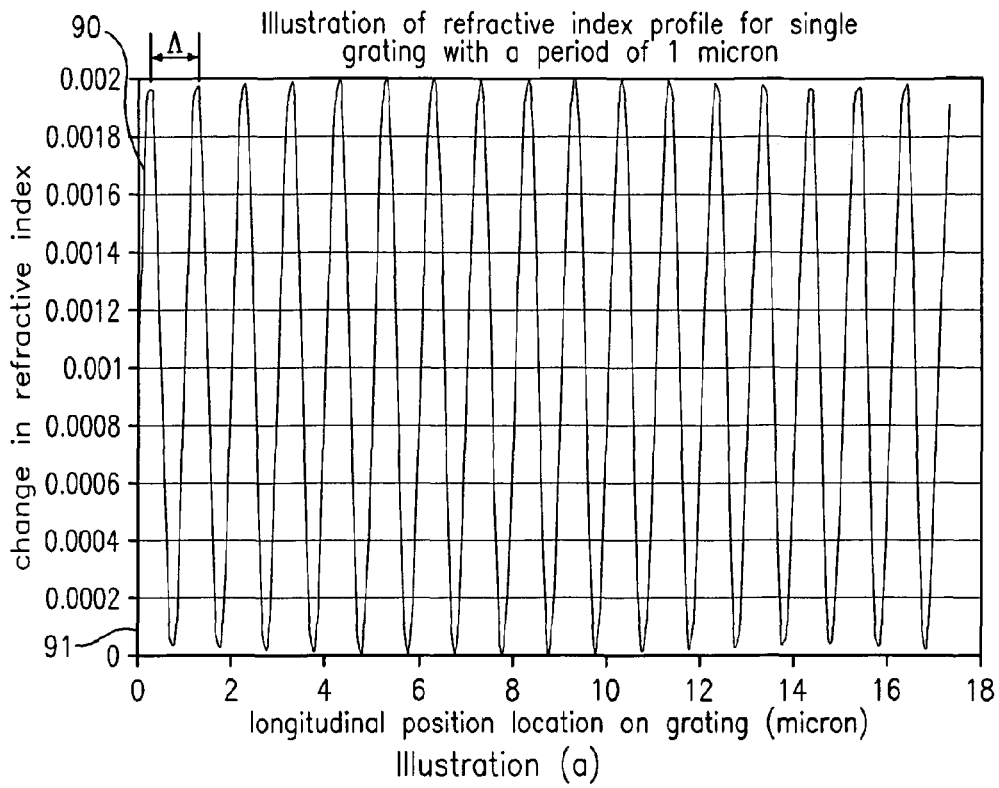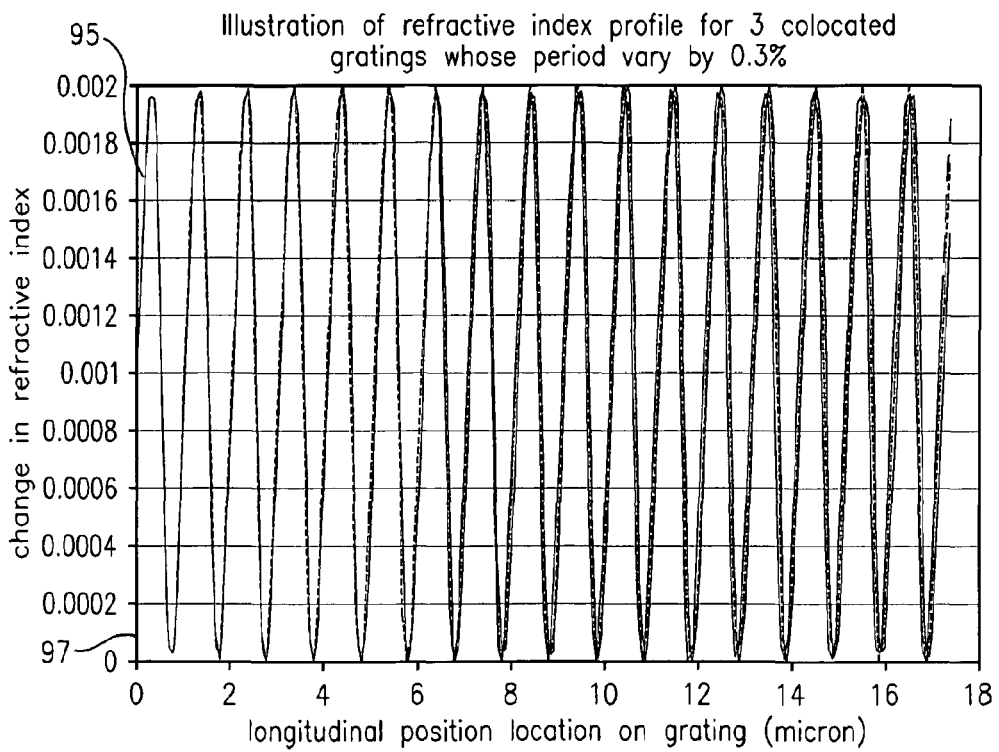
FIG. 27

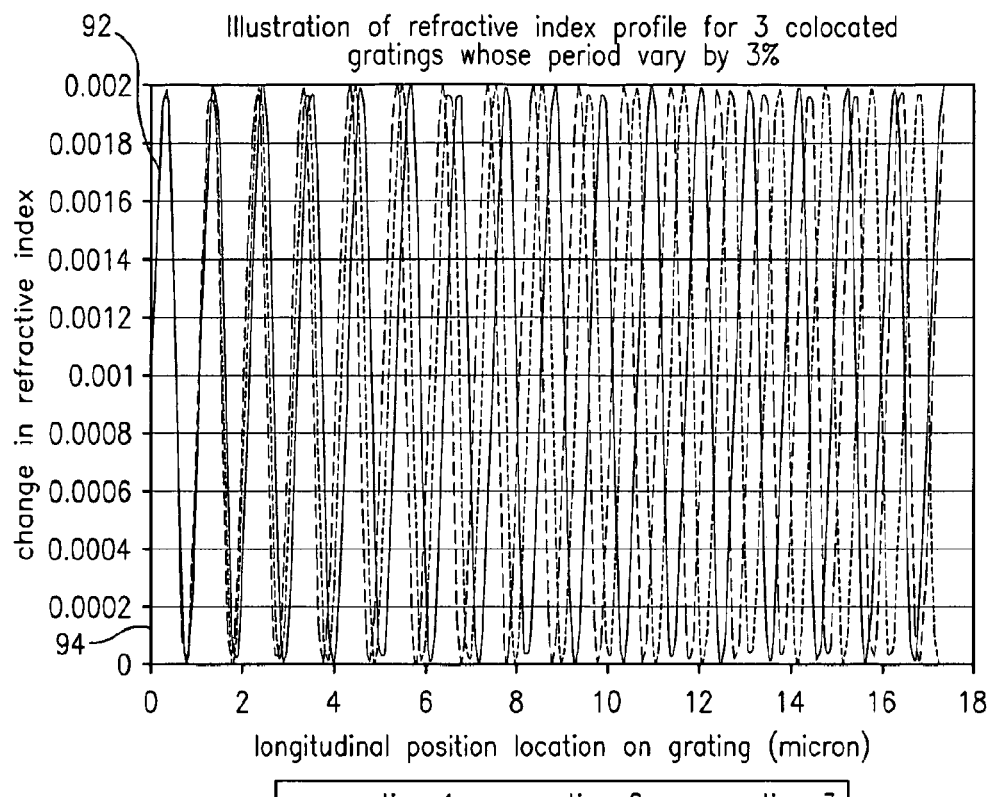
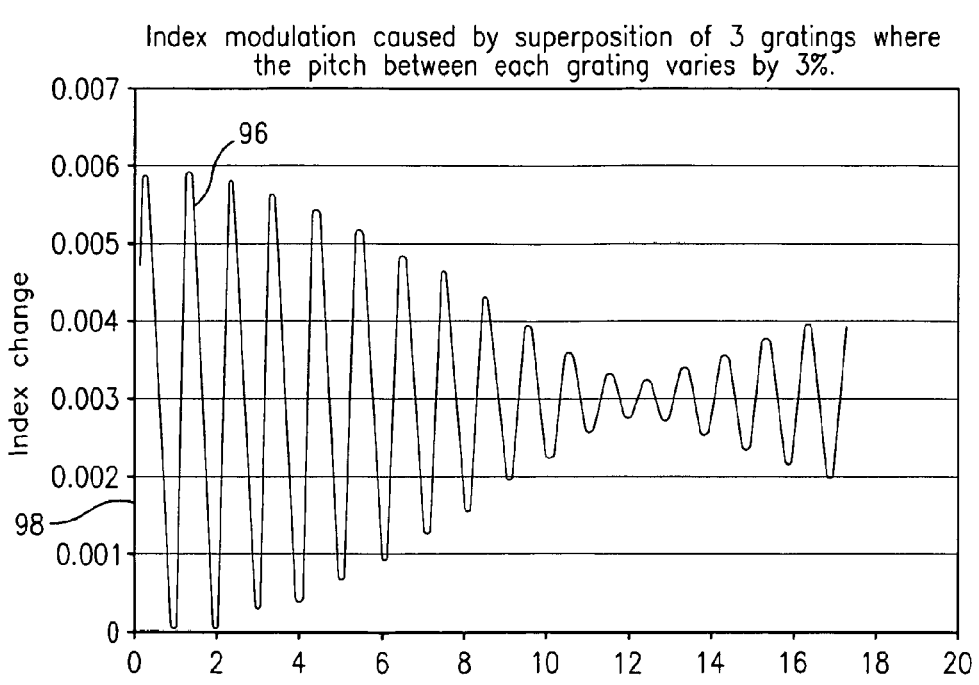
FIG. 27

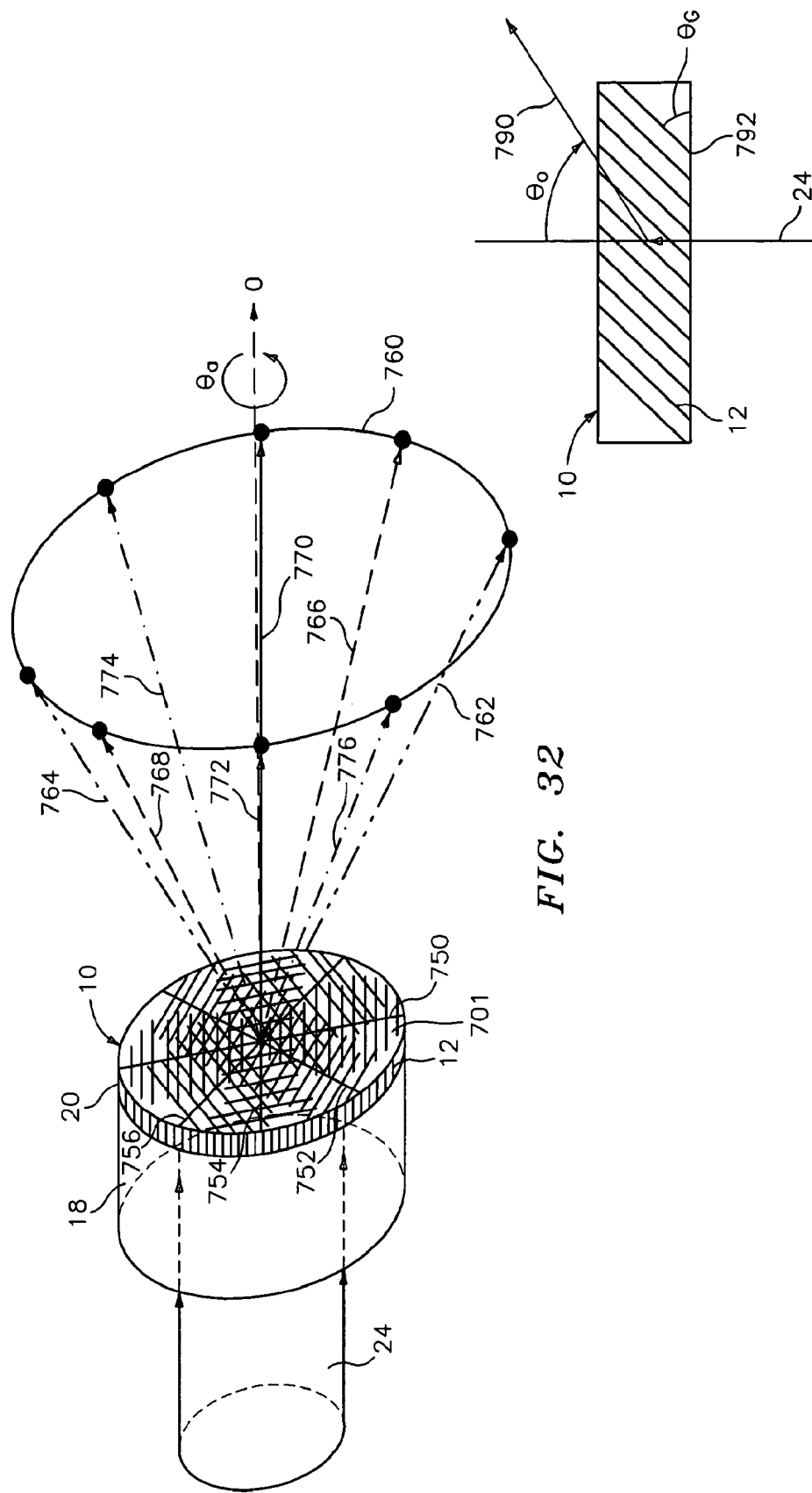

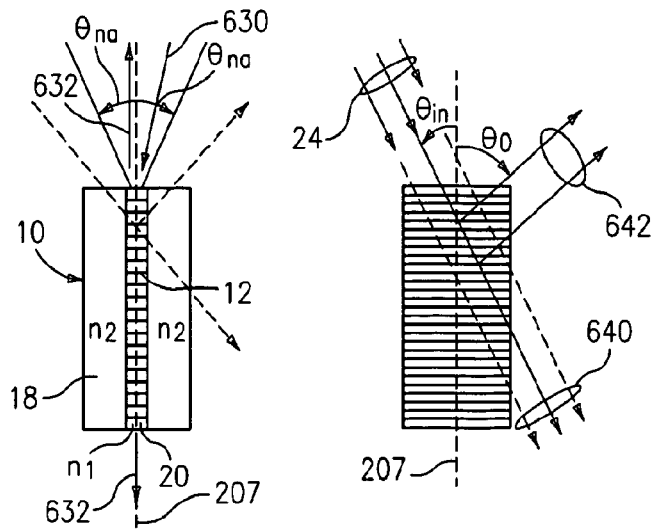
*FIG. 36*   *FIG. 37*
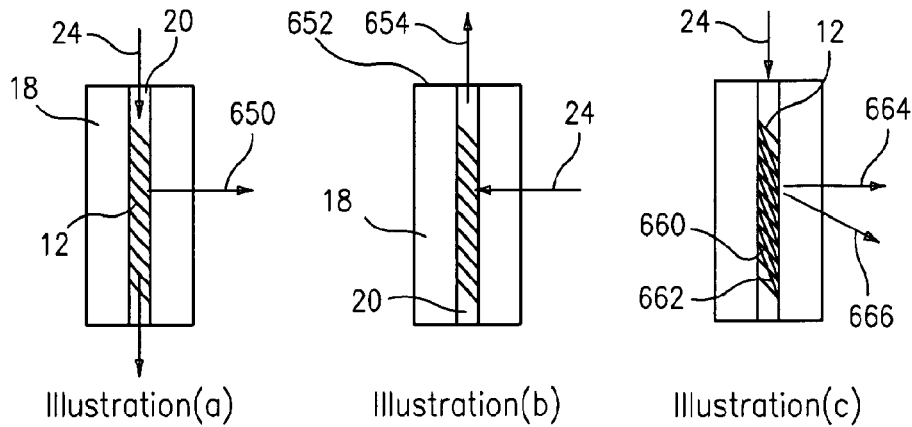
Illustration(a)   Illustration(b)   Illustration(c)
*FIG. 38*
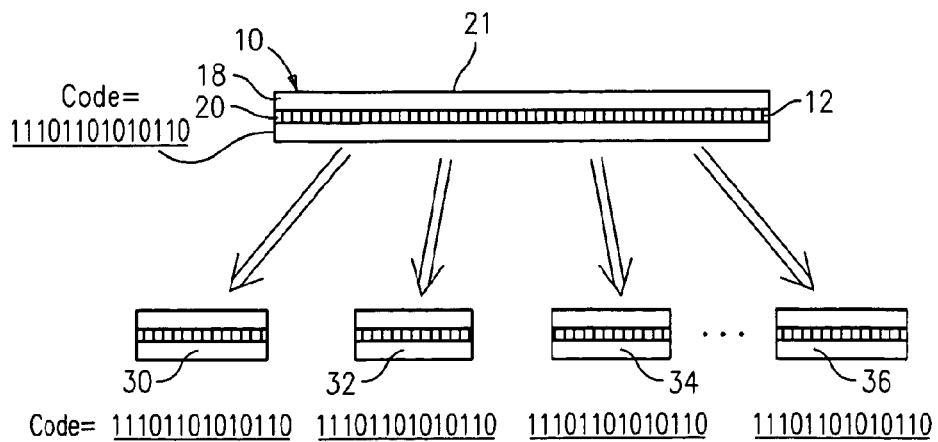
*FIG. 40*

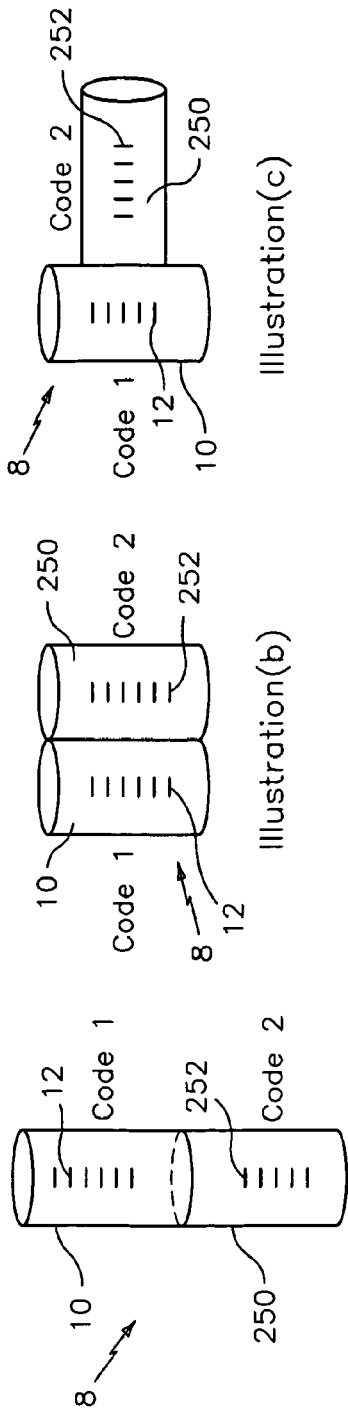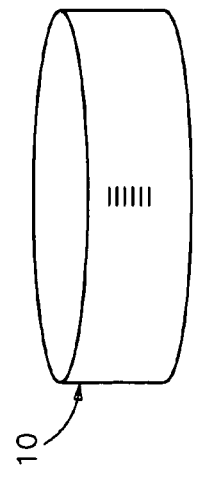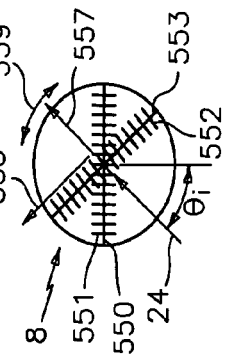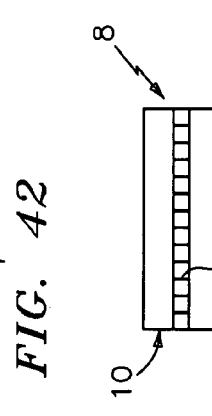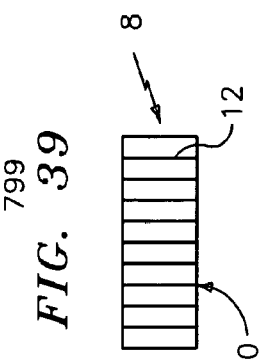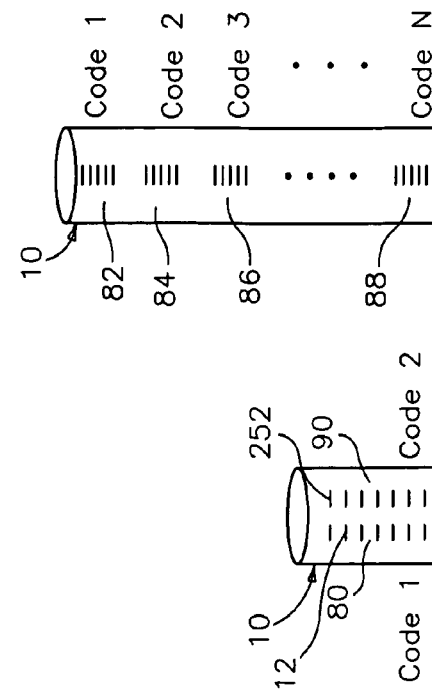

- Grooves formed in RIE Silica plate
- Entry/Exit ports on same centers as 96 well plate
- Bead/fluid entry and exit concepts exist

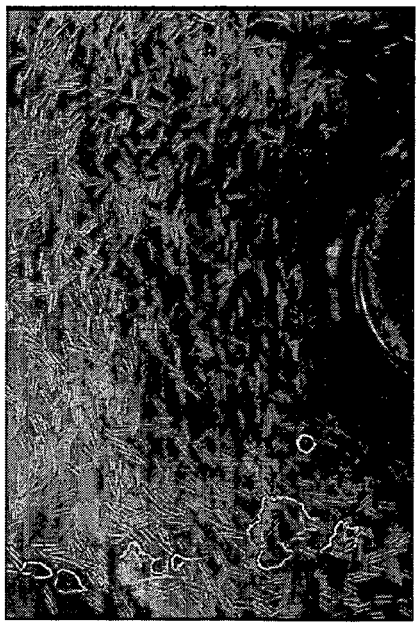
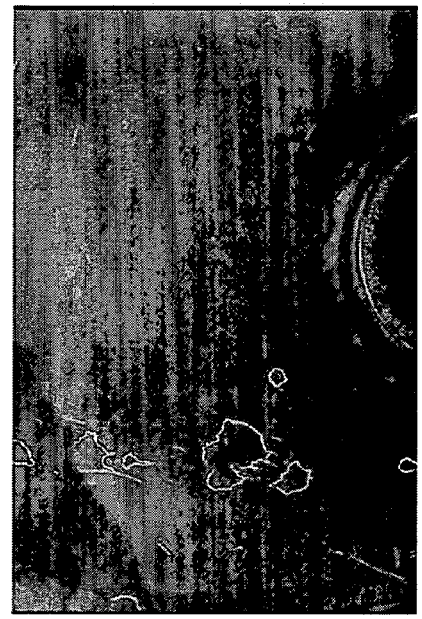
FIG. 73

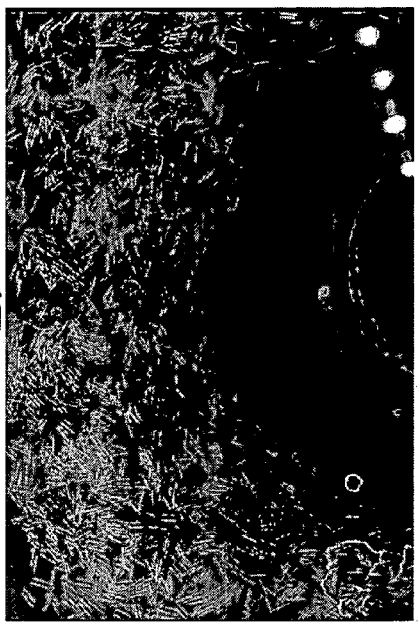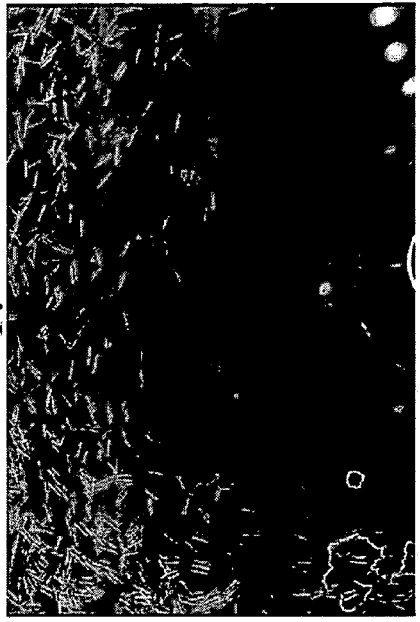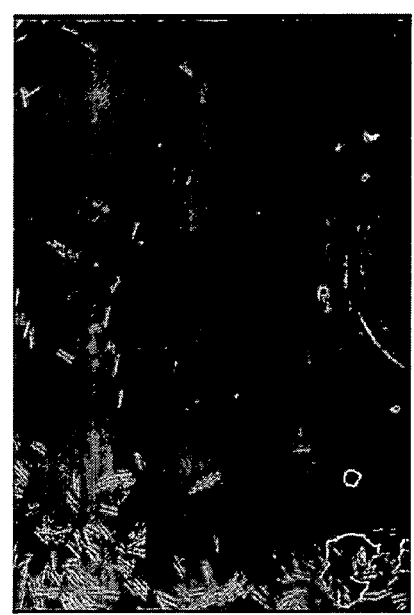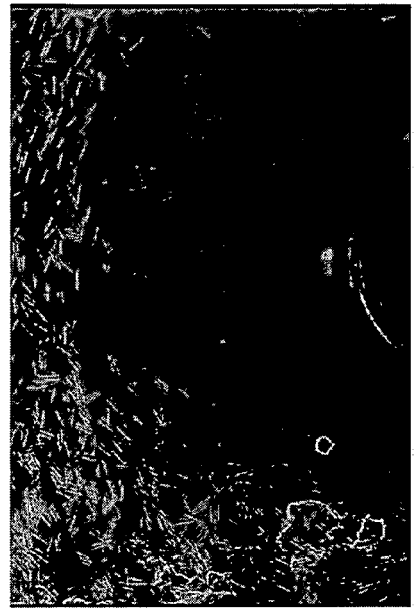
FIG. 74

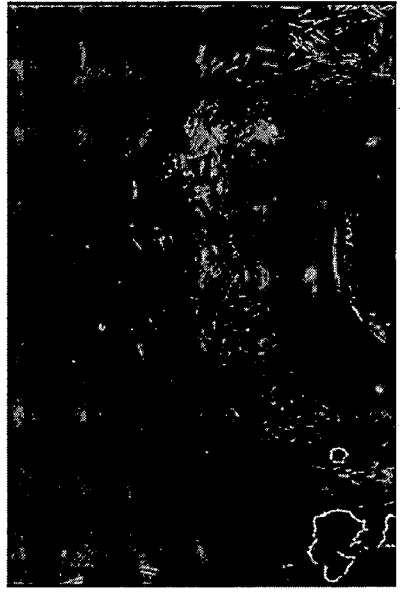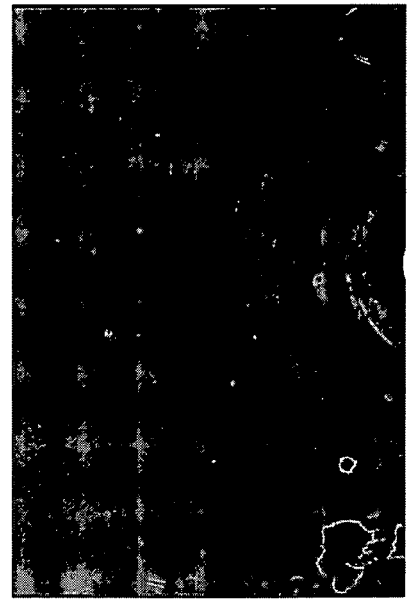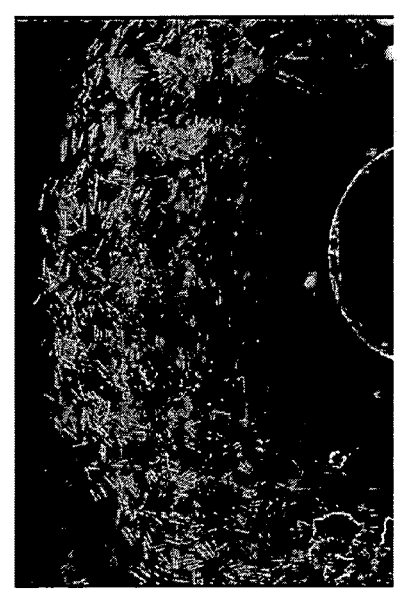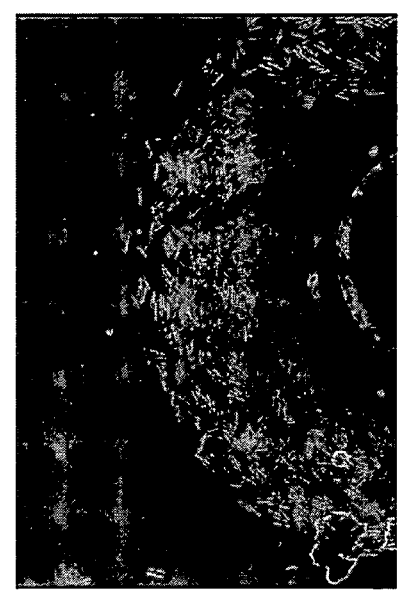
FIG. 76

Ultrasonic Probe for flush

- Flush may be enhanced with ultrasonic probe
- Probe makes contact with groove plate or top window of cell
- Ultrasonic energy (40 kHz) is transmitted to cell (run during the flush cycle; 1–2 seconds); drawing about 1–3 amps. Other frequencies and currents may be used.
- An interface material (e.g., silicone) may be used to increase the contact surface area (thickness of interface material should be minimized to reduce loss)
- Prototyped with probes, power supplies from Sonic & Materials Inc.
- Causes agitation of beads, enhances flush capability
- Also helps clean contamination off of the groove plate
- Probe must be held in contact with cell with sufficient force to maintain direct contact with the cell during operation
- Location may be at either end of sector or anywhere along the length; benefit of being on the end is you may be away from where the optical scanning occurs which minimizes any optical effects caused by the ultrasonic waves or the probe.
- Geometries; circular disk shaped probe of 2.75 in diameter; Bar Horn; 2 in x 0.18 in wide; placed between the sectors or at the end of a sector; May also use one or more dip stick probes which are dipped into the liquid in the cell.

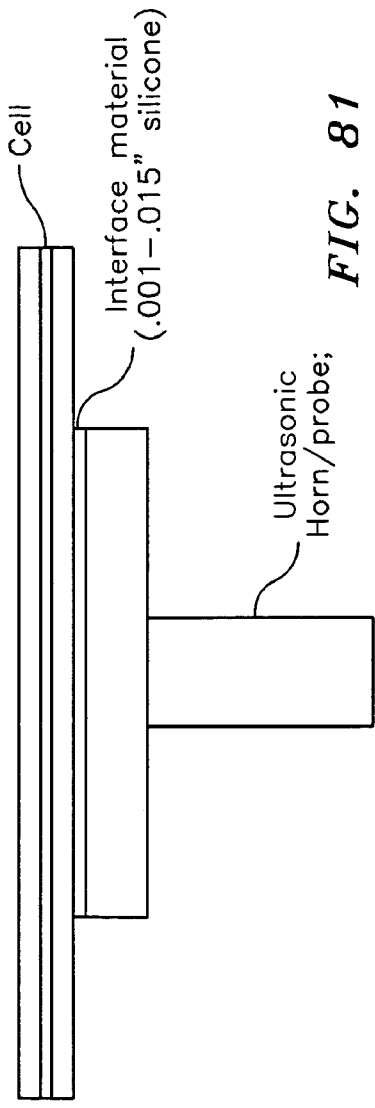

FIG. 81

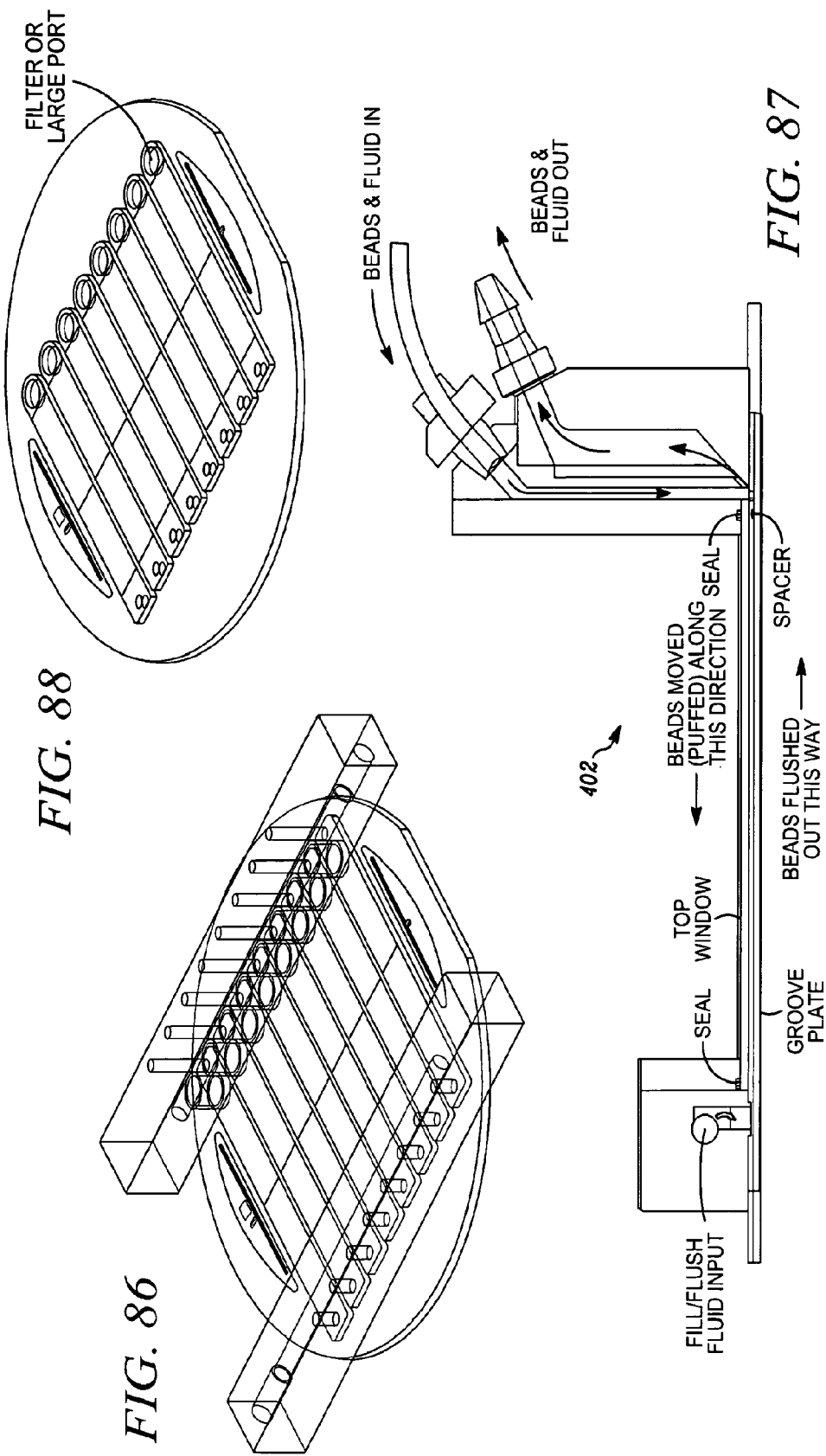

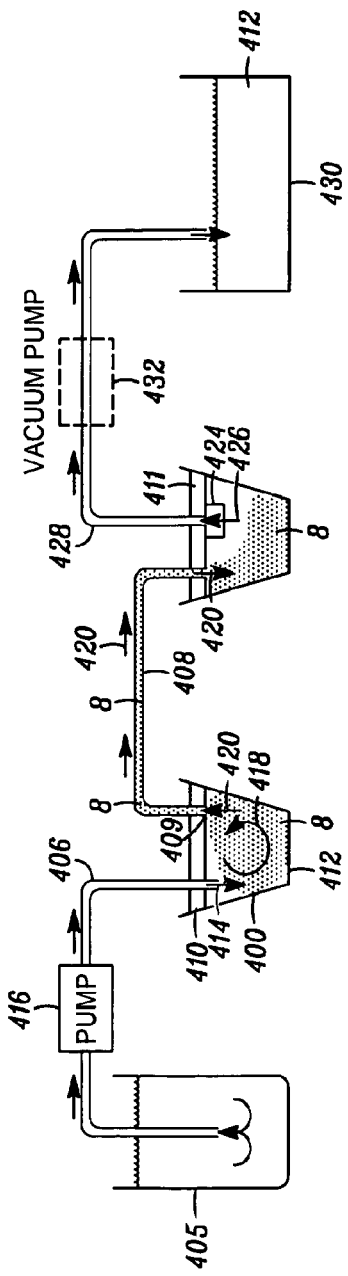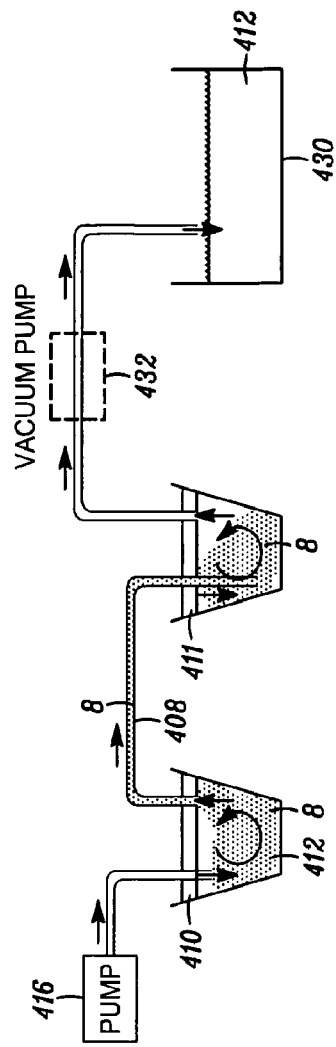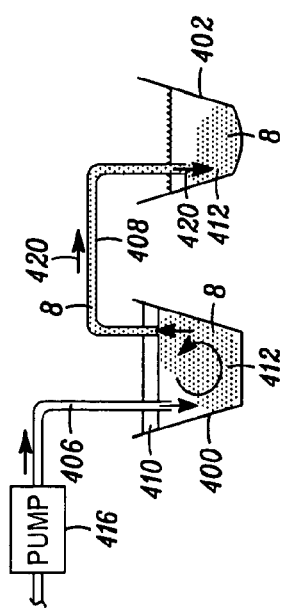

*FIG. 95*

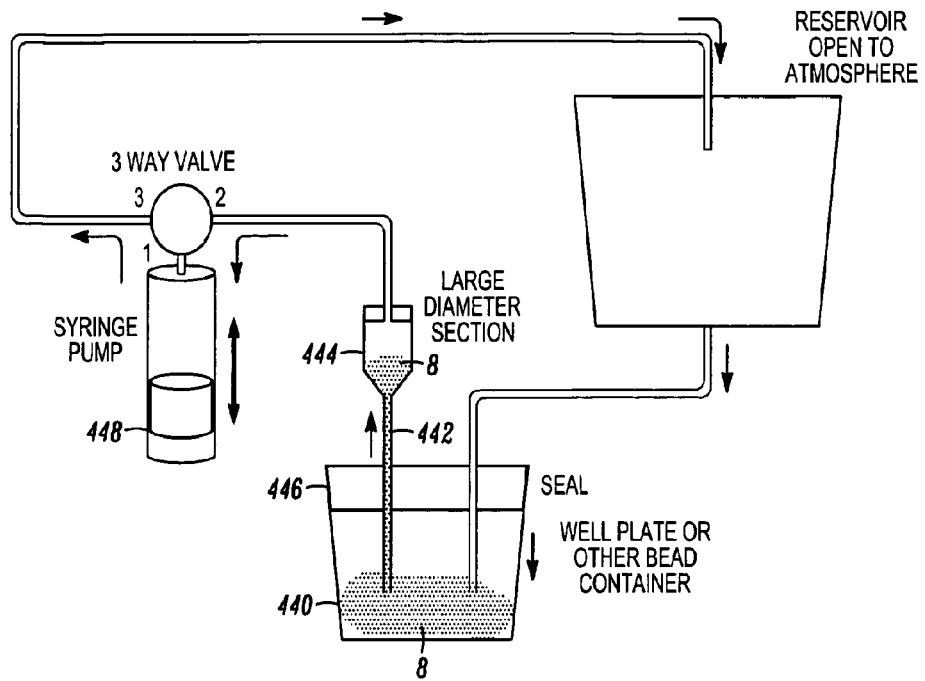

THIS CONFIGURATION SHOWS THAT THE RESERVOIR CAN BE COMBINED TO PROVIDE CLOSED LOOP FLUID MOVEMENT.

*FIG. 96*

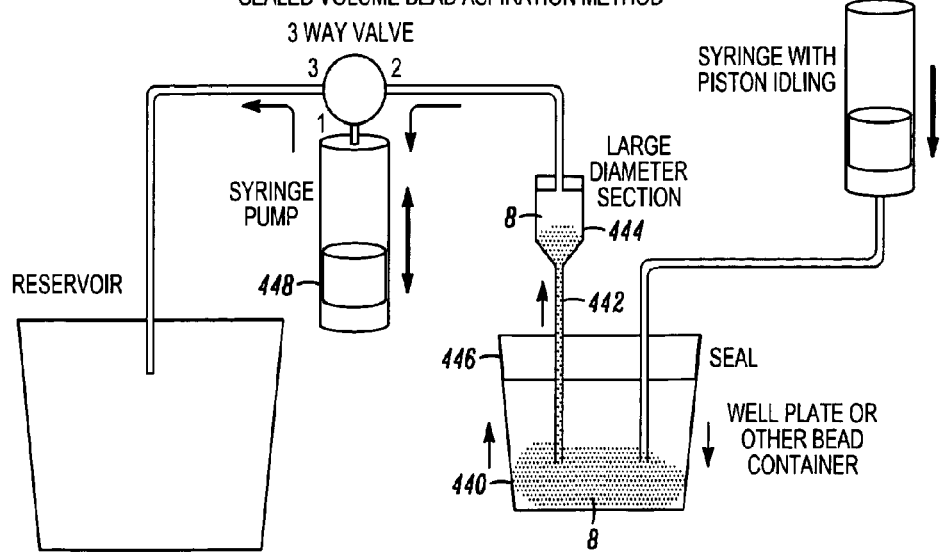

IN THIS CONFIGURATION A PISTON IS ADDED TO THE RESERVOIR OF THE 2ND TIP. THE FLUID WILL THEN NOT RUN OUT OF THE TIP WITHOUT THE PISTON MOVING. FRICTION BETWEEN THE PISTON AND SYRINGE BODY, THEN HOLDS THE PISTON IN PLACE. USE OF THE PISTON PREVENTED FLUID FROM DRIPPING OUT OF THE END OF THE 2ND TIP.

- ASPIRATION & DISPENSE W/A HAMILTON SYRINGE PUMP
- STORAGE BUFFER: 1X SSC, 0.1% SDS
- 28μm BEADS
- 200uL ULTRAFINE POINTS (VWR) PIPETTE TIPS

PIPETTE EXPERIMENTS

- BEAD DIAMETER: 28μm
- AGITATION VOLUME: 150μL
- FINAL ASPIRATION/DISPERSE VOLUME: 27μL
- STARTING BEAD CONCENTRATION: 0.68 BEADS/μL
- NUMBER OF TESTS: 36
- AVERAGE NUMBER BEADS/ASPIRATION: 18

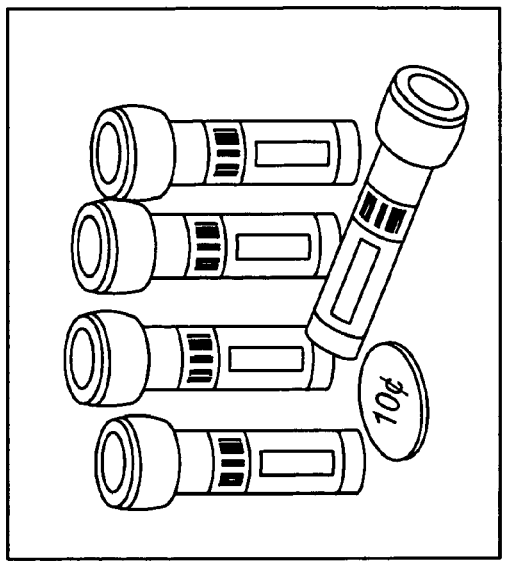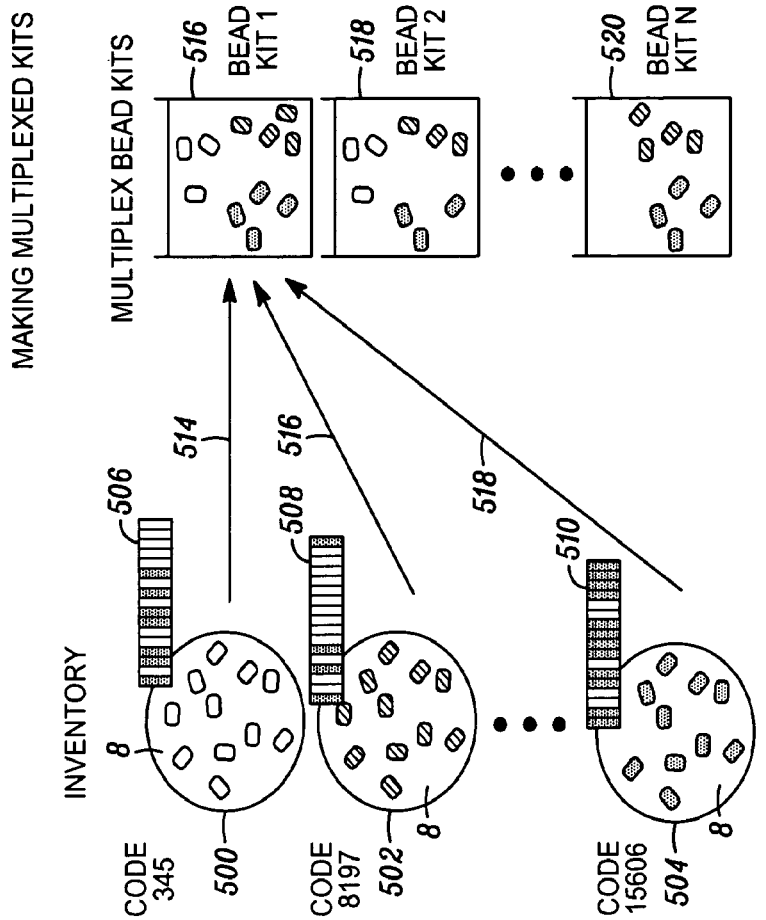
FIG. 107

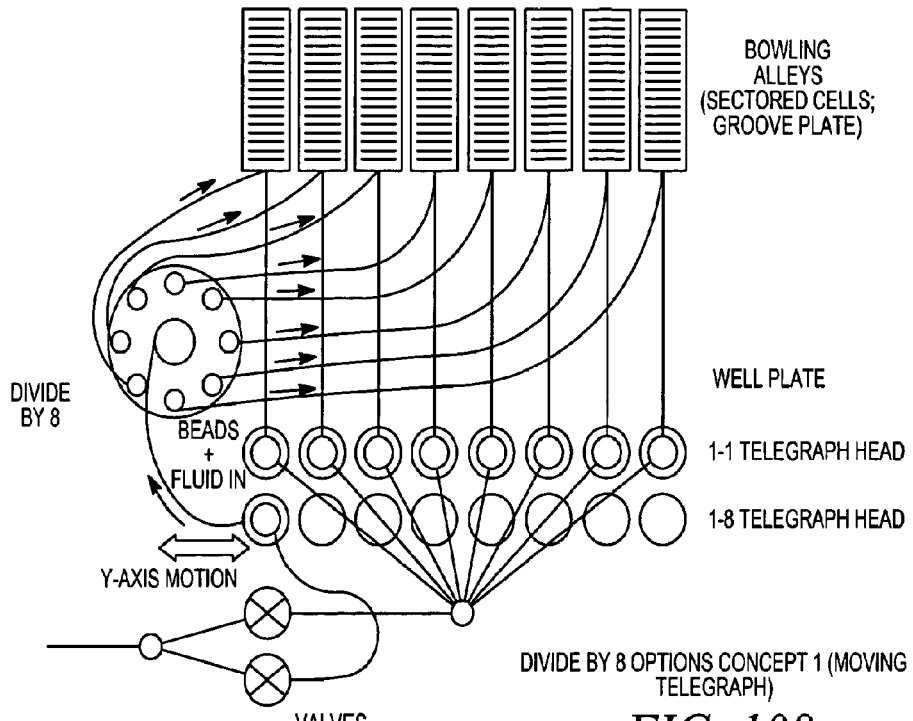
FIG. 108
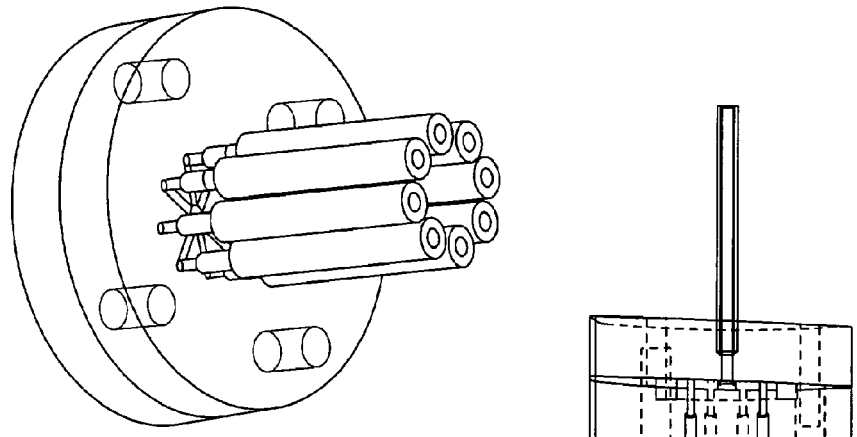
FIG. 109A
FIG. 109B

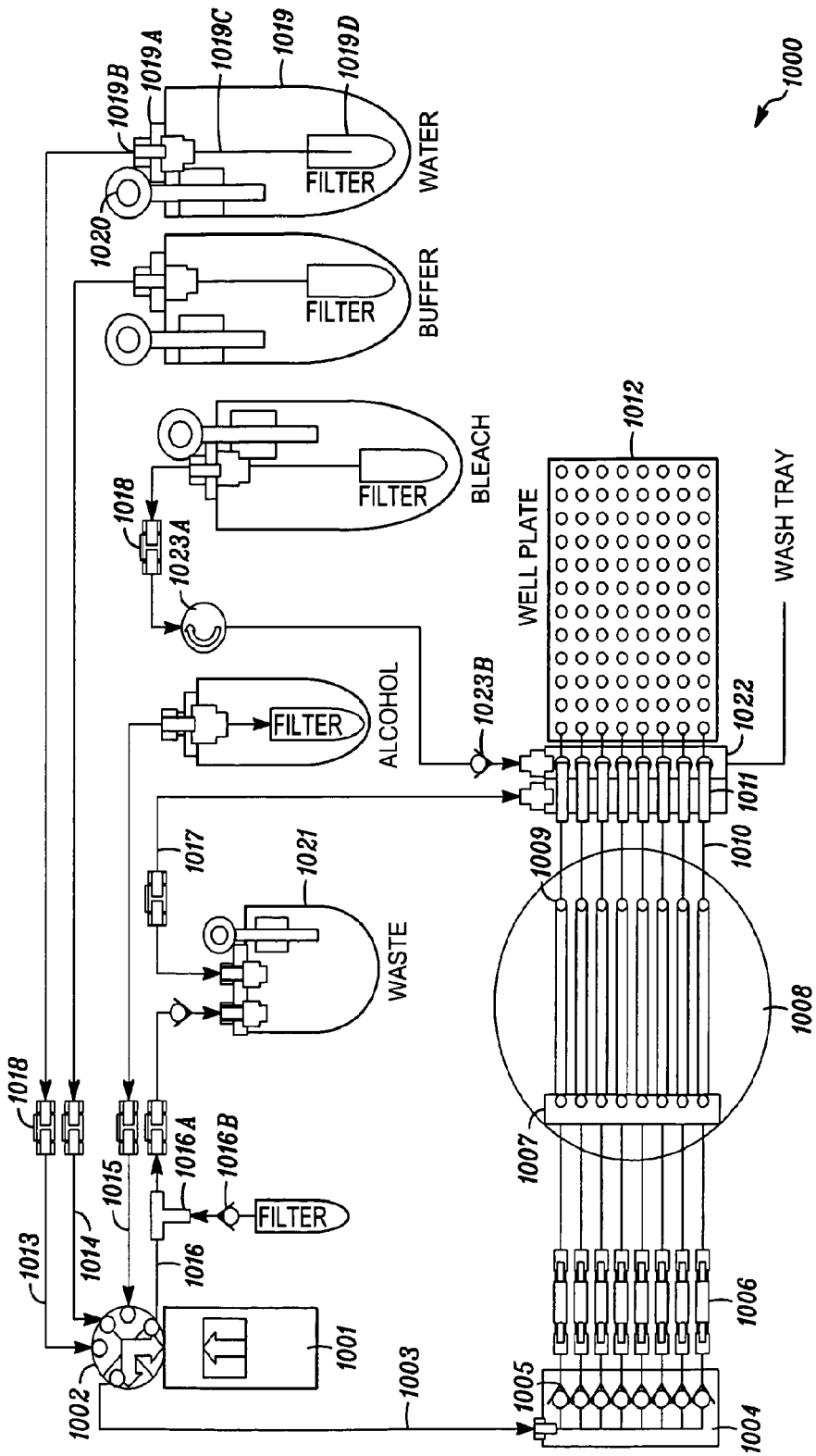
FIG. 118 FLUIDIC ARCHITECTURE

GOVERNING DESIGN PRINCIPLES

- UNIDIRECTIONAL FLUID FLOW, FROM PUMP TO TIPS
- BEADS SELF ASSEMBLED ON GROOVE PLATE
- GROOVE PLATE TILTED 10 DEG TO ENHANCE ALIGNMENT
- 8 INDEPENDENT FLUIDIC CELLS OPERATED SIMULTANEOUSLY TO ENHANCE THROUGHPUT
- BEADS ARE TRANSFERRED TO CELL WITH ZERO NET FLOW
- PRIMARY METHOD OF LOADING BEADS INTO GROOVES USES ZERO NET FLOW. SOME FLOW USED AT HIGHER PLEX

*FIG. 119*

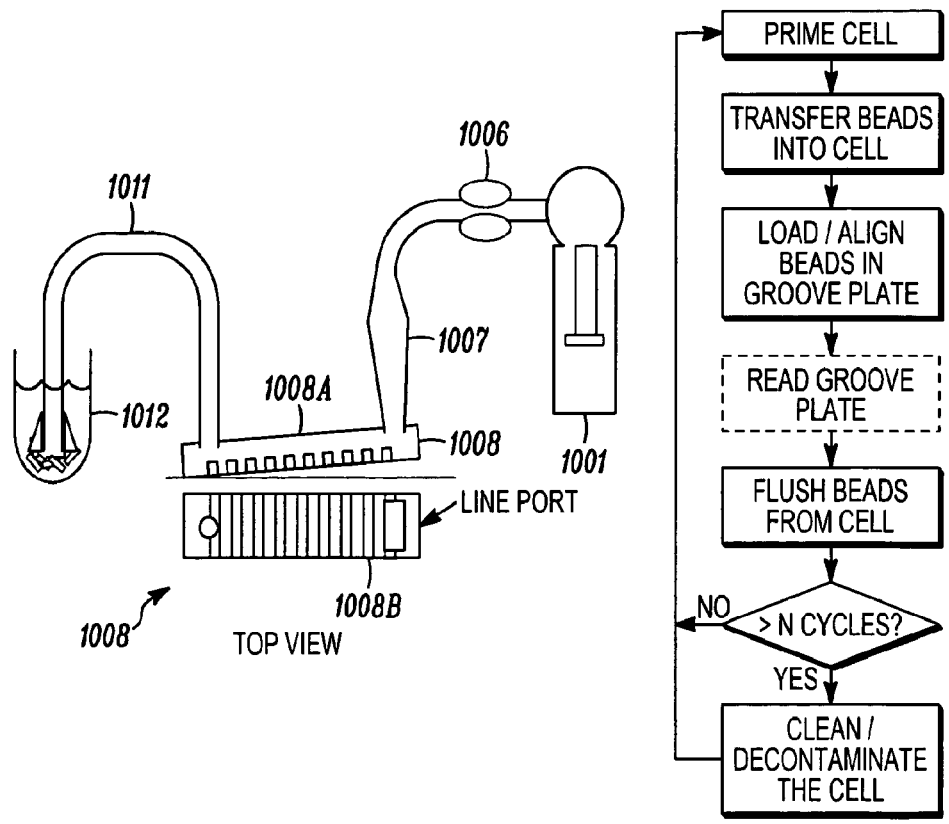

*FIG. 120*

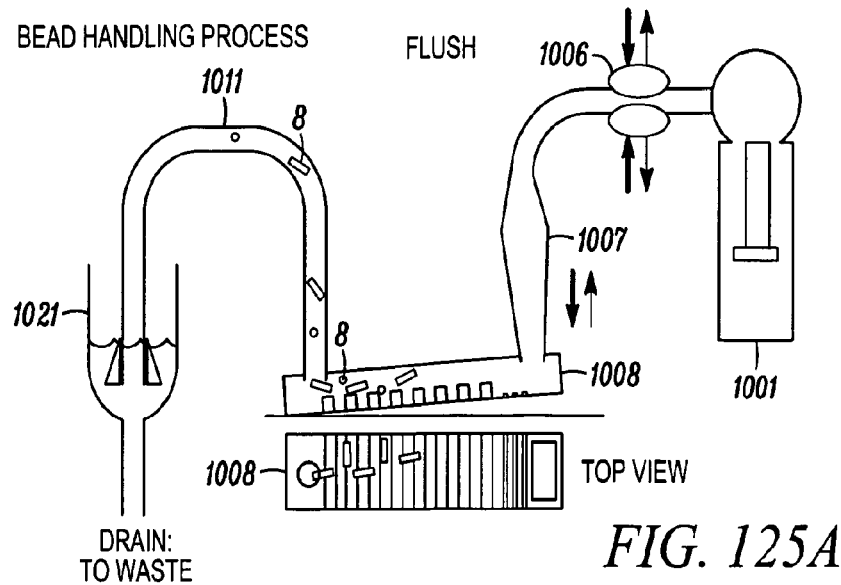
FIG. 125A
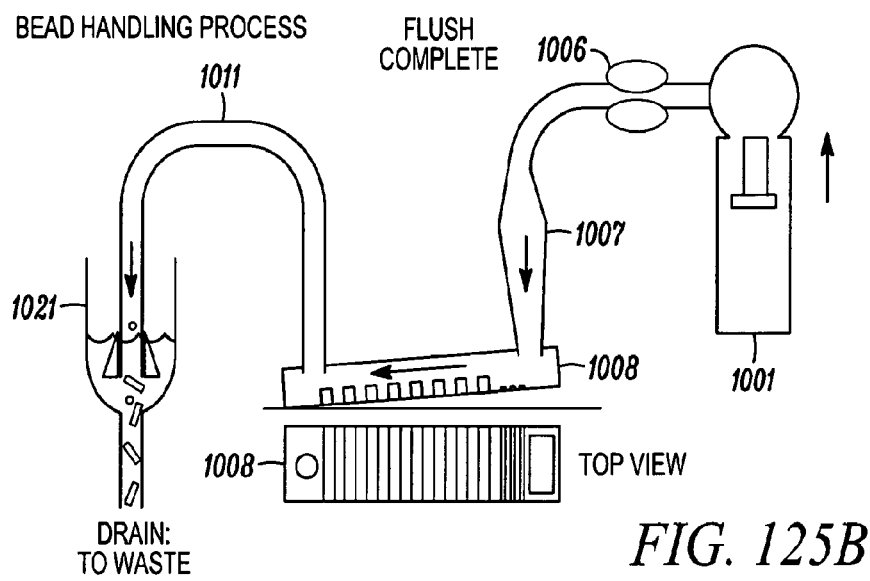
FIG. 125B
FIG. 126A
- 100 MM WATER
- 900 GROOVES
- 8 SECTORS
- SECTOR: 50 x 7 mm
- 25,200 BEADS / ALLEY @ 100%
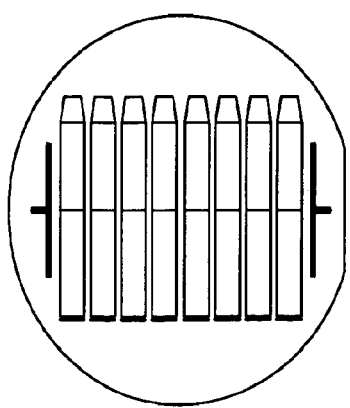

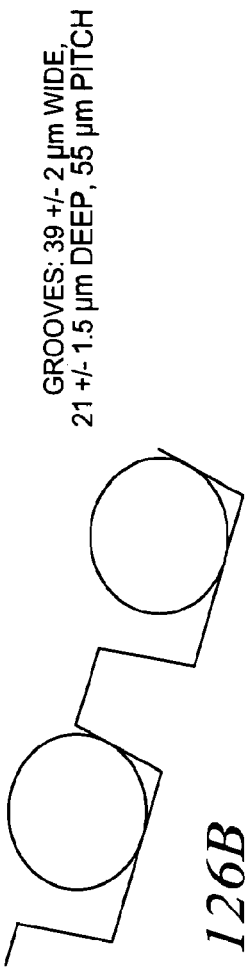

GROOVES: 39 +/- 2 μm WIDE,
21 +/- 1.5 μm DEEP, 55 μm PITCH

FIG. 126B

WHY TILT?
- WIDE GROOVES PROVIDE FOR FAST LOADING, HIGH DENSITY, EFFECTIVE FLUSH
- TILT PROVIDES CONSTRAINT

BEAD ALIGNMENT FEASIBILITY EXPERIMENTS

EXPERIMENT
- BEADS LOADED INTO CELL @ 10 DEG TILT
- HOSES CONNECTED TO CELL DURING CYCLING @ 2g
- BEADS IN IMAGE ASSESSED FOR TILT AND OFFSET
- POPULATION ~ 2000 BEADS

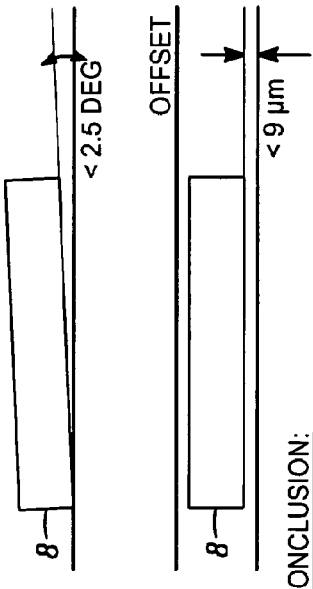

CONCLUSION:
- < 4% LOSS DUE TO ANGLE > 2.5 DEG @ 2g
- < 3% LOSS DUE TO OFFSET > 9 μm WINDOW @ 2g
- 5% TOTAL LOSS @ 1 APPEARS ACHIEVABLE (MANAGE DESIGN DETAILS)

PERFORMANCE REQUIREMENTS AND DRIVERS
- 2 COMPONENTS TO ALIGNMENT: ANGLE & OFFSET
- TOTAL LOSS ALLOCATION: 5%
- DRIVEN BY CODE ERROR BUDGET
- MAX ANGLE 2.5 DEG
- MAX OFFSET 9 μm FROM WALL

| TILT ALIGNMENT VALIDATION | | |
|---|---|---|
| EXPERIMENT | > 2.5 DEG | > 9 μm |
| AFTER LOAD | 2.0% | 2.0% |
| 100 CYCLE @ 2g | 2.0% | 2.0% |
| 650 CYCLE @ 2g | 4.0% | 3.0% |

(ACCELERATION / DECELERATION SPEC: 1g)

FIG. 127A

MULTIPLEX RANGE
415 PLEX (9100 BEADS), 60% DENSITY, 180 SEC LOAD
10 PLEX (200 BEADS), 15% DENSITY, 90 SEC LOAD
DENSITY REPORTED @ 95% OF ALIGNED BEADS
*FIG. 127B*

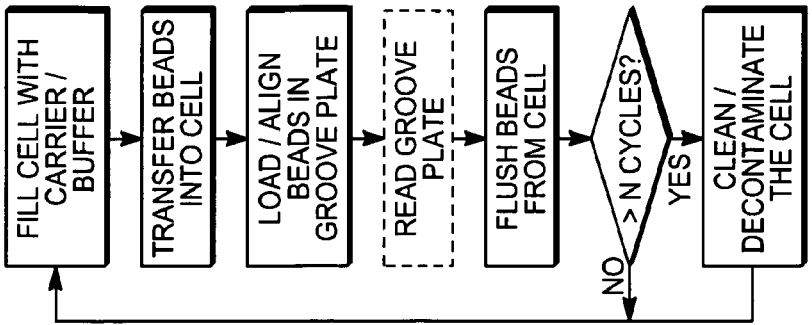

BEAD LOSS FEASIBILITY EXPERIMENTS
(TRANSFER OUT OF ROUND BOTTOM WELL PLATE, PUFF INTO GROOVES)

- CLEAN SURFACE AND OLIGO SURFACE BEADS
- QUANTITIES REPRESENTING ~10,100 AND 384 PLEX
- COUNTED BEADS IN WELL PRIOR TO TRANSFER (10 PLEX ONLY)
- 10 AND 100 PLEX - 5 EXPERIMENTS, 384 PLEX - 2 EXPERIMENTS

|  | 10 PLEX | 100 PLEX | 384 PLEX | REQUIREMENT |
|---|---|---|---|---|
| TRANSFER | 92.0% | 99.3% | 99.5% | 90.0% |
| READ IN-GROVES (*) | 78.5% | 89.0% | 86.6% | 80.0% |
| REMOVE EXCESS | 99.0% | 96.6% | 99.0% | 99.0% |
| TOTAL READABLE | 71.5% | 87.1% | 85.3% | >70% |

\* PROJECTED VALUE BASED ON LOADING MEASUREMENTS, 5% BEAD TILT/OFFSET, AND 5% CLIPPING OF THE BEAD POPULATION TO ENHANCE THROUGHPUT

CONCLUSION:
- LOW MARGIN AT LOW PLEX -> MITIGATE BY INCREASED REPLICATES
- PLENTY OF MARGIN AT HIGHER PLEX

FIG. 127C

BEAD FLUSH FEASIBILITY EXPERIMENTS

~ 50 PLEX BEFORE FLUSH    ~ 50 PLEX AFTER FLUSH

|  | 10 PLEX | 100 PLEX | 384 PLEX |
| --- | --- | --- | --- |
| # OF BEADS | 170 | 1900 | 8440 |
| LEFT BEHIND | 1 | 5 | 20 |
| LEFT BEHIND | 0.6% | 0.3% | 0.2% |

REQUIREMENT < 1% IN AFFECTED AREA

CONCLUSION: MULTIPLE FLUSHES OVER SHORT TIME NOT A PROBLEM
BUT UNCLEAR WHAT HAPPENS OVER LONG TIME SPAN

OPTICAL READER FOR READING ENCODED MICROPARTICLES

CROSS REFERENCES TO RELATED APPLICATIONS

The present application claims the benefit of: U.S. Provisional Application Ser. No. 60/609,583, filed Sep. 13, 2004, entitled "Improved Method and Apparatus for Aligning Microbeads in Order to Interrogate Same"; Ser. No. 60/610,910, filed Sep. 17, 2004, entitled "Method and Apparatus for Aligning Microbeads in Order to Interrogate Same"; and Ser. No. 60/610,833, filed Sep. 17, 2004, entitled "Method and Apparatus for Transporting and Kitting Microbeads"; and the present application is a continuation-in-part of U.S. patent application Ser. No. 10/661,836, filed Sep. 12, 2003, entitled "Method And Apparatus For Aligning Microbeads In Order To Interrogate The Same", which is a continuation-in-part of U.S. application Ser. No. 10/645,689, filed Aug. 20, 2003, and claims the benefit of U.S. Provisional Patent Application No. 60/410,541, filed Sep. 12, 2002. The present application is also a continuation-in-part of Ser. No. 11/063,665, filed Feb. 22, 2005, entitled "Multi-well Plate with Alignment Grooves for Encoded Microparticles", which claims the benefit of U.S. Provisional Patent Application No. 60/546,435, filed on Feb. 19, 2004. Each of U.S. application Ser. Nos. 60/609,583; 60/610,910; 60/610,833; 10/661,836; and 11/063,665 is incorporated herein by reference in their entirety.

The following cases contain subject matter related to that disclosed herein and are all incorporated herein by reference in their entirety: U.S. patent application Ser. No. 10/661,234, filed Sep. 12, 2003, entitled "Diffraction Grating-Based Optical Identification Element", Ser. No. 10/661,031, filed Sep. 12, 2003, entitled "Diffraction Grating-Based Encoded Micro-particles for Multiplexed Experiments", Ser. No. 10/661,082, filed Sep. 12, 2003, entitled "Method and Apparatus for Labeling Using Diffraction Grating based Encoded Optical Identification Elements"; U.S. patent application Ser. No. 10/661,115, filed Sep. 12, 2003, entitled "Assay Stick"; Ser. No. 10/661,254 filed Sep. 12, 2003, entitled "Chemical Synthesis Using Diffraction Grating-Based Encoded Optical Elements"; U.S. patent application Ser. No. 10/661,116, filed Sep. 12, 2003, entitled "Method Of Manufacturing Of A Diffraction Grating-Based Identification Element"; and U.S. patent application Ser. No. 10/763,995, filed Jan. 22, 2004, entitled, "Hybrid Random Bead/Chip Based Microarray"; and U.S. patent application Ser. No. 10/956,791, filed Oct. 1, 2004, entitled "Optical Reader for Diffraction Grating-Based Encoded Optical Identification Elements".

BACKGROUND OF THE INVENTION

1. Technical Field

The present invention generally relates to a method and apparatus for processing information contained on microbeads, each microbead having an elongated body with a code embedded therein along a longitudinal axis thereof to be read by a code reading device; and more particularly to a method and apparatus for aligning the microbeads so the longitudinal axis thereof is in a fixed orientation relative to the code reading or other device.

This invention also relates to transporting beads, and more particularly to transporting microbeads from one location to another.

2. Description of Related Art

Many industries have a need for uniquely identifiable objects or for the ability to uniquely identify objects, for sorting, tracking, and/or identification/tagging. Existing technologies, such as bar codes, electronic microchips/transponders, radio-frequency identification (RFID), and fluorescence and other optical techniques, are often inadequate. For example, existing technologies may be too large for certain applications, may not provide enough different codes, or cannot withstand harsh temperature, chemical, nuclear and/or electromagnetic environments.

Therefore, it would be desirable to obtain a coding element or platform that provides the capability of providing many codes (e.g., greater than 1 million codes), that can be made very small and/or that can withstand harsh environments.

Moreover, it would be desirable to provide a method and apparatus to position and align such encoded elements so as to identify the code to determine information about the process or application to which it is related and/or to better sense the chemical content on the elements and correlate it in relation to such process or application.

It is also well known that microbeads or microparticles may be used for various types of multiplexed chemical experiments or assays or for identifying, authenticating or sorting items. One challenge in transporting microbeads is being able to move them reliably from one location to another reliably and/or being able to move a predetermined number of beads.

Accordingly, it would be desirable to provide a reliable technique for transporting microbeads from one location to another.

SUMMARY OF THE INVENTION

In its broadest sense, the present invention provides a new and unique method and apparatus for aligning new and unique coding elements or microbeads, wherein each microbead has an elongated body with a code embedded therein along a longitudinal axis thereof to be read by a code reading or other detection device. The method features the step of aligning the microbeads with a positioning device so the longitudinal axis of the microbeads is positioned in a fixed orientation relative to the code reading or other detection device.

The new and unique microbeads are not spherical, but instead have an elongated shape and may be cylindrical, cubic, rectangular, or any other elongated shape. The microbeads are typically composed of silica glass with some germanium and/or boron doped region or regions that are photosensitive to ultraviolet light. Coded microbeads are individually identifiable via a single or series of spatially overlapping pitches written into them. The microbeads may be used in many different processes. After such processing, the microbeads have a resulting chemical content on the surface of each bead that is sensed and correlated in relation to the code contained with the microbead to determine information about the process.

When used in an assay process, the microbeads are typically cylindrically (i.e. tubular) shaped glass beads and between 25 and 250 μm in diameter and between 100 and 500 μm long. Other sizes may be used if desired. They have a holographic code embedded in the central region of the bead, which is used to identify it from the rest of the beads in a batch of beads with many different DNA or other chemical probes. A cross reference is used to determine which probe is attached to which bead, thus allowing the researcher to correlate the chemical content on each bead with the measured fluorescence signal. Because the code consists of a diffraction grating 12 typically disposed along an axis of the microbead, there is a particular alignment required between the incident readout laser beam and the readout detector in two of the three rotational axes. In aeronautical terms, the two of the three rotational axes include the pitch of the microbead in the front-to-back direction and the yaw of the microbead in a side-to-side direction. The third axis, rotation about the center axis of the cylinder, is azimuthally symmetric and therefore does not require alignment. The third axis is analogous to the roll axis.

The invention provides a method for aligning the microbeads in the two rotational axes to a fixed orientation relative to an incident laser beam and a readout camera, otherwise known as the code camera. The invention further provides a method for rapidly aligning a large number of microbeads, between 1,000 and 1,000,000 microbeads or more, economically, and with the necessary tolerances. The method is flexible as it relates to the size of the microbeads and can be integrated into a fully automated system, which prepares the microbeads for rapid readout by an automated code-reading machine.

In one embodiment of the present invention, the positioning device includes a plate with a series of parallel grooves (or channels), which could have one of several different shapes, including square, rectangular, v-shaped, semi-circular, etc., as well as a flat bottom groove with tapered walls. The grooves are formed into an optically transparent medium such as boro-silicate glass, fused silica, or other glasses, or plastic or other transparent support materials. The depth of the grooves will depend on the diameter of the microbead but generally they will be between 10 and 125 μm, but may be larger as discussed hereinafter, depending on the application. The spacing of the grooves is most optimal when it is between 1 and 2 times the diameter of the microbead, providing for both maximum packing density as well as maximum probability that a microbead will fall into a groove. The width of grooves is most optimal when the gap between the microbead and the walls of the grooves is sufficiently small to prevent the microbeads from rotating within the grooves by more than a few degrees. The bottom of the groove must also be maintained flat enough to prevent the microbeads from rotating, by more than a few tenths of a degree, relative to the incident laser beam. Another critical aspect of the grooved plate is the optical quality of the grooves. To prevent excess scatter of the readout laser beam, which could lead to low contrast between the code signal and the background scatter, it is important that the grooves exhibit high optical quality. The beads can be read in the groove plate from below, on top of, or the side of the plate, depending on the application and type of microbead used.

Some advantages of the groove plate approach include:

Rapid simultaneous alignment of microbeads. Alignment rates ~1000's per second.

Once the microbeads are aligned, they can be read as many times as necessary to get a good reading or improve statistics.

Microbeads naturally fall into groove (presumably by capillary forces) at very high packing densities.

Microbeads can be mixed after reading then re-read to enhance the statistics of readout process.

In an alternative embodiment of the present invention, the positioning device may includes a tube having a bore for receiving, aligning and reading the microbeads.

Moreover, the present invention also provides an apparatus for aligning an optical identification element. The optical identification element having an optical substrate having at least a portion thereof with at least one diffraction grating disposed therein, the grating having at least one refractive index pitch superimposed at a common location, the grating providing an output optical signal when illuminated by an incident light signal, the optical output signal being indicative of a code, and the optical identification element being an elongated object with a longitudinal axis. The apparatus also having an alignment device which aligns the optical identification element such that said output optical signal is indicative of the code.

The present invention also provides an optical element capable of having many optically readable codes. The element has a substrate containing an optically readable composite diffraction grating having one or more collocated index spacing or pitches Λ. The invention allows for a high number of uniquely identifiable codes (e.g., millions, billions, or more). The codes may be digital binary codes and thus are digitally readable or may be other numerical bases if desired.

Also, the elements may be very small "microbeads" (or microelements or microparticles or encoded particles) for small applications (about 1-1000 microns), or larger "macroelements" for larger applications (e.g., 1-1000 mm or much larger). The elements may also be referred to as encoded particles or encoded threads. Also, the element may be embedded within or part of a larger substrate or object.

The code in the element is interrogated using free-space optics and can be made alignment insensitive.

The gratings (or codes) are embedded inside (including on or near the surface) of the substrate and may be permanent non-removable codes that can operate in harsh environments (chemical, temperature, nuclear, electromagnetic, etc.).

The code is not affected by spot imperfections, scratches, cracks or breaks in the substrate. In addition, the codes are spatially invariant. Thus, splitting or slicing an element axially produces more elements with the same code. Accordingly, when a bead is axially split-up, the code is not lost, but instead replicated in each piece.

The invention is a significant improvement over prior art bead movement techniques in being able to repeatably move a predetermined number of beads from one location (or container or well) to another location (or container or well). Also, the invention provides for the reliable and repeatable transportation of all beads from one container or well to another or from one well to multiple wells using a "telegraph" technique. The invention is useful for creating multiplexed bead kits having a required number of beads of each code in a kit. The present invention may also be used to move the beads from a container to a reader to allow for the bead codes and/or chemistry on the beads to be read.

The invention may be used in any assay or multiplexed experiment, combinatorial chemistry or biochemistry assay process, or in a taggant application, or any other application where beads are in a liquid solution and need to be transported, kilted and/or read.

Advantages of the "telegraph" technique of the present invention are that it is low cost, fast, effective/reliable for moving beads, and low precision is required. Advantages of the pipetting techniques of the present invention is that the pippeter is a standard off the shelf product, it is flexible to be used with any type of well or container (e.g., sizes, shapes and other characteristics), or other fluid configurations, and does not require any sealing or physical connections to the wells.

The foregoing and other objects, features and advantages of the present invention will become more apparent in light of the following detailed description of exemplary embodiments thereof.

BRIEF DESCRIPTION OF THE DRAWING

The drawing is not drawn to scale and includes the following Figures:

FIG. 2 is a side view of an optical identification element, in accordance with the present invention.

FIG. 3 is a top level optical schematic for reading a code in an optical identification element, in accordance with the present invention.

FIG. 4 is a perspective view of a grooved plate for use with an optical identification element, in accordance with the present invention.

FIG. 5 is a diagram of the flat grooves and an example of the dimensionality thereof in accordance with the present invention.

FIG. 20(a) show an embodiment of a disk cytometer having radial channels for spin drying in accordance with the invention.

FIG. 20(b) show an alternative embodiment of a disk cytometer having a mechanical iris for providing a variable aperture for bead access to grooves in accordance with the invention.

FIG. 22 show an embodiment of an alignment tube in accordance with the invention.

FIG. 23 show an alternative embodiment of an alignment tube having a receiving flange in accordance with the invention.

FIG. 27 illustrations (a)-(d) show graphs of different refractive index pitches and a summation graph, in accordance with the present invention.

FIG. 32 is a perspective view showing azimuthal multiplexing of a thin grating for an optical identification element, in accordance with the present invention.

FIG. 33 is side view of a blazed grating for an optical identification element, in accordance with the present invention.

FIGS. 36-37 are side views of an optical identification element where light is incident on an end face, in accordance with the present invention.

FIG. 38, illustrations (a)-(c), are side views of an optical identification element having a blazed grating, in accordance with the present invention.

FIG. 39 is a side view of an optical identification element having a coating, in accordance with the present invention.

FIG. 40 is a side view of whole and partitioned optical identification element, in accordance with the present invention.

FIG. 41 is a side view of an optical identification element having a grating across an entire dimension, in accordance with the present invention.

FIG. 42, illustrations (a)-(c), are perspective views of alternative embodiments for an optical identification element, in accordance with the present invention.

FIG. 43, illustrations (a)-(b), are perspective views of an optical identification element having multiple grating locations, in accordance with the present invention.

FIG. 44, is a perspective view of an alternative embodiment for an optical identification element, in accordance with the present invention.

FIG. 45 is a view an optical identification element having a plurality of gratings located rotationally around the optical identification element, in accordance with the present invention.

FIGS. 55-83 are various alternative embodiments of the present invention.

FIGS. 84-133 describe other embodiments for reading, using, manipulating, storing, and/or moving encoded microparticles.

BEST MODE FOR CARRYING OUT THE INVENTION

Figure 1:
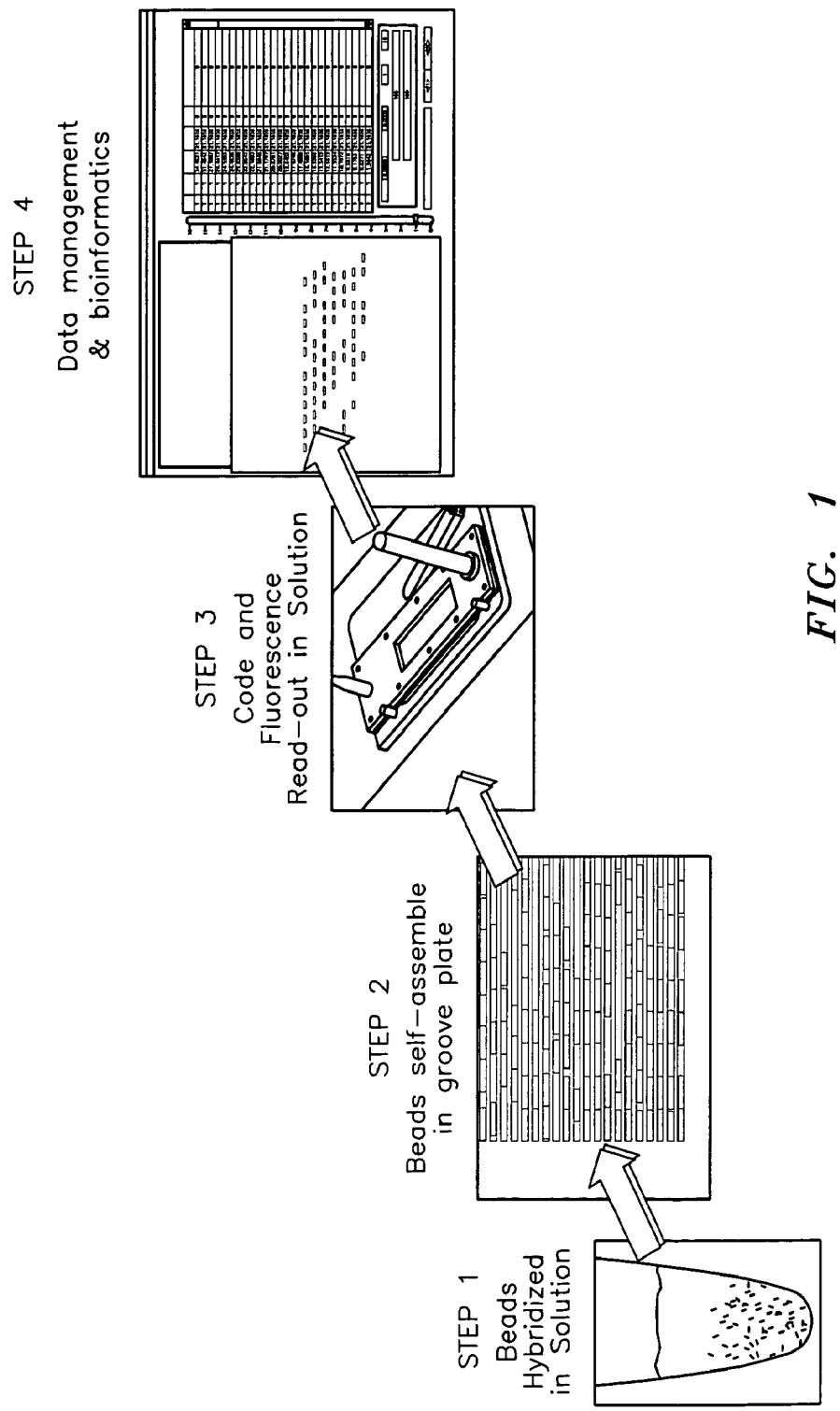
FIG. 1 shows the steps of a microbead platform assay process.

FIG. 1 shows, by way of example, steps of a microbead assay process which uses the microbead technology of the present invention. The steps of the assay process shown in FIG. 1 include a first step in which the microbeads are used in a solution; a second step in which the microbeads are aligned in a desired manner; a third step in which the code and florescence in and/or on the microbeads are read-out; and a fourth step in which the information related to the code and florescence is processed in relation to data management and bioinformatics. The present invention primarily relates to step 2 wherein the microbeads are uniquely aligned so the longitudinal axis of the microbeads is positioned in a fixed orientation relative to the code and florescence reading device, as well as relating to a lesser extent to step 3. It is important to note that the scope of the present invention is not intended to be limited to any particular type or kind of assay process or other process in which the microbead technology is used. The scope of the invention is intended to include embodiments in which the microbead technology of the present invention is used in many different processes.

Other processes/applications where the present invention may be used include use of the beads in taggant applications, where the encoded beads are used to identify, track, and/or authenticate, items such as is discussed in aforementioned copending U.S. patent application Ser. No. 10/661,082, filed Sep. 12, 2003, entitled "Method and Apparatus for Labeling Using Diffraction Grating-Based Encoded Optical Identification Elements".

FIG. 2: The Microbead Element 8

FIG. 2 shows a diffraction grating-based optical identification element 8 (or encoded element or coded element) that comprises a known optical substrate 10, having an optical diffraction grating 12 disposed (or written, impressed, embedded, imprinted, etched, grown, deposited or otherwise formed) in the volume of or on a surface of the substrate 10 along the length or longitudinal axis L of the element 8, which is otherwise known hereinafter as the microbead. The grating 12 is a periodic or aperiodic variation in the effective refractive index and/or effective optical absorption of at least a portion of the substrate 10.

The optical identification element 8 described herein is same as that described in Copending U.S. patent application Ser. No. 10/661,234, filed Sep. 12, 2003, entitled "Diffraction Grating-Based Optical Identification Element", which is incorporated herein by reference in its entirety.

In particular, the substrate 10 has an inner region 20 where the grating 12 is located. The inner region 20 may be photosensitive to allow the writing or impressing of the grating 12. The substrate 10 has an outer region 18, which does not have the grating 12 therein.

The grating 12 is a combination of one or more individual spatial periodic sinusoidal variations (or components) in the refractive index that are collocated at substantially the same location on the substrate 10 along the length of the grating region 20, each having a spatial period (or pitch) $\Lambda$. The resultant combination of these individual pitches is the grating 12, comprising spatial periods ($\Lambda 1$-$\Lambda n$) each representing a bit in the code. Thus, the grating 12 represents a unique optically readable code, made up of bits, where a bit corresponds to a unique pitch $\Lambda$ within the grating 12. Accordingly, for a digital binary (0-1) code, the code is determined by which spatial periods ($\Lambda 1$-$\Lambda n$) exist (or do not exist) in a given composite grating 12. The code or bits may also be determined by additional parameters (or additional degrees of multiplexing), and other numerical bases for the code may be used, as discussed herein and/or in the aforementioned patent application.

The grating 12 may also be referred to herein as a composite or collocated grating. Also, the grating 12 may be referred to as a "hologram", as the grating 12 transforms, translates, or filters an input optical signal to a predetermined desired optical output pattern or signal.

The substrate 10 has an outer diameter D1 and comprises silica glass ($SiO_2$) having the appropriate chemical composition to allow the grating 12 to be disposed therein or thereon. Other materials for the optical substrate 10 may be used if desired. For example, the substrate 10 may be made of any glass, e.g., silica, phosphate glass, borosilicate glass, or other glasses, or made of glass and plastic, or solely plastic. For high temperature or harsh chemical applications, the optical substrate 10 made of a glass material is desirable. If a flexible substrate is needed, plastic, rubber or polymer-based substrate may be used. The optical substrate 10 may be any material capable of having the grating 12 disposed in the grating region 20 and that allows light to pass through it to allow the code to be optically read.

The optical substrate 10 with the grating 12 has a length L and an outer diameter D1, and the inner region 20 diameter D. The length L can range from very small "microbeads" (or microelements, micro-particles, or encoded particles), about 1-1000 microns or smaller, to larger "macro beads" or "macroelements" for larger applications (about 1.0-1000 mm or greater). In addition, the outer dimension D1 can range from small (less than 1000 microns) to large (1.0-1000 mm and greater). Other dimensions and lengths for the substrate 10 and the grating 12 may be used.

The grating 12 may have a length Lg of about the length L of the substrate 10. Alternatively, the length Lg of the grating 12 may be shorter than the total length L of the substrate 10.

The outer region 18 is made of pure silica ($SiO_2$) and has a refractive index n2 of about 1.458 (at a wavelength of about 1553 nm), and the inner grating region 20 of the substrate 10 has dopants, such as germanium and/or boron, to provide a refractive index n1 of about 1.453, which is less than that of outer region 18 by about 0.005. Other indices of refraction n1,n2 for the grating region 20 and the outer region 18, respectively, may be used, if desired, provided the grating 12 can be impressed in the desired grating region 20. For example, the grating region 20 may have an index of refraction that is larger than that of the outer region 18 or grating region 20 may have the same index of refraction as the outer region 18 if desired.

FIG. 3: The Code Reader or Detector 29

FIG. 3 shows a configuration for reading or detecting the code in the microbead 8 using a code reader or other detector device 29, which is used in step 3 of the process shown in FIG. 1. In operation, an incident light 24 of a wavelength $\lambda$, e.g., 532 nm from a known frequency doubled Nd:YAG laser or 632 nm from a known Helium-Neon laser, is incident on the grating 12 in the substrate 10. Any other input wavelength $\lambda$ can be used if desired provided $\lambda$ is within the optical transmission range of the substrate (discussed more herein and/or in the aforementioned patent application). A portion of the input light 24 passes straight through the grating 12, as indicated by a line 25. The remainder of the input light 24 is reflected by the grating 12, as indicated by a line 27 and provided to a detector 29. The output light 27 may be a plurality of beams, each having the same wavelength $\lambda$ as the input wavelength $\lambda$ and each having a different output angle indicative of the pitches ($\Lambda 1$-$\Lambda n$) existing in the grating 12. Alternatively, the input light 24 may be a plurality of wavelengths and the output light 27 may have a plurality of wavelengths indicative of the pitches ($\Lambda 1$-$\Lambda n$) existing in the grating 12. Alternatively, the output light may be a combination of wavelengths and output angles. The above techniques are discussed in more detail herein and/or in the aforementioned patent application.

The code reader or detector 29 has the necessary optics, electronics, software and/or firmware to perform the functions described herein. In particular, the detector reads the optical signal 27 diffracted or reflected from the grating 12 and determines the code based on the pitches present or the optical pattern, as discussed more herein or in the aforementioned patent application. An output signal indicative of the code is provided on a line 31.

The dimensions, geometries, materials, and material properties of the substrate 10 are selected such that the desired optical and material properties are met for a given application. The resolution and range for the optical codes are scalable by controlling these parameters as discussed herein and/or in the aforementioned patent application. Also, the beads 8 may be made of any of the materials, geometries, and coatings described in copending U.S. patent application Ser. No. 10/661,234.

We have used the present invention with cylindrical beads having size of about 65 micron diameter and 400 microns long and about 28 microns diameter and about 250 microns long. However, other bead sizes may be used.

FIG. 4: The Grooved Tray or Plate

FIG. 4 shows one embodiment of a positioning device 200 for aligning the microbeads 8 so the longitudinal axis of the microbeads is in a fixed orientation relative to the code reading or other detection device. The positioning device 200 is shown in the form of a tray or plate 200 having v-grooves 205 for align the microbeads 8 and is used in step 2 of the process shown in FIG. 1.

As shown, the microbead elements 8 are placed in the tray 200 with v-grooves 205 to allow the elements 8 to be aligned in a predetermined direction for illumination and reading/detection as discussed herein. Alternatively, the grooves 205 may have holes 210 that provide suction to keep the elements 8 in position.

Forming The Grooves in the Groove Plate

The grooves in the groove plate may be made in many different ways, including being formed by SU8 photoresistant material, mechanically machining; deep reactive ion etching; or injection molding. One advantage of the injection molding approach is that the plate can be manufactured in volume at relatively low cost, and disposed of after the information about the beads is gathered in the assay process. The groove plate may be made of glass, including fused silica, low fluorescence glass, boro silicate glass, or other transparent glasses or plastic. Silicon is used because it is reflective so a reflective coating is typically not needed. Alternative, a mirror coating can be applied to the plate material to achieve the desired reflectivity.

FIG. 5: Flat Grooves

The scope of the invention is not intended to be limited to any particular groove shape. For example, FIG. 5 shows a diagram a plate 300 having flat grooves 302 instead of V-grooves as shown in FIG. 3. Some characteristics of the groove according to the present invention are as follows:

The groove width (w) should be at least as wide as the diameter of the bead (D) but not larger than D+15 µm.

The thickness of the depth of the groove (T) should be at least 0.5 times the diameter of the bead so that it sufficiently traps a bead once it falls into the groove even when it is subjected to mechanical agitation. The depth should not exceed 1.5 times the diameter of the bead so as to prevent more than one bead from falling into the same groove location.

Groove plates have been made using a thick photoresist called SU8 and is available from Microchem. The resist is both chemically inert and mechanically robust once fully cured. The groove walls are formed by the resist material, which is deposited onto a glass or substrate. Advantages of this process include the ability to tailor the depth of groove by controlling the thickness of the resist material, and virtually every other geometric attribute through the design of the photo mask. Because it is photolithographic process, essentially any shape profile can be made. For example grooves can be made in simple rows, concentric circles, or spirals. Other features such as discrete wells, spots and cross hatches can be made as fiducial marks for tracking and positional registration purposes.

The scope of the invention is also intended to include the grooves having a flat bottom as shown in FIG. 5 with outwardly tapered walls.

Figure 6:
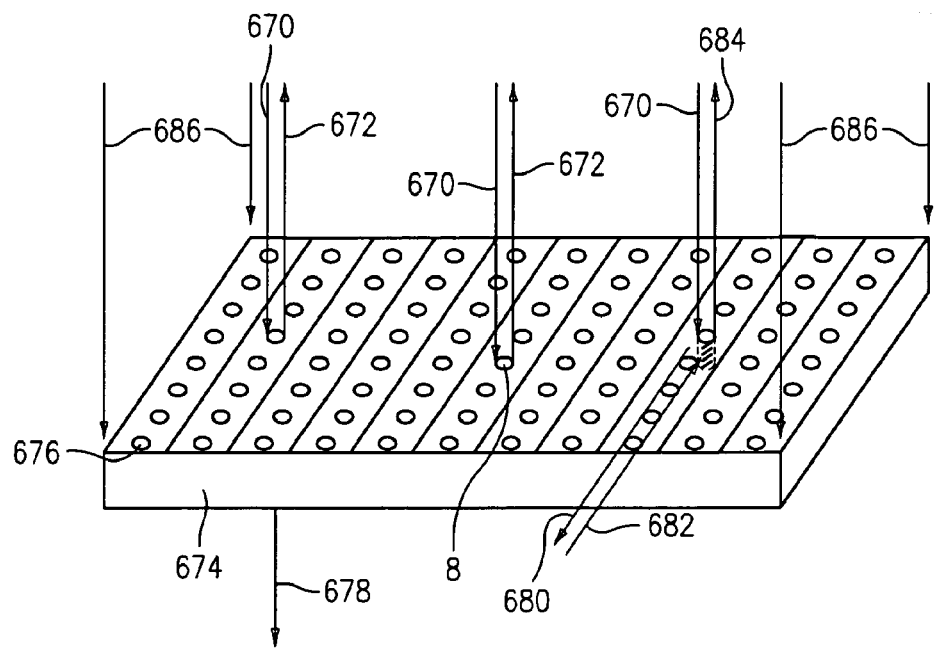
FIG. 6 is a perspective view of a plate with holes for use with an optical identification element, in accordance with the present invention.

FIG. 6: The Holey Plate 674

FIG. 6 shows an alternative embodiment, wherein alignment may be achieved by using a plate 674 having holes 676 slightly larger than the elements 8 if the light 24 (FIGS. 2 and 4) is incident along the grating axis 207. The incident light indicated as 670 is reflected off the grating and exits through the end as a light 672 and the remaining light passes through the grating and the plate 674 as a line 678. Alternatively, if a blazed grating is used, incident light 670 may be reflected out the side of the plate (or any other desired angle), as indicated by a line 680. Alternatively, input light may be incident from the side of the plate 674 and reflected out the top of the plate 674 as indicated by a line 684. The light 670 may be a plurality of separate light beams or a single light beam 686 that illuminates the entire tray 674 if desired.

Figure 7:
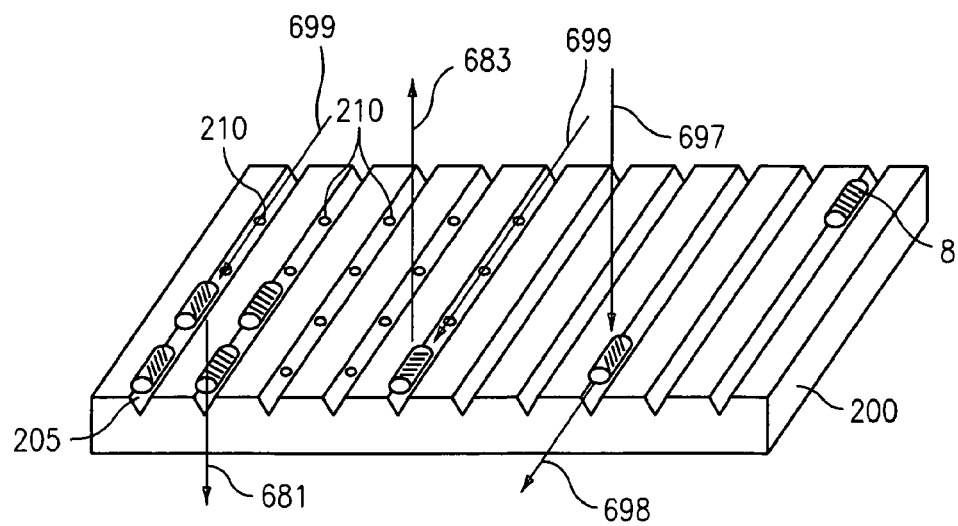
FIG. 7 is a perspective view of a grooved plate for use with an optical identification element, in accordance with the present invention.

FIG. 7: V-Groove Plate 200 with End Illumination

FIG. 7 shows an alternative embodiment, wherein the v-groove plate discussed hereinbefore with FIG. 4 may be used for the end illumination/readout condition. In this case, the grating 12 may have a blaze angle such that light incident along the axial grating axis will be reflected upward, downward, or at a predetermined angle for code detection. Similarly, the input light may be incident on the grating in a downward, upward, or at a predetermined angle and the grating 12 may reflect light along the axial grating axis for code detection.

Figure 8:
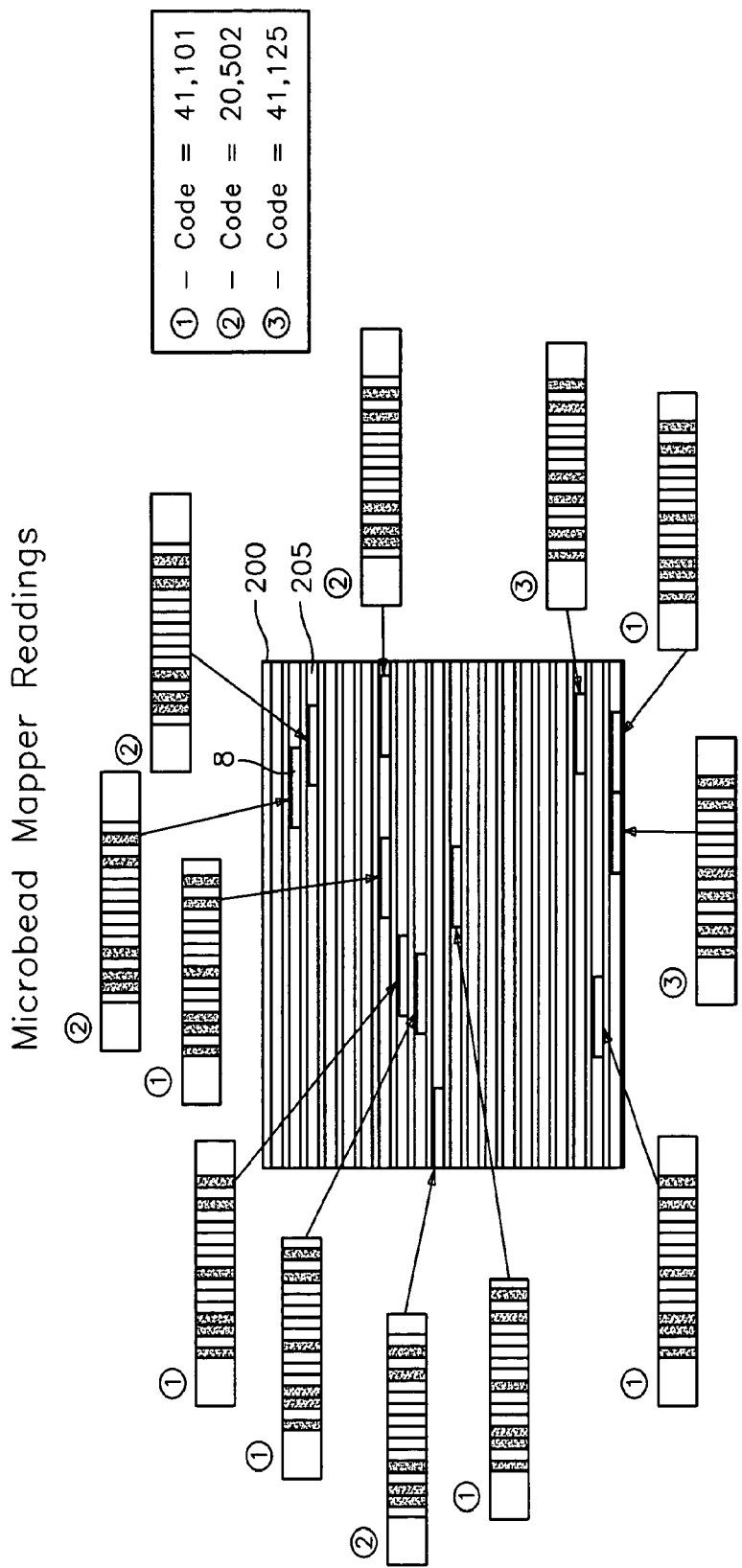
FIG. 8 is a diagram of a microbead mapper reading, in accordance with the present invention.

FIG. 8: Microbead Mapper Readings

FIG. 8 shows microbeads 8 arranged on a plate 200 having grooves 205. As shown, the microbeads 8 have different codes (e.g. "41101", "20502", "41125") using 16-bit, binary symbology), which may be read or detected using the reader or detector configuration described in relation to FIG. 3. The codes in the beads are used to provide a cross reference to determine which probe is attached to which bead, thus allowing the researcher to correlate the chemical content on each bead with the measured fluorescence signal in Step 3 of the process shown in FIG. 1.

Figure 8A:
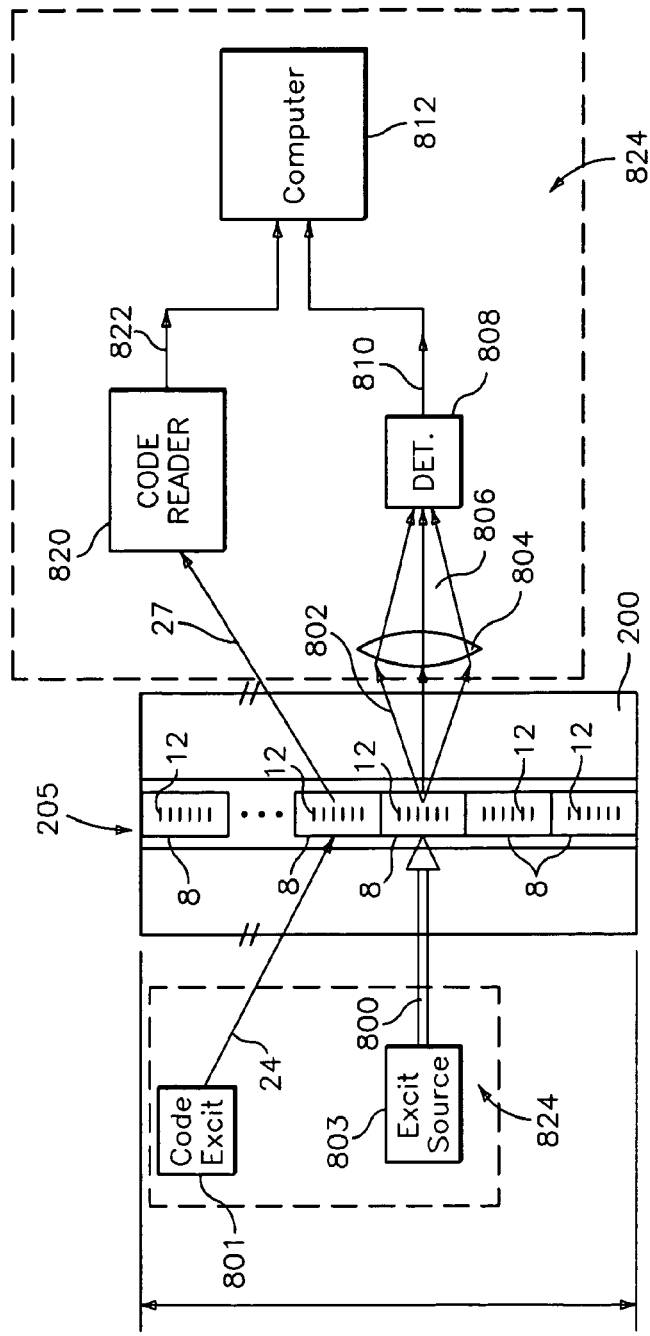
FIG. 8a is a diagram of a system for both detecting a material on and reading a code in a microbead, in accordance with the present invention.

FIG. 8a shows a code reader and detector for obtaining information from the microbead 8 in FIG. 8. The codes in the microbeads 8 are detected when illuminated by incident light 24 which produces a diffracted or output light signal 27 to a reader 820, which includes the optics and electronics necessary to read the codes in each bead 8, as described herein and/or in the aforementioned copending patent application. The reader 820 provides a signal on a line 822 indicative of the code in each of the bead 8. The incident light 24 may be directed transversely from the side of the grooved plate 200 (or from an end or any other angle) with a narrow band (single wavelength) and/or multiple wavelength source, in which case the code is represented by a spatial distribution of light and/or a wavelength spectrum, respectively, as described hereinafter and in the aforementioned copending patent application. Other illumination, readout techniques, types of gratings, geometries, materials, etc. may be used for the microbeads 8, as discussed hereinafter and in the aforementioned patent application.

For assays that use fluorescent molecule markers to label or tag chemicals, an optical excitation signal 800 is incident on the microbeads 8 on the grooved plate 200 and a fluorescent optical output signal 802 emanates from the beads 8 that have the fluorescent molecule attached. The fluorescent optical output signal 802 passes through a lens 804, which provides focused light 802 to a known optical fluorescence detector 808. Instead of or in addition to the lens 802, other imaging optics may be used to provide the desired characteristics of the optical image/signal onto the fluorescence detector 808. The detector 808 provides an output signal on a line 810 indicative of the amount of fluorescence on a given bead 8, which can then be interpreted to determine what type of chemical is attached to the bead 10.

Consistent with that discussed herein, the grooved plate 200 may be made of glass or plastic or any material that is transparent to the code reading incident beam 24 and code reading output light beams 27 as well as the fluorescent excitation beam 800 and the output fluorescent optical signal 802, and is properly suited for the desired application or experiment, e.g., temperature range, harsh chemicals, or other application specific requirements.

The code signal 822 from the bead code reader 820 and the fluorescent signal 810 from the fluorescence detector are provided to a known computer 812. The computer 812 reads the code associated with each bead and determines the chemical probe that was attached thereto from a predetermined table that correlates a predetermined relationship between the bead code and the attached probed. In addition, the computer 812 and reads the fluorescence associated with each bead and determines the sample or analyte that is attached to the bead from a predetermined table that correlates a predetermined relationship between the fluorescence tag and the analyte attached thereto. The computer 812 then determines information about the analyte and/or the probe as well as about the bonding of the analyte to the probe, and provides such information on a display, printout, storage medium or other interface to an operator, scientist or database for review and/or analysis, consistent with shown in step 4 of FIG. 1. The sources 801, 803 the code reader 820, the fluorescence optics 804 and detector 808 and the computer 812 may all be part of an assay stick reader 824.

Alternatively, instead of having the code excitation source 801 and the fluorescence excitation source 803, the reader 24 may have only one source beam which provides both the reflected optical signal 27 for determining the code and the fluorescence signal 802 for reading the tagged analyte attached to the beads 8. In that case the input optical signal is a common wavelength that performs both functions simultaneously, or sequentially, if desired.

The microbeads 8 may be coated with the desired probe compound, chemical, or molecule prior to being placed in the grooved plate 200. Alternatively, the beads 8 may be coated with the probe after being placed in the grooved plate 200. As discussed hereinbefore, the probe material may be an Oligo, cDNA, polymer, or any other desired probe compound, chemical, cell, or molecule for performing an assay.

The scope of the invention is not intended to be limited to using or detecting fluorescent molecule markers during the assay process. For example, embodiments of the invention are envisioned using and detection other types of molecular markers in other types of processes.

Modes of Microbead Alignment

There are at least two possible modes or approaches of use for the groove plate.

Figure 9:
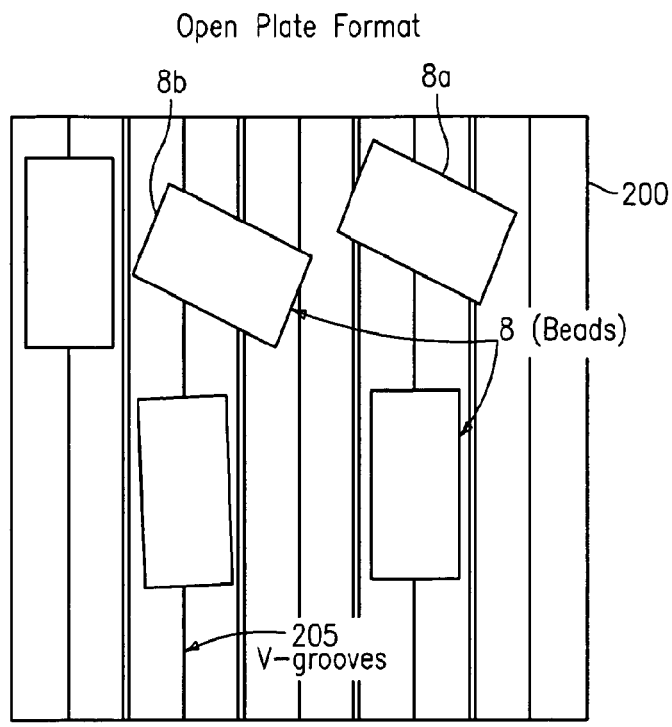
FIG. 9 is a diagram of a plate having microbeads thereon in relation to an open plate format for detection and reading of the microbead in accordance with the invention.

FIG. 9: Open Format Approach

FIG. 9 shows the first, or open plate format, meaning there is no top to cover the microbeads 8 and the v-grooves 205. In this mode, the microbeads 8 are dispensed onto the plate 200 using, for example, a pipette tip or syringe tip, although the scope of the invention is not intended to be limited to the manner of depositing the microbeads on the plate. The microbeads 8 may be then agitated by a sonic transducer (not shown), or manipulated with a mechanical wiper (not shown) or some form of spray nozzle (not shown) to encourage all the microbeads 8 to line up in the grooves 205. It has been observed that substantially all the microbeads naturally line up in the grooves 205 without the need for encouragement. However, there are always some microbeads, such as microbead 8a, 8b, that do not fall naturally into the grooves, and these must either be removed from the plate 200 or forced to fall into a groove 205. The open format approach has the advantages that grooves plate consists just of the plate and no other complicated features such as walls and a top, and possibly other chambers or channels to allow fluid flow and bubble removal. It also has the advantage that it can easily be made with a standard microscope slide, which is designed to fit conventional micro array readers or microscopes. However, the open format approach would most likely require the microbeads to be dried out prior to reading, to prevent non-uniform and unpredictable optical aberrations caused by the uneven evaporation of the buffer solution.

FIGS. 10-17: The Closed Format Approach

Figure 10:
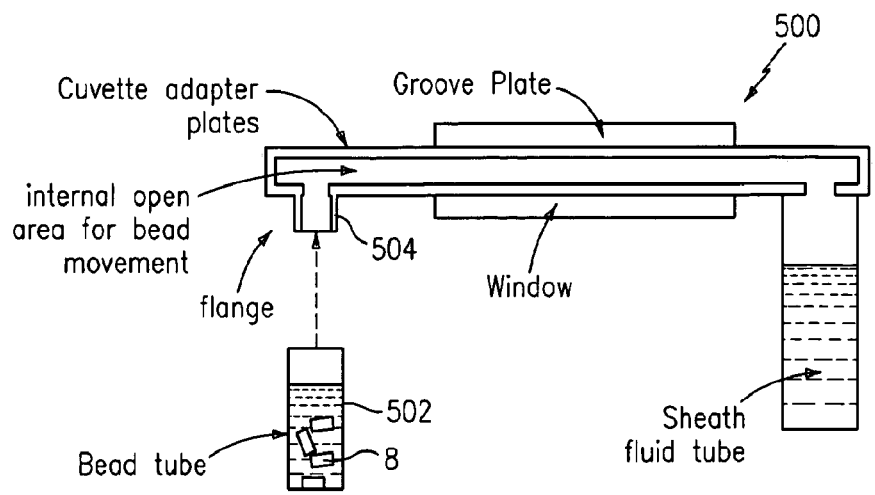
FIG. 10 is a diagram of a starting point for handling microbeads for readout in a cuvette process in accordance with the invention.

FIGS. 10-17 show the second mode which is called a closed format, that consists of not only of a groove plate but also a top and at least three walls to hold the solution and the microbeads in a cuvette-like device (or cell or chamber) generally indicated as 500 shown, for example, in FIG. 10.

In summary, the closed format approach provides a method for effectively distributing and aligning microbeads during the readout process, as described below:

The basic process for handling microbeads with a curvette for readout consists of the following steps:

(1) FIG. 10 shows a starting point for handling microbeads for a readout. The microbeads start in a test tube. Typical test-tube volumes are 1.5 ml. The microbeads will generally be in a liquid (usually water with a small amount of other buffer chemicals to adjust pH and possibly a small amount [~0.01%] of detergent.) As shown, a bead tube 502 contains the microbeads in a solution, which forms part of step 1 of the process shown in FIG. 1.

Figure 11:
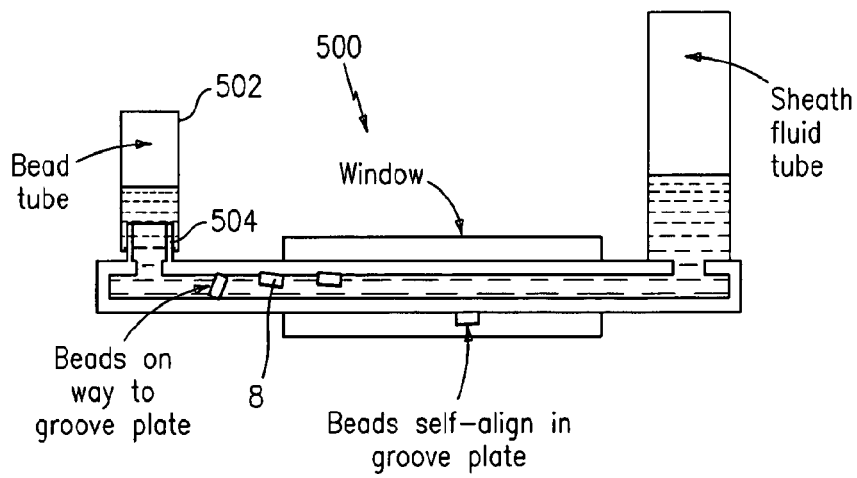
FIG. 11 is a diagram of a second step in the readout process in accordance with the invention.
Figure 14:
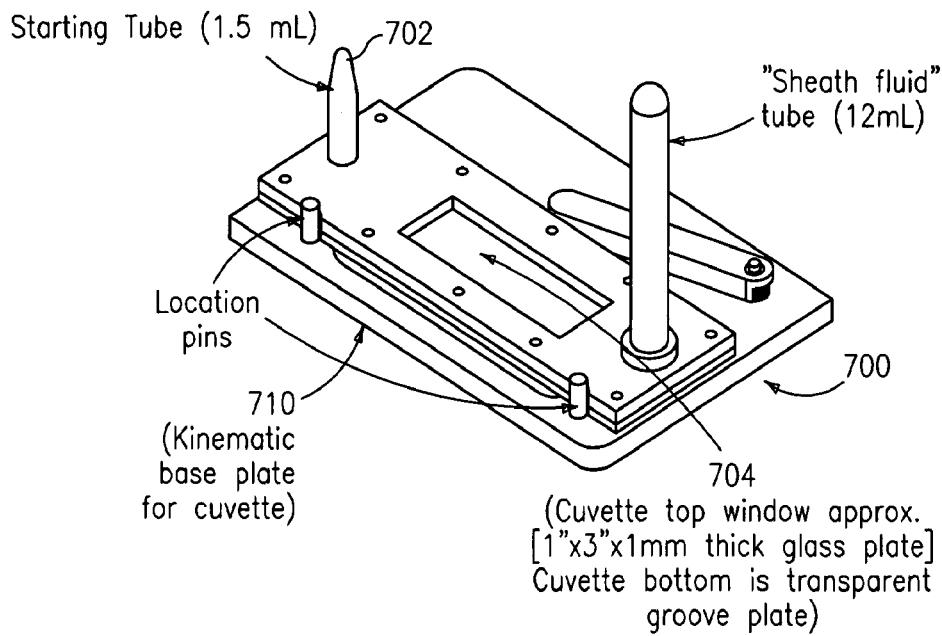
FIG. 14 is a diagram of an example of the cuvette showing its mount on a kinematic plate in accordance with the invention.

(2) FIG. 11 shows the bead tube 502 is coupled to a flange 504 of the cuvette 500 is inverted and the beads flow onto the groove plate. The cuvette consists of two round flanges that accept test-tubes, a transparent window, and an opposing groove plate. FIG. 14 shows a drawing of a prototype cuvette. The groove plate outer dimensions can be any size, but typical microscope slide dimensions are convenient (1"×3"). The grooves are mechanically or laser cut lengthwise, and have dimensions that are chosen for the exact size of cylindrical microbead. For instance, for a 125 μm diameter bead, grooves of approximately 150 μm wide by 150 μm deep are used. One tube carries the microbeads and a small amount of carrier fluid. The second tube may be larger and hold more fluid. The purpose of the second tube is to guarantee a certain fluid level in the next step.

(3) After the cuvette is inverted and the microbeads flow out onto the groove plate side of the cuvette, the microbeads naturally align in the grooves via a small amount of rocking or agitation, which forms part of step 2 of the process shown in FIG. 1.

Figure 12:
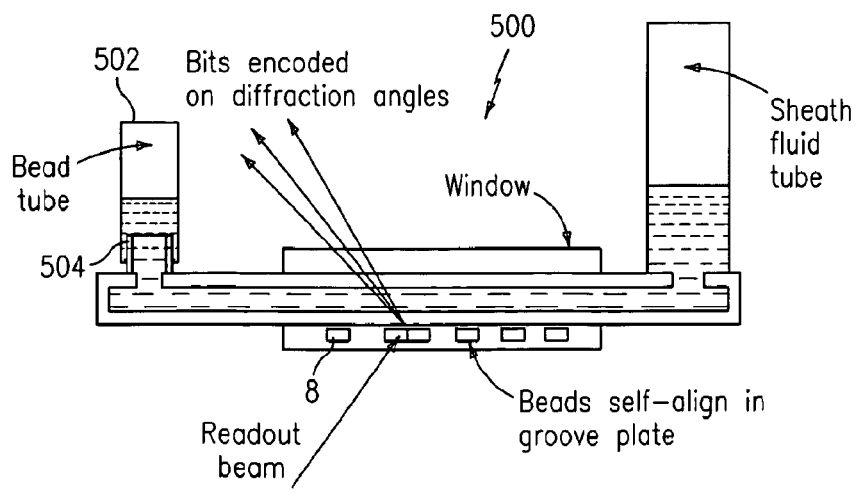
FIG. 12 is a diagram of the readout step in accordance with the invention.

(4) FIG. 12 shows the readout step, in which, after the beads are all (or nearly all) aligned in the groove plate, the entire plate is moved (or the readout laser beam is scanned) in order to read the codes of each beam, which forms part of step 3 of the process shown in FIG. 1. In effect, once the microbeads are in the grooves, the entire cuvette is moved back and forth across a readout beam. The readout beam is transmitted through the cuvette and contains the code bits encoded on the scattering angles.

Figure 13:
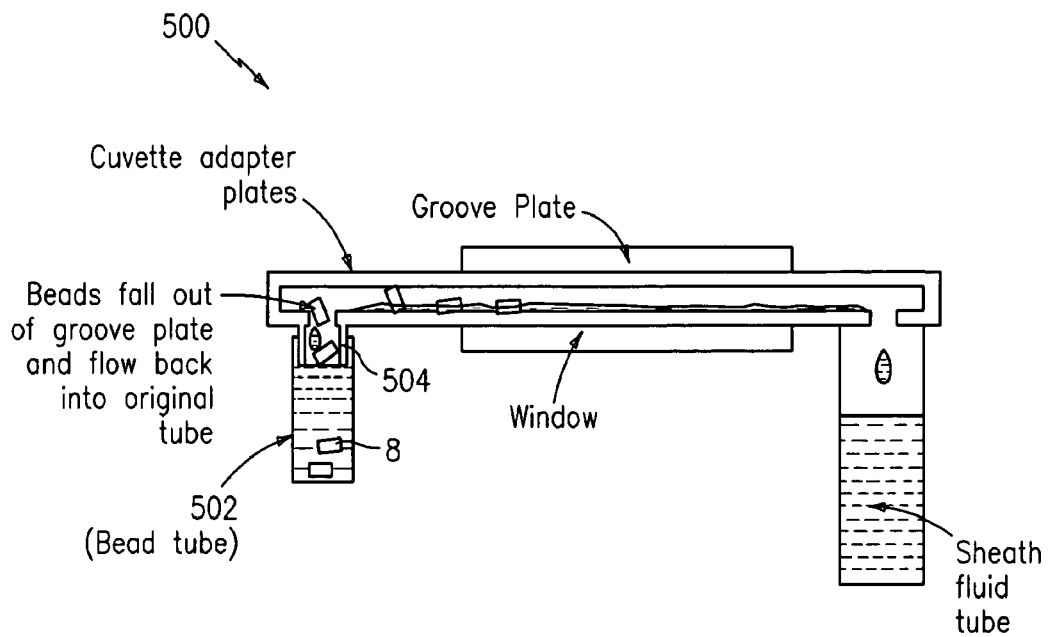
FIG. 13 is a diagram of final steps in the cuvette process in accordance with the invention.

(5) FIG. 13 shows a final step, in which the cuvette is inverted to its original position and the beads flow back into the original tube 502, which forms part of step 3 of the process shown in FIG. 1. In other words, after the readout process, the cuvette is re-inverted and the microbeads flow back into the original test tube.

FIG. 14 shows an example of a cuvette generally indicated as 700 that is mounted on a kinematic base plate 710. As shown, the cuvette 700 has a tube 702 for holding the solution with the beads and a top window 704 that is a 1 mm thick glass plate having dimensions of about 1" by 3". The cuvette also has a bottom plate that is a transparent groove plate. The location pins 712 and lever arm 714 hold the cuvette 700 in place on the kinematic plate 710.

One of the key advantages of using the cuvette device is that the potential to nearly index match the glass microbeads with a buffer solution thereby reducing the divergence of the laser beam caused by the lensing effect of the microbeads, and minimizing scatter form the groove plate itself.

Another advantage involves the potential to prevent microbeads from ever stacking up on top of each other, by limiting the space between the bottom and the top plate to be less than twice the diameter of the microbeads.

Another advantage is that the cover keeps the fluid from evaporating.

FIGS. 15-16

Figure 15:
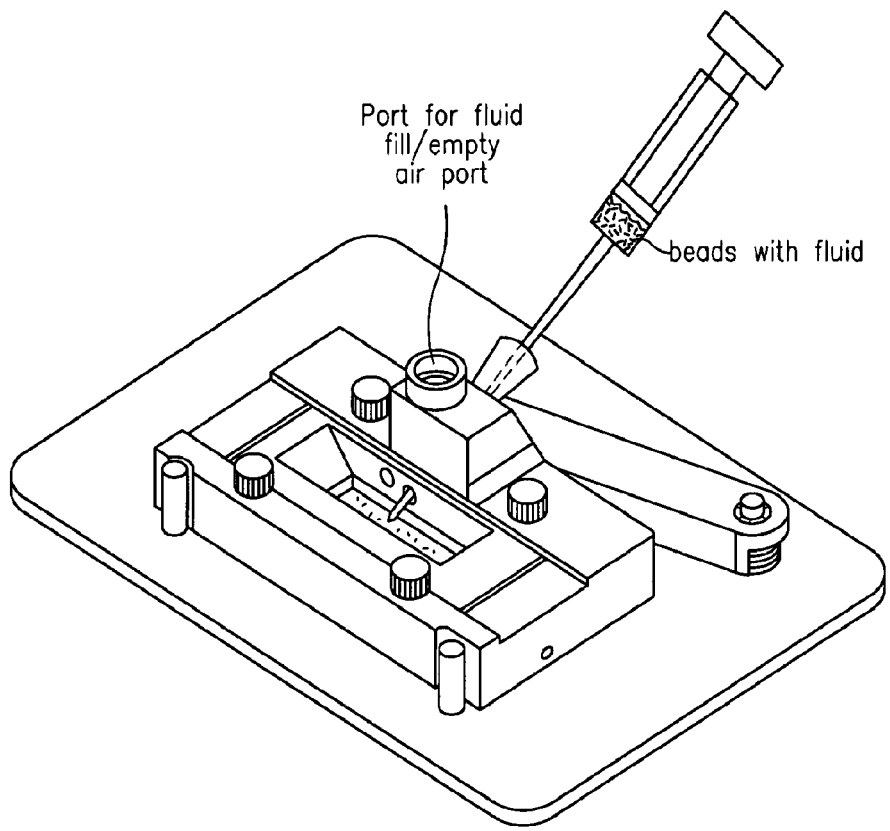
FIG. 15 is a diagram of an alternative embodiment of a cuvette showing a port for fluid filling/emptying using a pipette in accordance with the invention.
Figure 16:
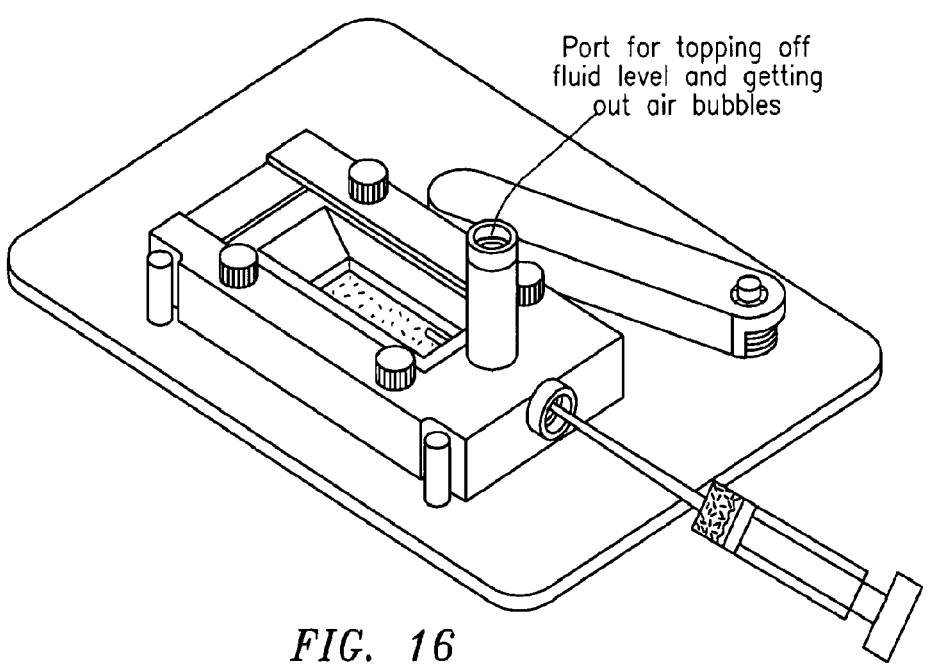
FIG. 16 is a diagram of an alternative embodiment of a cuvette showing an alternative port for fluid filling/emptying using a pipette in accordance with the invention.

FIGS. 15-16 show alternative embodiments of the cuvette shown in FIGS. 10-14. As shown, the microbeads are injected into the cuvette by placing them near the edge of the opening and allowing the surface tension, or an induced fluid flow, to pull the microbeads into the cuvette, where, because of the limited height between the floor and the ceiling of the cuvette, they are confined to move around in a plane, albeit with all the rotational degrees of freedom unconstrained. Once in the cuvette the microbeads are quickly and sufficiently constrained by the grooves as the microbeads fall into them. As in the case of the open format there is still the finite probability that some number of microbeads will not fall into the grooves and must be coaxed in by some form of agitation (ultrasonic, shaking, rocking, etc.).

Figure 17:
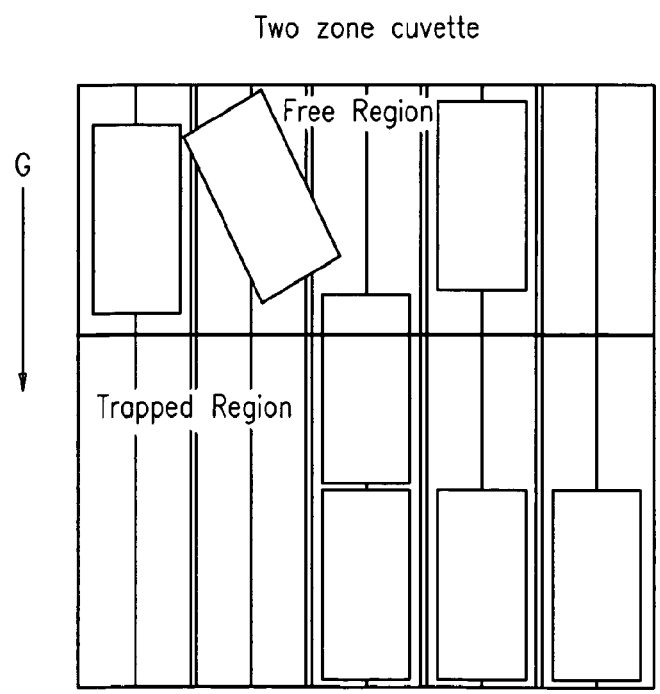
FIG. 17 is a diagram of a two zone cuvette showing a free region and a trapped region in accordance with the invention.

FIG. 17: Two Region Approach

FIG. 17 shows an alternative embodiment of the closed approach, which involves sectioning the closed region into two regions, one where the microbeads are free to move about in a plane, either in a groove or not, and a second region where the microbeads are trapped in a groove and can only move along the axes of a groove. Trapping the microbeads in a groove is accomplished by further reducing the height of the chamber to the extent that the microbeads can no longer hop out of a groove. In this embodiment, the free region is used to pre-align the microbeads into a groove, facilitating the introduction of microbeads into the trapped section. By tilting this type of cuvette up gravity can be used to pull the microbeads along a groove from the free region to the trapped region. Once in the trapped region the microbeads move to the end of the groove where they stop. Subsequent microbeads will begin to stack up until the groove is completely full of microbeads, which are stacked head to tail. This has the advantage of packing a large number of microbeads into a small area and prevents the microbeads from ever jumping out of the grooves. This approach could also be used to align the microbeads prior to injection into some form of flow cytometer, or a dispensing apparatus.

FIGS. 18-23: The Cytometer

FIGS. 18-23 show method and apparatus related to using a cytometer.

Figures 18A, 18B:
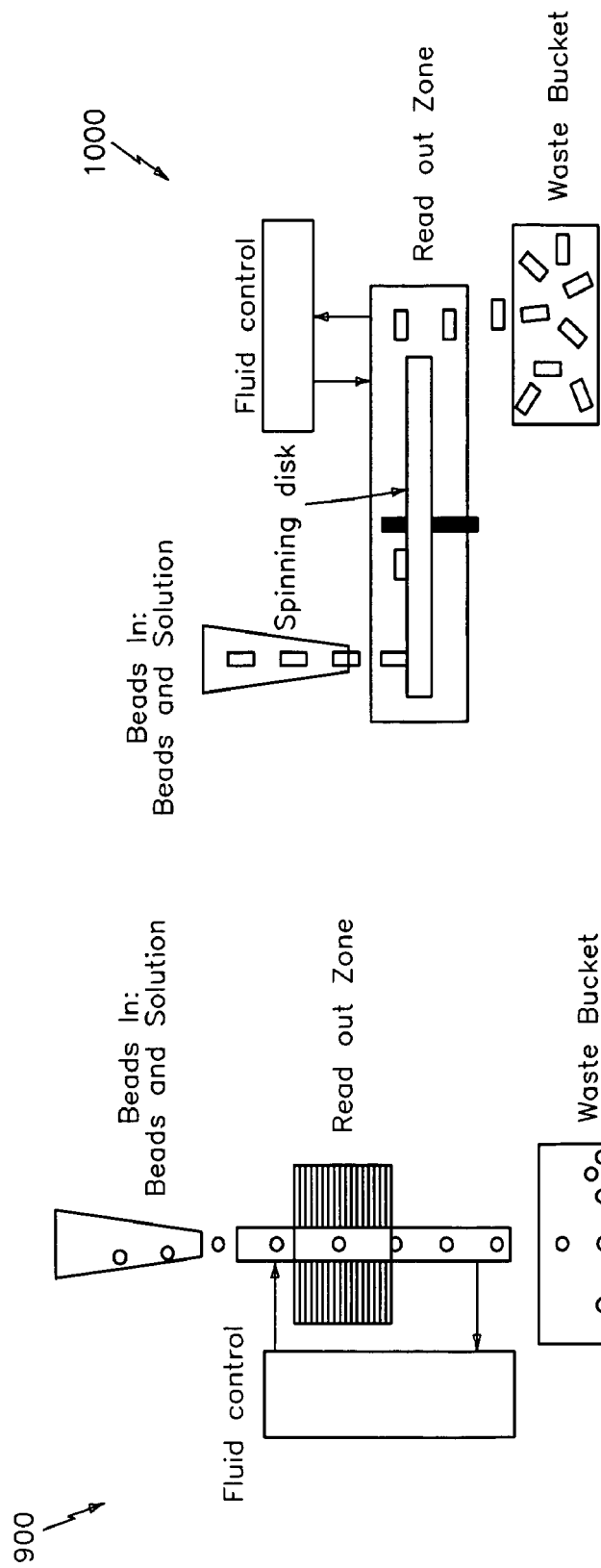
FIG. 18(a) is a diagram of steps for a conventional flow cytometer reader in a single pass cytometer process in accordance with the invention.
FIG. 18(b) is a diagram of steps for a disk cytometer reader in a multipass cytometer process in accordance with the invention.

FIG. 18(a) shows steps for a method related to a conventional (single pass) flow cytometer reader and FIG. 18(b) shows a method related to a disk cytometer reader (multipass).

In FIG. 18(a), the method generally indicated as 900 has a step for providing beads and a solution similar to step 1 in FIG. 1; and a step for reading information from the beads similar to steps 2 and 3 in FIG. 1.

In FIG. 18(b), the method generally indicated as 1000 has a step for providing beads and solution similar to step 1 in FIG. 1; and a step for spinning and reading information from the beads similar to steps 2 and 3 in FIG. 1.

Figures 19A, 19B, 19C:
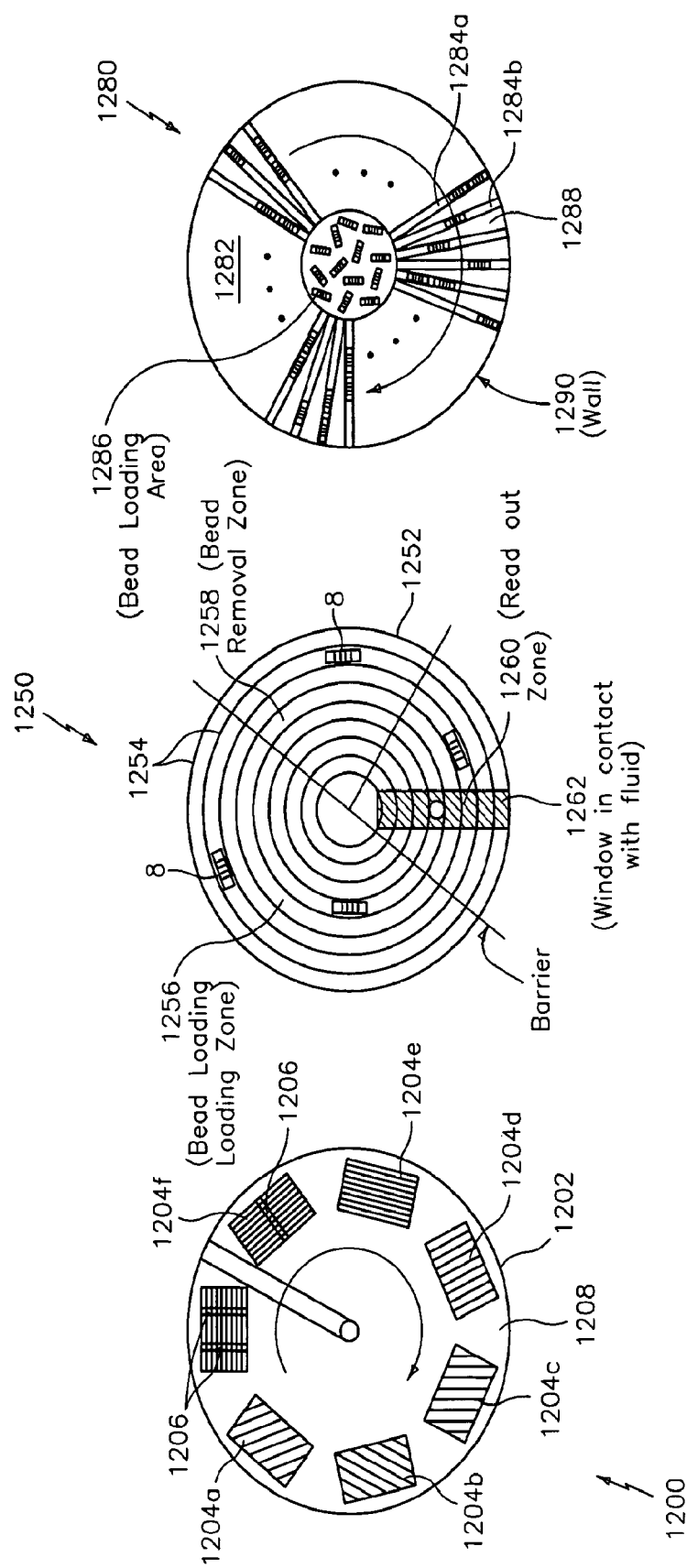
FIGS. 19(a), (b) and (c) show embodiments of a disk cytometer in accordance with the invention.

In the methods shown in FIGS. 18(a) and (b), a rotating disk (see FIGS. 19(a), (b) and (c) and 20) is used for aligning the microbeads consistent with step 2 of the process shown in FIG. 1.

FIG. 19(a) shows an embodiment of a cytometer bead reader having a rotating disk generally indicated as 1250, having a disk platform 1252 with circumferential, concentric, grooves 1254 for aligning microbeads 8. As shown, the rotating disk 1250 has various sectors for processing the microbeads, including a bead loading zone 1256, a bead removal zone 1258 and a readout zone 1260, as well as a barrier 1259 for preventing the microbeads from flying off the plate. As shown, a window 1262 for reading the beads is in contact with the fluid containing the beads.

FIG. 19(b) shows an alternative embodiment of a rotating disk generally indicated as 1200, having a disk platform 1202 with planar groove plates 1204a, b, c, d, e, f that are shown with grooves oriented in any one or more different ways. One or more of the planar groove plates 1204a, b, c, d, e, f may have an optional channel for fluid run-off, as shown, and a barrier (FIG. 19(a)) for preventing the microbeads from flying off the plate. All other attributes may be the same as described in FIG. 19(a). A window 1263 may be used for loading and/or reading the beads on the groove plates 1204a, b, c, d, e, f.

FIG. 19(c) shows an alternative embodiment of a rotating disk generally indicated as 1280, having a disk platform 1282 with radial grooves 1284a, 1284b. The disk platform 1282 has a bead loading zone 1286 in the center of the disk. One advantage of this embodiment is that the opening of the bead loading zone 1286 will also serve to allow the release of air bubbles that will naturally collect in the center of the disk due the reduced density of the fluid, which results from the centrifugal force pushing the fluid radially outwardly. The rotating disk 1280 has tight bead packing due to the centrifugal forces due to the spinning action of the disk. The rotating disk 1280 has a wedge shape spacer 1288 that keeps the channel at a constant gap width and a wall 1290.

FIG. 20(a) shows an alternative embodiment of a rotating disk generally indicated as 1300 having narrow radial channels 1302 for spin drying so liquid is forced out of the circumferential grooves through the radial channels. The plate 1300 may have a mechanical catcher 1320 coupled thereto for moving radially outwardly in direction 1320a if desired, for recirculating loose beads.

FIG. 20(b) show an alternative embodiment of a disk cytometer 1400 having a mechanical iris 1402 for providing a variable aperture for bead access to grooves in accordance with the invention.

Figure 21:
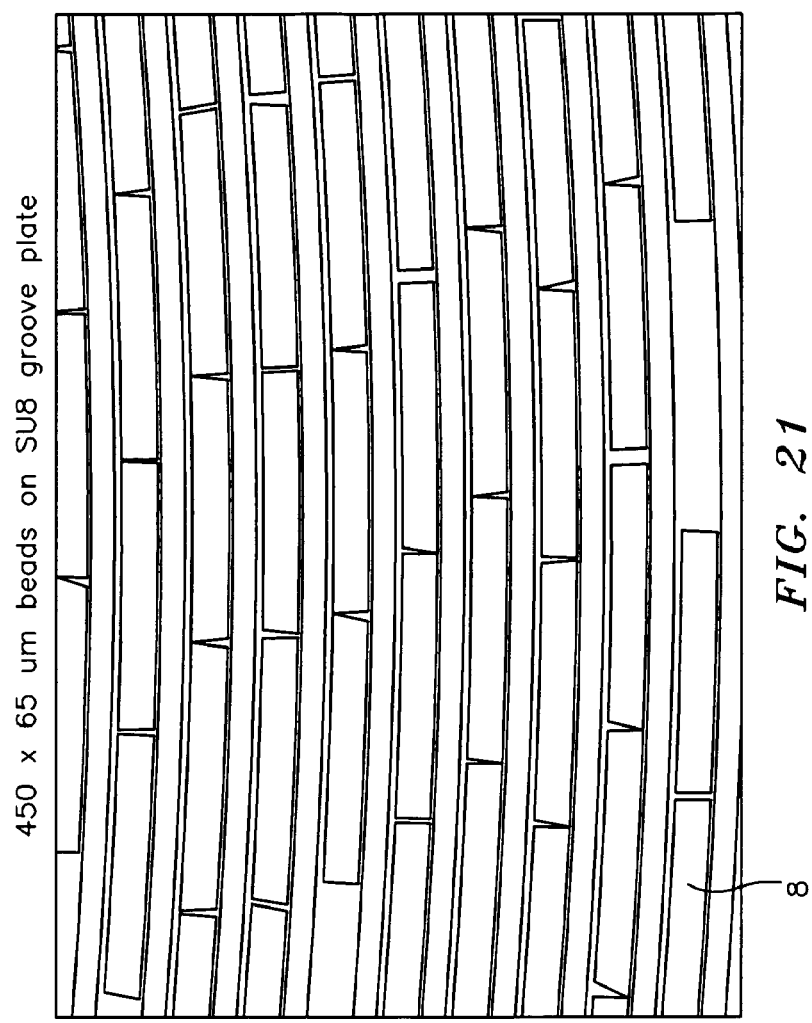
FIG. 21 shows an embodiment of a SU8 cylindrical grooved plate having 450×65 microns beads in accordance with the invention.

FIG. 21 shows a rotating groove plate having 450 by 65 microns beads arranged in the rotating SU8 circumferential channels.

For any of the circular groove plates shown herein, the disk may rotate as discussed above and/or the reader excitation laser(s)/detector(s) may rotate to read the code and/or the fluorescence on the beads 8.

Continuous Mode—Process Steps

The following are the processing steps for a continuous mode of operation:
1. Dispense batch of microbeads onto plate.
2. Spin slowly while agitating the plate theta x and y to get microbeads into grooves. The agitation can be performed using rocking, ultrasound, airflow, etc.
3. Once sufficient number of microbeads are in grooves, spin up plate to remove excess microbeads (microbeads that did not go into a groove).
4. Spin disk to read code and fluorescence.
5. To remove microbeads, purge with high velocity aqueous solution (enough to knock microbeads out of groove) and vacuum up, or spin microbeads off plate while they are not in a groove.
6. Inspect disk (probably with code camera) to verify that all microbeads have been removed.
7. Inject next batch of microbeads.

FIGS. 22-23: The Alignment Tube 502

In FIG. 22, instead of a flat grooved plate 200 (FIG. 3), the microbeads may be aligned in a tube 502 that has a diameter that is only slightly larger than the substrate 10, e.g., about 1-50 microns, and that is substantially transparent to the incident light 24. In that case, the incident light 24 may pass through the tube 502 as indicated by the light 500 or be reflected back due to a reflective coating on the tube 502 or the substrate as shown by return light 504. Other techniques can be used for alignment if desired.

FIG. 23 shows the tube 502 has an opening flange 512 for receiving the microbeads. FIG. 23 also shows an excitation laser 550, a diode laser 552 and a CCD camera 554 for gathering information from the bead 8 consistent with that discussed above. If desired, the beads 8 may be aligned and flowed through the tube 502 (similar to that discussed with FIG. 18(a) flow cytometer). In that case, fluid (liquid and/or gas) may flow through the tube 508 to move the beads 8 along the tube 502, using a flow cytometer approach.

FIGS. 24-44: Reading the Microbead Code and Alternative Embodiments

FIGS. 24-44 provide a method and apparatus for reading the code in the microbeads 8, as well as a more detailed description of the microbeads 8 and certain alternative embodiments therefore. The scope of the invention is not intended to be limited in any way to the manner in which the code is read, or the method of doing the same.

Figure 24:
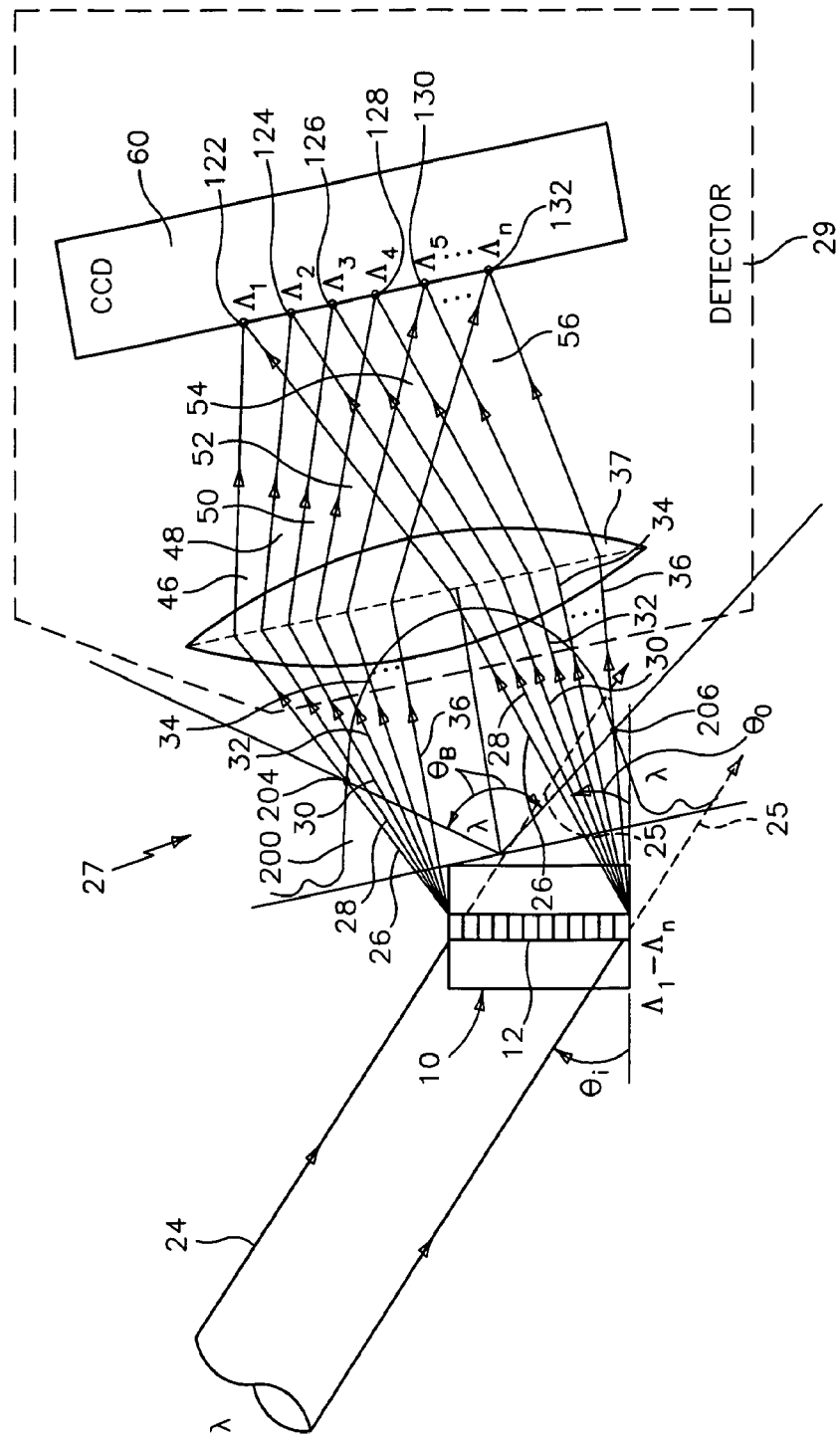
FIG. 24 is an optical schematic for reading a code in an optical identification element, in accordance with the present invention.

Referring to FIG. 24, The reflected light 27, comprises a plurality of beams 26-36 that pass through a lens 37, which provides focused light beams 46-56, respectively, which are imaged onto a CCD camera 60. The lens 37 and the camera 60, and any other necessary electronics or optics for performing the functions described herein, make up the reader 29. Instead of or in addition to the lens 37, other imaging optics may be used to provide the desired characteristics of the optical image/signal onto the camera 60 (e.g., spots, lines, circles, ovals, etc.), depending on the shape of the substrate 10 and input optical signals. Also, instead of a CCD camera other devices may be used to read/capture the output light.

Figure 25A:
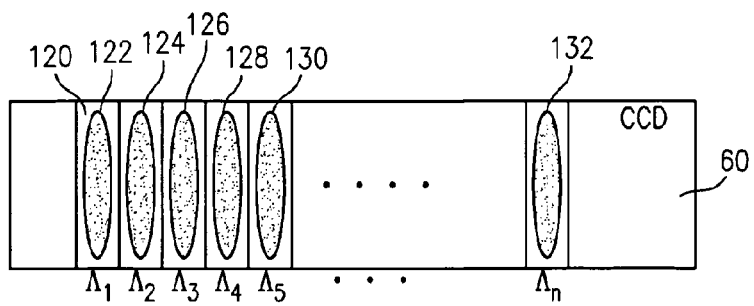
FIG. 25(a) is an image of a code on a CCD camera from an optical identification element, in accordance with the present invention.
Figure 25B:
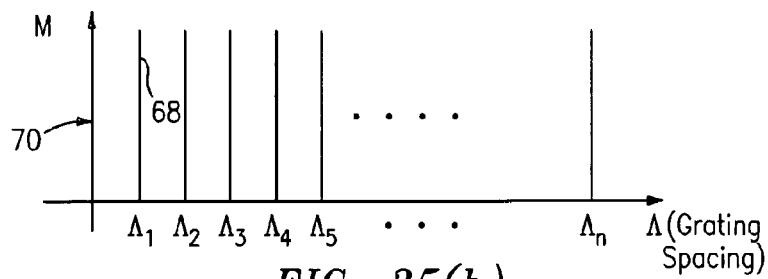
FIG. 25(b) is a graph showing an digital representation of bits in a code in an optical identification element, in accordance with the present invention.
Figure 26:
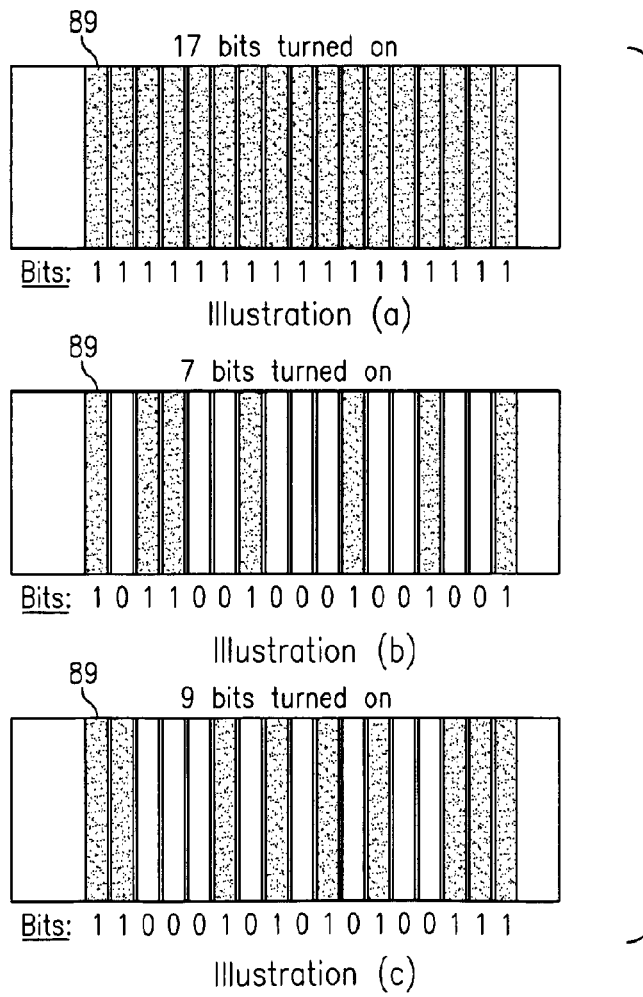
FIG. 26 illustrations (a)-(c) show images of digital codes on a CCD camera, in accordance with the present invention.

Referring to FIG. 25, the image on the CCD camera 60 is a series of illuminated stripes indicating ones and zeros of a digital pattern or code of the grating 12 in the element 8. Referring to FIG. 26, lines 68 on a graph 70 are indicative of a digitized version of the image of FIG. 25 as indicated in spatial periods ($\Lambda 1$-$\Lambda n$).

Each of the individual spatial periods ($\Lambda 1$-$\Lambda n$) in the grating 12 is slightly different, thus producing an array of N unique diffraction conditions (or diffraction angles) discussed more hereinafter. When the element 8 is illuminated from the side, in the region of the grating 12, at an appropriate input angle, e.g., about 30 degrees, with a single input wavelength $\lambda$ (monochromatic) source, the diffracted (or reflected) beams 26-36 are generated. Other input angles $\theta i$ may be used if desired, depending on various design parameters as discussed herein and/or in the aforementioned patent application, and provided that a known diffraction equation (Eq. 1 below) is satisfied:

$$\sin(\theta_i) + \sin(\theta_o) = m\lambda/n\Lambda \qquad \text{Eq. 1}$$

where Eq. 1 is diffraction (or reflection or scatter) relationship between input wavelength $\lambda$, input incident angle $\theta i$, output incident angle $\theta o$, and the spatial period $\Lambda$ of the grating 12. Further, m is the "order" of the reflection being observed, and n is the refractive index of the substrate 10. The value of m=1 or first order reflection is acceptable for illustrative purposes. Eq. 1 applies to light incident on outer surfaces of the substrate 10 which are parallel to the longitudinal axis of the grating (or the $k_B$ vector). Because the angles $\theta i, \theta o$ are defined outside the substrate 10 and because the effective refractive index of the substrate 10 is substantially a common value, the value of n in Eq. 1 cancels out of this equation.

Thus, for a given input wavelength $\lambda$, grating spacing $\Lambda$, and incident angle of the input light $\theta i$, the angle $\theta o$ of the reflected output light may be determined. Solving Eq. 1 for $\theta o$ and plugging in m=1, gives:

$$\theta_o = \sin^{-1}(\lambda/\Lambda - \sin(\theta i)) \qquad \text{Eq. 2}$$

For example, for an input wavelength $\lambda$=532 nm, a grating spacing $\Lambda$=0.532 microns (or 532 nm), and an input angle of incidence $\theta i$=30 degrees, the output angle of reflection will be $\theta o$=30 degrees. Alternatively, for an input wavelength $\lambda$=632 nm, a grating spacing $\Lambda$=0.532 microns (or 532 nm), and an input angle $\theta i$ of 30 degrees, the output angle of reflection $\theta o$ will be at 43.47 degrees, or for an input angle $\theta i$=37 degrees, the output angle of reflection will be $\theta o$=37 degrees. Any input angle that satisfies the design requirements discussed herein and/or in the aforementioned patent application may be used.

In addition, to have sufficient optical output power and signal to noise ratio, the output light 27 should fall within an acceptable portion of the Bragg envelope (or normalized reflection efficiency envelope) curve 200, as indicated by points 204,206, also defined as a Bragg envelope angle $\theta B$, as also discussed herein and/or in the aforementioned patent application. The curve 200 may be defined as:

$$I(ki, ko) \approx [KD]^2 \text{sinc}^2\left[\frac{(ki-ko)D}{2}\right] \qquad \text{Eq. 3}$$

where K=$2\pi\delta n/\lambda$, where, $\delta n$ is the local refractive index modulation amplitude of the grating and $\lambda$ is the input wavelength, sin c(x)=sin(x)/x, and the vectors $k_i = 2\pi \cos(\theta_i)/\lambda$ and $k_o = 2\pi \cos(\theta_o)/\lambda$ are the projections of the incident light and the output (or reflected) light, respectively, onto the line 203 normal to the axial direction of the grating 12 (or the grating vector $k_B$), D is the thickness or depth of the grating 12 as measured along the line 203 (normal to the axial direction of the grating 12). Other substrate shapes than a cylinder may be used and will exhibit a similar peaked characteristic of the Bragg envelope. We have found that a value for $\delta n$ of about $10^{-4}$ in the grating region of the substrate is acceptable; however, other values may be used if desired.

Rewriting Eq. 3 gives the reflection efficiency profile of the Bragg envelope as:

$$I(ki, ko) \approx \left[\frac{2\pi \cdot \delta n \cdot D}{\lambda}\right]^2 \left[\frac{\sin(x)}{x}\right]^2 \qquad \text{Eq. 4}$$

where:

$$x = (ki-ko)D/2 = (\pi D/\lambda)^*(\cos\theta i - \cos\theta o)$$

Thus, when the input angle $\theta i$ is equal to the output (or reflected) angle $\theta_o$ (i.e., $\theta i = \theta_o$), the reflection efficiency I (Eqs. 3 & 4) is maximized, which is at the center or peak of the Bragg envelope. When $\theta i = \theta o$, the input light angle is referred to as the Bragg angle as is known. The efficiency decreases for other input and output angles (i.e., $\theta i \neq \theta_o$), as defined by Eqs. 3 & 4. Thus, for maximum reflection efficiency and thus output light power, for a given grating pitch $\Lambda$ and input wavelength, the angle $\theta i$ of the input light 24 should be set so that the angle $\theta o$ of the reflected output light equals the input angle $\theta i$.

Also, as the thickness or diameter D of the grating decreases, the width of the sin(x)/x function (and thus the width of the Bragg envelope) increases and, the coefficient to or amplitude of the sin $c^2$ (or $(\sin(x)/x)^2$ function (and thus the efficiency level across the Bragg envelope) also increases, and vice versa. Further, as the wavelength $\lambda$ increases, the half-width of the Bragg envelope as well as the efficiency level across the Bragg envelope both decrease. Thus, there is a trade-off between the brightness of an individual bit and the number of bits available under the Bragg envelope. Ideally, $\delta n$ should be made as large as possible to maximize the brightness, which allows D to be made smaller.

From Eq. 3 and 4, the half-angle of the Bragg envelope $\theta_B$ is defined as:

$$\theta_B = \frac{\eta\lambda}{\pi D \sin(\theta_i)} \qquad \text{Eq. 5}$$

where $\eta$ is a reflection efficiency factor which is the value for x in the sin $c^2(x)$ function where the value of sin $c^2(x)$ has decreased to a predetermined value from the maximum amplitude as indicated by points 204,206 on the curve 200.

We have found that the reflection efficiency is acceptable when $\eta \leq 1.39$. This value for n corresponds to when the amplitude of the reflected beam (i.e., from the sin $c^2(x)$ function of Eqs. 3 & 4) has decayed to about 50% of its peak value. In particular, when x=1.39=$\eta$, sin $c^2(x)$=0.5. However, other values for efficiency thresholds or factor in the Bragg envelope may be used if desired.

The beams 26-36 are imaged onto the CCD camera 60 to produce the pattern of light and dark regions 120-132 representing a digital (or binary) code, where light=1 and dark=0 (or vice versa). The digital code may be generated by selectively creating individual index variations (or individual gratings) with the desired spatial periods $\Lambda 1$-$\Lambda n$. Other illumination, readout techniques, types of gratings, geometries, materials, etc. may be used as discussed in the aforementioned patent application.

Referring to FIG. 26, illustrations (a)-(c), for the grating 12 in a cylindrical substrate 10 having a sample spectral 17 bit code (i.e., 17 different pitches Λ1-Λ17), the corresponding image on the CCD (Charge Coupled Device) camera 60 is shown for a digital pattern of 7 bits turned on (10110010001001001); 9 bits turned on of (11000101010100111); all 17 bits turned on of (11111111111111111).

For the images in FIG. 26, the length of the substrate 10 was 450 microns, the outer diameter D1 was 65 microns, the inner diameter D was 14 microns, δn for the grating 12 was about $10^{-4}$, n1 in portion 20 was about 1.458 (at a wavelength of about 1550 nm), n2 in portion 18 was about 1.453, the average pitch spacing Λ for the grating 12 was about 0.542 microns, and the spacing between pitches ΔΛ was about 0.36% of the adjacent pitches Λ.

Referring to FIG. 27, illustration (a), the pitch Λ of an individual grating is the axial spatial period of the sinusoidal variation in the refractive index n1 in the region 20 of the substrate 10 along the axial length of the grating 12 as indicated by a curve 90 on a graph 91. Referring to FIG. 27, illustration (b), a sample composite grating 12 comprises three individual gratings that are co-located on the substrate 10, each individual grating having slightly different pitches, Λ1, Λ2, Λ3, respectively, and the difference (or spacing) ΔΛ between each pitch Λ being about 3.0% of the period of an adjacent pitch Λ as indicated by a series of curves 92 on a graph 94. Referring to FIG. 27, illustration (c), three individual gratings, each having slightly different pitches, Λ1, Λ2, Λ3, respectively, are shown, the difference ΔΛ between each pitch Λ being about 0.3% of the pitch Λ of the adjacent pitch as shown by a series of curves 95 on a graph 97. The individual gratings in FIG. 27, illustrations (b) and (c) are shown to all start at 0 for illustration purposes; however, it should be understood that, the separate gratings need not all start in phase with each other. Referring to FIG. 27, illustration (d), the overlapping of the individual sinusoidal refractive index variation pitches Λ1-Λn in the grating region 20 of the substrate 10, produces a combined resultant refractive index variation in the composite grating 12 shown as a curve 96 on a graph 98 representing the combination of the three pitches shown in FIG. 27, illustration (b). Accordingly, the resultant refractive index variation in the grating region 20 of the substrate 10 may not be sinusoidal and is a combination of the individual pitches Λ (or index variation).

The maximum number of resolvable bits N, which is equal to the number of different grating pitches Λ (and hence the number of codes), that can be accurately read (or resolved) using side-illumination and side-reading of the grating 12 in the substrate 10, is determined by numerous factors, including: the beam width w incident on the substrate (and the corresponding substrate length L and grating length Lg), the thickness or diameter D of the grating 12, the wavelength λ of incident light, the beam divergence angle $\theta_R$, and the width of the Bragg envelope $\theta_B$ (discussed more in the aforementioned patent application), and may be determined by the equation:

$$N \cong \frac{\eta \beta L}{2D \sin(\theta_i)} \qquad \text{Eq. 6}$$

Figure 28:
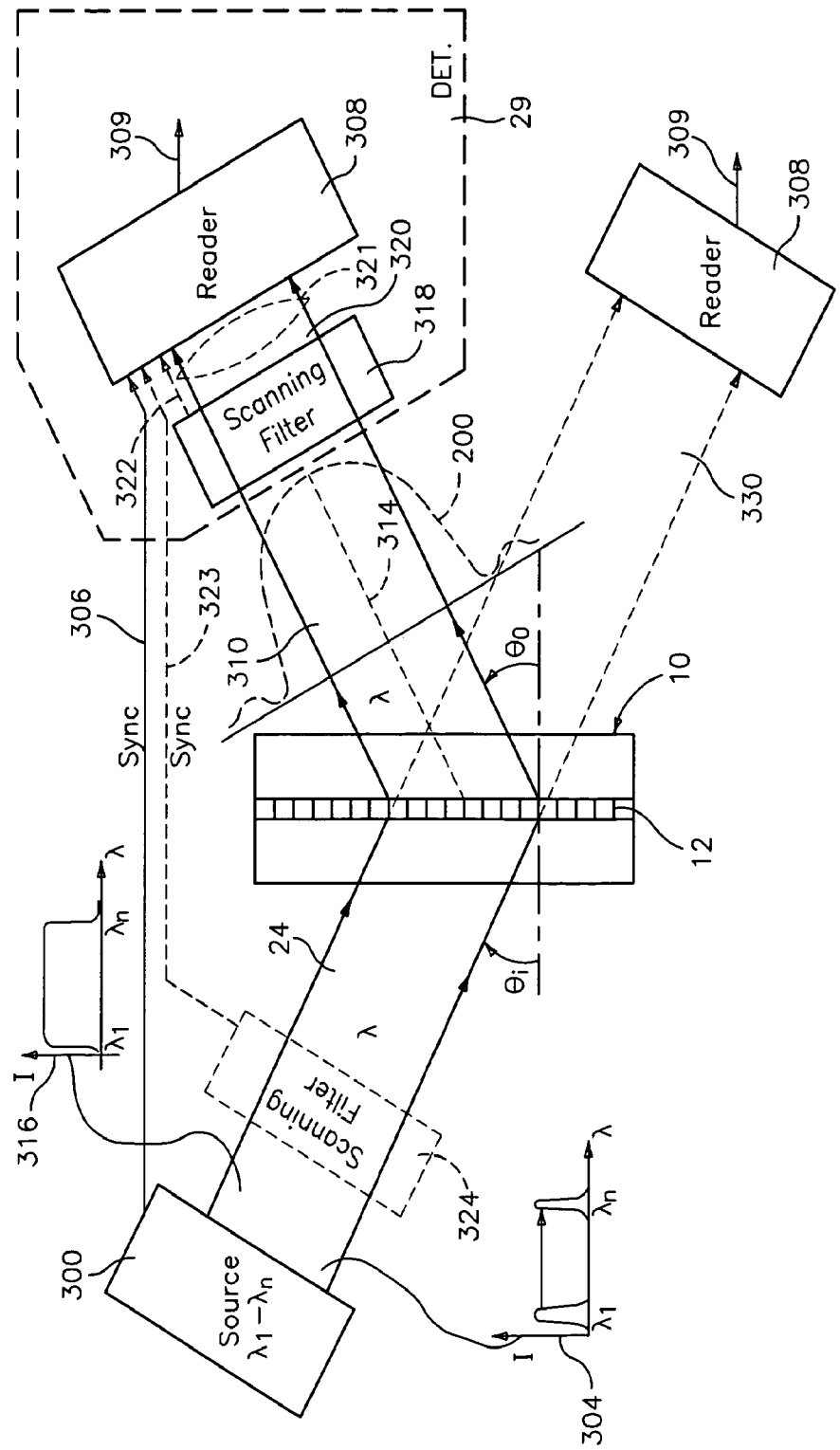
FIG. 28 is an alternative optical schematic for reading a code in an optical identification element, in accordance with the present invention.

Referring to FIG. 28, instead of having the input light 24 at a single wavelength λ (monochromatic) and reading the bits by the angle θo of the output light, the bits (or grating pitches Λ) may be read/detected by providing a plurality of wavelengths and reading the wavelength spectrum of the reflected output light signal. In this case, there would be one bit per wavelength, and thus, the code is contained in the wavelength information of the reflected output signal.

In this case, each bit (or Λ) is defined by whether its corresponding wavelength falls within the Bragg envelope, not by its angular position within the Bragg envelope 200. As a result, it is not limited by the number of angles that can fit in the Bragg envelope 200 for a given composite grating 12, as in the embodiment discussed hereinbefore. Thus, using multiple wavelengths, the only limitation in the number of bits N is the maximum number of grating pitches Λ that can be superimposed and optically distinguished in wavelength space for the output beam.

Figure 29:
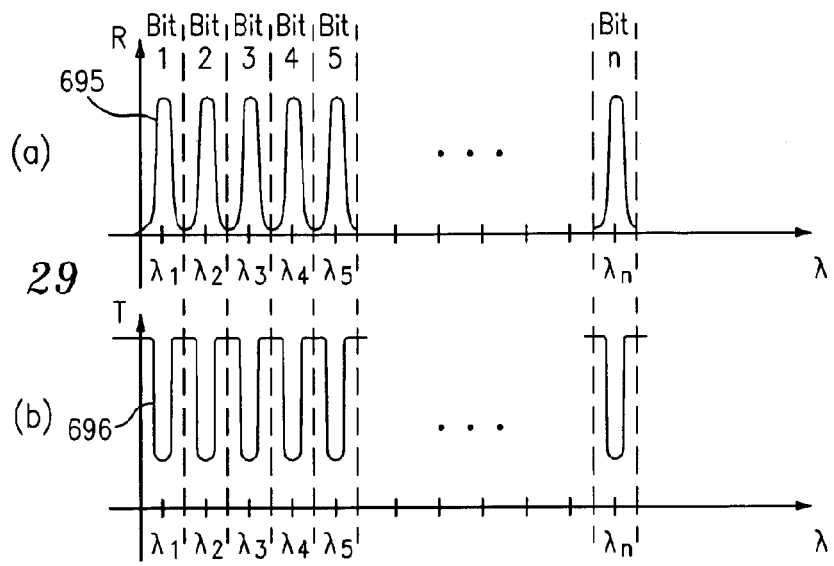
FIG. 29 illustrations (a)-(b) are graphs of reflection and transmission wavelength spectrum for an optical identification element, in accordance with the present invention.

Referring to FIGS. 28 and 29, illustration (a), the reflection wavelength spectrum (λ1-λn) of the reflected output beam 310 will exhibit a series of reflection peaks 695, each appearing at the same output Bragg angle θo. Each wavelength peak 695 (λ1-λn) corresponds to an associated spatial period (Λ1-Λn), which make up the grating 12.

One way to measure the bits in wavelength space is to have the input light angle θi equal to the output light angle θo, which is kept at a constant value, and to provide an input wavelength λ that satisfies the diffraction condition (Eq. 1) for each grating pitch Λ. This will maximize the optical power of the output signal for each pitch Λ detected in the grating 12.

Referring to 29, illustration (b), the transmission wavelength spectrum of the transmitted output beam 330 (which is transmitted straight through the grating 12) will exhibit a series of notches (or dark spots) 696. Alternatively, instead of detecting the reflected output light 310, the transmitted light 330 may be detected at the detector/reader 308. It should be understood that the optical signal levels for the reflection peaks 695 and transmission notches 696 will depend on the "strength" of the grating 12, i.e., the magnitude of the index variation n in the grating 12.

In FIG. 28, the bits may be detected by continuously scanning the input wavelength. A known optical source 300 provides the input light signal 24 of a coherent scanned wavelength input light shown as a graph 304. The source 300 provides a sync signal on a line 306 to a known reader 308. The sync signal may be a timed pulse or a voltage ramped signal, which is indicative of the wavelength being provided as the input light 24 to the substrate 10 at any given time. The reader 308 may be a photodiode, CCD camera, or other optical detection device that detects when an optical signal is present and provides an output signal on a line 309 indicative of the code in the substrate 10 or of the wavelengths present in the output light, which is directly related to the code, as discussed herein. The grating 12 reflects the input light 24 and provides an output light signal 310 to the reader 308. The wavelength of the input signal is set such that the reflected output light 310 will be substantially in the center 314 of the Bragg envelope 200 for the individual grating pitch (or bit) being read.

Alternatively, the source 300 may provide a continuous broadband wavelength input signal such as that shown as a graph 316. In that case, the reflected output beam 310 signal is provided to a narrow band scanning filter 318 which scans across the desired range of wavelengths and provides a filtered output optical signal 320 to the reader 308. The filter 318 provides a sync signal on a line 322 to the reader, which is indicative of which wavelengths are being provided on the output signal 320 to the reader and may be similar to the sync signal discussed hereinbefore on the line 306 from the source

300. In this case, the source 300 does not need to provide a sync signal because the input optical signal 24 is continuous. Alternatively, instead of having the scanning filter being located in the path of the output beam 310, the scanning filter may be located in the path of the input beam 24 as indicated by the dashed box 324, which provides the sync signal on a line 323.

Alternatively, instead of the scanning filters 318,324, the reader 308 may be a known optical spectrometer (such as a known spectrum analyzer), capable of measuring the wavelength of the output light.

The desired values for the input wavelengths λ (or wavelength range) for the input signal 24 from the source 300 may be determined from the Bragg condition of Eq. 1, for a given grating spacing Λ and equal angles for the input light θi and the angle light θo. Solving Eq. 1 for λ and plugging in m=1, gives:

$$\lambda = \Lambda[\sin(\theta o) + \sin(\theta i)] \quad \text{Eq. 7}$$

It is also possible to combine the angular-based code detection with the wavelength-based code detection, both discussed hereinbefore. In this case, each readout wavelength is associated with a predetermined number of bits within the Bragg envelope. Bits (or grating pitches Λ) written for different wavelengths do not show up unless the correct wavelength is used.

Accordingly, the bits (or grating pitches Λ) can be read using one wavelength and many angles, many wavelengths and one angle, or many wavelengths and many angles.

Figure 30:
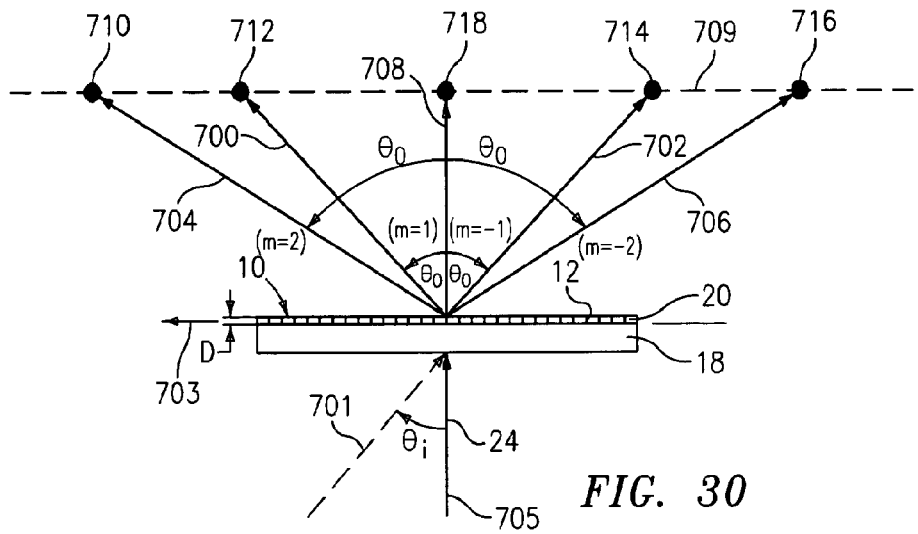
FIGS. 30-31 are side views of a thin grating for an optical identification element, in accordance with the present invention.

Referring to FIG. 30, the grating 12 may have a thickness or depth D which is comparable or smaller than the incident beam wavelength λ. This is known as a "thin" diffraction grating (or the full angle Bragg envelope is 180 degrees). In that case, the half-angle Bragg envelope θB is substantially 90 degrees; however, δn must be made large enough to provide sufficient reflection efficiency, per Eqs. 3 and 4. In particular, for a "thin" grating, $D \cdot \delta n \approx \lambda/2$, which corresponds to a π phase shift between adjacent minimum and maximum refractive index values of the grating 12.

It should be understood that there is still a trade-off discussed hereinbefore with beam divergence angle $\theta_R$ and the incident beam width (or length L of the substrate), but the accessible angular space is theoretically now 90 degrees. Also, for maximum efficiency, the phase shift between adjacent minimum and maximum refractive index values of the grating 12 should approach a π phase shift; however, other phase shifts may be used.

In this case, rather than having the input light 24 coming in at the conventional Bragg input angle θi, as discussed hereinbefore and indicated by a dashed line 701, the grating 12 is illuminated with the input light 24 oriented on a line 705 orthogonal to the longitudinal grating vector 705. The input beam 24 will split into two (or more) beams of equal amplitude, where the exit angle $\theta_o$ can be determined from Eq. 1 with the input angle $\theta_i = 0$ (normal to the longitudinal axis of the grating 12).

In particular, from Eq. 1, for a given grating pitch Λ1, the +/−1$^{st}$ order beams (m=+1 and m=−1), corresponds to output beams 700,702, respectively. For the +/−2$^{nd}$ order beams (m=+2 and m=−2), corresponds to output beams 704,706, respectively. The 0$^{th}$ order (undefracted) beam (m=0), corresponds to beam 708 and passes straight through the substrate. The output beams 700-708 project spectral spots or peaks 710-718, respectively, along a common plane, shown from the side by a line 709, which is parallel to the upper surface of the substrate 10.

For example, for a grating pitch Λ=1.0 um, and an input wavelength λ=400 nm, the exit angles $\theta_o$ are ~+/−23.6 degrees (for m=+/−1), and +/−53.1 degrees (from m=+/−2), from Eq. 1. It should be understood that for certain wavelengths, certain orders (e.g., m=+/−2) may be reflected back toward the input side or otherwise not detectable at the output side of the grating 12.

Alternatively, one can use only the +/−1$^{st}$ order (m=+/−1) output beams for the code, in which case there would be only 2 peaks to detect, 712, 714. Alternatively, one can also use any one or more pairs from any order output beam that is capable of being detected. Alternatively, instead of using a pair of output peaks for a given order, an individual peak may be used.

Figure 31:
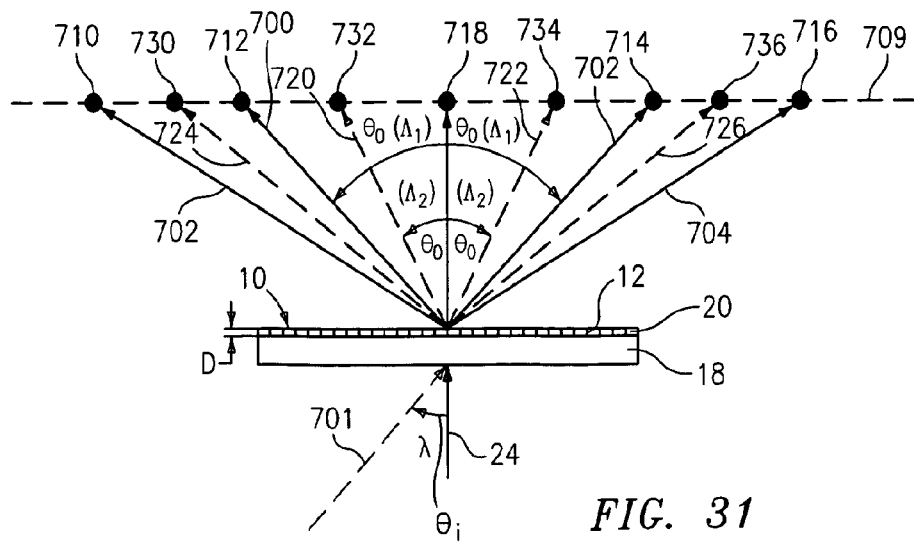

Referring to FIG. 31, if two pitches Λ1,Λ2 exist in the grating 12, two sets of peaks will exist. In particular, for a second grating pitch Λ2, the +/−1$^{st}$ order beams (m=+1 and m=−1), corresponds to output beams 720,722, respectively. For the +/−2$^{nd}$ order beams (m=+2 and m=−2), corresponds to output beams 724,726, respectively. The 0$^{th}$ order (un-defracted) beam (m=0), corresponds to beam 718 and passes straight through the substrate. The output beams 720-726 corresponding to the second pitch Λ2 project spectral spots or peaks 730-736, respectively, which are at a different location than the point 710-716, but along the same common plane, shown from the side by the line 709.

Thus, for a given pitch Λ (or bit) in a grating, a set of spectral peaks will appear at a specific location in space. Thus, each different pitch corresponds to a different elevation or output angle which corresponds to a predetermined set of spectral peaks. Accordingly, the presence or absence of a particular peak or set of spectral peaks defines the code.

In general, if the angle of the grating 12 is not properly aligned with respect to the mechanical longitudinal axis of the substrate 10, the readout angles may no longer be symmetric, leading to possible difficulties in readout. With a thin grating, the angular sensitivity to the alignment of the longitudinal axis of the substrate 10 to the input angle θi of incident radiation is reduced or eliminated. In particular, the input light can be oriented along substantially any angle θi with respect to the grating 12 without causing output signal degradation, due the large Bragg angle envelope. Also, if the incident beam 24 is normal to the substrate 10, the grating 12 can be oriented at any rotational (or azimuthal) angle without causing output signal degradation. However, in each of these cases, changing the incident angle θi will affect the output angle θo of the reflected light in a predetermined predictable way, thereby allowing for accurate output code signal detection or compensation.

Referring to FIG. 32, for a thin grating, in addition to multiplexing in the elevation or output angle based on grating pitch Λ, the bits can also be multiplexed in an azimuthal (or rotational) angle θa of the substrate. In particular, a plurality of gratings 750,752,754,756 each having the same pitch Λ are disposed in a surface 701 of the substrate 10 and located in the plane of the substrate surface 701. The input light 24 is incident on all the gratings 750,752,754,756 simultaneously. Each of the gratings provides output beams oriented based on the grating orientation. For example, the grating 750 provides the output beams 764,762, the grating 752 provides the output beams 766,768, the grating 754 provides the output beams 770,772, and the grating 756 provides the output beams 774, 776. Each of the output beams provides spectral peaks or spots (similar to that discussed hereinbefore), which are located in a plane 760 that is parallel to the substrate surface plane 701. In this case, a single grating pitch Λ can produce many bits depending on the number of gratings that can be placed at different azimuthal (rotational) angles on the surface of the substrate 10 and the number of output beam spectral peaks that can be spatially and optically resolved/detected. Each bit may be viewed as the presence or absence of a pair of peaks located at a predetermined location in space in the plane 760. Note that this example uses only the m=+/−1$^{st}$ order for each reflected output beam. Alternatively, the detection may also use the m=+/−2$^{nd}$ order. In that case, there would be two additional output beams and peaks (not shown) for each grating (as discussed hereinbefore) that may lie in the same plane as the plane 760 and may be on a concentric circle outside the circle 760.

In addition, the azimuthal multiplexing can be combined with the elevation or output angle multiplexing discussed hereinbefore to provide two levels of multiplexing. Accordingly, for a thin grating, the number of bits can be multiplexed based on the number of grating pitches Λ and/or geometrically by the orientation of the grating pitches.

Furthermore, if the input light angle θi is normal to the substrate 10, the edges of the substrate 10 no longer scatter light from the incident angle into the "code angular space", as discussed herein and/or in the aforementioned patent application.

Also, in the thin grating geometry, a continuous broadband wavelength source may be used as the optical source if desired.

Referring to FIG. 33, instead of or in addition to the pitches Λ in the grating 12 being oriented normal to the longitudinal axis, the pitches may be created at a angle θg. In that case, when the input light 24 is incident normal to the surface 792, will produce a reflected output beam 790 having an angle θo determined by Eq. 1 as adjusted for the blaze angle θg. This can provide another level of multiplexing bits in the code.

Figure 34:
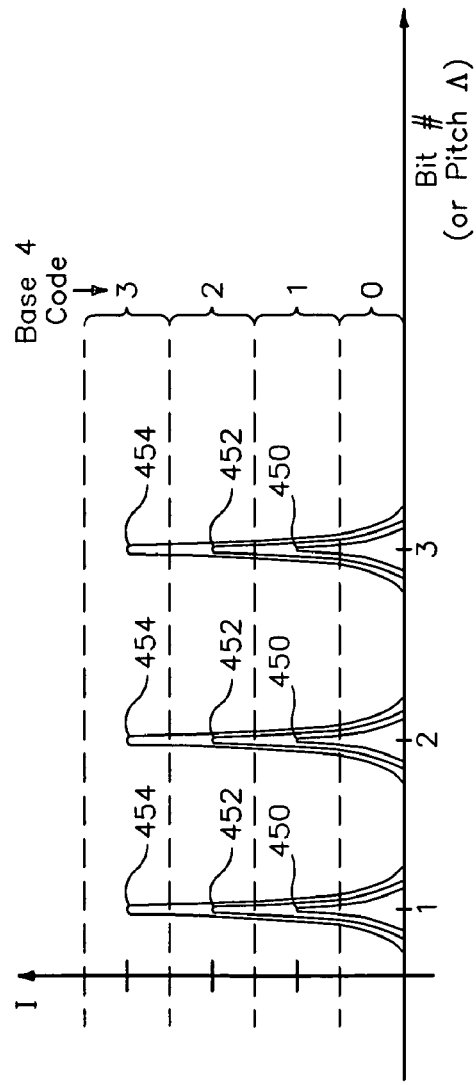
FIG. 34 is a graph of a plurality of states for each bit in a code for an optical identification element, in accordance with the present invention.

Referring to FIG. 34, instead of using an optical binary (0-1) code, an additional level of multiplexing may be provided by having the optical code use other numerical bases, if intensity levels of each bit are used to indicate code information. This could be achieved by having a corresponding magnitude (or strength) of the refractive index change (δn) for each grating pitch Λ. Four intensity ranges are shown for each bit number or pitch Λ, providing for a Base-4 code (where each bit corresponds to 0, 1, 2, or 3). The lowest intensity level, corresponding to a 0, would exist when this pitch Λ is not present in the grating 12. The next intensity level 450 would occur when a first low level δn1 exists in the grating that provides an output signal within the intensity range corresponding to a 1. The next intensity level 452 would occur when a second higher level δn2 exists in the grating 12 that provides an output signal within the intensity range corresponding to a 2. The next intensity level 452, would occur when a third higher level δn3 exists in the grating 12 that provides an output signal within the intensity range corresponding to a 3.

Figure 35:
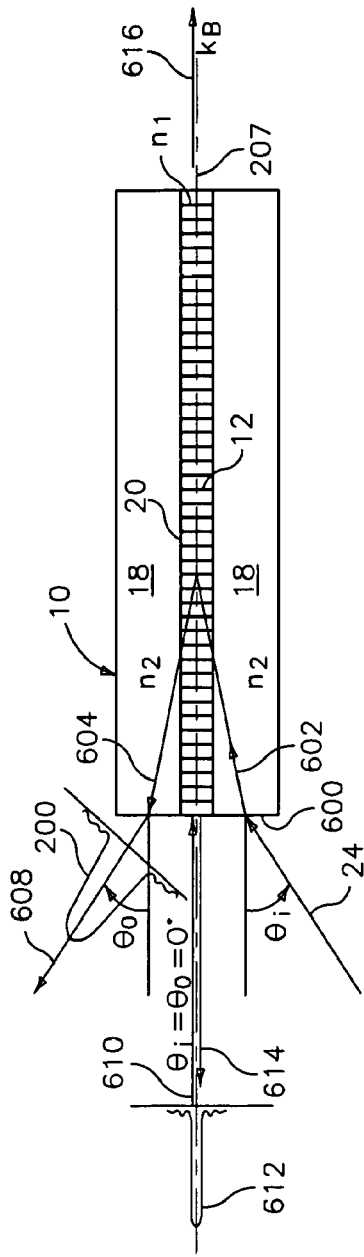
FIG. 35 is a side view of an optical identification element where light is incident on an end face, in accordance with the present invention.

Referring to FIG. 35, the input light 24 may be incident on the substrate 10 on an end face 600 of the substrate 10. In that case, the input light 24 will be incident on the grating 12 having a more significant component of the light (as compared to side illumination discussed hereinbefore) along the longitudinal grating axis 207 of the grating (along the grating vector $k_B$), as shown by a line 602. The light 602 reflects off the grating 12 as indicated by a line 604 and exits the substrate as output light 608. Accordingly, it should be understood by one skilled in the art that the diffraction equations discussed hereinbefore regarding output diffraction angle θo also apply in this case except that the reference axis would now be the grating axis 207. Thus, in this case, the input and output light angles θi,θo, would be measured from the grating axis 207 and length Lg of the grating 12 would become the thickness or depth D of the grating 12. As a result, a grating 12 that is 400 microns long, would result in the Bragg envelope 200 being narrow. It should be understood that because the values of n1 and n2 are close to the same value, the slight angle changes of the light between the regions 18,20 are not shown herein.

In the case where incident light 610 is incident along the same direction as the grating vector (Kb) 207, i.e., θi=0 degrees, the incident light sees the whole length Lg of the grating 12 and the grating provides a reflected output light angle θo=0 degrees, and the Bragg envelope 612 becomes extremely narrow, as the narrowing effect discussed above reaches a limit. In that case, the relationship between a given pitch Λ in the grating 12 and the wavelength of reflection λ is governed by a known "Bragg grating" relation:

$$\lambda = 2n_{eff}\Lambda \qquad \text{Eq. 8}$$

where $n_{eff}$ is the effective index of refraction of the substrate, λ is the input (and output wavelength) and Λ is the pitch. This relation, as is known, may be derived from Eq. 1 where θi=θo=90 degrees.

In that case, the code information is readable only in the spectral wavelength of the reflected beam, similar to that discussed hereinbefore for wavelength based code reading. Accordingly, the input signal in this case may be a scanned wavelength source or a broadband wavelength source. In addition, as discussed hereinbefore for wavelength based code reading, the code information may be obtained in reflection from the reflected beam 614 or in transmission by the transmitted beam 616 that passes through the grating 12.

It should be understood that for shapes of the substrate 10 or element 8 other than a cylinder, the effect of various different shapes on the propagation of input light through the element 8, substrate 10, and/or grating 12, and the associated reflection angles, can be determined using known optical physics including Snell's Law, shown below:

$$n_{in} \sin \theta in = n_{out} \sin \theta out \qquad \text{Eq. 9}$$

where $n_{in}$ is the refractive index of the first (input) medium, and $n_{out}$ is the refractive index of the second (output) medium, and θin and θout are measured from a line 620 normal to an incident surface 622.

Referring to FIG. 36, if the value of n1 in the grating region 20 is greater than the value of n2 in the non-grating region 18, the grating region 20 of the substrate 10 will act as a known optical waveguide for certain wavelengths. In that case, the grating region 20 acts as a "core" along which light is guided and the outer region 18 acts as a "cladding" which helps confine or guide the light. Also, such a waveguide will have a known "numerical aperture" (θna) that will allow light that is within the aperture θna to be directed or guided along the grating axis 207 and reflected axially off the grating 12 and returned and guided along the waveguide. In that case, the grating 12 will reflect light having the appropriate wavelengths equal to the pitches Λ present in the grating 12 back along the region 20 (or core) of the waveguide, and pass the remaining wavelengths of light as the light 632. Thus, having the grating region 20 act as an optical waveguide for wavelengths reflected by the grating 12 allows incident light that is not aligned exactly with the grating axis 207 to be guided along and aligned with the grating 12 axis 207 for optimal grating reflection.

If an optical waveguide is used any standard waveguide may be used, e.g., a standard telecommunication single mode optical fiber (125 micron diameter or 80 micron diameter fiber with about a 8-10 micron diameter), or a larger diameter waveguide (greater than 0.5 mm diameter), such as is describe in U.S. patent application Ser. No. 09/455,868, filed Dec. 6, 1999, entitled "Large Diameter Waveguide, Grating". Further, any type of optical waveguide may be used for the optical substrate 10, such as, a multi-mode, birefringent, polarization maintaining, polarizing, multi-core, multi-cladding, or microstructured optical waveguide, or a flat or planar waveguide (where the waveguide is rectangular shaped), or other waveguides. Any other dimensions may be used for the waveguide if desired, provided they meet the functional and performance requirements of the application taking into account the teachings herein.

Referring to FIG. 37, if the grating 12 extends across the entire dimension D of the substrate, the substrate 10 does not behave as a waveguide for the incident or reflected light and the incident light 24 will be diffracted (or reflected) as indicated by lines 642, and the codes detected as discussed hereinbefore for the end-incidence condition discussed hereinbefore with FIG. 45, and the remaining light 640 passes straight through.

Referring to FIG. 38, illustrations (a)-(c), in illustration (a), for the end illumination condition, if a blazed or angled grating is used, as discussed hereinbefore, the input light 24 is coupled out of the substrate 10 at a known angle as shown by a line 650. Referring to FIG. 38, illustration (b), alternatively, the input light 24 may be incident from the side and, if the grating 12 has the appropriate blaze angle, the reflected light will exit from the end face 652 as indicated by a line 654. Referring to FIG. 38, illustration (c), the grating 12 may have a plurality of different pitch angles 660,662, which reflect the input light 24 to different output angles as indicated by lines 664, 666. This provides another level of multiplexing (spatially) additional codes, if desired.

The grating 12 may be impressed in the substrate 10 by any technique for writing, impressed, embedded, imprinted, or otherwise forming a diffraction grating in the volume of or on a surface of a substrate 10. Examples of some known techniques are described in U.S. Pat. Nos. 4,725,110 and 4,807,950, entitled "Method for Impressing Gratings Within Fiber Optics", to Glenn et al; and U.S. Pat. No. 5,388,173, entitled "Method and Apparatus for Forming Aperiodic Gratings in Optical Fibers", to Glenn, respectively, and U.S. Pat. No. 5,367,588, entitled "Method of Fabricating Bragg Gratings Using a Silica Glass Phase Grating Mask and Mask Used by Same", to Hill, and U.S. Pat. No. 3,916,182, entitled "Periodic Dielectric Waveguide Filter", Dabby et al, and U.S. Pat. No. 3,891,302, entitled "Method of Filtering Modes in Optical Waveguides", to Dabby et al, which are all incorporated herein by reference to the extent necessary to understand the present invention.

Alternatively, instead of the grating 12 being impressed within the substrate material, the grating 12 may be partially or totally created by etching or otherwise altering the outer surface geometry of the substrate to create a corrugated or varying surface geometry of the substrate, such as is described in U.S. Pat. No. 3,891,302, entitled "Method of Filtering Modes in Optical Waveguides", to Dabby et al, which is incorporated herein by reference to the extent necessary to understand the present invention, provided the resultant optical refractive profile for the desired code is created.

Further, alternatively, the grating 12 may be made by depositing dielectric layers onto the substrate, similar to the way a known thin film filter is created, so as to create the desired resultant optical refractive profile for the desired code.

FIGS. 39-50: Alternative Microbead Geometries

The substrate 10 (and/or the element 8) may have end-view cross-sectional shapes other than circular, such as square, rectangular, elliptical, clam-shell, D-shaped, or other shapes, and may have side-view sectional shapes other than rectangular, such as circular, square, elliptical, clam-shell, D-shaped, or other shapes. Also, 3D geometries other than a cylinder may be used, such as a sphere, a cube, a pyramid or any other 3D shape. Alternatively, the substrate 10 may have a geometry that is a combination of one or more of the foregoing shapes.

The shape of the element 8 and the size of the incident beam may be made to minimize any end scatter off the end face(s) of the element 8, as is discussed herein and/or in the aforementioned patent application. Accordingly, to minimize such scatter, the incident beam 24 may be oval shaped where the narrow portion of the oval is smaller than the diameter D1, and the long portion of the oval is smaller than the length L of the element 8. Alternatively, the shape of the end faces may be rounded or other shapes or may be coated with an antireflective coating.

It should be understood that the size of any given dimension for the region 20 of the grating 12 may be less than any corresponding dimension of the substrate 10. For example, if the grating 12 has dimensions of length Lg, depth Dg, and width Wg, and the substrate 12 has different dimensions of length L, depth D, and width W, the dimensions of the grating 12 may be less than that of the substrate 12. Thus, the grating 12, may be embedded within or part of a much larger substrate 12. Also, the element 8 may be embedded or formed in or on a larger object for identification of the object.

The dimensions, geometries, materials, and material properties of the substrate 10 are selected such that the desired optical and material properties are met for a given application. The resolution and range for the optical codes are scalable by controlling these parameters as discussed herein and/or in the aforementioned patent application.

Referring to FIG. 39, the substrate 10 may have an outer coating 799, such as a polymer or other material that may be dissimilar to the material of the substrate 10, provided that the coating 799 on at least a portion of the substrate, allows sufficient light to pass through the substrate for adequate optical detection of the code. The coating 799 may be on any one or more sides of the substrate 10. Also, the coating 799 may be a material that causes the element 8 to float or sink in certain fluids (liquid and/or gas) solutions.

Also, the substrate 10 may be made of a material that is less dense than certain fluid (liquids and/or gas) solutions, thereby allowing the elements 8 to float or be buoyant or partially buoyant. Also, the substrate may be made of a porous material, such as controlled pore glass (CPG) or other porous material, which may also reduce the density of the element 8 and may make the element 8 buoyant or partially-buoyant in certain fluids.

Referring to FIG. 40, the grating 12 is axially spatially invariant. As a result, the substrate 10 with the grating 12 (shown as a long substrate 21) may be axially subdivided or cut into many separate smaller substrates 30-36 and each substrate 30-36 will contain the same code as the longer substrate 21 had before it was cut. The limit on the size of the smaller substrates 30-36 is based on design and performance factors discussed herein and/or in the aforementioned patent application.

Referring to FIG. 41, one purpose of the outer region 18 (or region without the grating 12) of the substrate 10 is to provide mechanical or structural support for the inner grating region 20. Accordingly, the entire substrate 10 may comprise the grating 12, if desired. Alternatively, the support portion may be completely or partially beneath, above, or along one or more sides of the grating region 20, such as in a planar geometry, or a D-shaped geometry, or other geometries, as described herein and/or in the aforementioned patent application. The non-grating portion 18 of the substrate 10 may be used for other purposes as well, such as optical lensing effects or other effects (discussed herein or in the aforementioned patent application). Also, the end faces of the substrate 10 need not be perpendicular to the sides or parallel to each other. However, for applications where the elements 8 are stacked end-to-end, the packing density may be optimized if the end faces are perpendicular to the sides.

Referring to FIG. 42, illustrations (a)-(c), two or more substrates 10,250, each having at least one grating therein, may be attached together to form the element 8, e.g., by an adhesive, fusing or other attachment techniques. In that case, the gratings 12,252 may have the same or different codes.

Referring to FIG. 43, illustrations (a) and (b), the substrate 10 may have multiple regions 80,90 and one or more of these regions may have gratings in them. For example, there may be gratings 12,252 side-by-side (illustration (a)), or there may be gratings 82-88, spaced end-to-end (illustration (b)) in the substrate 10.

Referring to FIG. 44, the length L of the element 8 may be shorter than its diameter D, thus, having a geometry such as a plug, puck, wafer, disc or plate.

Referring to FIG. 45 to facilitate proper alignment of the grating axis with the angle θi of the input beam 24, the substrate 10 may have a plurality of the gratings 12 having the same codes written therein at numerous different angular or rotational (or azimuthal) positions of the substrate 10. In particular, two gratings 550, 552, having axial grating axes 551, 553, respectively may have a common central (or pivot or rotational) point where the two axes 551,553 intersect. The angle θi of the incident light 24 is aligned properly with the grating 550 and is not aligned with the grating 552, such that output light 555 is reflected off the grating 550 and light 557 passes through the grating 550 as discussed herein. If the element 8 is rotated as shown by the arrows 559, the angle θi of incident light 24 will become aligned properly with the grating 552 and not aligned with the grating 550 such that output light 555 is reflected off the grating 552 and light 557 passes through the grating 552. When multiple gratings are located in this rotational orientation, the bead may be rotated as indicated by a line 559 and there may be many angular positions that will provide correct (or optimal) incident input angles θi to the grating. While this example shows a circular cross-section, this technique may be used with any shape cross-section.

Figure 46:
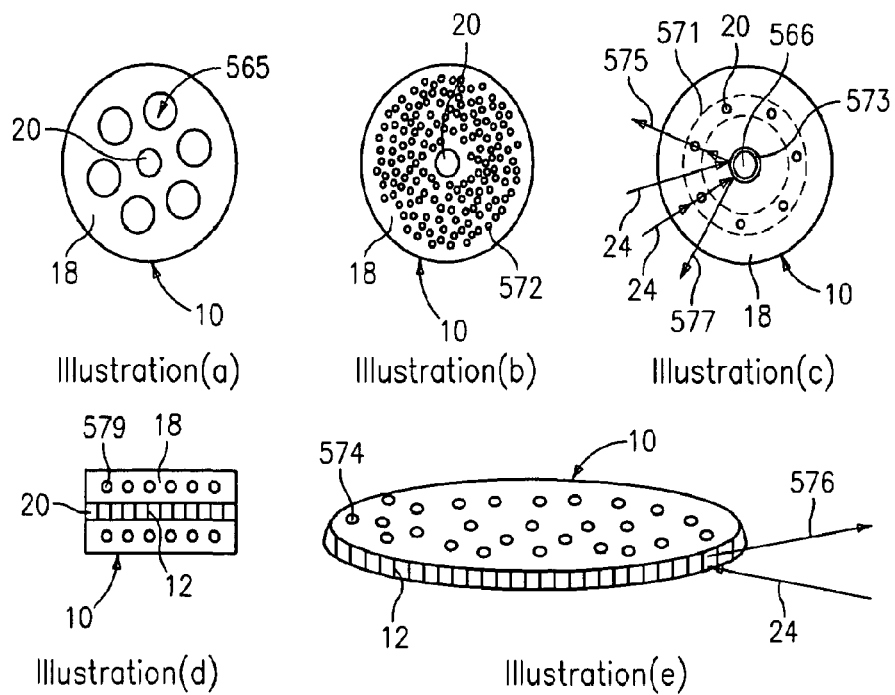
FIG. 46, illustrations (a)-(e), show various geometries of an optical identification element that may have holes therein, in accordance with the present invention.

Referring to FIG. 46, illustrations (a), (b), (c), (d), and (e) the substrate 10 may have one or more holes located within the substrate 10. In illustration (a), holes 560 may be located at various points along all or a portion of the length of the substrate 10. The holes need not pass all the way through the substrate 10. Any number, size and spacing for the holes 560 may be used if desired. In illustration (b), holes 572 may be located very close together to form a honeycomb-like area of all or a portion of the cross-section. In illustration (c), one (or more) inner hole 566 may be located in the center of the substrate 10 or anywhere inside of where the grating region(s) 20 are located. The inner hole 566 may be coated with a reflective coating 573 to reflect light to facilitate reading of one or more of the gratings 12 and/or to reflect light diffracted off one or more of the gratings 12. The incident light 24 may reflect off the grating 12 in the region 20 and then reflect off the surface 573 to provide output light 577. Alternatively, the incident light 24 may reflect off the surface 573, then reflect off the grating 12 and provide the output light 575. In that case the grating region 20 may run axially or circumferentially 571 around the substrate 10. In illustration (d), the holes 579 may be located circumferentially around the grating region 20 or transversely across the substrate 10. In illustration (e), the grating 12 may be located circumferentially around the outside of the substrate 10, and there may be holes 574 inside the substrate 10.

Figure 47:
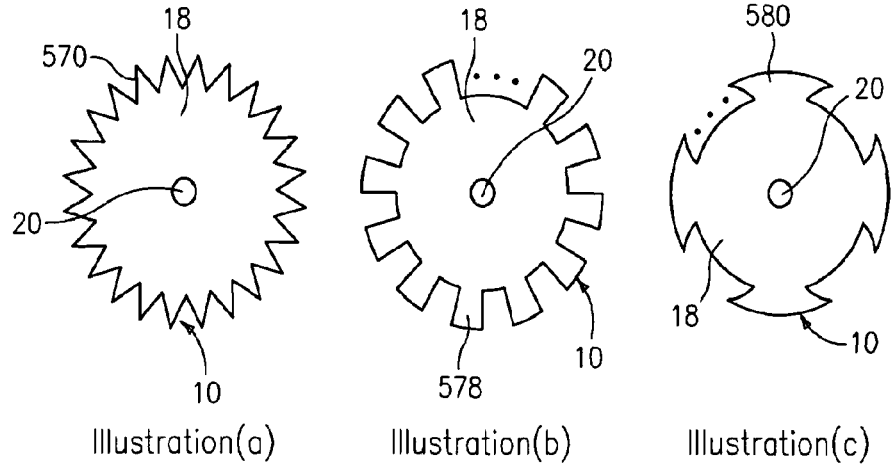
FIG. 47, illustrations (a)-(c), show various geometries of an optical identification element that may have teeth thereon, in accordance with the present invention.

Referring to FIG. 47, illustrations (a), (b), and (c), the substrate 10 may have one or more protruding portions or teeth 570, 578,580 extending radially and/or circumferentially from the substrate 10. Alternatively, the teeth 570, 578, 580 may have any other desired shape.

Figure 48:
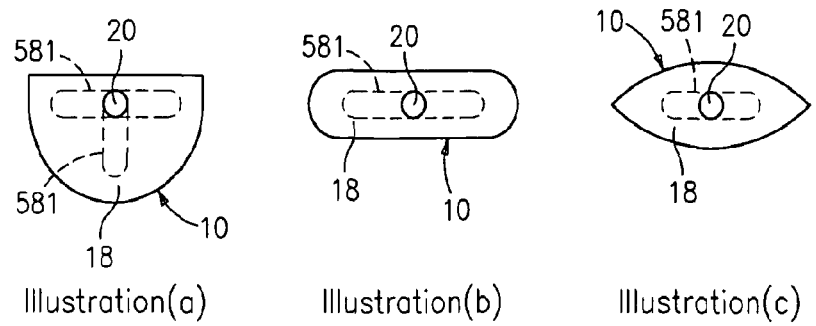
FIG. 48, illustrations (a)-(c), show various geometries of an optical identification element, in accordance with the present invention.

Referring to FIG. 48, illustrations (a), (b), (c) a D-shaped substrate, a flat-sided substrate and an eye-shaped (or clamshell or teardrop shaped) substrate 10, respectively, are shown. Also, the grating region 20 may have end cross-sectional shapes other than circular and may have side cross-sectional shapes other than rectangular, such as any of the geometries described herein for the substrate 10. For example, the grating region 20 may have a oval cross-sectional shape as shown by dashed lines 581, which may be oriented in a desired direction, consistent with the teachings herein. Any other geometries for the substrate 10 or the grating region 20 may be used if desired, as described herein.

Figure 49:
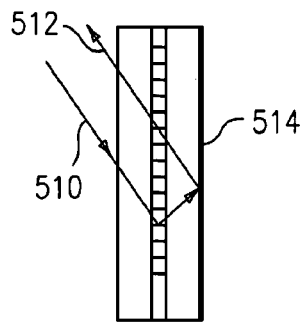
FIG. 49 is a side view an optical identification element having a reflective coating thereon, in accordance with the present invention.

Referring to FIG. 49, at least a portion of a side of the substrate 10 may be coated with a reflective coating to allow incident light 510 to be reflected back to the same side from which the incident light came, as indicated by reflected light 512.

Figure 50:
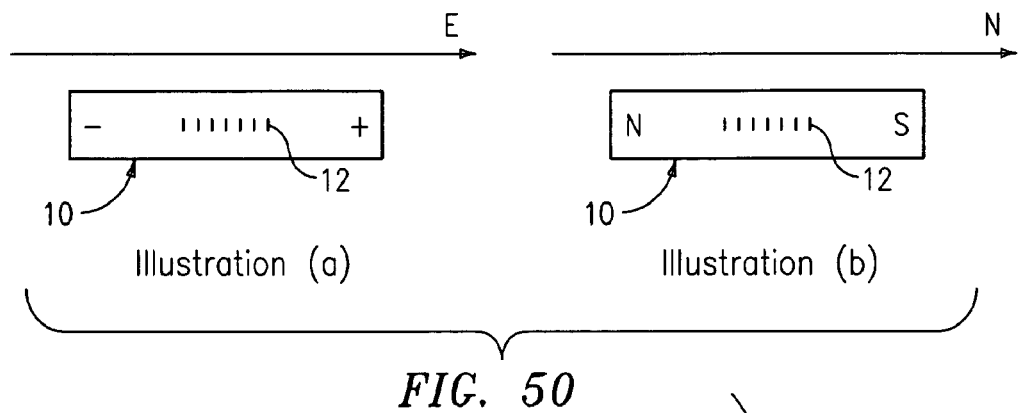
FIG. 50, illustrations (a)-(b), are side views of an optical identification element polarized along an electric or magnetic field, in accordance with the present invention.
Figure 51:
FIGS. 51 and 52 are diagrams of bead reads from flat retro-reflector trays, in accordance with the present invention.
Figure 52:
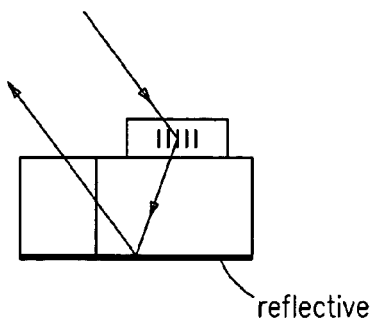
Figure 53:
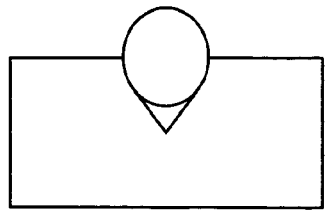
FIGS. 53 and 54 are diagrams of beads read thru V-grooves, in accordance with the present invention.
Figure 54:
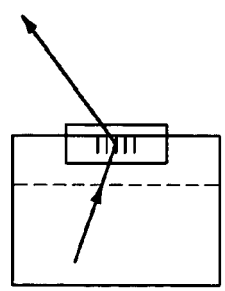

Referring to FIG. 50, illustrations (a) and (b), alternatively, the substrate 10 can be electrically and/or magnetically polarized, by a dopant or coating, which may be used to ease handling and/or alignment or orientation of the substrate 10 and/or the grating 12, or used for other purposes. Alternatively, the bead may be coated with conductive material, e.g., metal coating on the inside of a holy substrate, or metallic dopant inside the substrate. In these cases, such materials can cause the substrate 10 to align in an electric or magnetic field. Alternatively, the substrate can be doped with an element or compound that fluoresces or glows under appropriate illumination, e.g., a rare earth dopant, such as Erbium, or other rare earth dopant or fluorescent or luminescent molecule. In that case, such fluorescence or luminescence may aid in locating and/or aligning substrates.

Further Alternative Embodiments for Groove Plates and Loading/Unloading Beads

Figure 55:
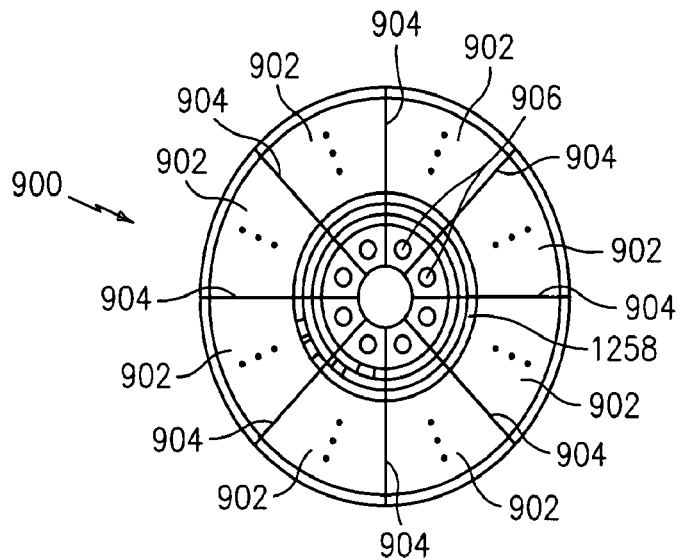
Figure 56:
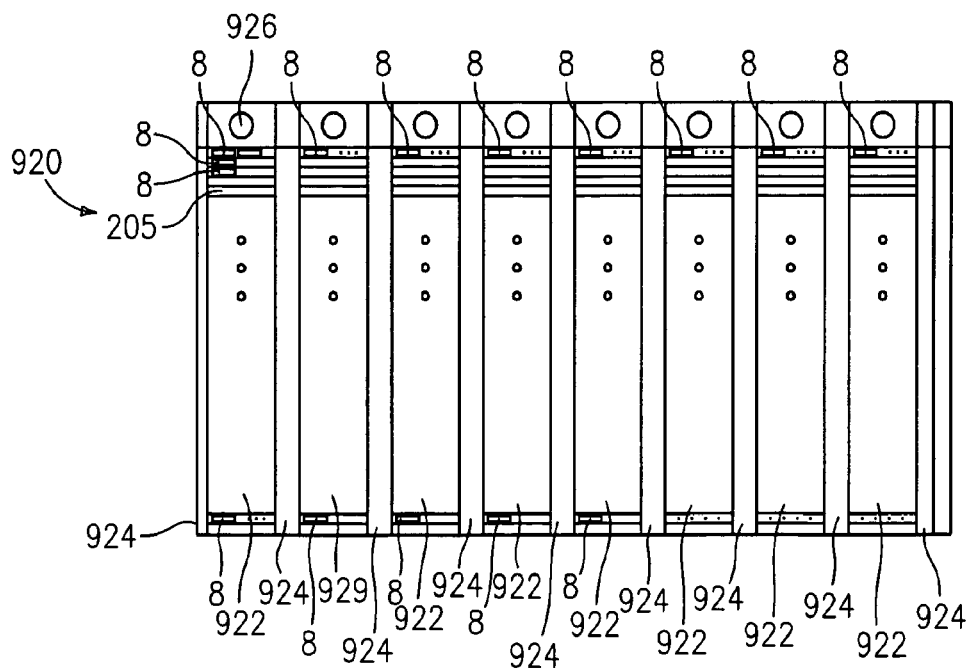

Referring to FIGS. 55 and 56, the bead cell, chamber, or cuvettes 900, 920, respectively, may be segmented into regions each associated with a different reaction or used for a different identification process/application. In particular, referring to FIG. 55, for a cell having circular grooves 1258, the cell may have a plurality of separate sections 902 which are physically separated from each other by barriers, 904. In that case, the beads may be loaded through separate holes or ports 906, which communicate only with an associated section 902. The sections 902 may be mechanically isolated, so that the beads 8 placed in a given section 902 all remain in that section, and/or fluidically isolated, so that any fluid with the beads 8 placed in a given section 902 remains in that section with no cross-over into any other section 902.

Further, referring to FIG. 56, for a cell having straight grooves 205, the cell 940 may have a plurality of separate sections 942 which are physically separated from each other by barriers, 944. In that case, the beads may be loaded through separate holes or ports 946, which communicate only with an associated section 942. The sections 942 may be mechanically isolated, so that the beads 8 placed in a given section 942 all remain in that section, and/or fluidically isolated, so that any fluid with the beads 8 placed in a given section 942 remains in that section with no cross-over into any other section 942.

Figure 57:
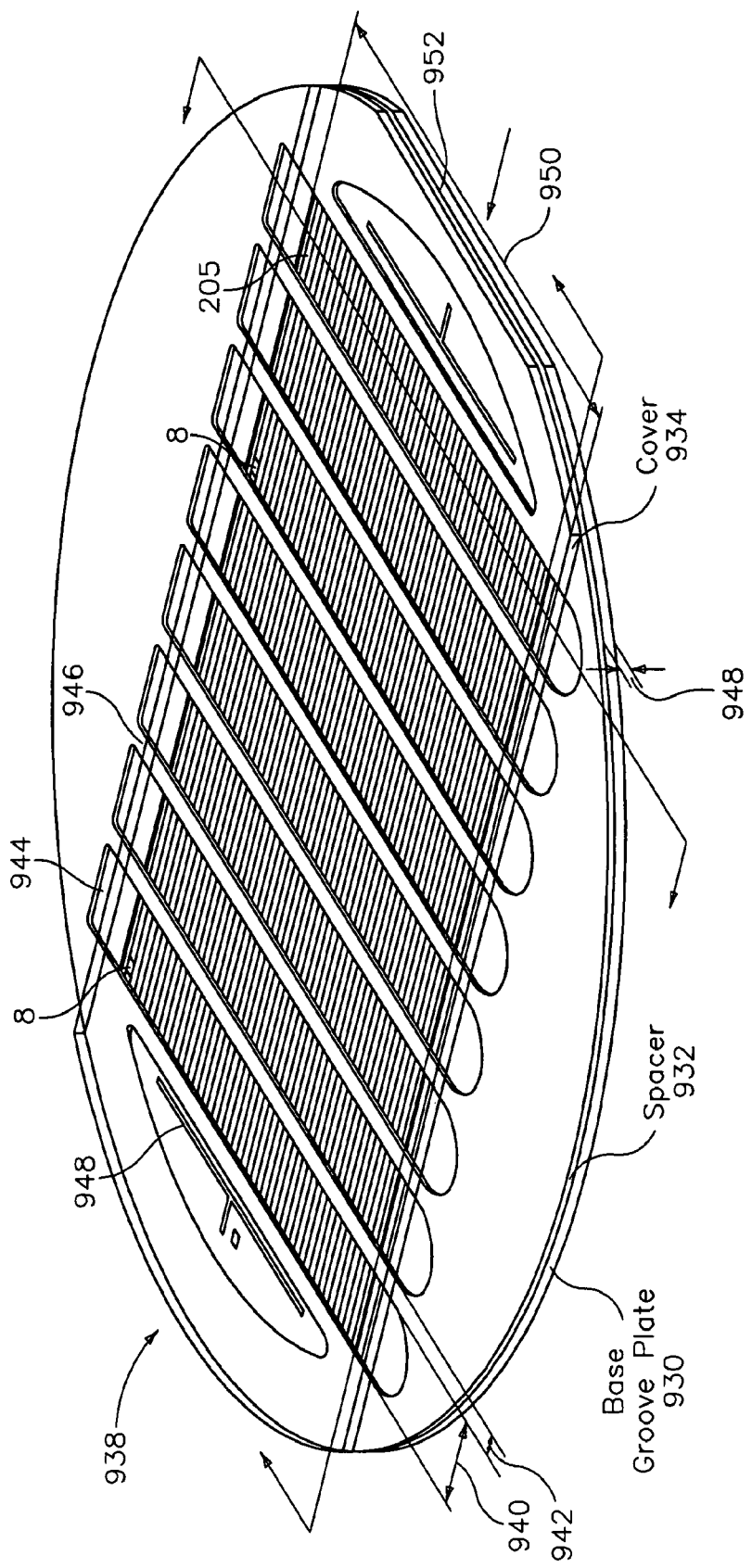

Referring to FIG. 57, one example of a sectored cell 920 with straight grooves 205 has a base groove plate 930, a spacer 932, and a cover 934. The groove plate may be made of fused silica, borosilicate glass, or plastic, acrylic, Zeonex made by Zeon Corp. or any other support material that is transparent or substantially transparent to desired incident wavelength light or can be made of reflective by coating a transparent material or using a reflective material, such as silicon or other support material that reflects the desired wavelengths of incident light. Also, the groove plate 930 may be made of a material that has minimal fluorescence to minimize background fluorescence in the desired fluorescence wavelength range, for applications where fluorescence of the beads 8 is measured.

The base plate 930 has a substantially circular shape having a diameter of about 100 mm, with a mechanical alignment key or notch 952 about 32.5 mm long, which may be used for mechanical alignment during wafer fabrication of the groove plate 930. The thickness 948 is about 1 mm. The base plate 930 has the grooves 205 therein, which may be formed by direct reactive ion etching (REI) of the glass base plate 930, photo-patterning with photoresist, photoresist and plating process, or any other process that provides the grooves 205 that meet the requirements for the application. The sectors 944 have a length 950 of about 50 mm. Also, one or more reference lines 948 (or fiducials) may be provided for reader head alignment with the grooves 205. The length 940 of each grooved section or sector 944 is about 7 mm and the space 946 between each section 944 is about 2 mm. The grooves 205 are about 34 microns by 24 microns deep and have about a 55 micron pitch spacing. For a 7 mm long groove, each groove 205 would hold about 28 cylindrically shaped beads 8 each bead 8 having a dimension of about 30 microns in diameter and 250 microns in length. The sectors 944 having a length of about 50 mm, may have about 900 grooves and hold a total capacity about 25,200 beads 8. While the number of physically separated sectors 944 in the cell 938 shown is eight, any number of sectors may be used if desired.

Figure 58:
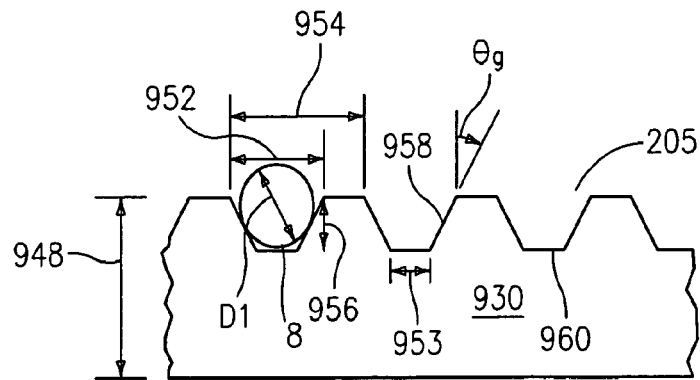
Figure 59:
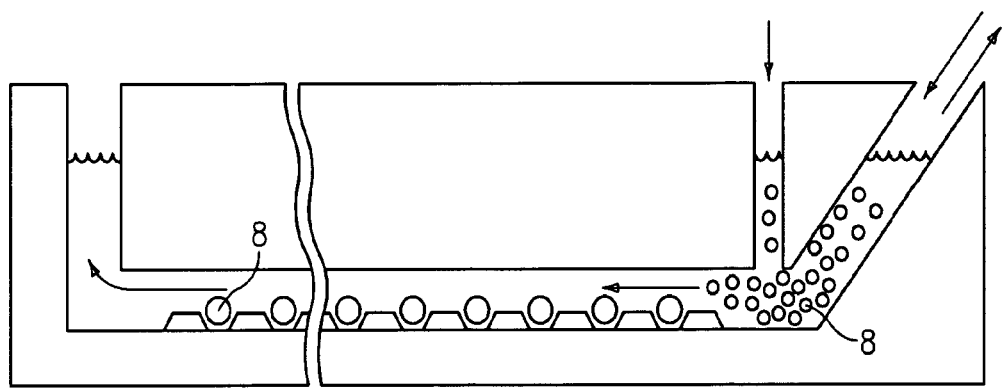
Figure 60A:
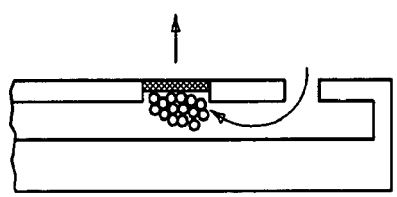
Figure 60B:
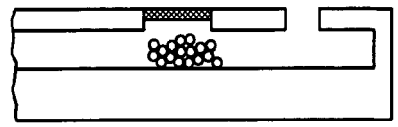
Figure 61A:
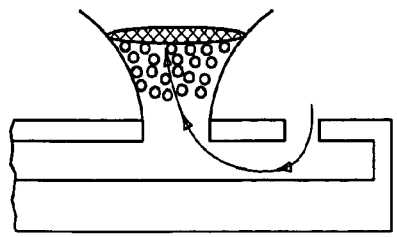
Figure 61B:
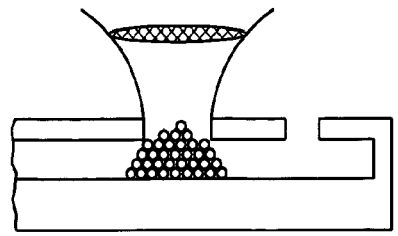

Referring to FIG. 58, the grooves 205 have a depth of about 22 to 24 microns, and have a top width of about 34 microns, and a base width 953 of about 30 microns for θg=5 deg., and a spacing pitch of about 55 microns, for a bead 8 having a diameter D1 of about 28 microns. The side walls 958 may have an angle θg of about 0 to 10 degrees. Other angles may be used, depending on the application, e.g., whether the beads will be removed from the plate and how they will be removed.

For example, referring to FIG. 58, with the angle θg is between 0 and about 10 degrees the beads may be flushed or washed out of the grooves 205 with fluid flow transversely across the top of the grooves 205, using a fluid flow rate of about 3 to 6 ml/second cleans out the beads. The flush may be done with dionized water, regular water, saline, detergent with water, or other liquid. Using a detergent reduces the viscosity and surface tension so beads do not stick to the surface of the cell. The angle θg may be greater than 10 degrees if desired, depending on certain design parameters, including, flush flow rate, groove-to-groove separation, and groove depth. Alternatively, if the angle θg is less than 0 deg., the beads will be more likely to stay in the grooves 205.

Other dimensions and geometries for the groove plate 930, grooves 205, spacer 932, and cover 934 and/or for any features or characteristics thereof may be used if desired.

Loading/Moving Beads Using Pressure Wave/Vibrations

The present invention, which is predicated on two observations, eliminates the need for mechanically distributing beads. The first observation is that small particles are easily moved by a fluid stream, and the orientation of cylindrical particles is generally with the long axis of the particle perpendicular to the direction of the flow. And the second is that particles in a liquid can be moved in a particular direction by a temporally asymmetric oscillatory flow. Regarding the later, it was observed that when an oscillatory flow was used in a closed fluidic cell containing cylindrical glass particles, whereby the rate of the outgoing wave was higher than the return wave, the particles would acquire a net displacement in the direction of the outgoing wave. When the flow rates were reversed, i.e. when the outgoing wave was slower than the return wave, the particles moved inward. Again it was observed that the particles would tend to orient perpendicular to the direction of the pressure wave.

This behavior was first observed using a closed fluidic cell in the shape of a round disk with a floor and ceiling spaced by approximately 500 micron. The cell was entirely closed except for a hole in the center of the top, which allowed the particles (400×40 um cylindrical glass "beads") to be inserted into the center of the cell. An asymmetric flow was established by tapping the bottom of the cell with a blunt object. A time sequence is shown FIG. 1(a-f), illustrating how the particles form a ring shaped pattern and how the size of the ring increased, indicating that the particles were moving outward, after a series of pulses were applied in one direction. FIG. 1(g-l), illustrate how the size of the ring decreased after the direction of the pulses was reversed. In subsequent experiments, oscillatory flow was established by coupling fluid through the open port in the top of the cell. The general behavior of the cell was the same in either case. By applying rapid pressure pulses, coupled through a flexible tube inserted into the center hole, and allowing the waves to slowly return, beads were made to move outward, thereby forming the familiar circular shape. The radius of the circle depended on such things as: the number of pulses, the amplitude of the pulses, the separation between the floor and the ceiling, the size of the beads and the geometry of the cell. An important feature of the cell was an air buffer around the perimeter of the cell to allow the fluid a place to move, since the fluid itself is non-compressible, the air gap acted as a pneumatic spring. Another important feature was the space between the floor and ceiling. It was important to maintain a small gap (<500 um) between the floor and the ceiling to keep the velocity of the fluid in the cell high enough to move the particles.

Other experiments relating to the general behavior of fluidic-induced particle movement include placing cylindrical beads on the bottom of a an open vessel such as a beaker, then moving the beads by introducing the tip of a syringe into the pile of beads and blowing the liquid out through the tip. In this experiment, the beads all moved radially away from the tip, leaving behind a region void of all beads. Again, it was observed that the beads tended to generally align parallel to the wave front. FIG. 11 shows a schematic of a concept that uses two such flow-generating tips. The flow from the tips can be operated such that they oppose each other, thus acting to push the beads into the region half way between the tips. Or they can be operated in a push-pull fashion whereby the beads tend to move toward one tip or the other. A synthetic circular force field can be generated by rotating the plate while operating the tips in either of the previously mentioned methods.

Figure 70:
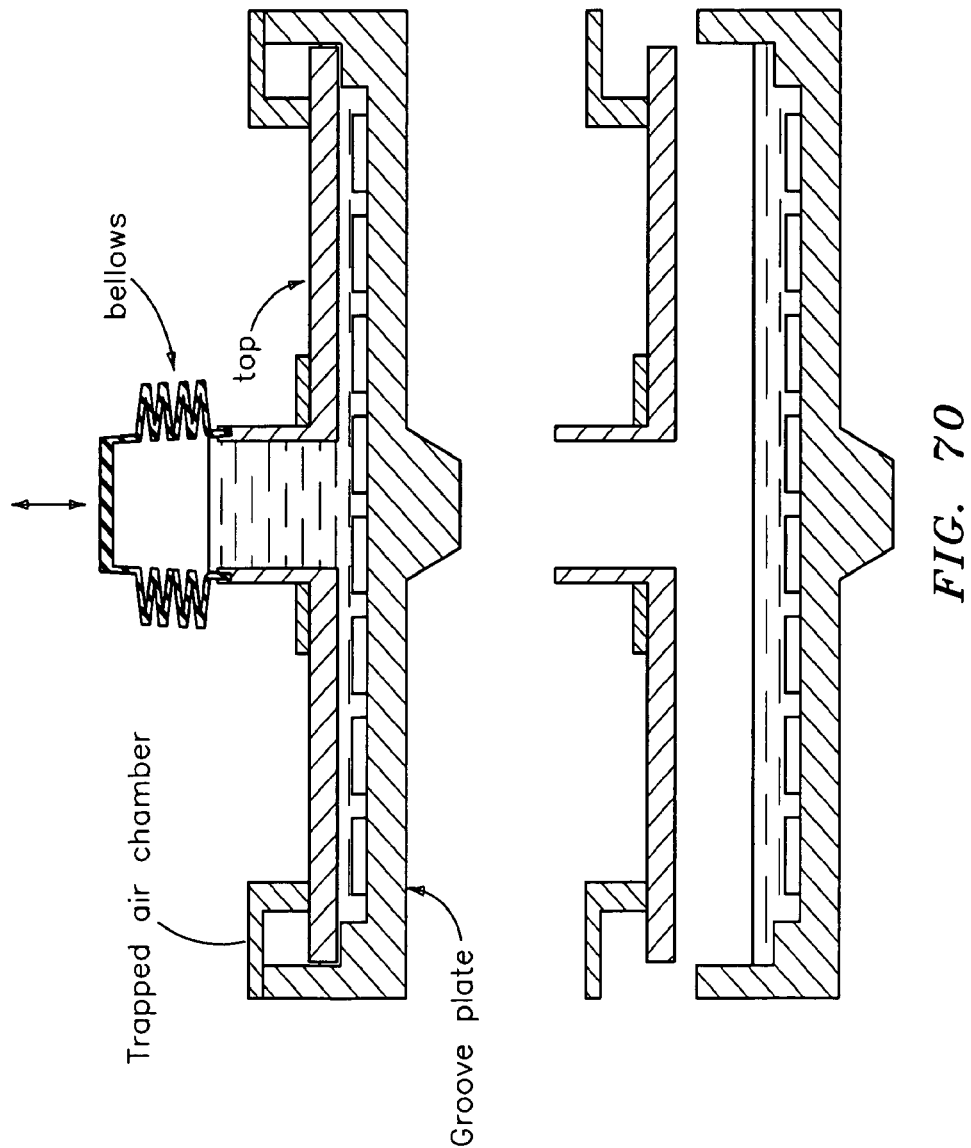
Figure 71:
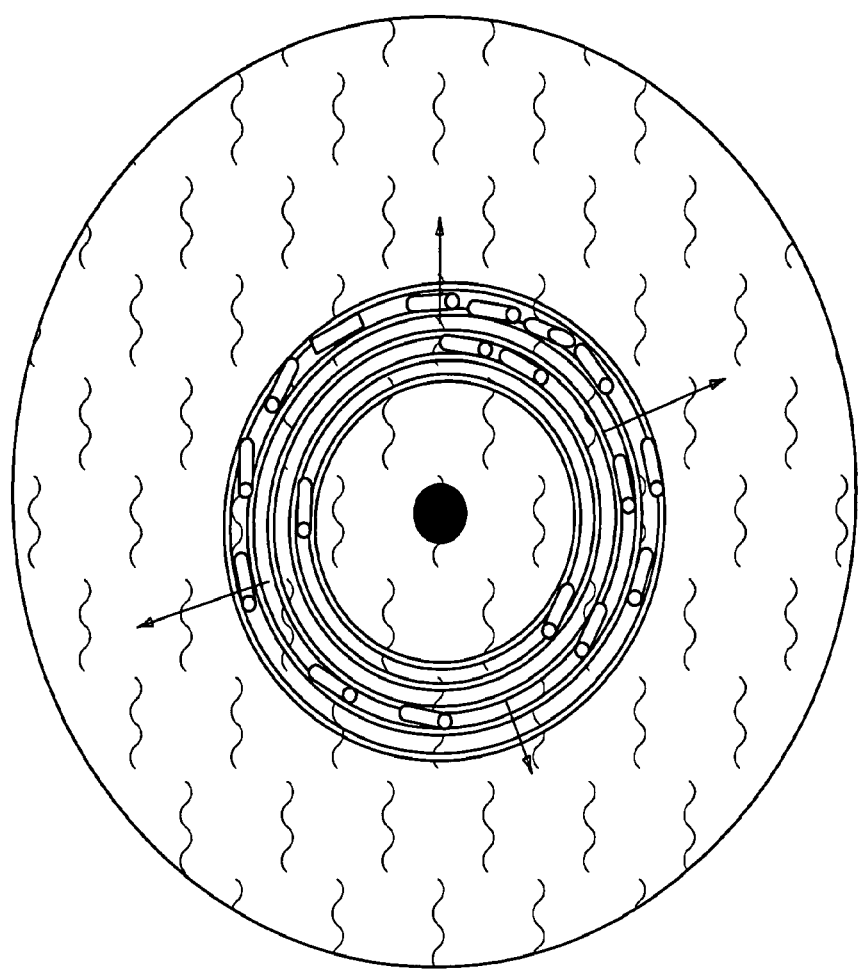
Figure 72:
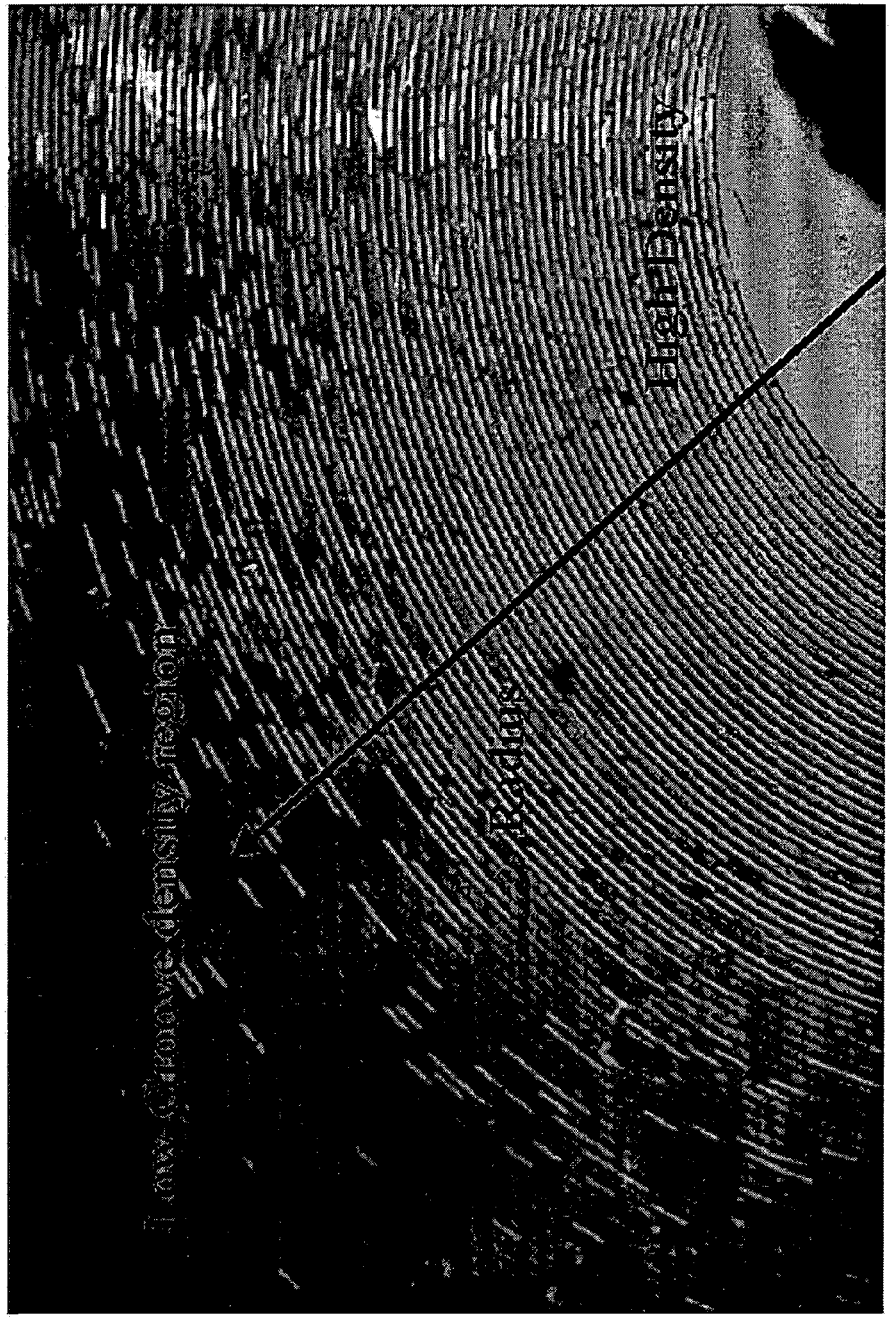
Figure 75:
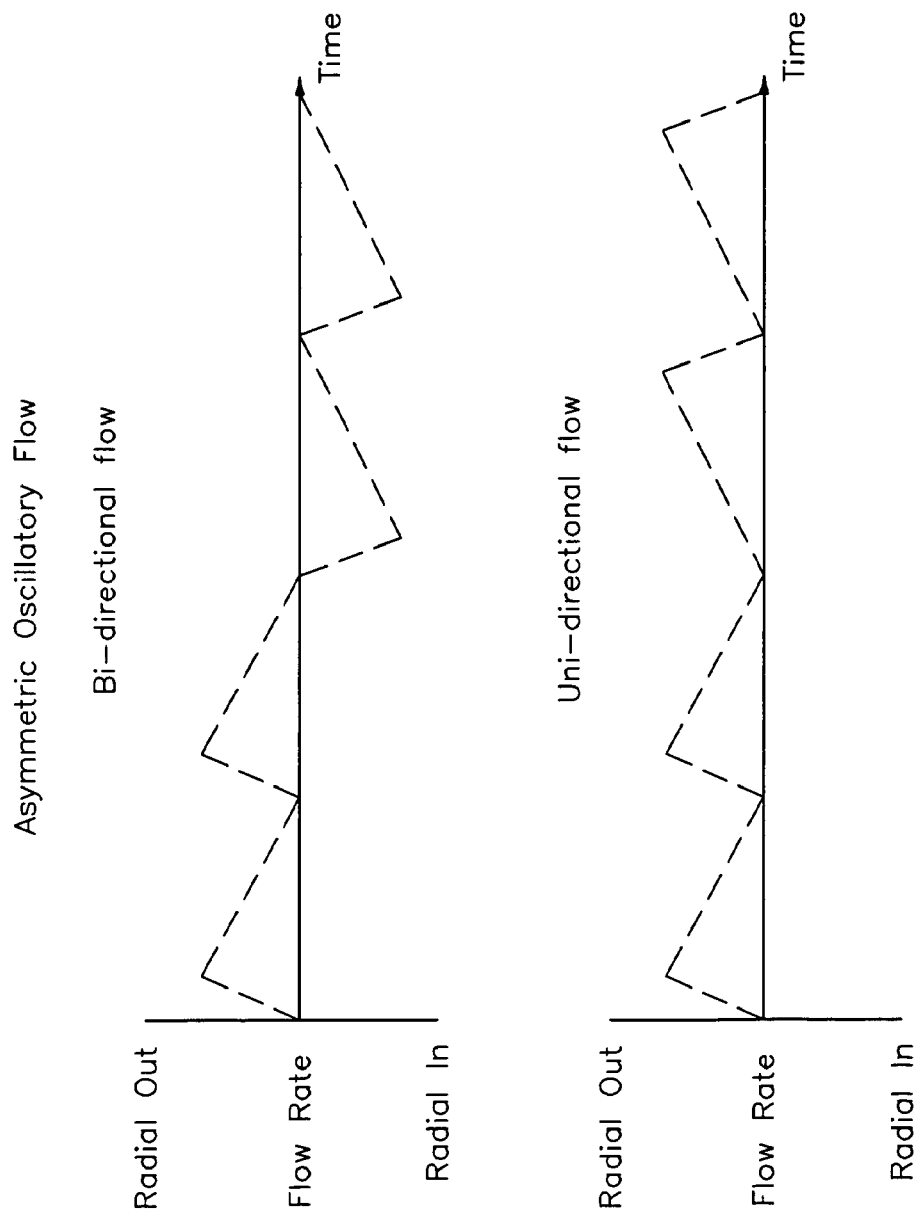

An of the invention involves combining the ability to transport beads across the floor of a substrate using either continuous fluid flow or a type of asymmetric oscillatory flow, with the technology for trapping beads, such as the previously described groove plate. This would enable a highly efficient assembly of beads with precise orientations in the smallest possible area. With respect to reduced operating cost and high throughput, all three of these attributes are important elements of a commercial encoded particle reader. FIG. 70 shows a schematic of a concept that incorporates a closed liquid cell and the elements required to load the cell efficiently. Key elements of the method include: a closed cell including a top and a bottom, the bottom contains a plate with grooves for aligning beads, both the top and the bottom are transparent, the top has an opening in the center for loading beads and for coupling a pressure generating device such as a bellows or a tube, and finally a region of trapped air around the perimeter adjacent to and in contact with the fluid in the cell. The loading operation consists of: filling the cell with a liquid such as water, spinning the cell to remove the air bubbles, dispensing beads through the center hole in the lid, applying a pulsating flow such that the rate of the outward going pulse is higher the return pulse. This will tend to move the pile of beads away from the center of the cell. As the beads move outward they populate the grooves. The direction of the pulsation can be reversed to move the pile of beads back toward the center to enhance the probability that the grooves are fully populated before allowing beads to move out to a larger radius. By moving the beads in and out it should be possible to fully populate the inner most grooves, thus maximizing the overall loading density. It may further be desirable to include an azimuthal (or circumferential) agitation or vibration to stimulate the beads to move along the channels of the grooves once they have fallen in, thereby enhancing the probability that an open space is created to allow room for additional beads to fall into the groove.

Figure 77:
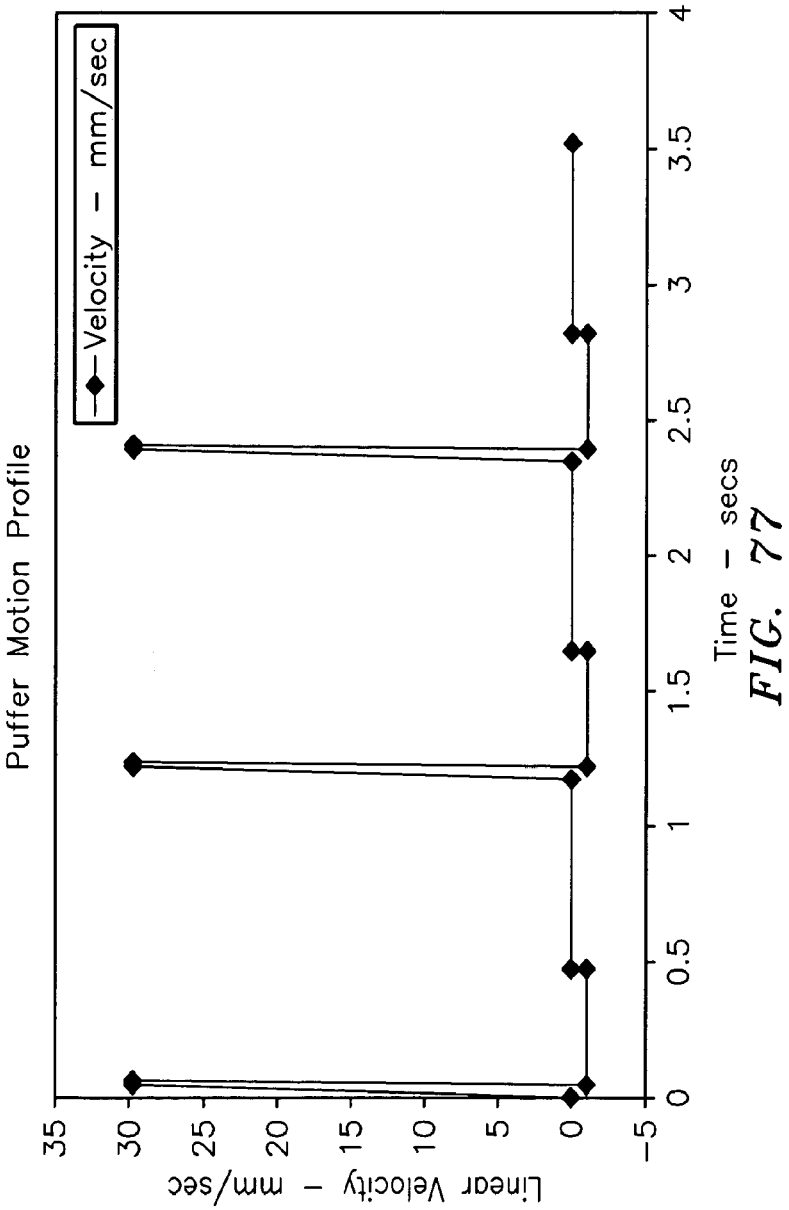
Figure 78:
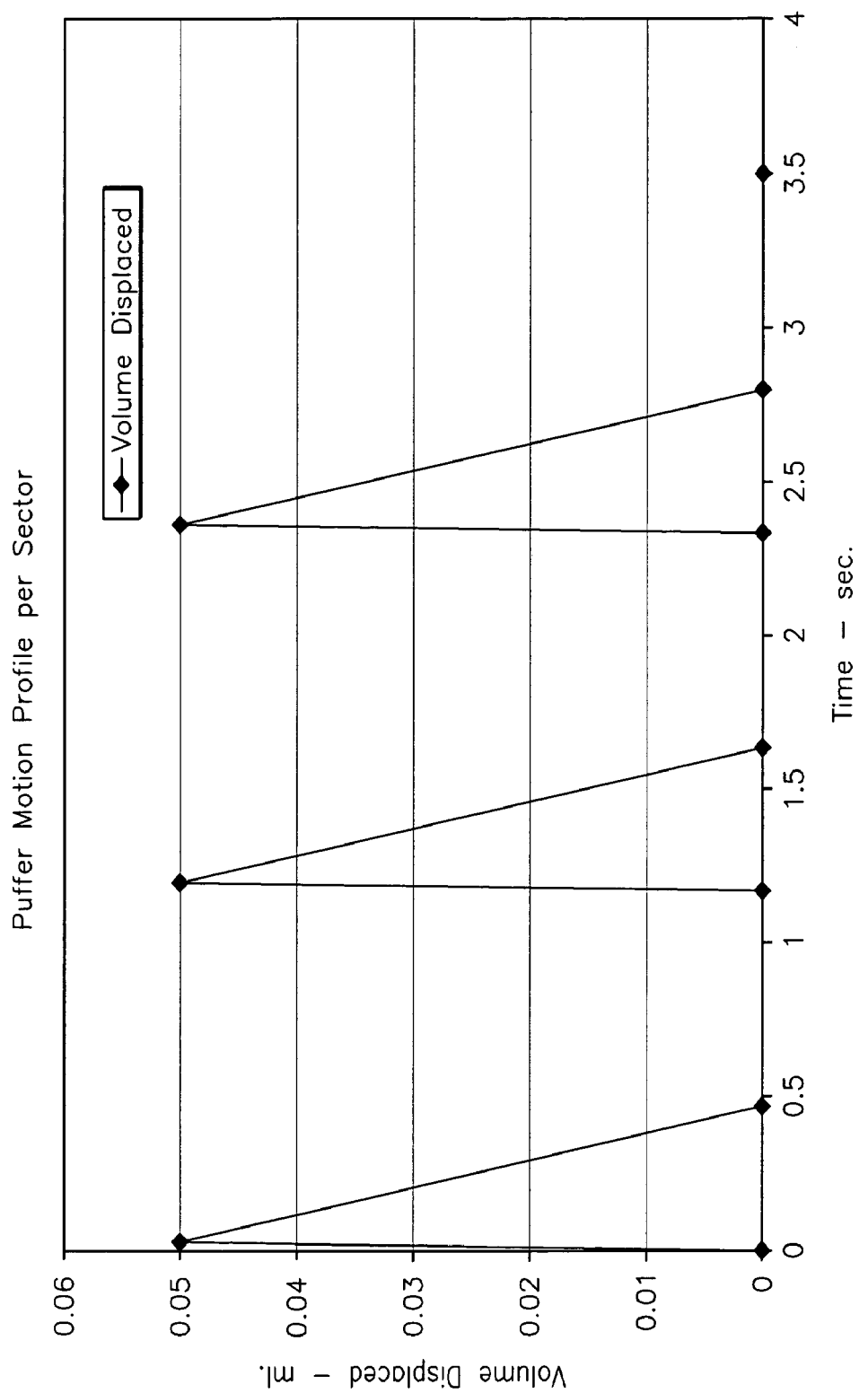
Figure 79:
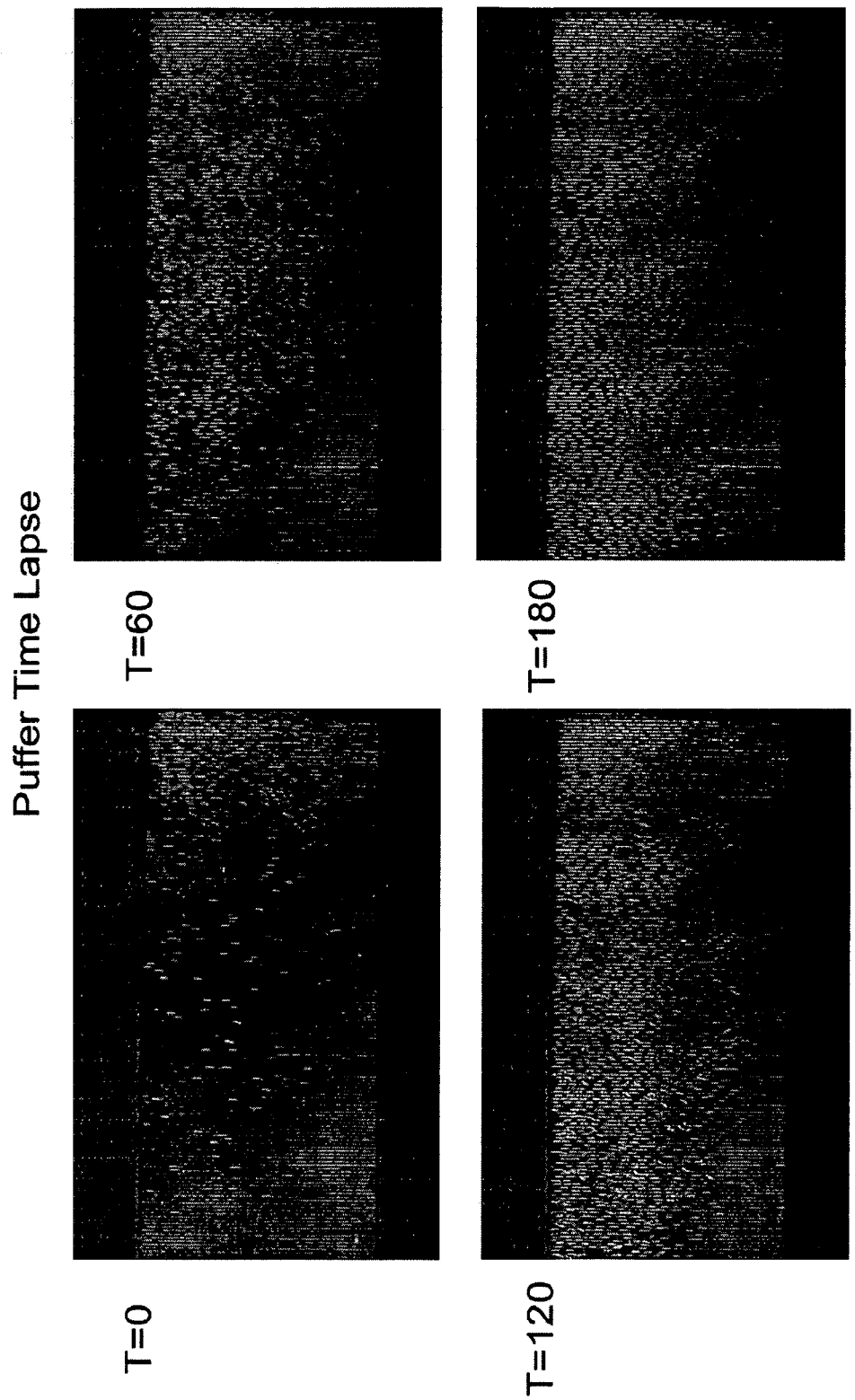

Also see FIGS. 77-79 for "puffing" (pressure pulses) done with straight grooves with the actuator on one end.

Unloading Beads

Figure 80:
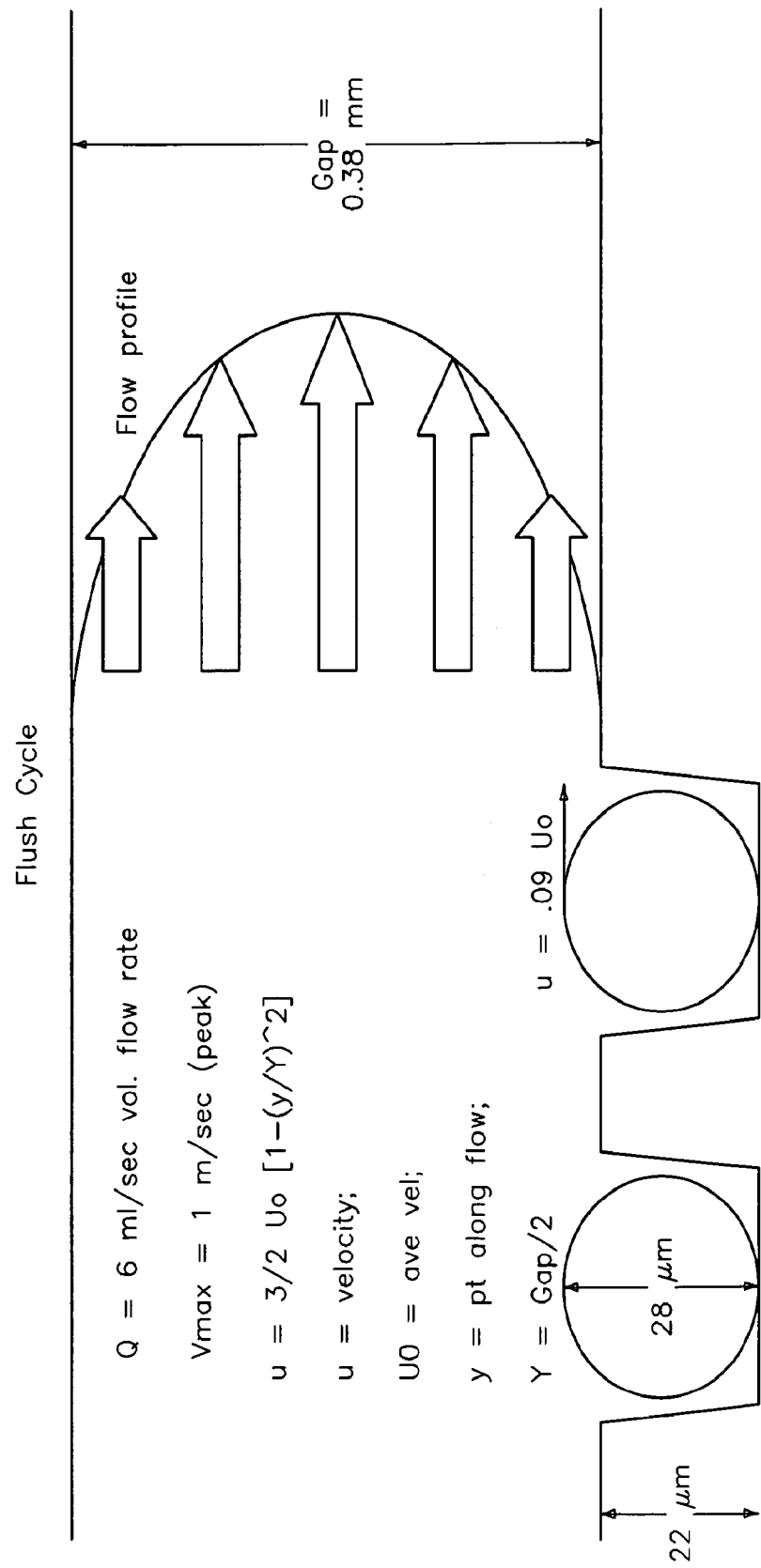
Figure 82:
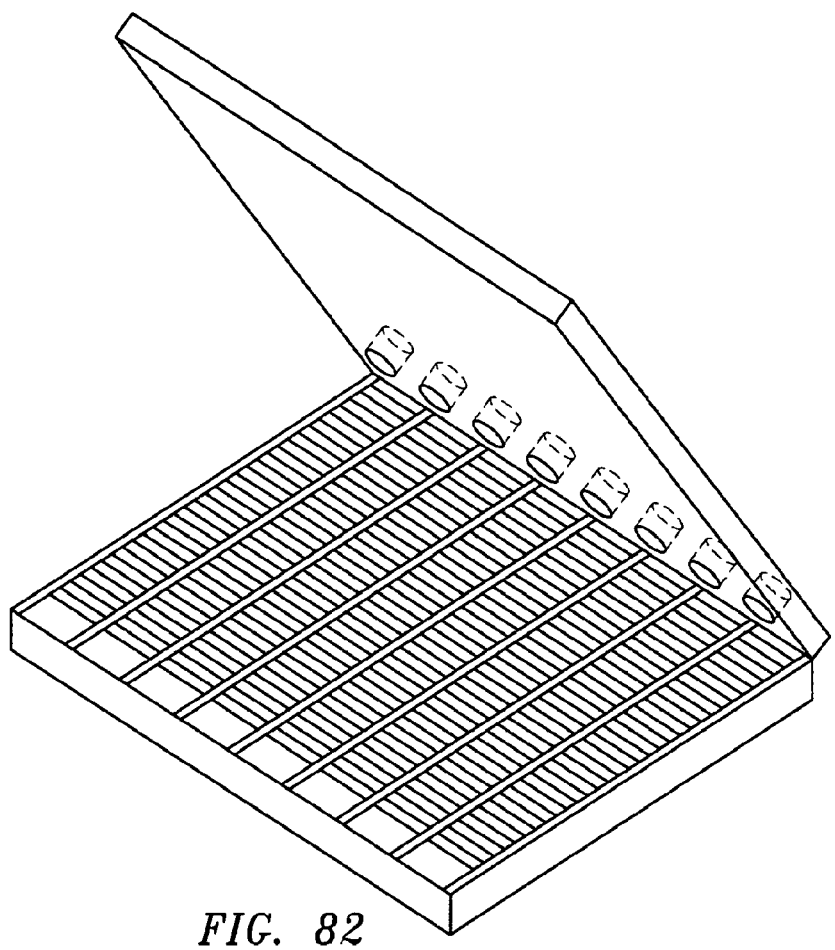
Figure 83:
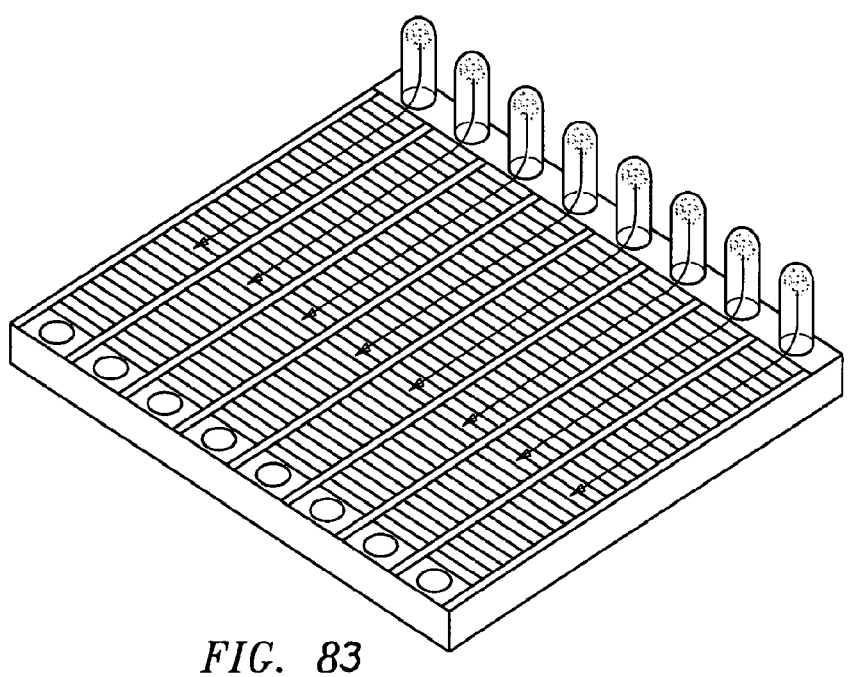
Figure 84:
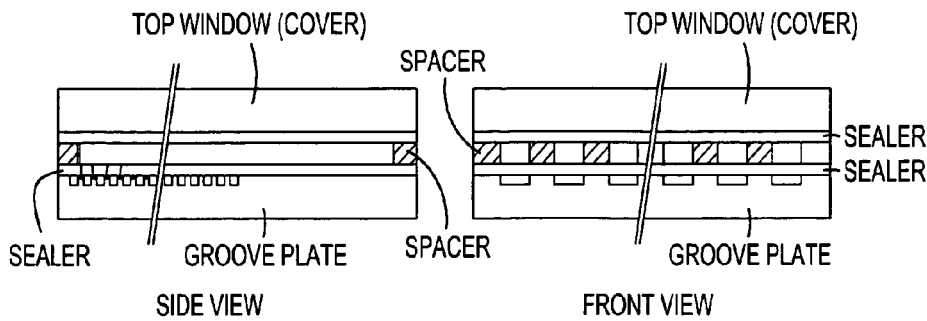
Figure 85:
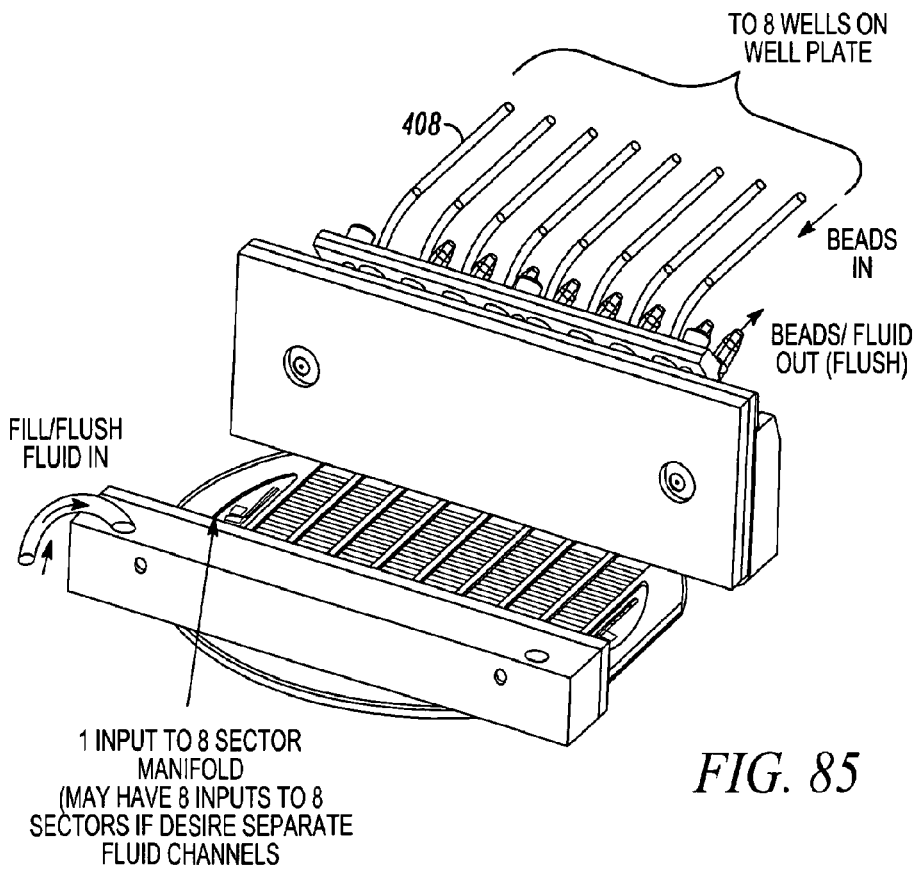

Referring to FIG. 80-81, the beads may be unloaded by flushing with fluid as shown and discussed herein before.

Cylindrical Groove Platform

Figure 62:
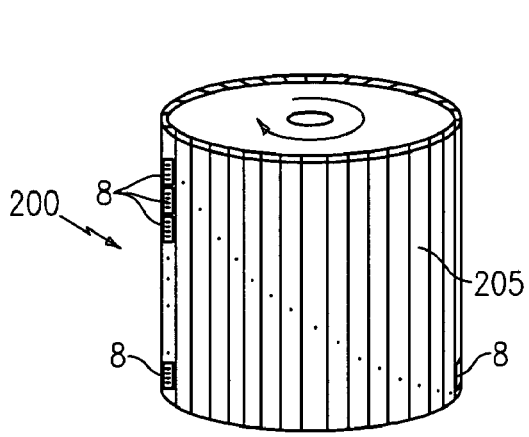
Figure 63:
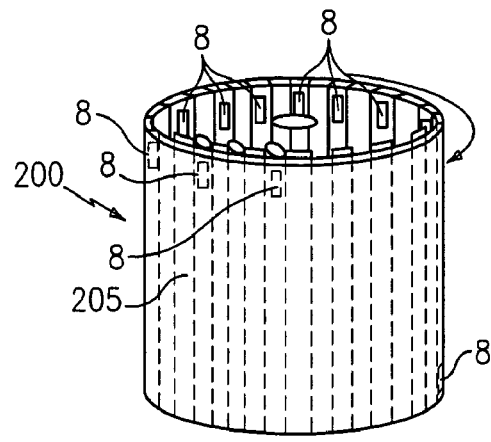
Figure 64:
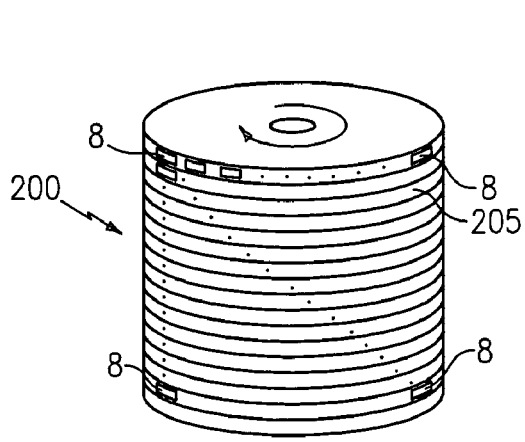
Figure 65:
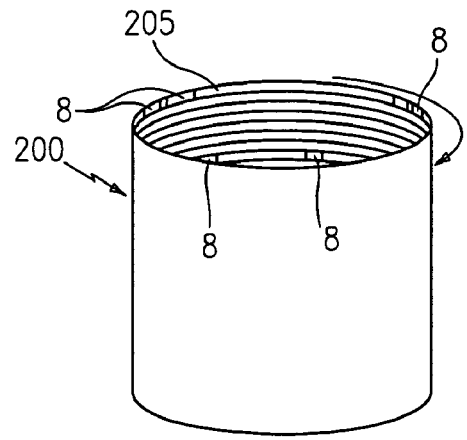
Figure 66:
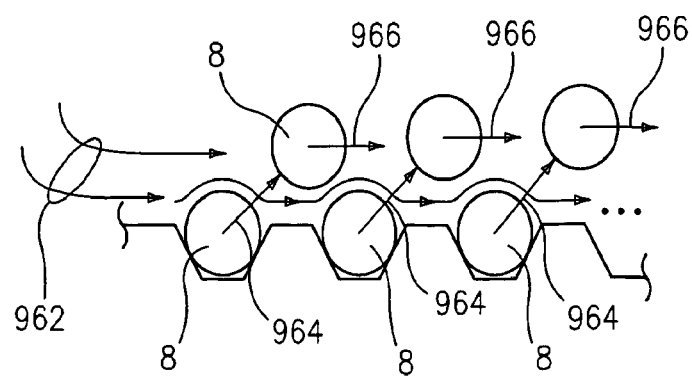
Figure 67:
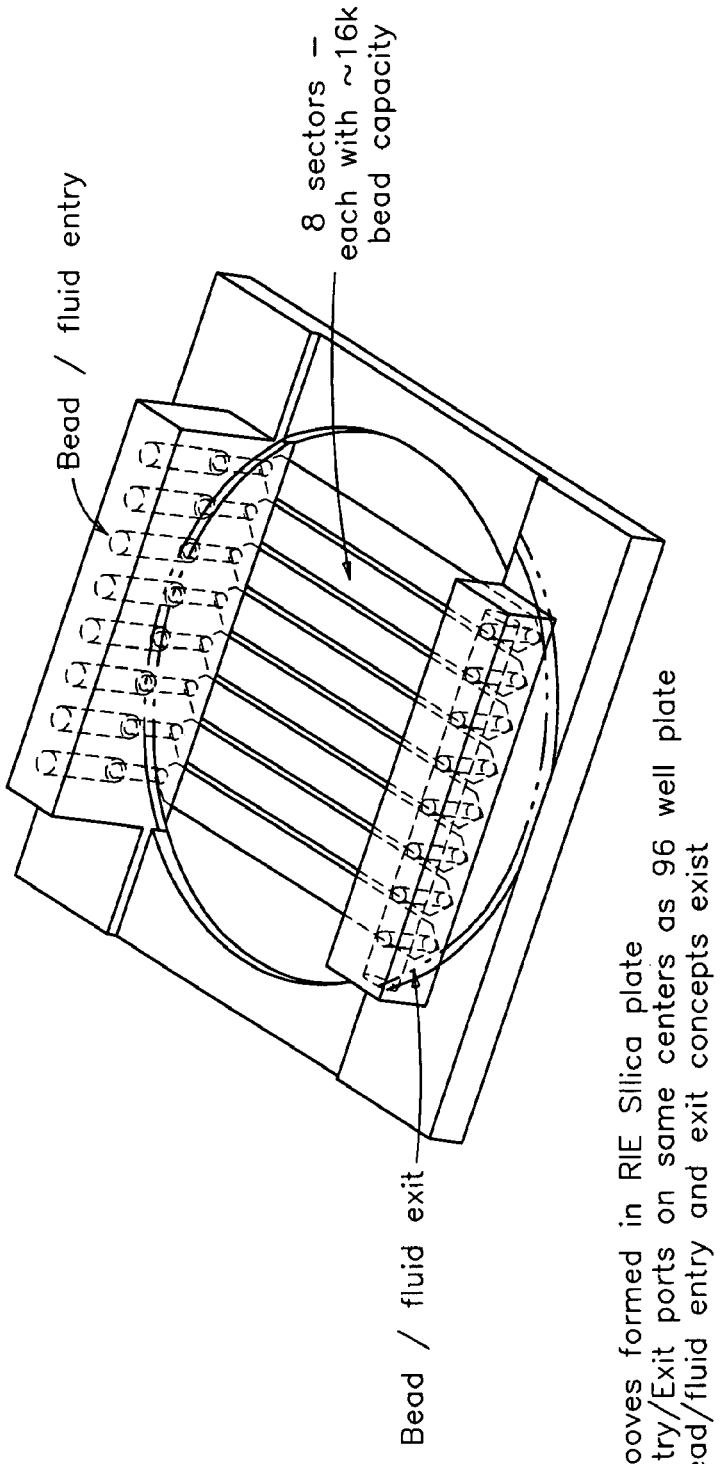
Figure 68:
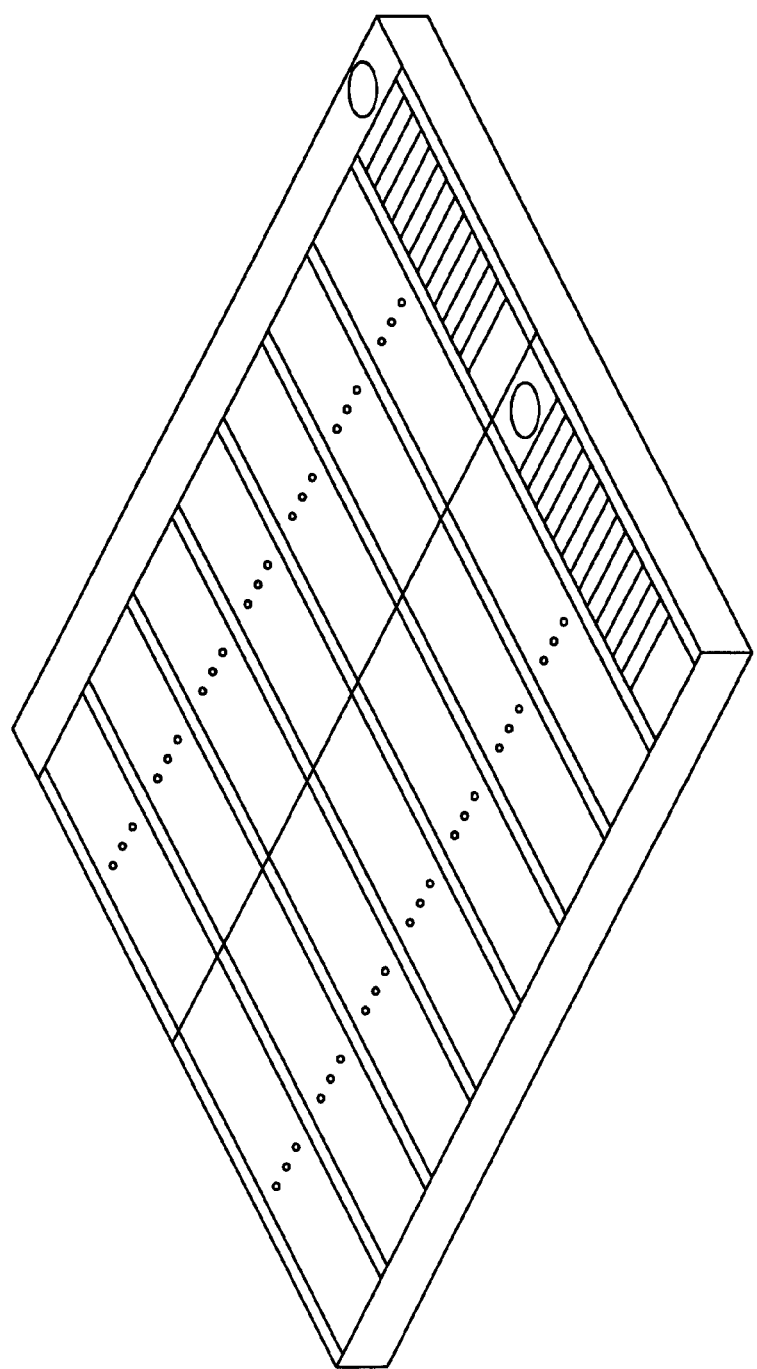
Figure 69:
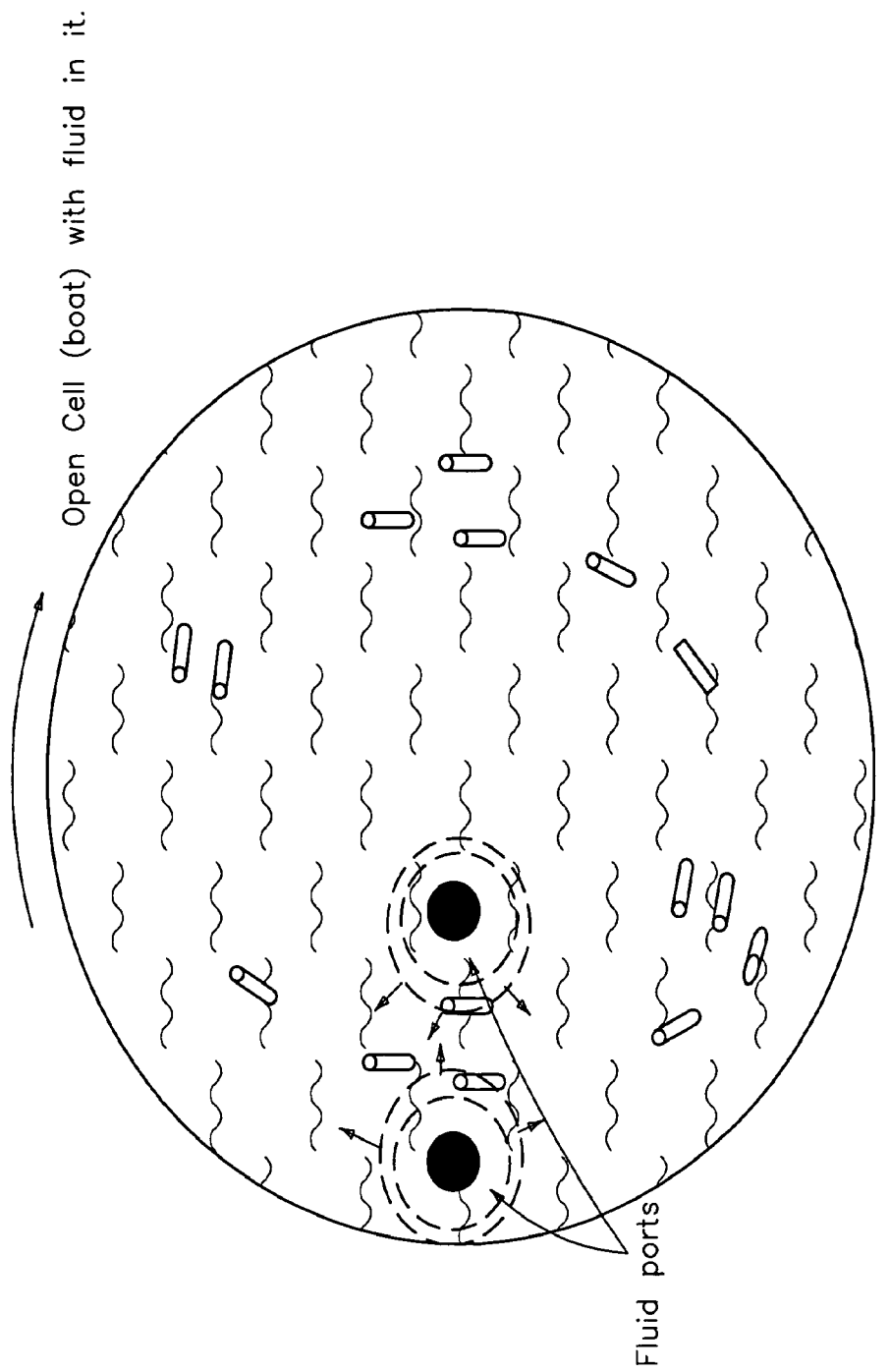

Alternatively, referring to FIGS. 62-65, the groove plate may be cylindrical shaped. In that case, the grooves 205 may run along the longitudinal axis as shown in FIGS. 62,63 or circumferentially as shown in FIGS. 64,65. The grooves 205 may be oriented in any other direction along the cylindrical groove if desired. Also, the grooves 205 may be located on the outside of the cylinder as shown in FIGS. 62,64. Alternatively, the grooves 205 may be located on the inside of the cylinder as shown in FIGS. 63,65. When the grooves 205 are located on the inside, the cylinder may be spun about the longitudinal axis to locate the beads 8 within the grooves 205. The orientation of the longitudinal axis of the cylinder may be such that the longitudinal axis is vertical or horizontal or at any other desired angle.

Referring to FIG. 89, an apparatus for transporting microbeads for the present invention includes a container or well 400 with a sealed lid 410 having microbeads 8 and liquid 412 therein and a second container 402 having a sealed lid 411 with liquid 412 therein. Two tubes 406,408 penetrate the lid 410, the first tube 406 connects the first container 400 to a pump 416 and the second tube 408 connects the first container to the second container 402 for receiving the beads from the first container 200. The first container 400 is filled with a liquid 412, and one end or tip 414 of the first tube 406 is in the liquid 412 a predetermined distance into the container 400, e.g., 20% to 50% of the full depth of the container. A tip 409 of the tube 408 is mounted substantially flush with the bottom surface of the lid 410. The pump 416 pumps liquid 412 from a reservoir 405 into the tube 406 to the first container 400. When the pump 416 pumps the liquid 412 into the container 400, the beads 8 are agitated as indicated by the lines 418. The liquid 412 and the beads 8 exit the container 400 through the tube 408 as indicated by a line 420 and are emptied into the container 402. The liquid 412 enters the container 402 and exits the container 402 through a filter 424 then through a tube 428, as indicated by a line 426. The filter 424 prevents the beads 8 from exiting the container 402. The liquid 412 that exits the container 402 is dispensed via the tube 428 into a waste pan or container 430.

Instead of the pump 416 being connected to the tube 406, a vacuum pump 432 may draw a vacuum on the tube 428. In that case the tube 406 would be open ended. We have found that this technique transports all the beads 8 from the container 400 to the second container 402.

The tip 409 of the tube 408 may be placed further into the container (i.e., not flush with inner surface of the lid 410), if desired. In that case, some air may be pumped along the tube 408 with the liquid and the beads 8. If air exists at the top of the container 400, the beads 8 may stick to the wall or inner surface of the lid 410 and not be transported to the other container 402.

Referring to FIG. 90, instead of the second container 402 being a sealed container, it may be an open container. In that case, the container 402 should have sufficient volume to receive the fluid from the pump 416.

Referring to FIGS. 90 and 91, instead of having the filter 424 on the exit port of the sealed container 402, the container may have a volume that is large enough such that when the beads 8 enter from the tube 408, they stay substantially near the bottom of the container 402 and do not get sucked out of the tube 428 to the waste container 430. This technique for transporting the beads 8 may be referred to as the "telegraph" technique.

The seal between the lids 410,411 and the containers 400, 402, may be any type of seal that retains the liquid inside the container, e.g., a radial seal/inner surface seal on the inside wall of the container, a top surface/axial seal to the top surface of the container, or any other seal that will perform the function required.

We have found that a flow rate of 1.0 to 2.0 ml/sec., with a tube inner diameter of 0.031 to 0.063 inches, and a total transport time of about 0.73 seconds will transport all the beads from a well of a 96 well plate to a bead reader cell, such as that described in copending U.S. patent application, Ser. No. 60/609,583. In that case, the first container 400 would be an individual well in the well plate, and the second container 402 would be the reader cell.

Also, this can be automated such that the lid 410 is a probe head which comes down on top of the well to create a seal on the well. The probe would contain the two tubes 406, 406, the tube 406 would be an aspirate tube and the tube 408 would be a dispense tube for dispensing or transporting the beads 8 from the first container 400 to the second container 402. As discussed herein, the system can operate under pressure or a vacuum. For a system operating under pressure, the liquid 412 is driven into the dispense line, pressurizing the well and sending the fluid out of the aspirate tube 408. This permits use of drive pressure greater than 1 atm. However, there is a risk that fluid (and possibly beads) will leak out of the well if the lid seal fails. In a vacuum configuration, the aspirate tube 408 is connected to negative pressure, and drive pressure is limited to 1 atmosphere. However, in that case, if a seal fails, air leaks into the system instead of liquid (and possibly beads) leaking out.

Figure 92:
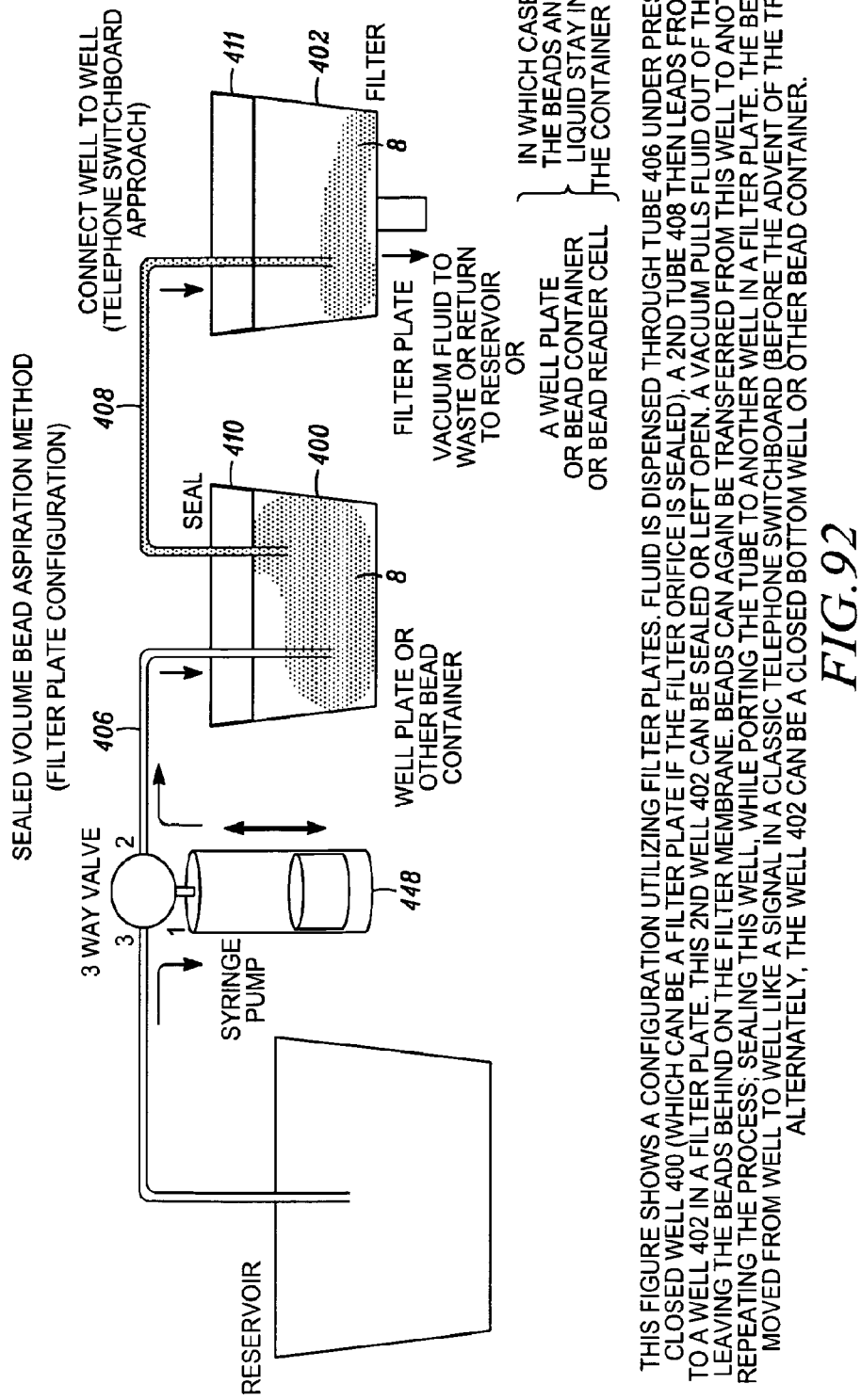
Figure 93:
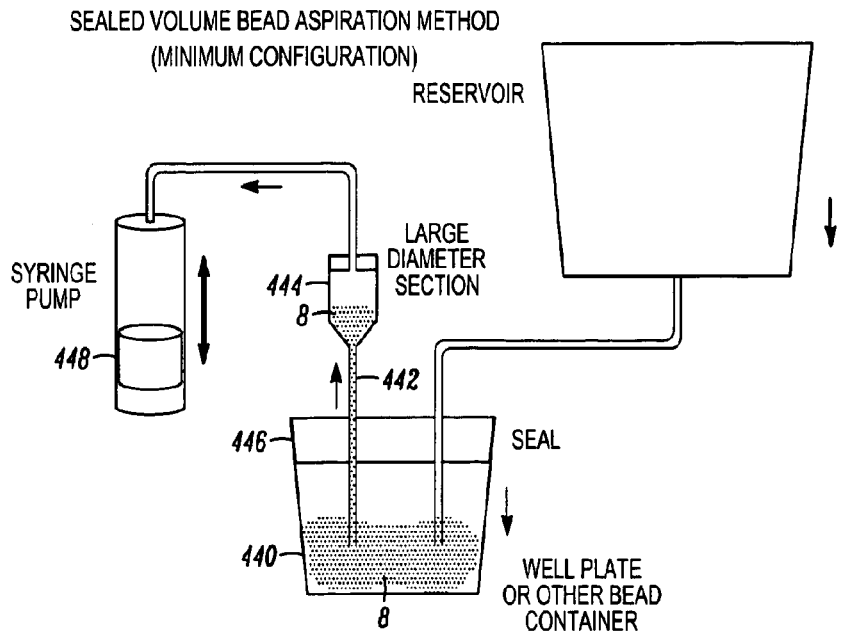

Referring to FIG. 92, a similar configuration to that shown in FIG. 91, using a syringe pump.

Referring to FIGS. 93-97, various alternative configurations for pulling or pushing the beads 8 out of a well 440 having a sealed lid 446, through a tube 442, to a larger diameter holding area 440, using a syringe pump 448. In each case, once the beads 8 are in the holding area 440, the lid 446 is removed from the container 440 and placed in the target or destination well or container (not shown).

In particular, two tips penetrate the upper seal on the container as discussed hereinbefore, with one tip connected to a syringe pump and the other connected to a reservoir. When the syringe pump is aspirated, fluid will be pulled from the reservoir through the second tip. The fluid is thus dispensed from the second tip, agitating the slurry, and aspirated by the first tip. In this way, an arbitrary volume of fluid can be dispensed and aspirated using only a single pump, without overflowing the well or prematurely emptying the well of fluid. The dispensing head is then moved to the new location desired. To dispense the beads, flow is reversed. The flow rate is set lower to avoid re-aspirating the beads into the reservoir. Also, in general, the volume can be set much lower to simply dispense the beads into a new well. The volume can be set the same, however, to refill the reservoir to the original volume. Alternatively, the actuation direction can be reversed. The second tip can be connected to a pump, while the first tip is connected to the reservoir. When fluid is dispensed under pressure through the second tip, fluid will flow up through the first tip, providing an effective aspiration. Re-dispense then involves aspiration through the second tip.

Figure 98:
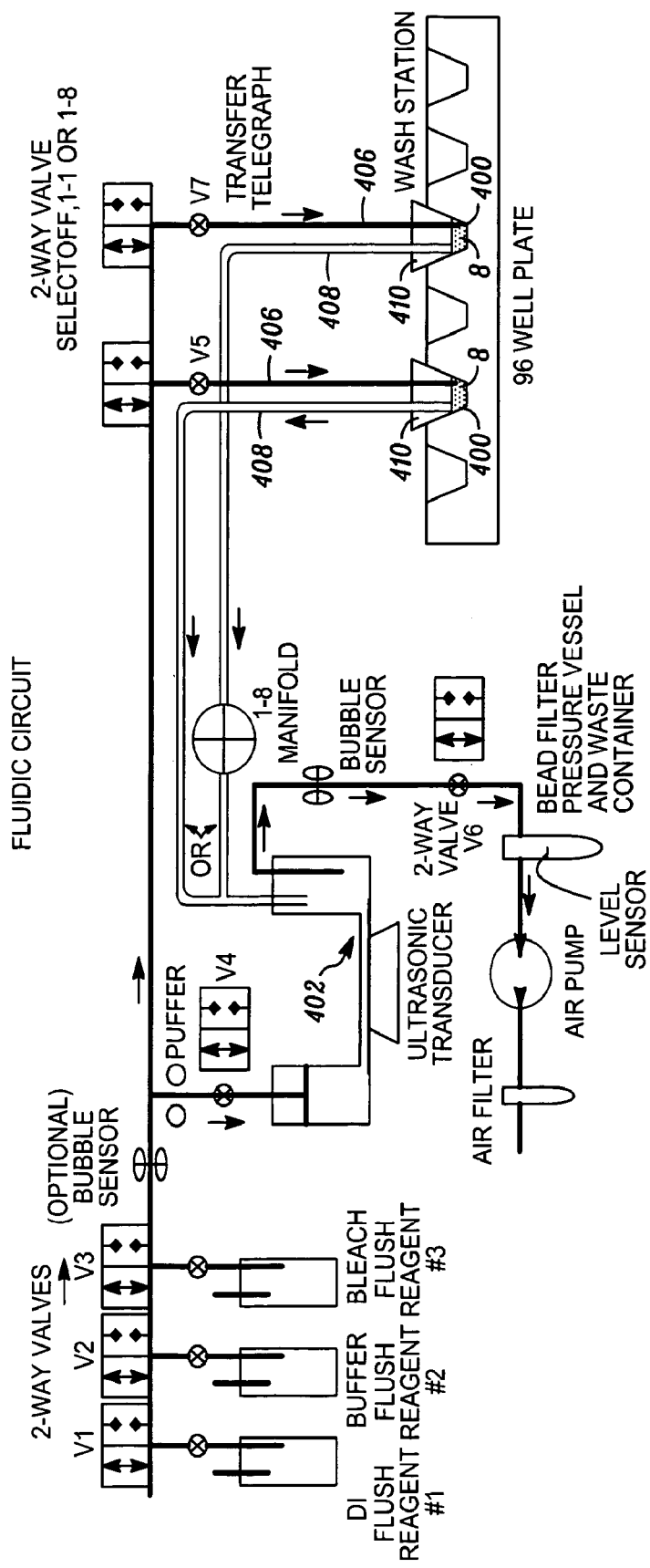

Referring to FIG. 98, a fluidic circuit for loading beads 8 from wells 400 in a known multi-well plate (e.g., a 96 well plate having 8 rows and 12 columns) to a multi-segmented bead cell/chamber, such as is discussed in copending U.S. patent application Ser. Nos. 60/609,583 and 60/610,910, is shown. This system uses an air pump to create a vacuum to pull the beads into the cell 402 (second container) from the wells 400 (first container).

In particular, source fluid is contained in reagent bottles. A bottle is selected by opening the valve which leads by a tubing connection through the bottle cap to the desired bottle. Three bottles are shown, actuated by valves V1, V2 and V3. Additional bottles could be added, each with a companion valve. All valves are electrically operated solenoid valves, such as clean valves sold by Takasago Corp. Valve V6 is ideally a tubing pinch type valve for reliability as beads may damage a conventional solenoid valve.

The prime mover in this embodiment is an air pump, such as that made by Boxer Corp., which creates a vacuum condition in a pressure vessel that acts as a vacuum trap. Fluid is then pulled into this container when valve V6 is open.

Figure 94:
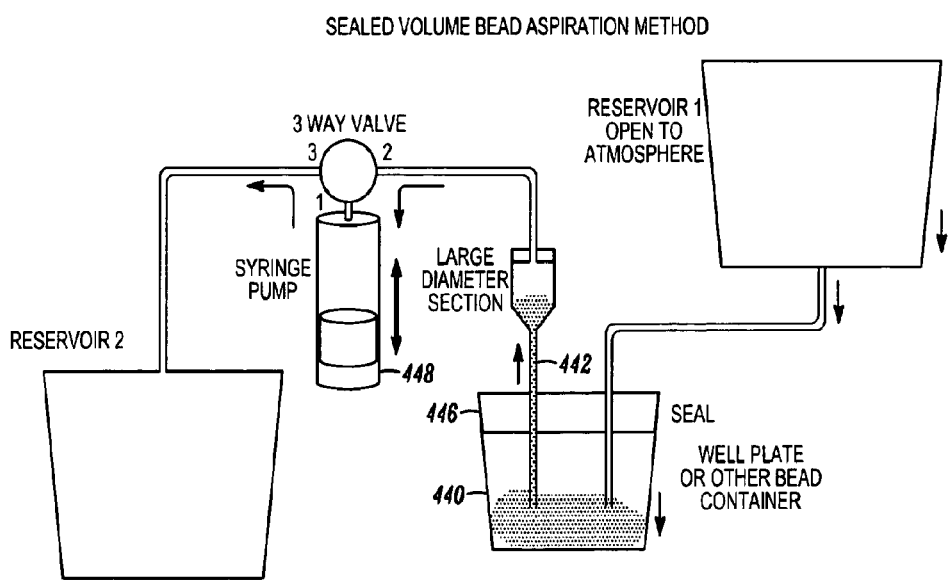
Figure 97:
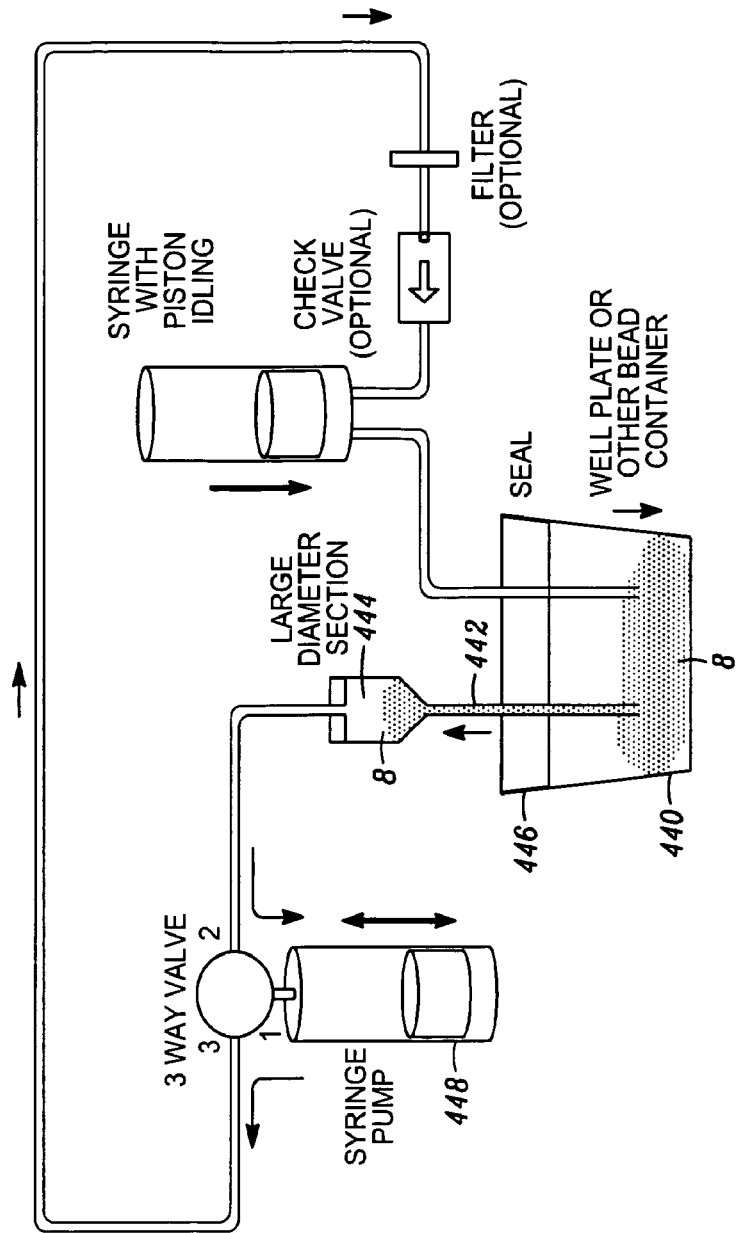

Alternatively, a liquid pump can serve as the prime mover. In this case, a filter should be placed in front of the pump to block beads from entering the pump. If a liquid pump is used, the pressure vessel is unnecessary as an unsealed waste container can be used. Alternatively, a syringe pump, such as that sold by Kloehn Inc., can serve as the prime mover (as shown in FIG. 94). In this case, a filter should be placed in front of the syringe pump to block beads from entering the syringe. A three way valve must be used with the syringe pump so that after filling the syringe, fluid the valve can be switched to then dump fluid to waste. If a syringe pump is used, the pressure vessel is unnecessary as an unsealed waste container can be used.

Referring to the valve state table shown as Table 1 below, to describe the process of filling the cell, begin with a null state of all valves closed and the pump off. The pump is turned on to stabilize a vacuum condition in the pressure vessel. One of valves V1, V2 or V3 is opened. Valve V4 is opened to direct fluid into the cell. Valve V6 is opened, thereby pulling fluid from the reagent bottles, through the cell and into the pressure vessel. Valve V6 controls the fill cycle time and is held open for a specified length of time, e.g., 1 second, calibrated to pull the desired volume of fluid through the cell.

A bubble sensor, such as that made by Introtek, may be used to aid in filling the cell with fluid, by ensuring that the fluid line is free of air before ending the fill cycle. The bubble sensor may also be used to detect if air is being pulled into the cell or system by an improperly seated lid 410 or other air leak. An optional bubble sensor may also be used near the reagent bottles to detect when one of the reagent bottles are empty. Alternatively, a level sensor, such as that made by The Madison Company, in each reagent bottle may be used instead of the bubble sensor to detect empty bottles. Also, another level sensor may be used to in the waste container to detect a full container.

Continuing the cycle, with the pump on, valve V6 closed and V4 open, to move beads from the well plate into the cell, valve V4 is closed and either valve V5 or valve V7 is opened. Valve V7 is only used if the single well to 8 output divider is intended to be used. Valve V6 is opened, thereby pulling fluid from the reagent bottles, into the sealed well plate, out the well plate into the cell, pushing fluid out of the cell into the pressure vessel. Beads are pulled along with the fluid from the well plate into the cell. While excess fluid exits the cell, the beads remain due to the manifold design within the cell.

To flush beads from the cell, the process of filling the cell is repeated. Cycle time is set longer, e.g., 2 to 5 seconds, for flush than for filling the cell, as several volume changes are desired to clean fluid and beads from the cell. As the flush volume is several times greater than the volume held within the cell, and the fluid velocity is high, the beads are propelled out of the cell, pass through valve V6 and enter the pressure vessel. A filter in the pressure vessel can be used to capture the beads. Standard household or industrial water filter housing makes an excellent pressure vessel, as does bag filter housing, such as the Giant Bag Housings by MetPro Corporation, Keystone Filter Division.

TABLE 1

|  | Valve Number | | | | | | |
| --- | --- | --- | --- | --- | --- | --- | --- |
|  | V1 | V2 | V3 | V4 | V5 | V6 | V7 |
| Fill Cell With Fluid | OPEN | OFF | OFF | OPEN | OFF | OPEN | OFF |
| Transfer Beads from 1 Well to 1 Sector in Cell | OFF | OPEN | OFF | OFF | OPEN | OPEN | OFF |

TABLE 1-continued

|  | Valve Number | | | | | | |
| --- | --- | --- | --- | --- | --- | --- | --- |
|  | V1 | V2 | V3 | V4 | V5 | V6 | V7 |
| Transfer Beads from 1 Well to 8 Sectors in Cell | OFF | OPEN | OFF | OFF | OFF | OPEN | OPEN |
| Load Beads | OFF | OFF | OFF | OFF | OPEN | OFF | OFF |
| Flush Reagent #1 | OPEN | OFF | OFF | OPEN | OFF | OPEN | OFF |
| Flush Reagent #2 | OFF | OPEN | OFF | OPEN | OFF | OPEN | OFF |
| Flush Reagent #3 | OFF | OFF | OPEN | OPEN | OFF | OPEN | OFF |

In Table 1,
Off = fluid flow is blocked;
Open = valve passes fluid flow.

Figure 99:
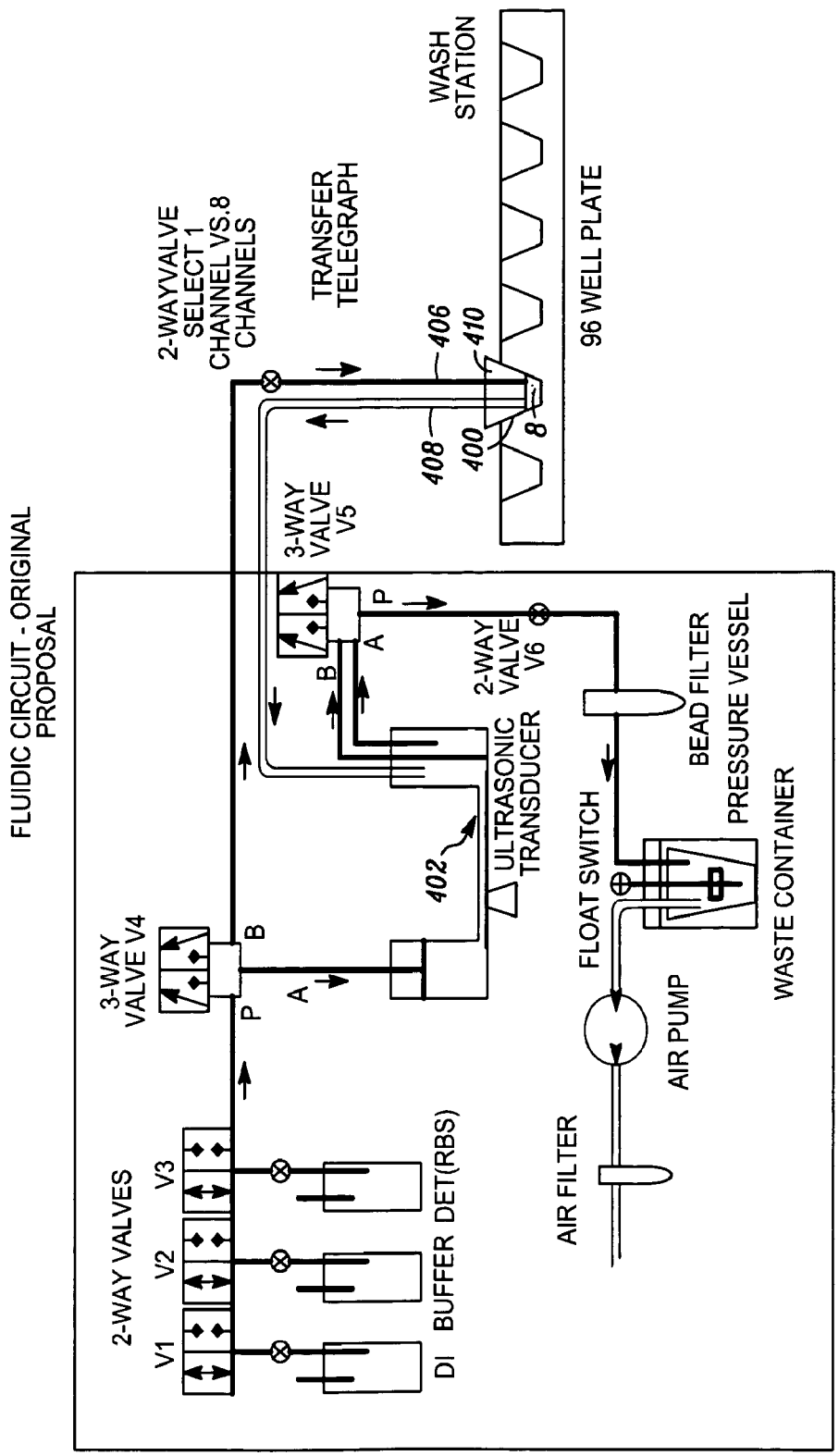

Referring to FIG. 99, an alternative fluidic circuit for loading beads 8 from wells 400 in a known multi-well plate (e.g., a 96 well plate having 8 rows and 12 columns) to a multi-segmented bead cell/chamber is shown. The bead cell is similar to that described in copending U.S. patent application Ser. Nos. 60/609,583 and 60/610,910. This system uses an air pump to create a vacuum to pull the beads into the cell 402 (second container) from the wells 400 (first container). This system also uses a 3-way valve to route the various fluids into the cell 402 or into the wells 400.

Figure 100:
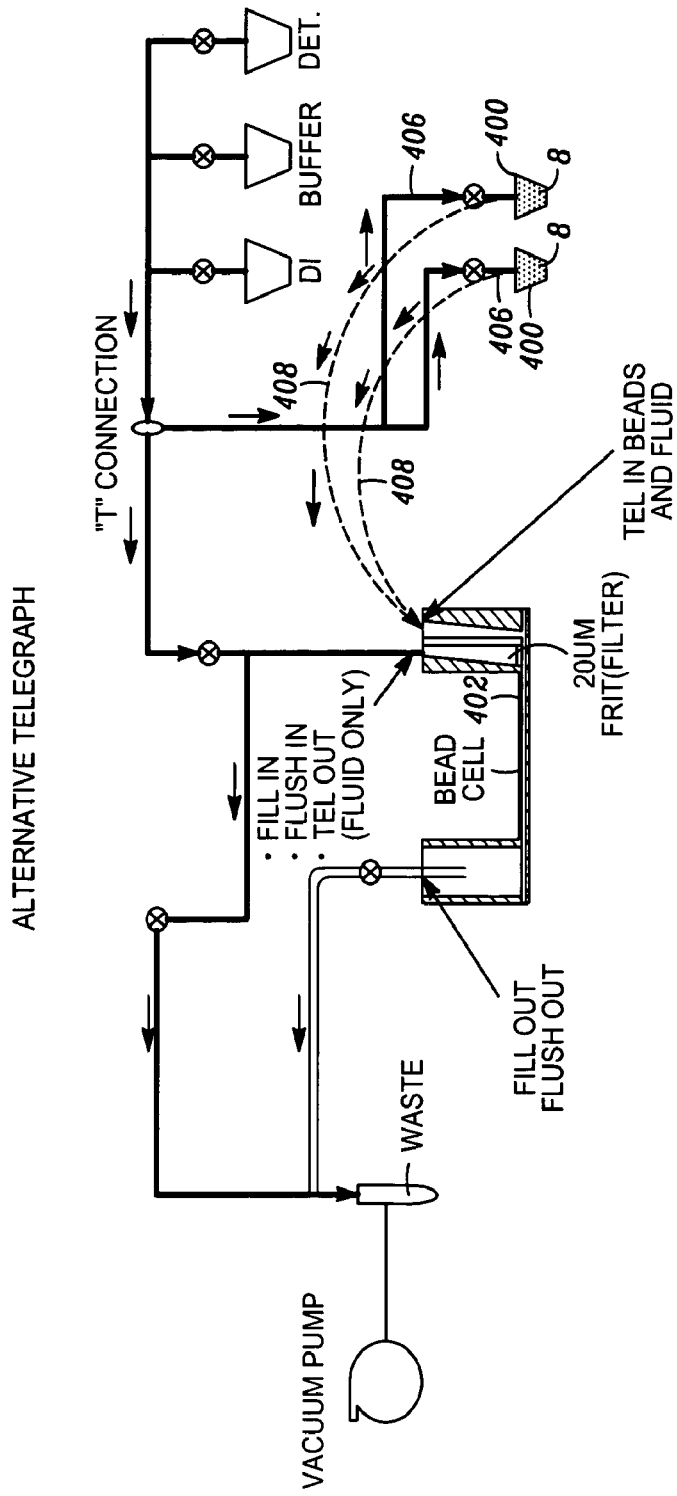

Referring to FIG. 100, an alternative fluidic circuit for loading beads 8 from wells 400 in a known multi-well plate (e.g., a 96 well plate having 8 rows and 12 columns) to a multi-segmented bead cell/chamber 402 is shown. The bead cell is similar to that described in copending U.S. patent application Ser. Nos. 60/609,583 and 60/610,910. This system uses an air pump to create a vacuum to pull the beads into the cell 402 (second container) from the wells 400 (first container). This system also uses a cell having a filter or frit as described in the aforementioned patent application to help collect the beads at the entry of the cell prior to distributing the beads across the cell for reading.

Figure 101:
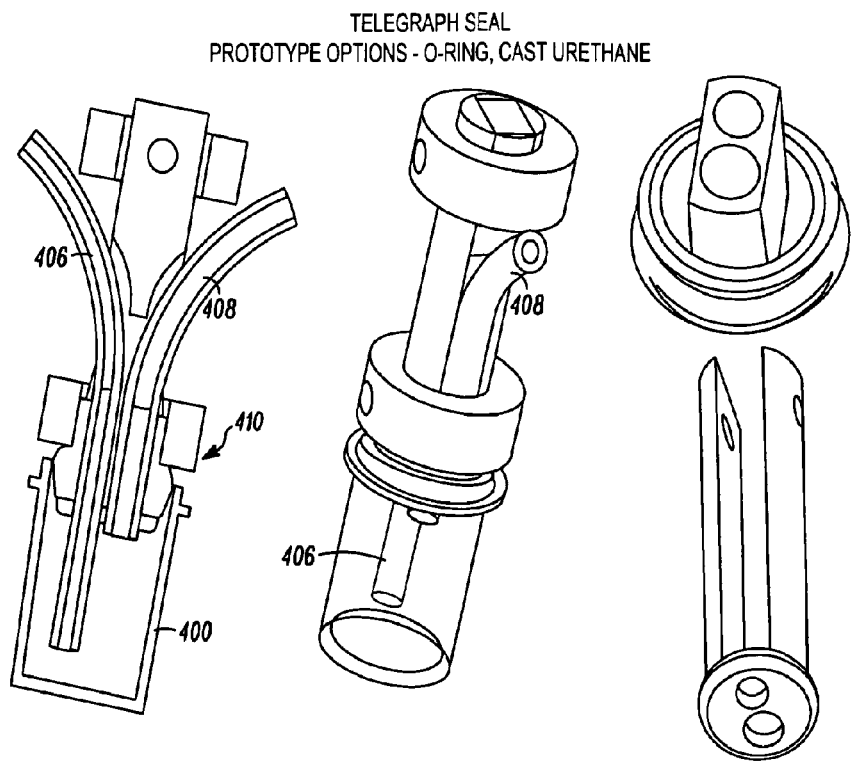
Figure 102:
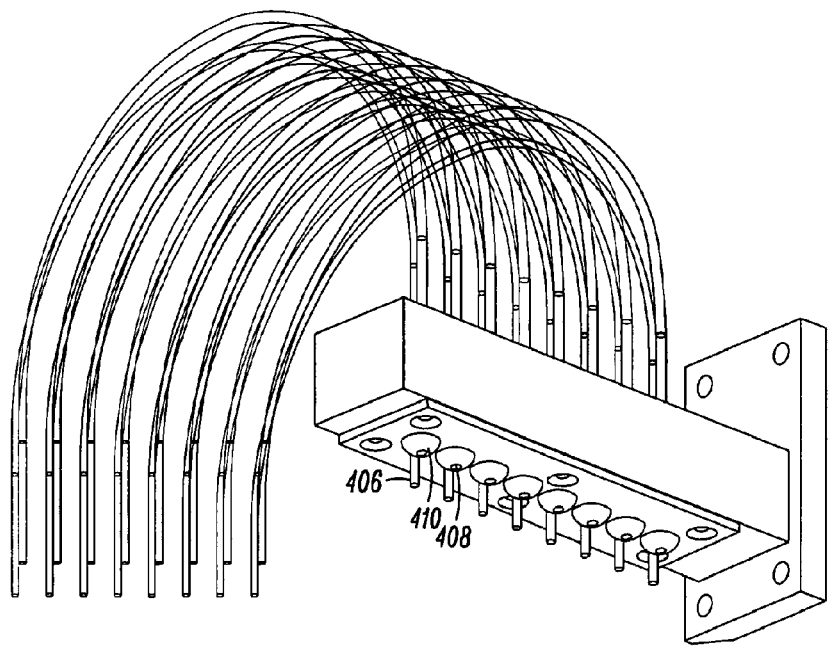

Referring to FIGS. 101-102, an example of an O-ring sealed lid 410 that fits on top of the well (or first container) 400 that would contain the beads 8. FIG. 102 shows a head having eight lids 410, one for each well of an eight row well plate and the tubes 406,408, as well as a housing to which they are all mounted.

Figure 110:
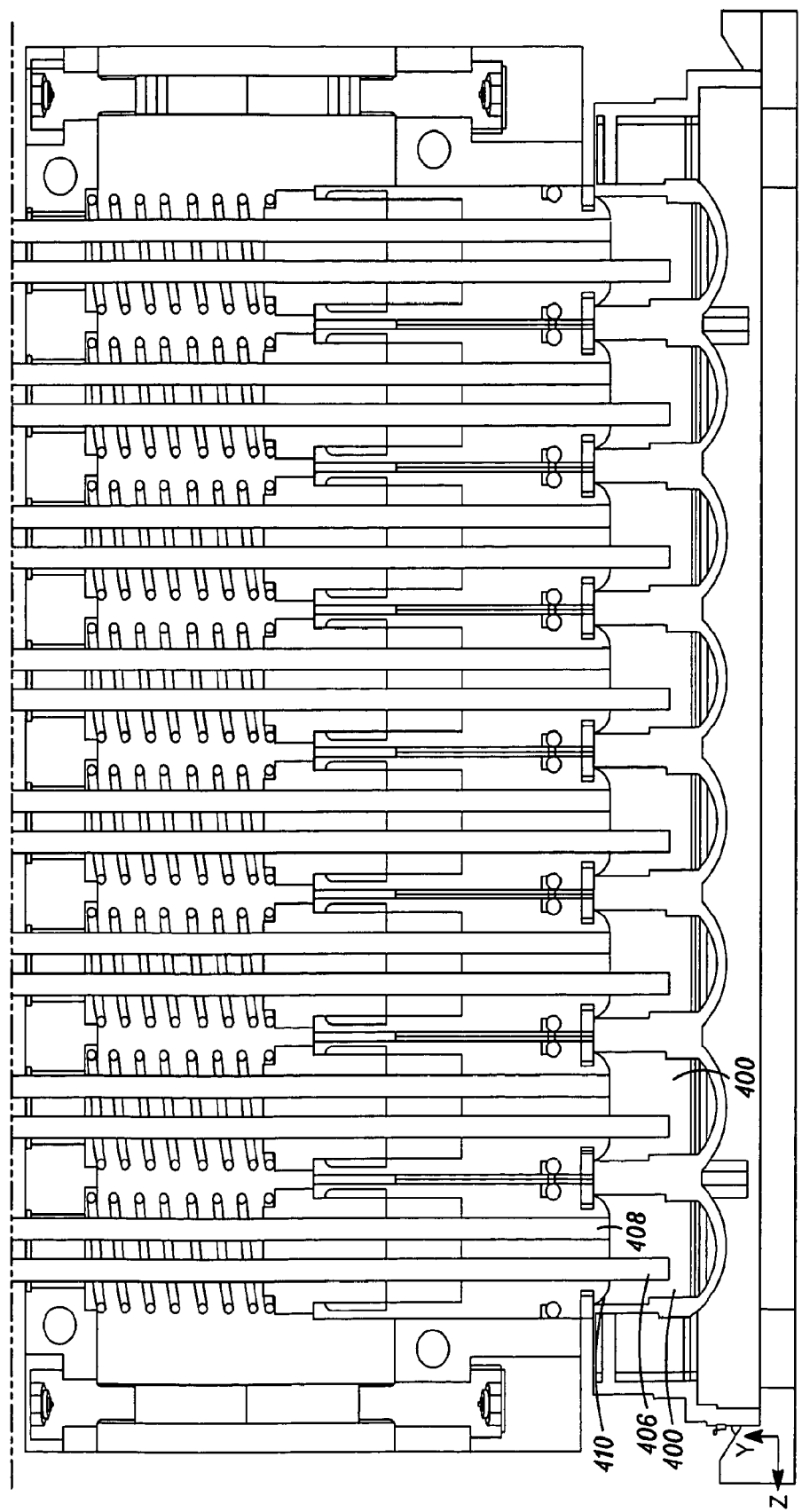

Referring to FIG. 110, a cross-section of a head having 8 lids 410, engaged with eight wells, and also showing a housing and springs and the tubes 406, 408.

Figure 103:
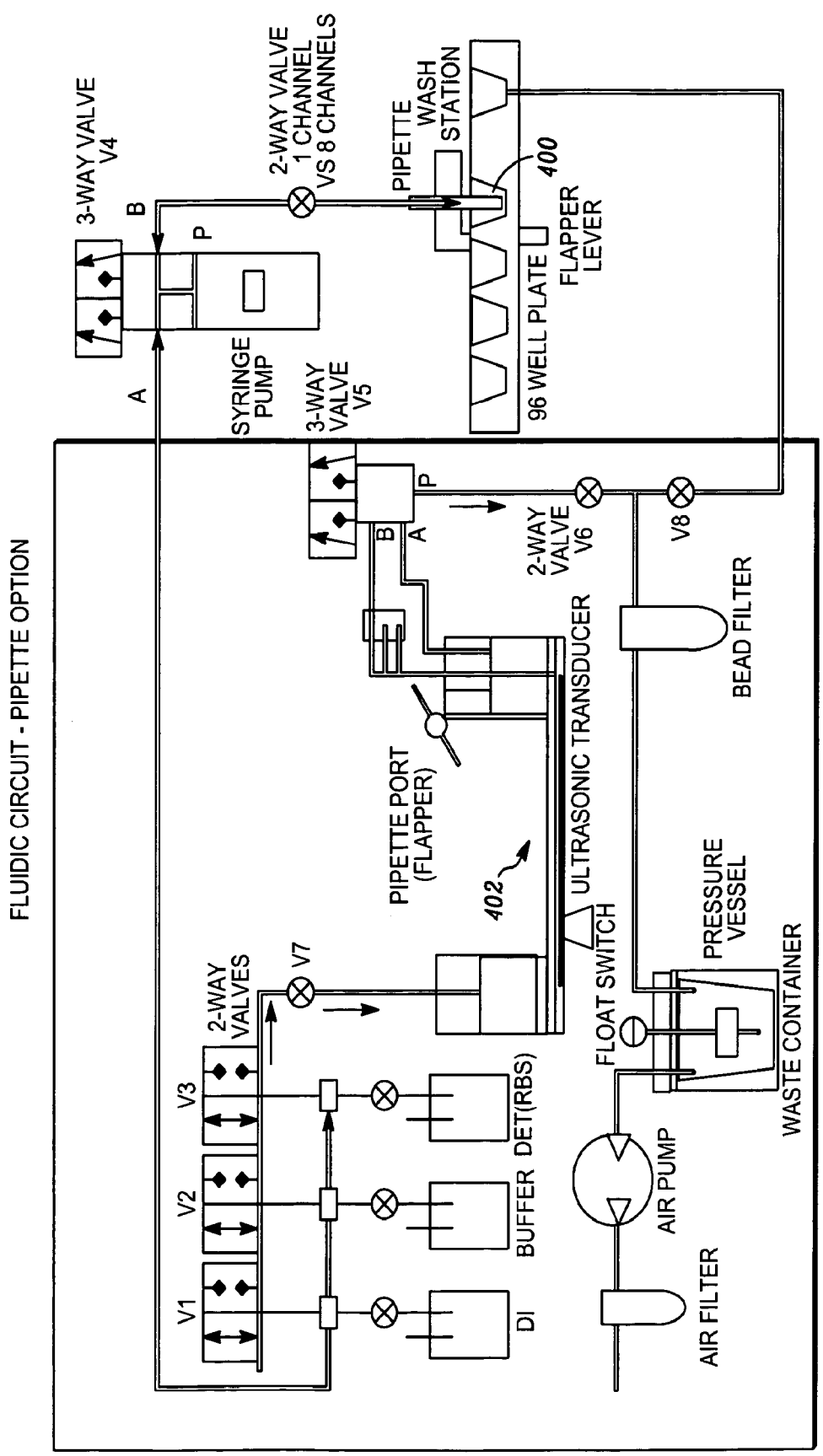

Referring to FIG. 103, a fluidic circuit for loading beads 8 from wells 400 in a known multi-well plate (e.g., a 96 well plate having 8 rows and 12 columns) to a multi-segmented bead cell/chamber 402, similar to that described herein with FIGS. 98 and 99, except that this system uses a pipetting technique instead of a "telegraph" technique for moving the beads. In that case, the pipette is placed in a well 400 and beads are extracted into the pipette tip. Then the pipette tip is moved and inserted into a pipette port on the cell 402. Also, this embodiment uses a 3-way valve for flow management.

Referring to FIGS. 108-109, instead of moving beads from one well to one of the sectored cells in the cell 402, a 1 to 8 flow manifold may be used to distribute beads from one well to eight separated sectors in the cell. FIG. 109 (a) is a perspective view and FIG. 109 (b) is a side cross-section view of the 1 to 8 fluid manifold. This 1 to 8 manifold is also shown as one option in the fluidics schematic if FIG. 98. The 1 to 8 manifold may be used to move fluid (with or without beads) from one well or port to 8 wells or port or used in as an 8 to 1 manifold to move fluid (with our without beads) from 8 wells or ports to 1 well or port.

Figure 104:
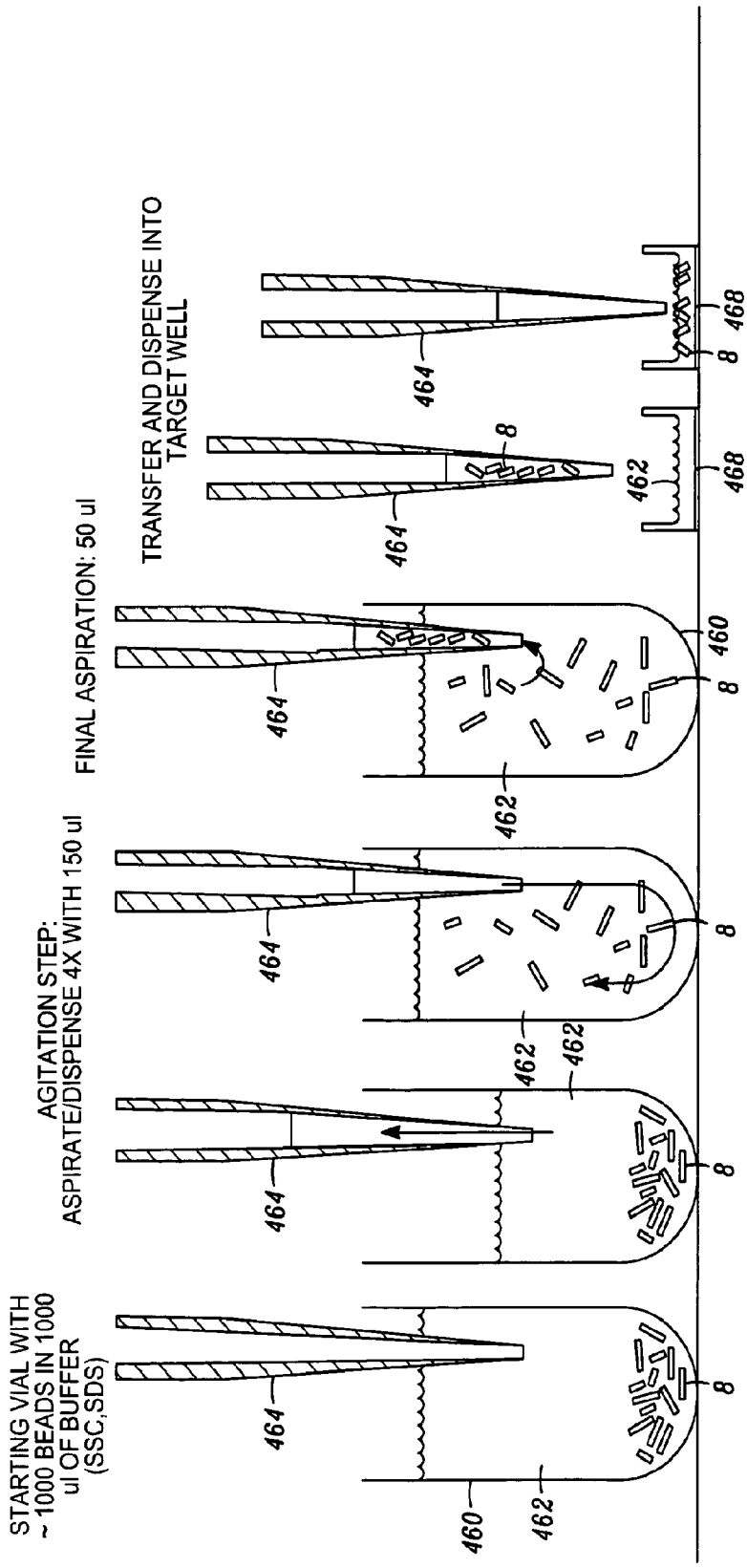
Figure 105:
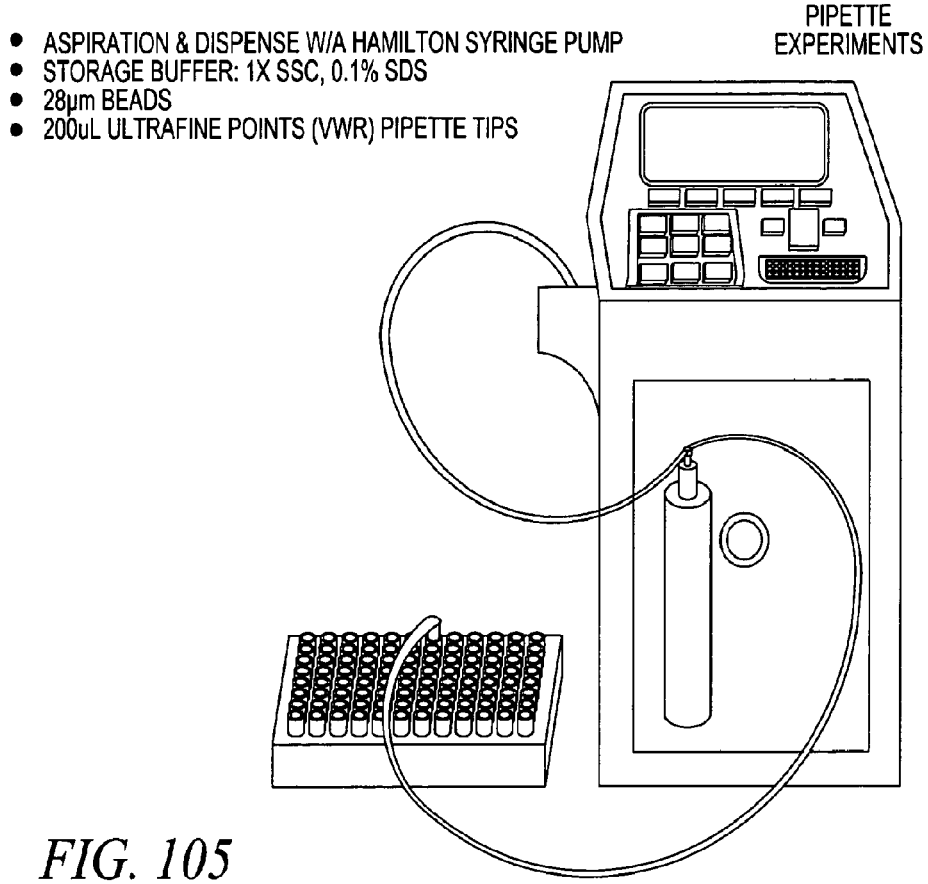
Figure 106:
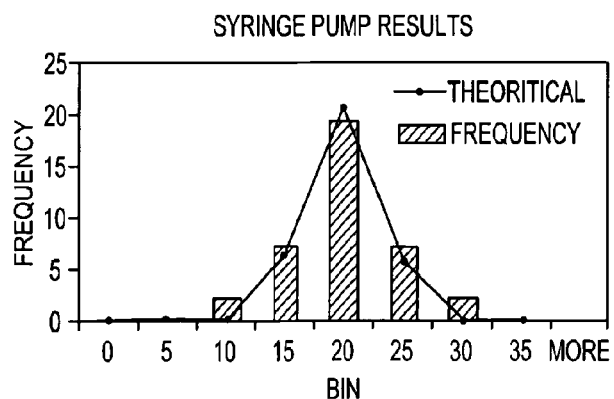

Referring to FIGS. 104-106, one technique for pipetting a predetermined number of the beads 8 from a well 462 is as follows:

1. Start with a highly accurate estimate of the total number of beads 8 in a large population in a separate container (not shown). This can be done by aspirating a certain volume of beads 8 and knowing the packing density is around 40%. N=volume of beads (ul)×40%/volume per bead (ul/bead).

2. Dispense the beads 8 into a known volume of buffer solution, e.g., SSC, SDS, or any other buffer solution or desired fluid in a vial or well 462.

3. Calculate the concentration of the beads 8.

4. Agitate the mixture of the beads 8 in the vial 462 by repeatably and rapidly cycling the pipette 464 in the buffer solution 462, thereby causing the beads 8 to mix and suspend substantially "homogeneously" in the solution 462. The agitation volume should be about 2-10% of the total volume and the rate of agitation should be fast enough to suspend the beads in solution. Also, it was found that in order to generate good fluid currents and, thus, good bead mixing/suspension, the pipette tip should be placed away from the center of the well 460, and near to the side wall if possible. Note that the pipette tip should be inserted into the liquid 462 such that the pipette tip is near the top of the liquid when the fluid is fully aspirated. Therefore, as the liquid level decreases from successive aspirations, the tip will need to be placed deeper into the vial each time a new group of beads is removed. Also, the size of the opening in the pipette tip opening/orifice determines the velocity of the mixing currents for a given agitation volume and rate. For example, a larger orifice will result in lower velocities for the same rate and volume. We have found that a tip with a small orifice (<about 600 um) works well for the 28×250 micron beads, solution and volume used. However, the tip orifice should not be so small (<about 300 um) that the flow through the tip for the pressure generated and decreased to the point where the velocities are too low to generate good mixing and suspension of the beads.

5. When the beads 8 are substantially "homogeneously" mixed and suspended in the liquid, then the next (final) aspiration of beads 8 should determine how many of the beads 8 are drawn from the vial 460. The number of beads 8 drawn=concentration (beads/ul)×aspiration volume (ul).

6. Dispensing the beads 8 into the target well 468 should include a brief time delay of about 1-3 sec to allow the beads 8 to fall to the bottom of the pipette tip before they are completely dispensed into the target well 468.

In particular, referring to FIG. 104, for example, starting with the vial 460 with about 1000 beads having a diameter of about 28 microns and a length of about 250 microns, in about 1000 microliters of known buffer solution 462, e.g., SCC, SDS. First insert a pipette tip 464 into the liquid 462 such that the pipette tip is near the top of the liquid when the fluid is fully aspirated. Then, holding the pipette tip substantially still, aspirate/dispense about 4 times with about 150 microliters over a period of about 4 seconds; however other times may be used provided sufficient bead mixing and suspension is achieved. Then, draw a final aspiration of about 50 microliters. Then, transfer the pipette to a target well 468 and wait about 1-3 seconds to allow the beads to settle to the end of the pipette tip, then dispense the beads 8 into the well 468. The size of the opening in the pipette tip was 400 microns (0.4 mm) and the size of the well 460 was about 1000 micron liters, and the pipette tip was placed about mid way between the center of the well 460 and the side wall.

Referring to FIG. 105, a picture of a Hamilton Syringe Pump syringe pump used to pipette beads with the present invention is shown. The pump having a storage buffer of 1×SSC, 0.1% SDS, and using 200 microliter ultrafine points (VWR) pipette tips.

Referring to FIG. 106, a graph of syringe pump bead pipetting results is shown using the process described herein. For 36 tests, the average number of beads removed each time was 18, with a bead diameter of about 28 microns and length of 250 microns, agitation volume of 150 microliters, final aspiration volume of 27 microliters, and a starting bead concentration of 0.68 beads per microliter.

Referring to FIG. 107, a diagram of how a kitting process may be performed with the present invention. A plurality of containers or wells 500-504 are provided, each well having beads with a specific code. For example, the well 500 has beads 8 with a code of 345, as shown by the digital representation image 506, the well 502 has beads 8 having the code of 8197, as shown by the digital representation image 508, and the well 504 has beads 8 having the code of 15606, as shown by the digital representation image 510. The plurality of wells 500-504 having the beads 8 can create Multiplex Bead Kits 1 through N, each Kit in a separate container 516-520, and each Kit having a predetermined number of any one or more of the codes in the wells 500-504. The beads 8 may be transported from the wells 500-504 using the any embodiment of the present invention or using any technique now known or later developed to move a predetermined number the beads 8 into the containers 516-520 for the Kits. The predetermined number of beads 8 of each code in each kit may have a tolerance, e.g., +/−10 beads. Other bead kit tolerances may be used depending on the application. Referring to FIGS. 111-114, a method for making a "kit" consisting of N unique codes, where N may range from 1 to 5000, represented by M replicates (beads), where M may range from 5-100, can be accomplished by a two step process, consisting of transferring a small number (M) of beads from a vial or well containing beads of all the same code to a target well or vial, then, combining the small number of beads representing each code in the kit to a single vial or well, thus forming the "kit". The first step, transferring M beads from the source, could be performed in a 48, 96 or 384 well format using the pipetting approach previously described, or from an arbitrary configuration of individual vials. It is recognized that this can be done in parallel with a conventional multi-head pipetting machine such as those found in many laboratories. The second step of combining individual sets of N codes together to form the final "kit" may be accomplished by either dispensing the individual sets into a funnel-like device where the beads are flushed into a single well or vial containing a filter bottom such that copious amounts of fluid may be used to sufficiently flush all the beads through the funnel, leaving substantially no beads behind. Another approach, which accomplishes the combining effect, is to "telegraph" (previously described) the beads representing individual codes into a single vial or well all at once. This process is very fast and highly efficient in terms of transferring all the beads from the source to the destination. This two-step process would enable "kits" to be made with an arbitrary number of codes and represented by an arbitrary number of beads per code, in a rapid and efficient manner.

Figure 115:
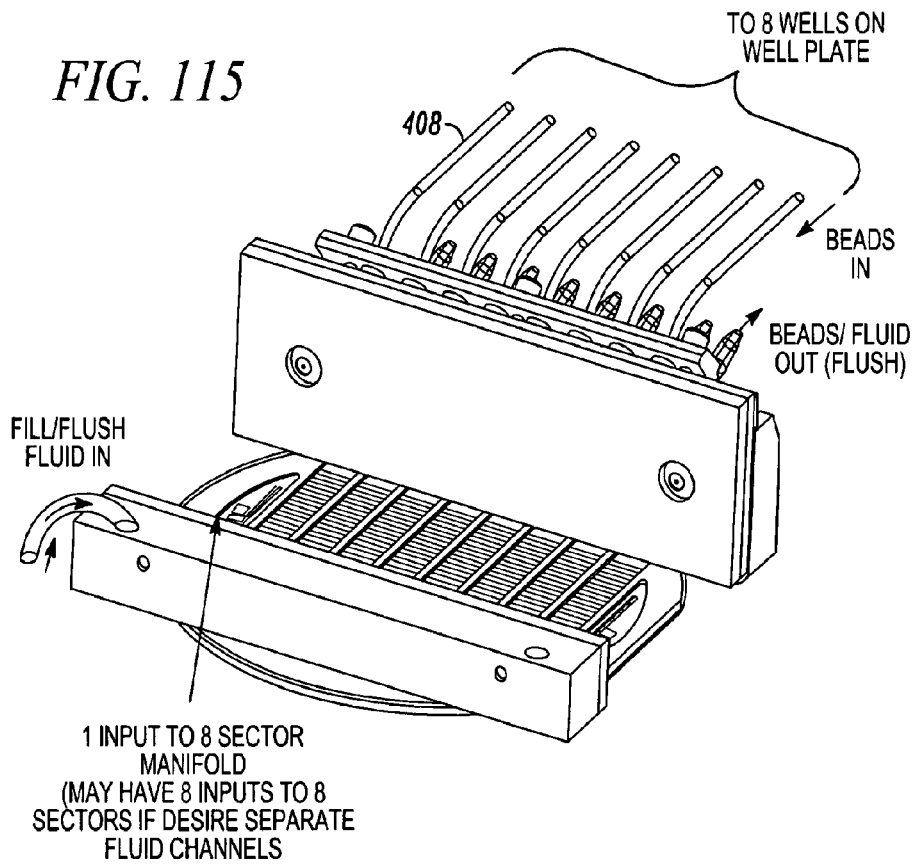
Figure 116:
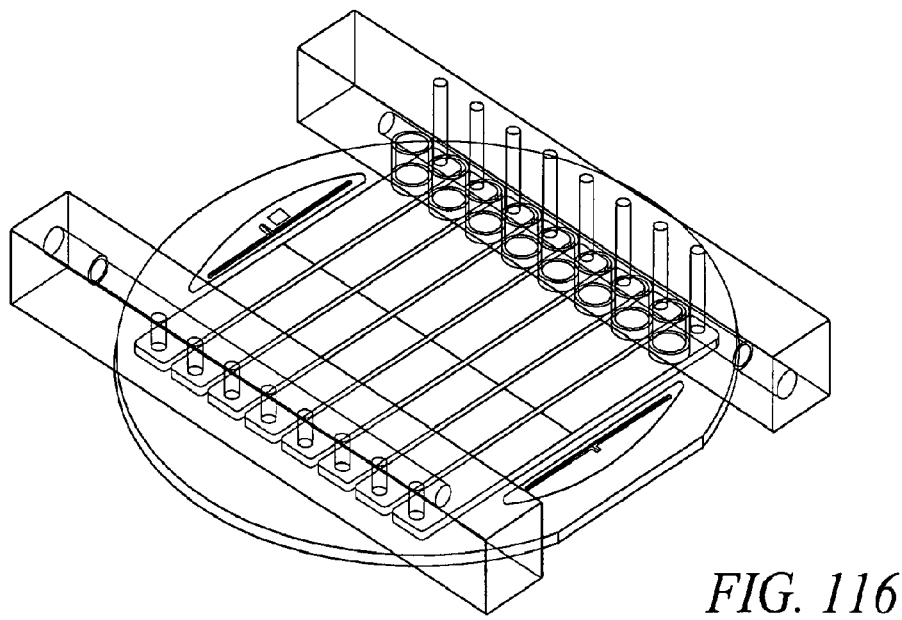
Figure 117:
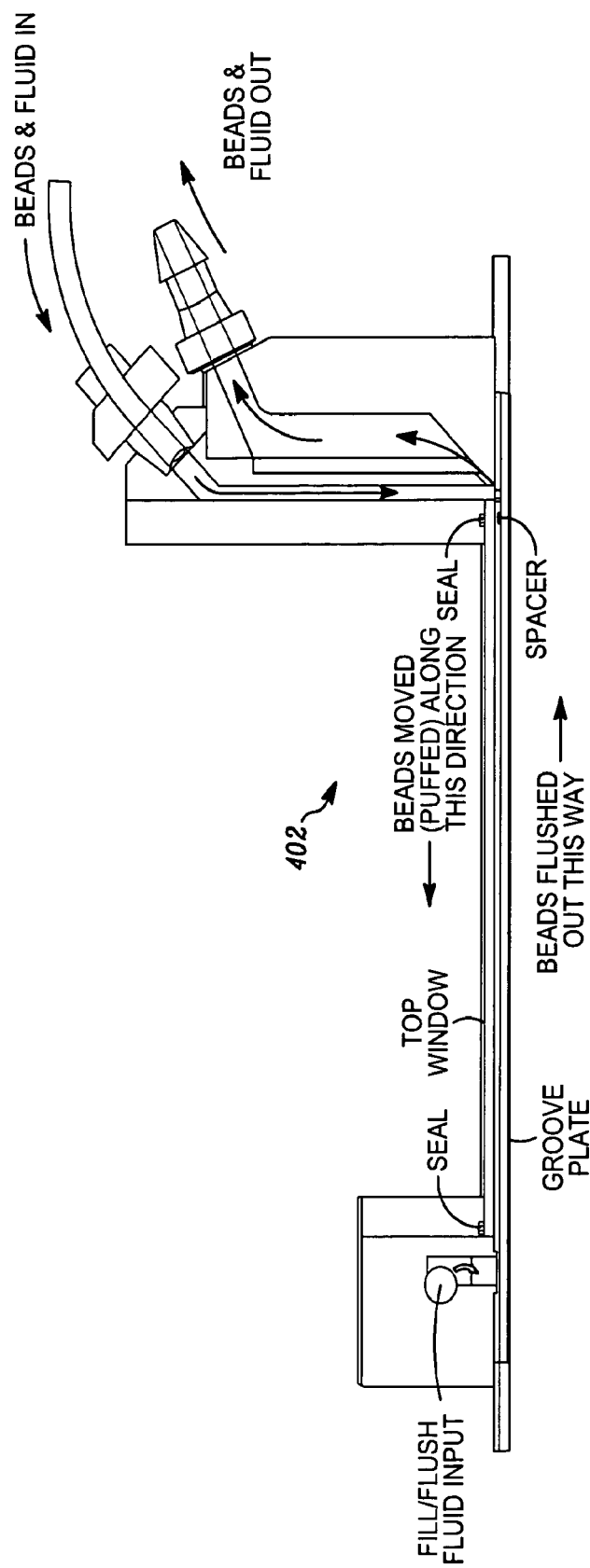

Referring to FIG. 115 shows a perspective view of the 8 sector bead cell having 8 input tubes 408 which transport beads and fluid from 8 cells to 8 corresponding sectors of the bead cell. It also shows a 1 to 8 flow manifold which takes in fluid and distributes it to 8 sectors in the cell.

Figure 111:
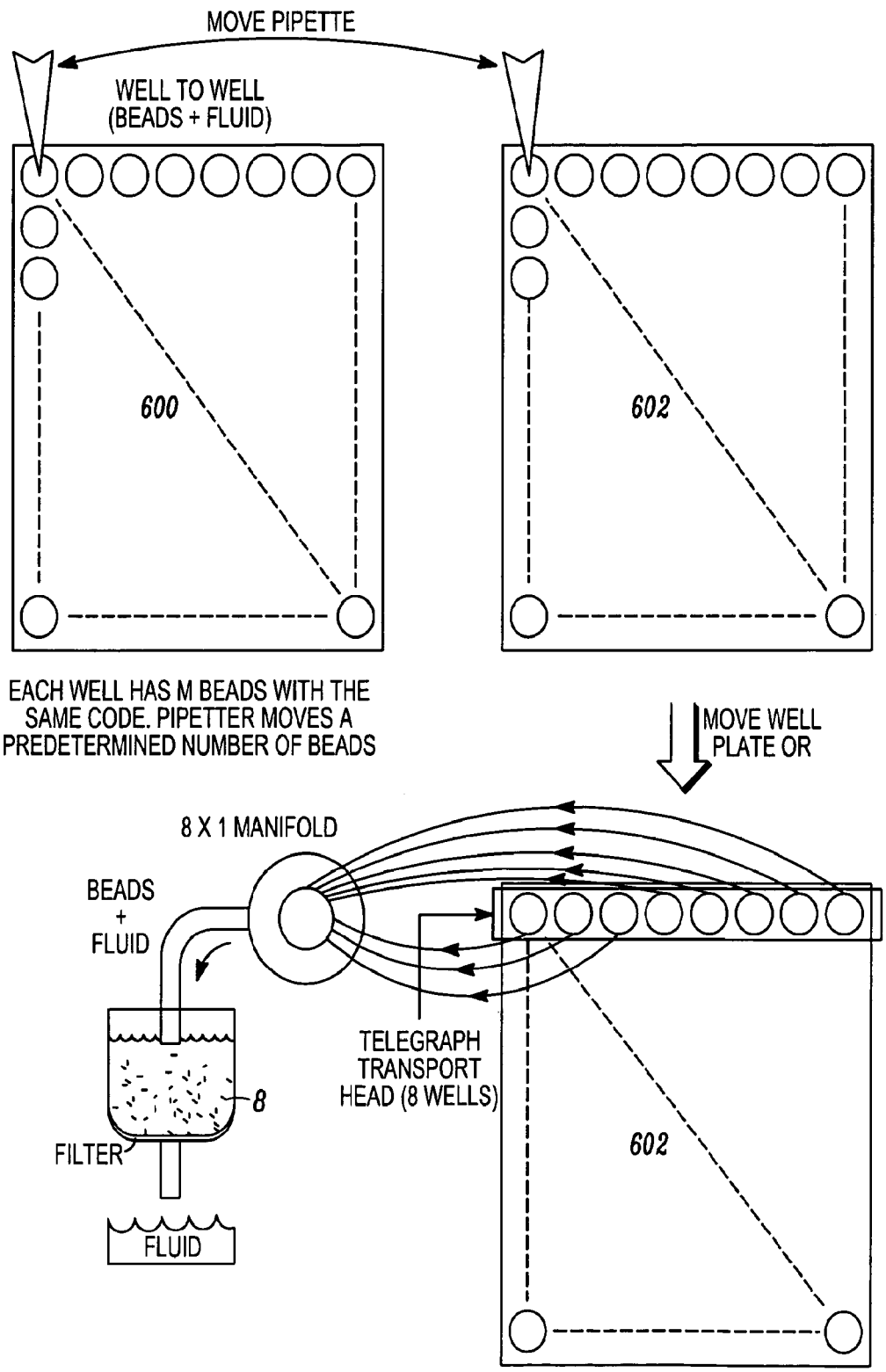
Figure 112:
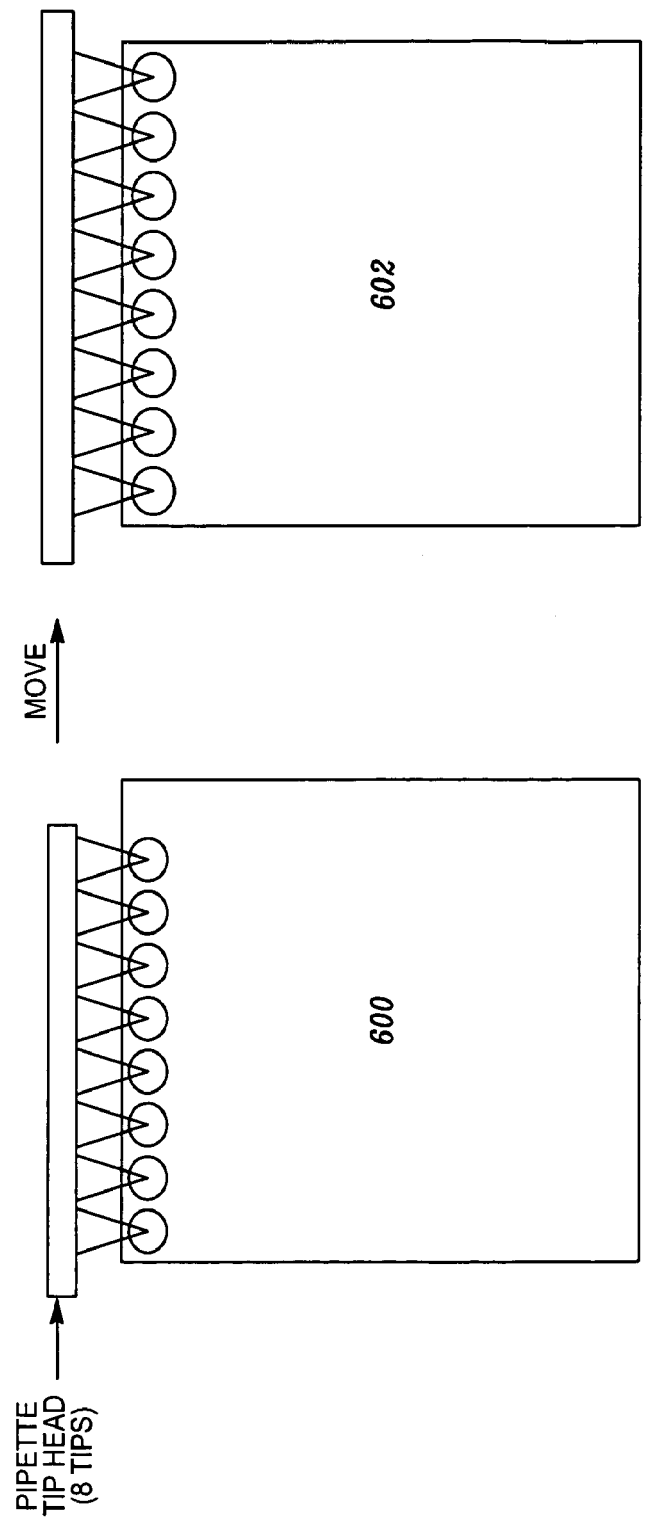
Figure 113:
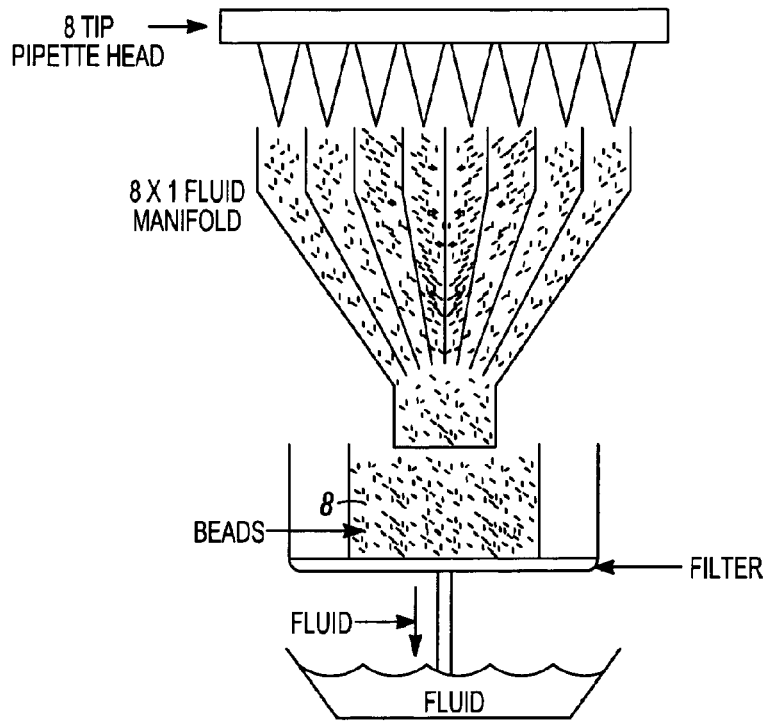
Figure 114:
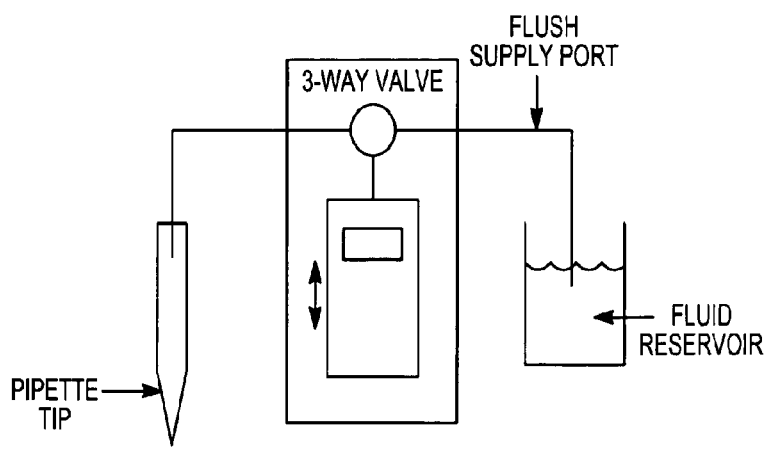

In particular, FIG. 111 shows a multi-well plate having beads which are pipetted individually to another multi-well plate which are then telegraphed as a group of wells (as described herein) to a filter well Kit container. FIG. 112 shows a multi-well plate having beads which are pipetted as a predetermined group or individual pipette tips to another multi-well plate, which are then telegraphed as a group of wells (as described herein) to a filter well Kit container. FIG. 113 shows an 8 to 1 manifold for receiving 8 pipette tips which will simultaneously dispense fluid and beads into the manifold and the manifold combines the received fluid and beads to a single output port which dispenses the fluid and beads into the Kit container having a filter on the bottom to catch the beads. The beads are then transferred to a final kitting container. FIG. 114 shows a pipetting machine having a flush port for flushing fluid through the pipette tip, which can be used after the beads 8 are dispensed into the manifold shown in FIG. 113, or whenever flushing with a fluid is needed. In each of the above cases, the Kit container may have a filter on the bottom to catch the beads and allow the fluid to exit. The beads are then transferred to a final kitting container. Alternatively, the container may be large enough to hold the fluid and the beads and then the beads and a portion of the fluid may be transported (e.g., by the telegraph method described herein) to a smaller kit container if needed.

An Alternative Embodiment of the Fluidic Subsystem

FIGS. 118-133 show an alternative embodiment of the present invention. In summary, FIGS. 118-121 show the basic architecture and governing design principles; FIGS. 122*a* to 125 show steps of the overall method and the sequencing thereof; FIG. 126 shows details related to a groove plate design; FIG. 127*a-d* show basic experiments; and FIGS. 128-133 show more detailed diagrams of components of the basic architecture.

Consistent with that discussed above, the microbead platform will perform biological assays on beads by attaching a type of biomolecule to the beads then placing the beads in a vessel containing sample material, which will react in varying degrees to the biomolecules. The extent to which the sample reacts is determined by measuring the intensity of a fluorescent tag molecule, and the identity of the fluorescent beads is determined by reading its holographic code. Both fluorescence and code detection methods place requirements on how beads are oriented relative to the interrogation lasers and collection optics. The purpose of the fluidic sub-system is to manage all fluid and bead manipulation activities entailed in the interrogation process. These include movement of beads from the microliter plate to the cell, alignment of beads in the cell and finally removal of beads from the cell so that the next batch can be interrogated. The fluidic system must also provide a means by which it can be cleaned of all biological and chemical contamination.

The following 6 steps describe the basic functions of the reader from a fluidic point of view:
1) Prime Cell
2) Transfer Beads
3) Load beads into grooves
4) Scan beads
5) Flush
6) Clean cell (after N cycles)

Steps 2-5 are performed every cycle on 8 wells at a time on an 8×12 well plate. Therefore a full 96 well plate requires 12 cycles to complete. Step 1 is performed on start up and whenever the fluidic system either accumulates too much air or to remove persistent beads from grooves. Likewise, step 6 is performed when an unacceptable level of fluorescent contamination has accumulated.

FIG. 119 shows the governing design principles.

FIG. 120 shows a diagram of the fluidic system process flow including the 6 basic steps.

Figure 121:
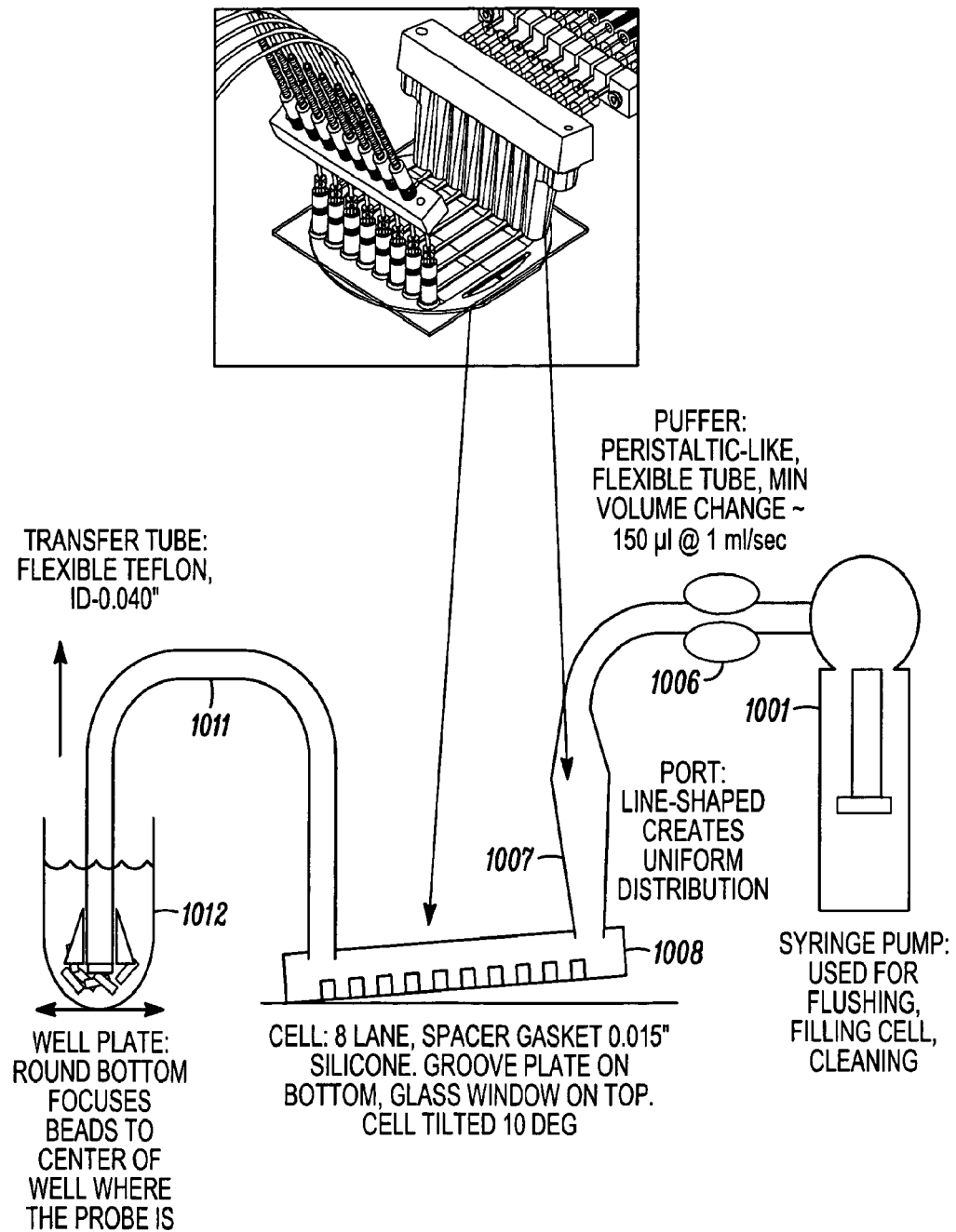
Figure 122A:
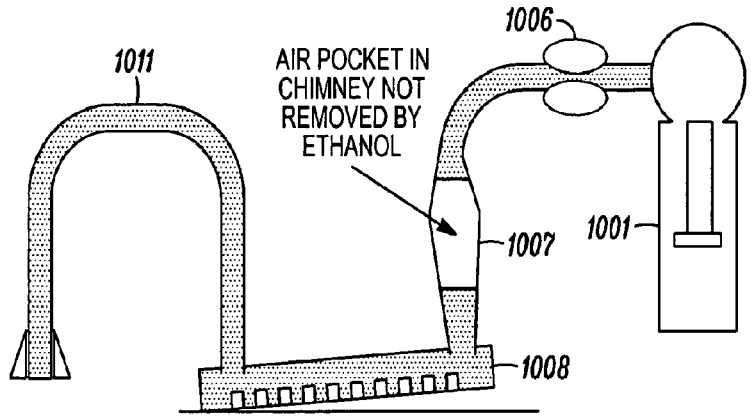
Figure 122B:
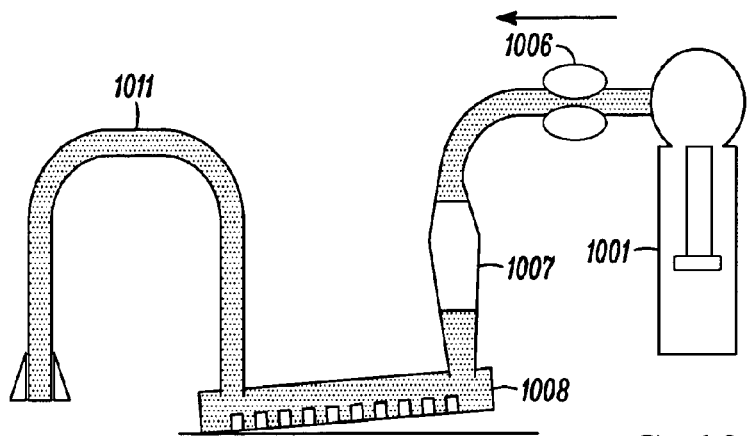
Figure 122C:
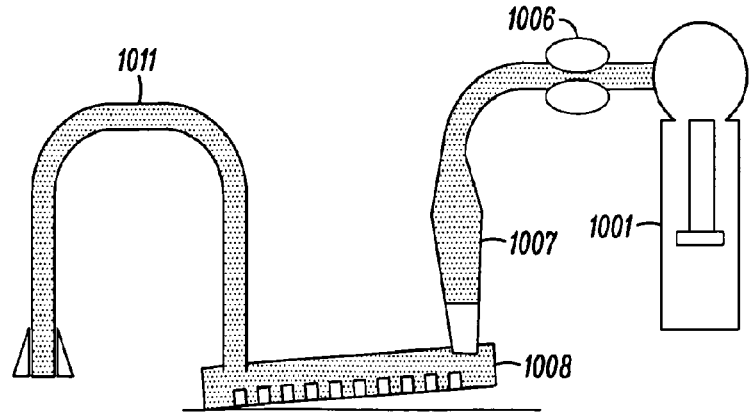
Figure 122D:
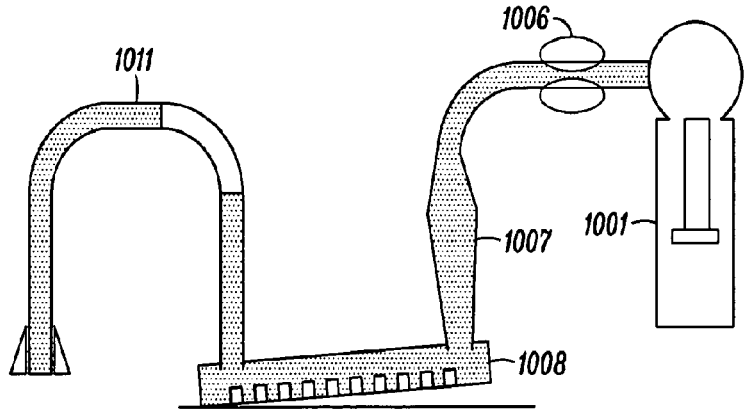
Figure 122E:
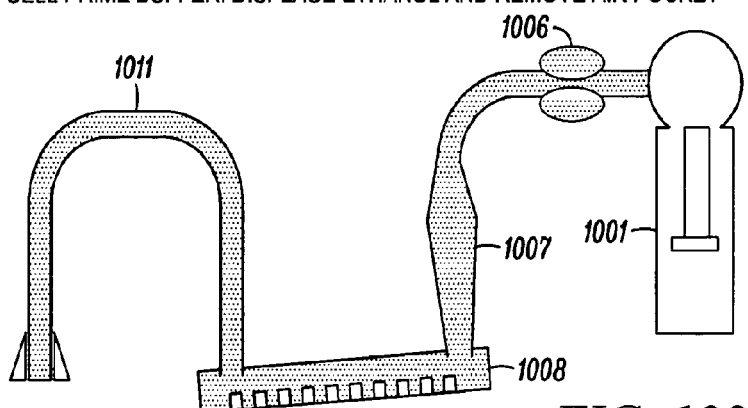
Figure 123A:
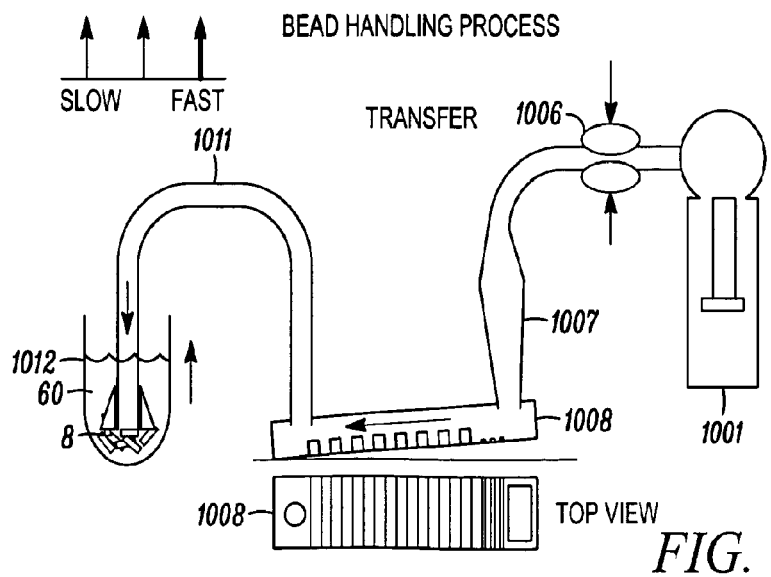
Figure 123B:
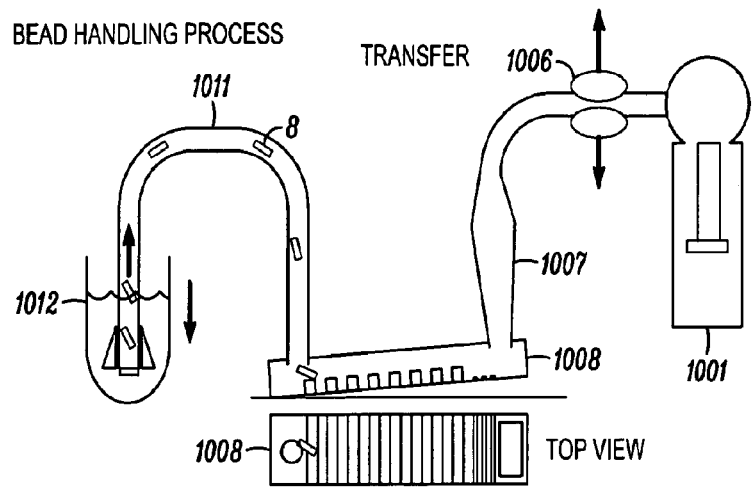
Figure 123C:
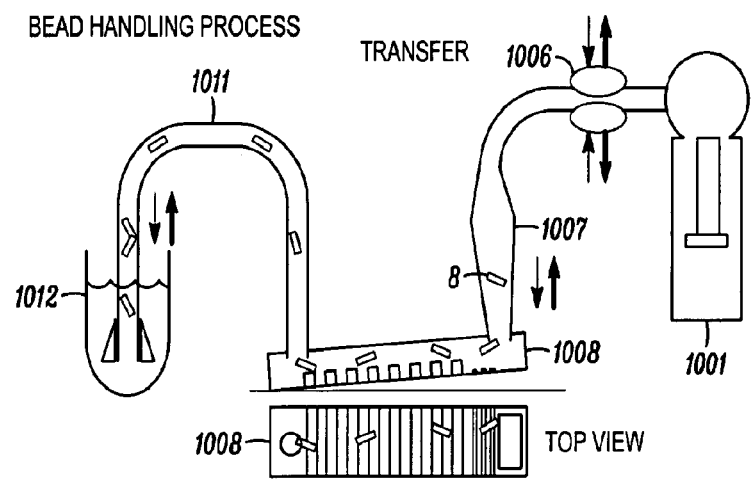
Figure 123D:
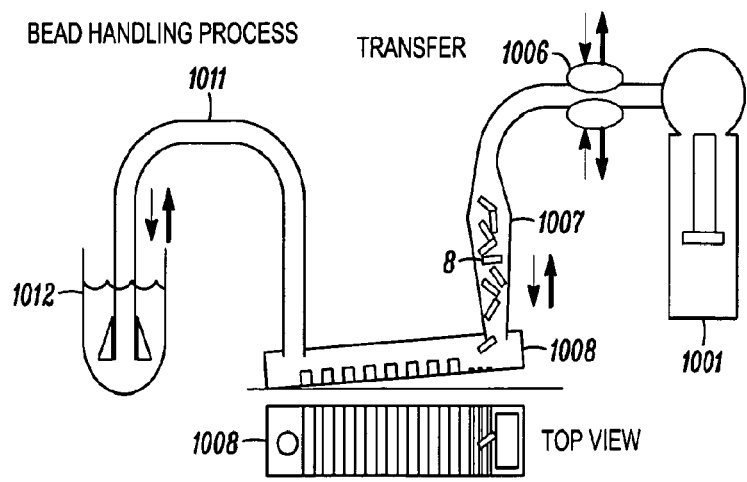
Figure 123E:
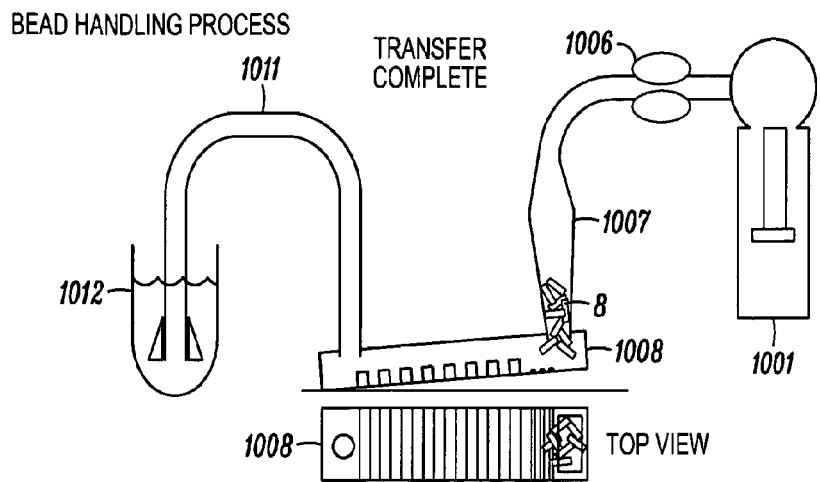

FIG. 121 shows the fluidic system including the architecture generally indicated as 1000 and major subsystems, including a transfer tube or probe assembly 1012, a well plate 1012, a cell or cell assembly 1008, a puffer tube or puffer tube assembly 1006 and syringe pump 1001, consistent with that shown in detail below in FIG. 118.

Fluidics Architecture

FIG. 118 shows in detail the basic fluidics architecture generally indicated as 1000 for performing the 6 steps of the alternative embodiment of the present invention, and includes the following elements and functionality as set forth below:

The Syringe pump 1001 aspirates or dispenses from selected valve position.

The Rotary valve 1002 rotates to select from 5 positions—Output to cell, Reagent 1, Reagent 2, Reagent 3, Dispense Excess/Aspirate Air.

The Tube Assembly, Output to Cell 1003 is fluoropolymer tubing to allow fluid to flow from syringe 1001 to the manifold leading to cell chimney 1007.

The Manifold (1×8) 1004 divides flow from 1 input line to 8 output lines leading to cell.

Check valves 1005: Check valves are connected to each of the 8 lines in the manifold. The check valves prevent fluid from siphoning between lanes of the cell. Without the check valves, a small height imbalance of the fluid in one probe versus another, could cause the siphoning of fluid out of the line carrying the shorter fluid path. This could then lead to a chain reaction where all the fluid siphons out of the cell.

Puffer tube assemblies 1006: The puffer tubes are constructed of silicone tubing with inner diameter 3/16 inch and outer diameter 5/16 inch. Compression of the tubing with the puffer block displaces fluid. The check valves prevent fluid from flowing back to the pump. Also, even without the check valves, the syringe is a stiff system which would prevent flow in this direction. Therefore all flow from compression moves out through the cell and out the probes. Release of the tubing then aspirates fluid through the probes back into the cell. The silicone tubes were selected for their elasticity and low compression set.

The Chimney 1007—The chimney 1007 is a molded part that is critical to the transfer of beads into the cell and loading of beads into grooves. The chimney 1007 terminates in the cell in a narrow line shaped nozzle which we call the line port. This shape provides a relatively flat flow velocity profile across the width of the alley. The narrowness of the port (generally less than 2 bead lengths at the narrowest portion), prevents large slow moving eddy regions when beads turn the corner from chimney to cell. Also, the spacer is aligned with the back of the nozzle to prevent significant dead zones of flow. Bead loading into grooves takes place at flow velocities that are in the laminar regime away from the immediate vicinity of the grooves. The chimney 1007 expands into a wider region. The height of the chimney and width of the expanded region were designed to limit the height to which beads rise in the chimney during transfer. By limiting this height, beads are not aspirated out of the chimney, which would lead to cross-contamination in later cycles.

Cell Assembly is labelled 1008.

Top Plate 1008a: The top plate is the top optical window of the cell sandwich. It contains a row of 8 holes for attachment of the chimney to the 8 lanes of the cell. At the opposite end of the alleys, it contains a row of 8 holes for attachment of the bead ports.

Spacer 1008b—The spacer maintains a gap between the groove plate and top window. It also seals and separates the 8 alleys from each other and from the outside world. The spacer is made of a silicone gasket. The gasket is attached to the two glass plates under compression and heat to create a seal. The spacer thickness is 0.015 inch or 380 microns. This thickness appears to be near an optimum value for balancing competing needs. On one hand, the thinner the gap the higher the velocity near the grooves, this aids in bead loading with the puffer and in bead removal. On the other hand, if the gap is too small, bubbles are not effectively cleared from the cell. Note that other materials could serve as a gasket.

Groove Plate 1008c—the groove plate arranges the beads in an orderly fashion to be read by the reader optics. The groove plate is made of fused silica and is produced by an RIE (reactive ion etch) process. Fused silica is used for its low fluorescence, permitting better sensitivity to low fluorescence signals. Several other processes have been explored for constructing a groove plate.

Bead Entrance/Exit Ports 1009—The bead tubes from the probes terminate in this port. The gasket taper to a rounded cone, with the port at the apex. The goal is to minimize dead volume, so that beads maintain momentum as they enter and exit the cell through the port. Each alley has a fluidically isolated port.

Bead Tubes, fluoropolymer 1010—The bead tubes carry beads into the cell through the transfer process, and carry them out of the cell during the flush process. Fluoropolymer tubing is used for inertness, to minimize friction and reduce bubble adhesion.

Probe Assemblies 1011—The probes are connected and integral with the bead tubes. The probes enter the well plate for transferring beads into the cell. The probes are designed to withstand "bottoming out" in the well plate and are spring loaded.

Well Plate 1012
Water Tube Assembly 1013
Tube Assembly, External, Water 1013a
Buffer Tube Assembly 1014
Tube Assembly, External, Buffer 1014a
Alcohol Tube Assembly 1015
Tube Assembly, External, Alcohol 1015a
Air & Fluid Excess Tube Assembly 1016
Tee 1016a
Air Inlet to Valve Check Valve 1016b—On syringe aspirate from this valve position, allows air to enter the syringe. The check valve blocks flow in the dispense direction Air Inlet to Valve Check Valve 1016c—This check valve allows flow in the dispense direction to waste, but blocks return flow, to prevent aspiration from waste.

Waste Drain Tube Assembly 1017

Tube Assembly, External, Waste Drain 1017*a*

Panel Connections 1018—Field connections for the customer. Luer locks are preferred.

Reagent Bottles 1019

Bottle Caps 1019*a*

Tube Connections 1019*b*

Straws 1019*c*

Filters 1019*d*

Level Switches 1020—Sense reagent bottles empty below a set point or waste bottle full over a maximum level.

Waste Bottle 1021

Waste/Wash Tray 1022—Divided into two sections—one for dumping waste fluid and beads, and a section for washing the probe tips. Spillage from the wash overflows into waste. Fluid may be pumped using the auxiliary pump into the wash section to augment cleaning and to add bleach.

Wash subsystem 1023

Auxiliary pump 1023*a*

Check Valve 1023*b*—Prevents back pressure on the auxiliary pump.

A rotary valve selects among reagent and waste bottles, or output to the cell. The syringe pump aspirates or dispenses to the selected valve.

Either by hand or using laboratory automation, the user places a 96 well micro-titre plate on the platform.

An actuator moves the platform with the plate into position.

Transfer beads into cell a) Probe assemblies descend to near top of well b) Slow compression of the puffer tubing to displace fluid into the wells c) Probe assemblies move to bottom of well d) Rapid release of puffer tubing to draw fluid and beads into the bead tubes FIG. 119 sets forth the governing design principles.

DESCRIPTION OF THE 6 STEPS

The 6 steps are described in detail, as follows:

1) The Prime Cell Step

FIG. 122*a-e* show the basic sequence of the prime cell step.

The purpose of the Prime Cell step is to configure the cell and its associated fluidic components in a state that allows effective transfer of beads from the well plate 1012 to the cell. Such a state is characterized by having the entire fluidic system, from the syringe pump to the probe tips filled with a buffer solution and having substantially all the air removed from the fluidic system, including both small air bubbles and larger cavities. Once in this state, the fluidic system is considered "stiff" from a fluidic point of view, and is capable of supporting bead transfer, bead loading and bead flushing operations.

The following sequence, which relies on a syringe pump as the motive for fluids through the system, is designed to prime the cell:

Displace fluid in system with air,

Displace Air with Ethanol,

Displace Ethanol with Water, and

Displace Water with Buffer.

Each of the four basic elements of the prime cycle has a specific purpose, as does the order of operations. The importance of the first step, pushing air through the system to displace any fluid that may already be in the system, was found to help with the second step, ethanol purge; though it is still unclear why it helps. Ethanol is the first fluid pushed through the system after purging with air. Ethanol has a very low surface tension and is a good wetting agent; properties that make it ideal for removing bubbles throughout the system, especially in the cell where bubbles trapped in the small cross-section device are most difficult to remove. Once the interior surfaces of the fluidic system are wetted with ethanol and the air bubbles are removed, water is pushed through. Although the ethanol is highly effective at removing air bubbles, the one source of trapped air ethanol cannot remove resides in the chimney. The pocket of air trapped in the chimney is a consequence of pushing fluid down the chimney rather than up the chimney. The natural tendency of the air in the chimney is to rise since it is less dense than all the fluids. When ethanol is pushed through, it simply spills around the air pocket as it travels from the top of the chimney to the bottom on its way to the cell. The spilling effect, a result of very low surface tension, prevents the air from being displaced by the liquid. To overcome this, water is pushed through the system next. Because the ethanol wets all surfaces the water can come through next and wet the surfaces by simply displacing the ethanol rather than trying the wet dry surfaces directly. Once the water displaces the ethanol, its high surface tension allows it to form a meniscus at the top of the chimney, which follows the shape of the chimney as it travel from the inlet at the top of the chimney to the cell at the bottom. Provided the inside diameter of the chimney never exceeds a critical diameter (approximately 9 mm for a round geometry and less for shapes that deviate from round), it is possible to support a column of water above the air without spilling around the air pocket. As the water is introduced into the chimney by the syringe pump the pocket of air is continuously pushed down toward the bottom of the chimney and eventually out through the cell and finally through the probe tips. In addition to the critical diameter, it is also important that surfaces and transitions inside the chimney be smooth and continuous; asperities will tend to break the meniscus as it travels slowly down the chimney. Once the water is pushed entirely through the system and the cell is free of all air both in the form of bubbles and cavities the sequence proceeds to the final step, which is to simply displace the water with a buffer solution. The system is now considered primed.

2) The Transfer Beads to Cell Step

FIG. 123*a-e* show the basic sequence of the step for transferring of beads 8 to the cell or well-plate 1008.

The transfer process refers to the movement of beads from the well-plate 1012 to the cell 1008 through a path, which includes the transfer tube, the cell and finally the chimney. In most cases, beads begin their journey at the bottom of a round bottom well; since they are denser than the buffer fluid they sink to the bottom of the well. The method of transferring beads from the well plate involves vacuuming them off the bottom of the well with an open-ended tube attached to the cell, called a transfer tube. At the distal end of the transfer tube is the probe tip which has attached to it a cone-shaped vestige designed to enhance the flow rate around beads that are more than a few tube diameters away from the center of the tube, thereby enhancing the efficiency of the transfer process. However, unlike a typical vacuum whereby the flow rate is always in the same direction (i.e. into the vacuum) the method employed here involves alternating the direction of the flow and varying the rate of flow.

Responsibility for this action is a device called a "puffer," which consists of a flexible silicone tube approximately 2" long by ¼" diameter. The tube is connected in-line between the syringe pump and the cell and is placed between two metal surfaces, on of which moves in order to squeezed the tube. Fluid rushes out of the tube when it's squeezed and back in when it's released. Since one end of the tube is dead-ended at the syringe and the other end (the part that goes into the well with the beads) is open, the net flow is always through the open end, both inward and outward.

Beads are transported from the well-plate to the cell by repeating a cycle of slow contractions and fast expansions of the puffer tube. Slow contractions re-set the puffer tube to a state whereby a vacuum can be applied to the transfer tube (expansion), thereby pulling beads toward the cell. While the flow rate is slow liquid moves past the beads without carrying them very far in the direction of the flow. While the flow is rapid, beads are effectively moved in the direction of the flow. Therefore, repeating the cycle causes the beads to acquire a net motion in the direction of the fast flow. This method is employed to lift beads out of the well plate and transport them to the cell during the transfer process and move beads out on the groove plate during the load process and remove beads from the grooves and flush them out of the cell during the flush process.

Another key element of the fluidic architecture with regard to the transfer process is the chimney. The chimney is made to have a rapidly increasing inner diameter starting from the point at which it is attached to the cell. The purpose of the large inner diameter is to decrease the flow rate to the extent that beads cannot travel past the chimney and become lost in tubing. The inner volume of the chimney is designed to be 2 to 5 times larger than the volume of fluid displaced by the puffer during the transfer process. It was found that beads entering the chimney at high rates of speed travel about ¾ the height of the chimney before the flow is reversed (slow contraction) which then pushes the beads to the bottom of the chimney and even out onto the groove plate. After a certain number of puffer cycles (10-15), the puffer stops and beads fall under their own weight to the bottom of the chimney and pile up in small rectangular opening called the line port. The distribution of beads in the port is uniform across the opening, which is important for the next step; bead load.

Beads are considered transferred after a set number of (empirically determined) puffer cycles. Once the beads are transferred excess cycles cause them to harmlessly rise and fall in the chimney. Therefore, without a means of feedback, the transfer process is always run with an excess number of cycles to ensure that a high percentage of beads are transferred. Efficiencies that range between 95 and 99.9% are obtained after about 15 cycles, approximately 40 seconds. The process concludes with beads settling to the bottom of the chimney on the groove plate in a pile substantially uniform in distribution within the port, a consequence of randomization caused by turbulent flow in the chimney.

The port, which is defined as the opening of the chimney to the cell, is rectangular in shape, approximately 6 mm long and 250 µm wide. It is surrounded on three edges by the gasket, which forms the perimeter of each of the 8 independent lanes. The fourth edge is open to the lane leading to the grooved region. The back edge of the port is aligned as closely as possible to the edge of the gasket so as to minimize dead zones in the flow field caused by eddy currents. Gaps that range from 0 to 50 µm were found to eliminate such dead regions behind the opening of the port where beads could potentially become stuck. Similarly, the width of the port opening is large enough to ensure beads don't form a log jam but small enough ensure the velocity of the flow through any portion of the opening is sufficiently large to carry beads out of the port region during the bead load process. The range of openings found to be effective were 200 to 400 µm. The length of the port opening, which spans nearly the entire 7 mm width of the lane, was found to produce the most uniform distribution of beads in the grooved region of any combination of port and gasket shapes. Other geometries tried involved ports of various sizes of circles with gaskets cut into linear tapers, horn shaped tapers and parabolic shaped taper, which depending on the flow rate, produced either narrow beam-like distributions or lobed distributions characterized by a low density region of beads in the middle of the lane and high density regions near the edges of the lane. Both types of profiles produced unacceptably low total packing densities, a feature that plays heavily into the overall throughput of the instrument. Unlike the circular port shapes that rely on the flow field to produce distribution functions, the rectangular port shape allows the beads to form a uniform distribution across the width of the lane by the simple process of mixing in the chimney then settling to the bottom.

Another feature of the cell that plays in important roll in the dynamics of bead transport is the thickness of the gasket. The gasket not only defines the perimeter of the lane around the grooved region and the ports, it also defines the height of the column of fluid in the cell. With a density of 2.2 glass beads sink in aqueous solutions, which means when they are in the cell they will lay on the surface of the groove plate (the bottom of the cell), where the velocity of the laminar flow is close to zero. When the height of the laminar flow field (thickness of the gasket) becomes very large compared with the diameter of the bead the velocity of the flow intercepting the bead approaches zero. Therefore, to maximize the interaction of the bead with the flow field the gasket thickness should be kept as thin as possible.

Countering this requirement are two issues that occur when the gasket is too thin. The first pertains to the persistence of small air bubbles. The smaller the gap between the groove plate and the top plate the harder it becomes to flush small air bubbles away. It was found that a gasket thickness of less than 300 µm resulted in such problems. The second relates to the pressure drop across the cell during the transfer cycle. Because the entire pressure generated by the puffer during transfer drops across both the cell and the transfer tube, since they're in series with each other, the impedance of the cell cannot be much larger than the transfer line. Otherwise the flow rate at the distal end of the transfer tube will be insufficient to cause bead transport out of the well. Therefore it is important to balance the impedance of the transfer tube with the cell. Again, the minimum gasket thickness was found to be around 300 m.

3) Load the Beads into the Grooves

Figure 124A:
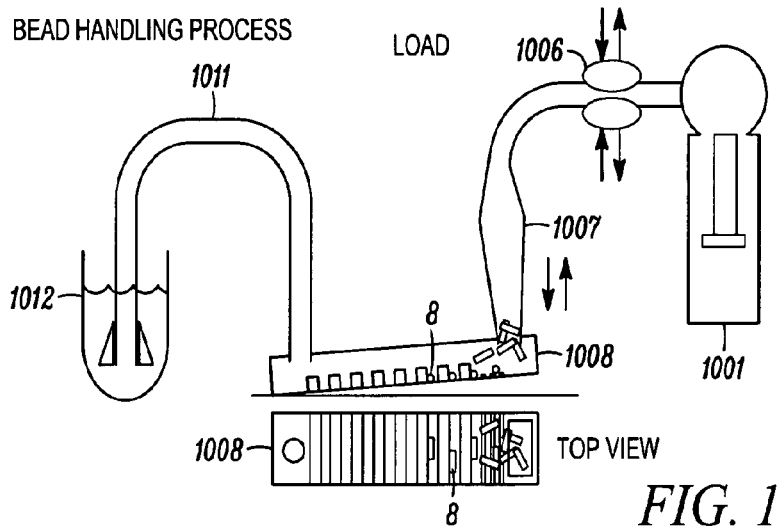
Figure 124B:
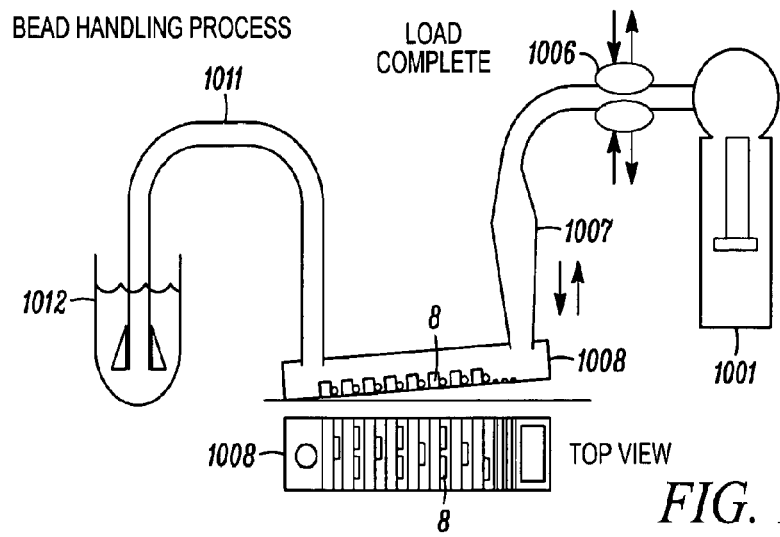

FIG. 124a-b show the basic sequence of the step for loading of the beads 8 into the grooves of the well-plate 1008.

4) Scan the Beads in the Well-Plate

The step for scanning the beads in the well-plate 1008 is consistent with that described above.

5) Flushing the Beads from the Grooves

FIGS. 125a-b show the basic sequence of the step for flushing the beads 8 from the grooves of the well-plate 1008.

FIG. 126: The Groove Plate Design

FIG. 126 a and b show the groove plate design.

FIG. 127a-d: Bead Alignment Feasibility Experiments

Figure 127D:
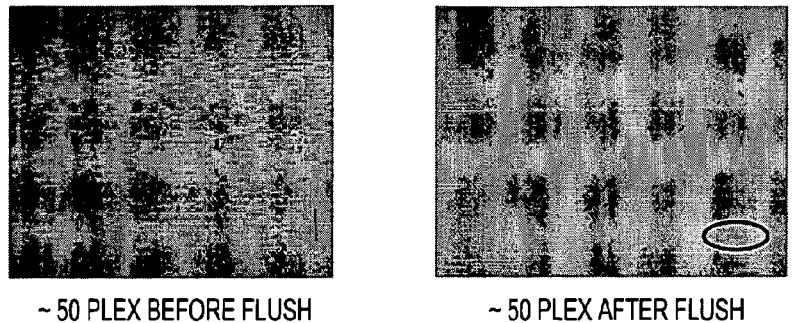
Figure 128:
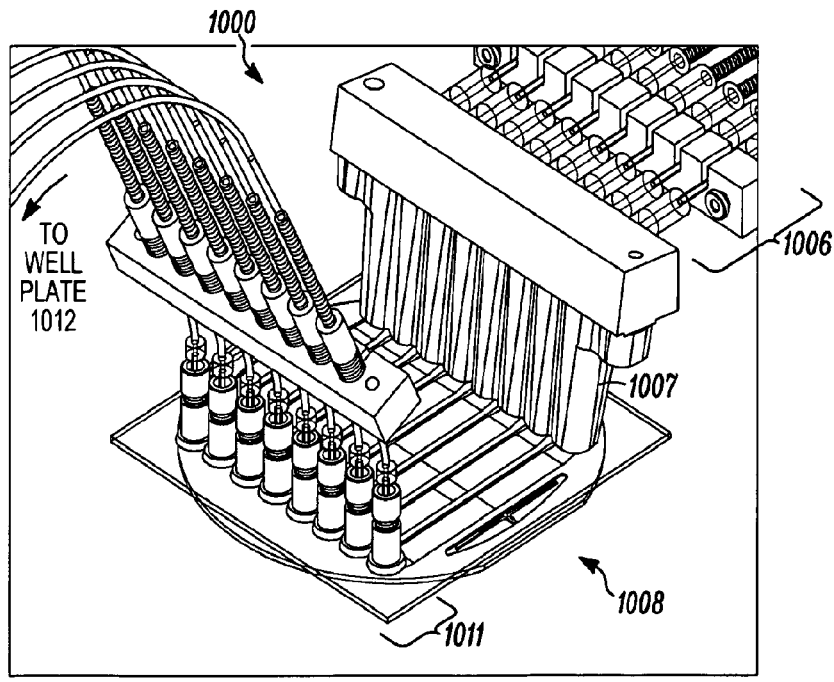
Figure 129:
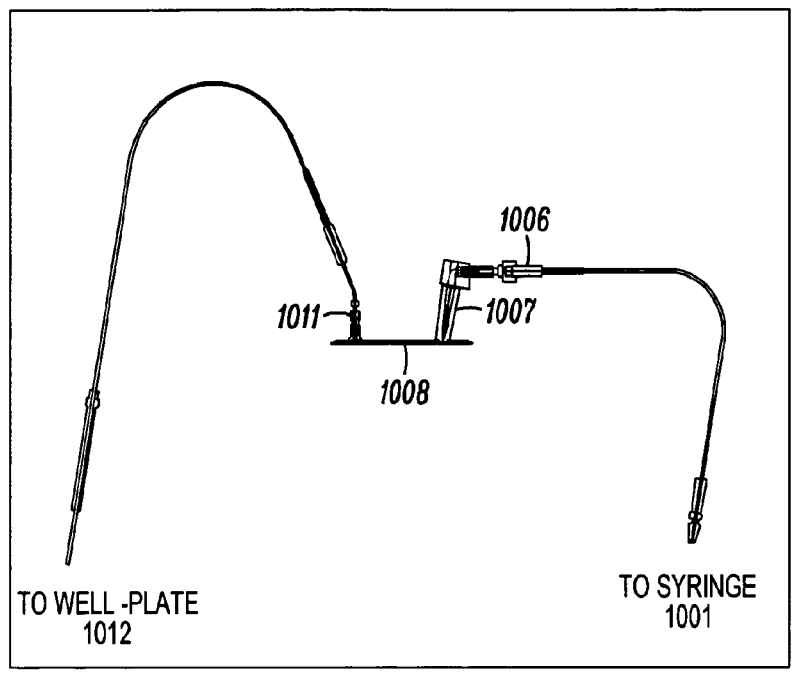
Figure 130A:
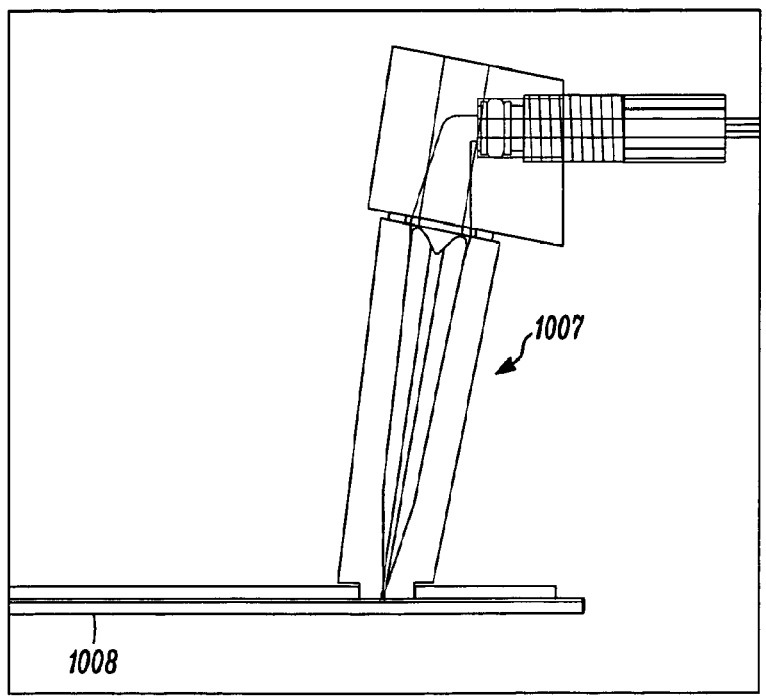
Figure 130B:
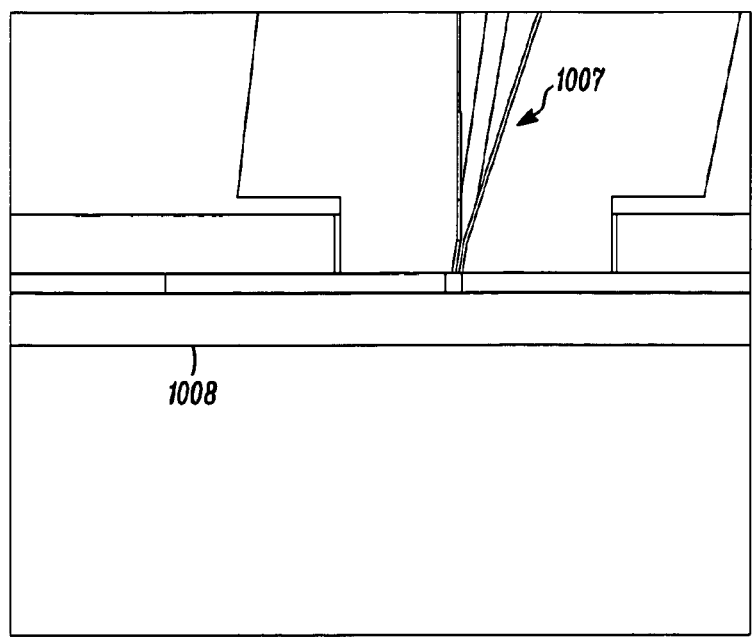
Figure 131:
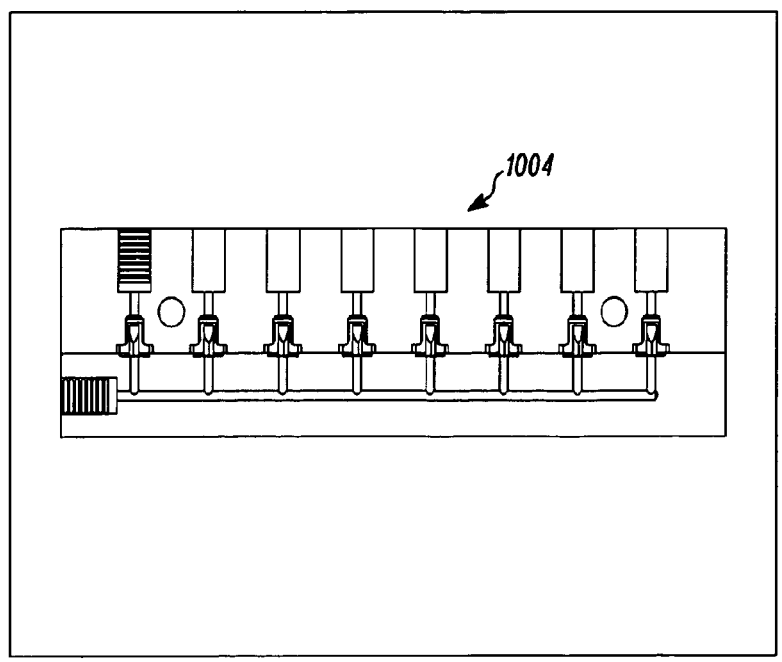
Figure 132:
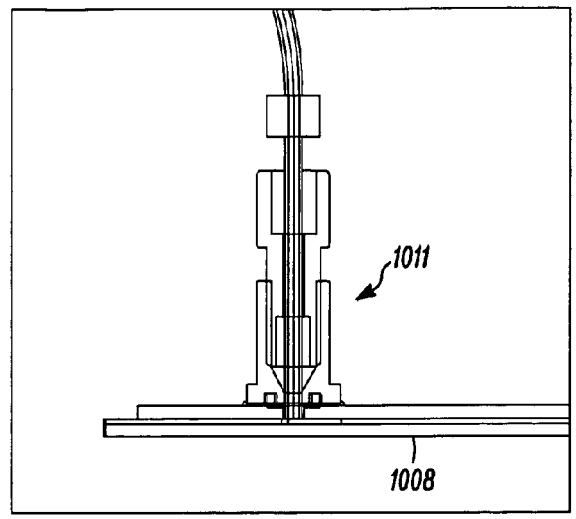
Figure 133:
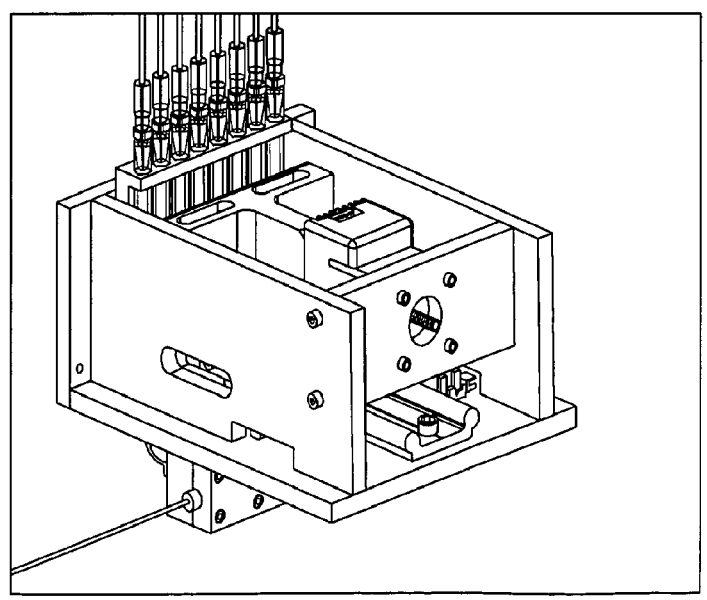

FIG. 127 a-d relate to bead feasibility experiments, including FIG. 127a that shows bead alignment feasibility experiments with performance requirements and drivers and the basic parameters of the experiment; FIG. 127b that shows multiplex ranges; FIG. 127c that shows bead loss feasibility experiments; and FIG. 127d that shows bead flush feasibility experiments.

FIGS. 128-133

FIGS. 128-133 show more detailed diagrams of components of the basic architecture 1001.

THE SCOPE OF THE INVENTION

Unless otherwise specifically stated herein, the term "microbead" is used herein as a label and does not restrict any embodiment or application of the present invention to certain dimensions, materials and/or geometries.

The dimensions and/or geometries for any of the embodiments described herein are merely for illustrative purposes and, as such, any other dimensions and/or geometries may be used if desired, depending on the application, size, performance, manufacturing requirements, or other factors, in view of the teachings herein.

It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof, the foregoing and various other additions and omissions may be made therein and thereto without departing from the spirit and scope of the present invention.

What is claimed is:

1. An optical reader for reading encoded microparticles, each microparticle having an elongated body with an optically detectable code extending along a longitudinal axis of the corresponding elongated body, the reader comprising:
   a plate having a plurality of channels extending lengthwise along a surface of the plate, each of the channels configured to receive and align a plurality of the microparticles so that the codes of the microparticles are in a common fixed orientation relative to each other and extend longitudinally along a length of the respective channel;
   an illumination source for illuminating the microparticles in the channels, the codes in the microparticles reflecting a portion of incident light and permitting a portion of the incident light to pass through the microparticles thereby providing an output signal indicative of the code; and
   a detection device configured to capture the output signals provided by the microparticles.

2. The reader in accordance with claim 1 wherein the channels have one of a square shape, a rectangular shape, a V-shape, and a semi-circular shape.

3. The reader in accordance with claim 1 wherein the plate is an optically transparent medium.

4. The reader in accordance with claim 1 wherein the channels are open-sided such that microparticles are free to move across a side of the plate until aligning with and coming to rest in the channels.

5. The reader in accordance with claim 1 further comprising an agitation device configured to agitate the plate to encourage alignment of the microparticles within the channels.

6. The reader in accordance with claim 1 wherein the illumination source comprises light for illuminating the codes and light for exciting labels on the microparticles.

7. The reader in accordance with claim 1 wherein the detection device is configured to read codes from light reflected by the microparticles in a predetermined optical output pattern.

8. The reader in accordance with claim 1 wherein the detection device is configured to capture an image.

9. The reader in accordance with claim 8 wherein the image comprises at least a first series of illuminated stripes indicating a digital pattern associated with a corresponding one of the microparticles.

10. The reader in accordance with claim 1 wherein the detection device constitutes a CCD camera that detects at least one of (i) light reflected from the microparticles and (ii) light passing through the microparticles.

11. The reader in accordance with claim 1 wherein the detection device includes an optical scanner that scans the channels to read the codes, the plate and the optical scanner moving relative to one another during a scan in a direction that is along the lengths of the channels.

12. The reader in accordance with claim 1 further comprising a computing device configured to identify a probe or an analyte attached to a corresponding microparticle based upon the code of the corresponding microparticle.

13. The reader in accordance with claim 1 further comprising a fluidic system configured to load the microparticles onto the plate and remove the microparticles from the plate.

14. The reader in accordance with claim 13 wherein the fluidic system includes liquid and is substantially free of air.

15. The reader in accordance with claim 13 wherein the fluidic system includes liquid and directs fluid flow across the plate, the channels being open-sided such that microparticles are free to move across a side of the plate until aligning with and coming to rest in the channels.

16. The reader in accordance with claim 1 further comprising the microparticles, each of the codes comprising a grating that provides a plurality of light beams when the incident light is incident upon the grating, the plurality of light beams projecting from the respective microparticle at different angles and constituting the output signal.

17. The reader in accordance with claim 1 wherein the illumination source and the plate are configured to be positioned relative to each other so that the microparticles have a common orientation relative to the incident light when illuminated.

18. The reader in accordance with claim 1 wherein the channels align the microparticles so that the microparticles have a common orientation relative to the detection device when the detection device captures the corresponding output signals.

19. The reader in accordance with claim 1 wherein each of the channels has a cross-section taken perpendicular to the length of the channel that is sized and shaped to accommodate only one microparticle.

20. An optical reader for reading encoded microparticles, each microparticle having an elongated body with an optically detectable code extending along a longitudinal axis of the corresponding elongated body, the reader comprising:

a plate having a plurality of channels extending lengthwise along a surface of the plate, each of the channels configured to receive and align a plurality of the microparticles;

an illumination source for illuminating the codes of the microparticles in the channels, the codes in the microparticles reflecting a portion of incident light and permitting a portion of the incident light to pass through the microparticles thereby providing an output signal indicative of the code; and a detection device configured to capture the output signals provided by the microparticles, wherein the plate, the illumination source, and the detection device are configured to be positioned so that the microparticles have a common orientation relative to the detection device when the detection device captures the corresponding output signals, the microparticles being in fixed positions with respect to the plate.

21. The reader in accordance with claim 20 wherein each of the channels has a cross-section taken perpendicular to the length of the channel that is sized and shaped to accommodate only one microparticle.

\* \* \* \* \*